US009376420B2

(12) United States Patent
Park et al.

(10) Patent No.: US 9,376,420 B2
(45) Date of Patent: Jun. 28, 2016

(54) 4,5-DIHYDRO-1H-PYRAZOLE DERIVATIVE OR SALTS THEREOF, AND PHARMACEUTICAL COMPOSITION COMPRISING SAME

(71) Applicant: YUHAN CORPORATION, Seoul (KR)

(72) Inventors: Chan-Sun Park, Gyeonggi-do (KR); Young-Hwan Kim, Gyeonggi-do (KR); Gyu-Jin Lee, Gyeonggi-do (KR); Youn Hur, Gyeonggi-do (KR); Eun-Hye Jung, Gyeonggi-do (KR); Hee-Jae Tak, Gyeonggi-do (KR); Seung-Yub Shin, Seoul (KR); Ho-Jin Lee, Seoul (KR); Chun-Ho Lee, Seoul (KR); Koo-Yeon Lee, Gangwon-do (KR)

(73) Assignee: YUHAN CORPORATION, Seoul (KR)

( * ) Notice: Subject to any disclaimer, the term of this patent is extended or adjusted under 35 U.S.C. 154(b) by 0 days.

(21) Appl. No.: 14/438,299

(22) PCT Filed: Oct. 23, 2013

(86) PCT No.: PCT/KR2013/009446
§ 371 (c)(1),
(2) Date: Apr. 24, 2015

(87) PCT Pub. No.: WO2014/065575
PCT Pub. Date: May 1, 2014

(65) Prior Publication Data
US 2015/0291563 A1    Oct. 15, 2015

(30) Foreign Application Priority Data

Oct. 25, 2012    (KR) .................. 10-2012-0119067
Oct. 25, 2012    (KR) .................. 10-2012-0119077

(51) Int. Cl.
*C07D 403/04* (2006.01)
*C07D 231/06* (2006.01)
*C07D 401/10* (2006.01)
*C07D 403/10* (2006.01)
*C07D 401/06* (2006.01)

(52) U.S. Cl.
CPC ............ *C07D 403/10* (2013.01); *C07D 231/06* (2013.01); *C07D 401/06* (2013.01); *C07D 401/10* (2013.01); *C07D 403/04* (2013.01)

(58) Field of Classification Search
CPC .. C07D 231/06; C07D 401/06; C07D 401/10; C07D 403/10; C07D 403/04; A61K 31/415; A61P 9/00
USPC ..................................................... 546/268.1
See application file for complete search history.

(56) References Cited

U.S. PATENT DOCUMENTS 8,044,053 B2    10/2011  Buschmann et al.
2004/0019222 A1*  1/2004  Alcon-Marrugat . C07D 231/06
                                        548/377.1
2009/0286758 A1   11/2009  McElroy et al.
2010/0184772 A1    7/2010  Buschmann et al.
2012/0022058 A1    1/2012  Arhancet et al.

FOREIGN PATENT DOCUMENTS

WO    2007/009698 A1    1/2007

OTHER PUBLICATIONS

Tanaka; Chemistry Letters 1983, 507-510.*
Murai; Tetrahedron Letters 2012, 53, 3746-3749, S1-S62.*
Dorwald; "Side Reactions in Organic Synthesis: A Guide to Successful Synthesis Design" 2005 Wiley-VCH Verlag GmbH & Co. KGaA, Wienheim, chapter 1.*
McKenna et al., "Minireview: Evolution of NURSA, the Nuclear Receptor Signaling Atlas", Mol Endocrinol, vol. 23, No. 6, pp. 740-746, (2009).
Lehmann et al., "Activation of the Nuclear Receptor LXR by Oxysterols Defines a New Hormone Response Pathway", J. Biol. Chem., vol. 272, No. 6, pp. 3137-3140, (1997).
Willy et al., "LXR, a nuclear receptor that defines a distinct retinoid response pathway", Genes Dev., vol. 9, No. 9, pp. 1033-1045, (1995).
Zelcer et al., "Liver X receptors as integrators of metabolic and inflammatory signaling", The Journal of Clinical Investigation, vol. 116, No. 3, pp. 607-614, (2006).
Singaraja et al., "Increased ABCA1 activity protects against atherosclerosis", J. Clin. Invest., vol. 110, No. 1, pp. 35-42, (2002).
Peet et al., "Cholesterol and Bile Acid Metabolism Are Impaired in Mice Lacking the Nuclear Oxysterol Receptor LXRα", Cell, vol. 93, pp. 693-704, (1998).
Tangirala et al., "Identification of macrophage liver X receptors as inhibitors of atherosclerosis", PNAS, vol. 99, No. 18, pp. 11896-11901, (2002).

(Continued)

*Primary Examiner* — Andrew D Kosar
*Assistant Examiner* — Daniel Carcanague
(74) *Attorney, Agent, or Firm* — Vorys, Sater, Seymour & Pease LLP; Mih Suhn Koh

(57) ABSTRACT

The present invention provides a 4,5-dihydro-1H-pyrazole derivative or its pharmaceutically acceptable salt, a process for the preparation thereof, and a pharmaceutical composition comprising the same. The 4,5-dihydro-1H-pyrazole derivative or its pharmaceutically acceptable salt effectively increases the LXR transcriptional activity, and therefore can be usefully applied for preventing or treating a dysfunction in cholesterol metabolism, such as cholesterol gallstone, hyperlipidemia, or coronary atherosclerosis.

17 Claims, No Drawings-

(56) References Cited

OTHER PUBLICATIONS

Diblasio-Smith et al., "Discovery and implementation of transcriptional biomarkers of synthetic LXR agonists in peripheral blood cells", Journal of Translational Medicine, vol. 6, No. 59, pp. 1-15, (2008).

Katz et al., "Safety, Pharmacokinetics, and Pharmacodynamics of Single Doses of LXR-623, a Novel Liver X-Receptor Agonist, in Healthy Participants", J Clin Pharmacol, vol. 49, pp. 643-649, (2009).

* cited by examiner

4,5-DIHYDRO-1H-PYRAZOLE DERIVATIVE OR SALTS THEREOF, AND PHARMACEUTICAL COMPOSITION COMPRISING SAME

TECHNICAL FIELD

The present invention relates to a 4,5-dihydro-1H-pyrazole derivative or its pharmaceutically acceptable salt, a process for the preparation thereof, and a pharmaceutical composition comprising the same.

BACKGROUND ART

Nuclear receptors (NR) are family of DNA transcription factors found within cells that are involved in various transcriptional programs in the body. There are 48 kinds of nuclear receptors identified depending upon the ligands. In normal state, NRs exist in inactive forms forming homodimer or heterodimer complexes with corepressors. Endogenous ligands in response to external stimuli or exogenous ligands activate NRs inducing dissociation of corepressors and recruit coactivators which lead to the DNA response element and interaction between NRs and transcription factors, thereby regulating the expression of target genes (McKenna, N. J. et al. Mol. Endocrinol. 2009, 23: 740-746). And also, post translational modifications, such as acetylation, phosphorylation, ubiquitination, etc., play a critical role in regulating the activities of nuclear receptors.

Liver X receptor (LXR), one of the NRs activated by endogenous ligand oxysterol, is a transcription factor involved in the control of cholesterol homeostasis in the body. Oxysterols, oxidized forms of cholesterols, are produced by the cholesterols metabolism in the body (Lehmann, et al. J. Biol. Chem. 1997, 272(6):3137-3140). There are two isoforms of LXR: LXRα and LXRβ. The two isoforms share about 77% sequence homology in their ligand binding domains (LBD). The LXRα is predominantly expressed in the liver, while the LXRβ is expressed ubiquitously in the body (Willy, et al. Gene Dev. 1995, 9(9):1033-1045). LXR facilitates the excretion of cholesterols through reverse cholesterol transport (RCT) from the peripheries to the liver. In the RCT, two cholesterol transporters, i.e., the ABC-A1 (ATP-binding cassette transporter A1) and the ABC-G1 (ATP-binding cassette transporter G1) expressed in peripheral macrophages, play a crucial role. LXR ligands increase the expressions of ABC-A1/G1, thereby stimulating the RCT (J Clin Invest 2006, 116(3):607-614).

The overexpression of ABC-A1 in an experimental model of atherosclerosis (i.e., apoE-knockout mice) showed 66% reduction in atherosclerotic lesion formation in the blood vessel (Singaraja, et al. J Clin Invest 2002, 110(1):35-42). The knockout of LXRα gene results in abnormal control of cholesterol levels, which leads to liver damages along with increased LDL level, decreased HDL level, and decreased expressions of lipid-related genes in the blood vessel (Peet et al. Cell 1998, 93:693-704). The double knockout of LXRα/β exhibits decreased expressions of cholesterol transporters and increased lipid accumulation in macrophages, thereby facilitating atherogenesis, which mimics the symptoms of Tangier disease, a human genetic HDL deficiency (Tangirala et al. PNAS 2002, 99(18):11896-11901). And also, it has been reported that, when human peripheral blood monocytes (PBMC) were treated with synthetic LXR ligands, the expressions of ABC-A1 and ABC-G1 genes were rapidly increased (Diblasio-Smith et al. J Transl Med 2008, 6(59):1-15). It has been reported that, when a synthetic ligand was single administered to healthy participants followed by measuring the relationship between the blood concentration and the expressions of ABC-A1/G1, the expressions of ABC-A1/G1 were increased in a dose-proportional manner (Katz et al. J Clin pharmacol 2009, 49:643-649).

Therefore, a ligand capable of increasing the LXR transcriptional activity is expected to be useful for preventing or treating a dysfunction in cholesterol metabolism, including e.g., cholesterol gallstone, hyperlipidemia, or coronary atherosclerosis.

DETAILED DESCRIPTION OF THE INVENTION

Technical Problem

The present inventors found that a 4,5-dihydro-1H-pyrazole derivative and its pharmaceutically acceptable salt increases the LXR transcriptional activity, and therefore can be usefully applied for preventing or treating a dysfunction in cholesterol metabolism.

Therefore, the present invention provides the above 4,5-dihydro-1H-pyrazole derivative or its pharmaceutically acceptable salt, a process for the preparation thereof, and a pharmaceutical composition comprising the same.

Technical Solution

According to an aspect of the present invention, there is provided a 4,5-dihydro-1H-pyrazole derivative and its pharmaceutically acceptable salt.

According to another aspect of the present invention, there is provided a process for preparing said compound and its pharmaceutically acceptable salt.

According to still another aspect of the present invention, there is provided a pharmaceutical composition for preventing or treating a dysfunction in cholesterol metabolism, including cholesterol gallstone, hyperlipidemia, and coronary atherosclerosis, comprising said compound or its pharmaceutically acceptable salt as an active ingredient.

Advantageous Effects

The compound of the present invention, i.e., the 4,5-dihydro-1H-pyrazole derivative or its pharmaceutically acceptable salt, effectively increases the LXR transcriptional activity. Therefore, said 4,5-dihydro-1H-pyrazole derivative or its pharmaceutically acceptable salt can be usefully applied for preventing or treating a dysfunction in cholesterol metabolism, such as cholesterol gallstone, hyperlipidemia, or coronary atherosclerosis.

BEST MODE FOR CARRYING OUT THE INVENTION

As used herein, the term "alkyl" refers to a straight or branched aliphatic hydrocarbon radical. For example, the $C_1$-$C_6$ alkyl means a straight or branched aliphatic hydrocarbon having 1 to 6 carbon atoms, such as methyl, ethyl, propyl, n-butyl, n-pentyl, n-hexyl, isopropyl, isobutyl, sec-butyl, tert-butyl, neopentyl, and isopentyl.

The term "alkoxy" refers to a radical formed by substituting the hydrogen atom of a hydroxyl group with an alkyl. For example, the $C_1$-$C_6$ alkoxy includes methoxy, ethoxy, propoxy, n-butoxy, n-pentyloxy, isopropoxy, sec-butoxy, tert-butoxy, neopentyloxy, and isopentyloxy.

The term "aryl" refers to an organic radical derived from an aromatic hydrocarbon, through removing one hydrogen atom therefrom, including mono or poly-fused ring systems such as 6- to 12-membered substituted or unsubstituted rings. The "aryl" includes, for example, phenyl, naphthyl, biphenyl, etc.

The term "heteroaryl" refers to a 5- to 12-membered aromatic radical having one or more, preferably 1 to 4, heteroatoms selected from oxygen (O) atom, nitrogen (N) atom, and sulfur (S) atom, including a 5- or 6-membered monocyclic heteroaryl radical and a poly-cyclic heteroaryl radical formed by fusing the 5- or 6-membered monocyclic heteroaryl radical with one or more benzene rings. The 'heteroaryl' may be also partially saturated. For example, the "heteroaryl" includes pyridine, pyridazine, pyrimidine, pyrazine, triazine, thiophene, furan, thiazole, oxazole, pyrazole, imidazole, pyrrole, isothiazole, isoxazole, triazole, thiadiazole, tetrazole, oxadiazole, benzothiazole, bezoxazole, benzimidazole, benzofuran, benzothiophene, benzisoxazole, indole, indoline, quinoline, isoquinoline, quinazoline, imidazopyridine, oxazolopyridine, etc.

The term "heterocycle" refers to a 3- or 12-membered mono- or poly-cyclic ring having one or more, preferably 1 to 4, heteroatoms selected from oxygen (O) atom, nitrogen (N) atom, and sulfur (S) atom, but not containing an aromatic ring. For example, the "heterocycle" includes tetrahydropyridine, tetrahydropyrimidine, dihydropyridine, dihydropyrazine, piperidine, piperazine, diazepane, pyrrolidine, tetrahydrofuran, hexahydropyrimidine, hexahydropyridazine, etc.

The present invention provides a compound of Formula 1 or its pharmaceutically acceptable salt:

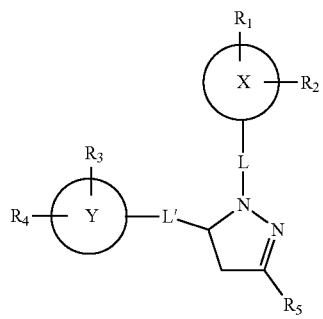

<Formula 1> wherein,

L and L' are, independently each other, —(CH$_2$)$_n$—, n is 0, 1, 2, or 3,

Ring X and Ring Y are, independently each other, a C$_3$~C$_6$ cycloalkyl ring, an aryl ring, a heteroaryl ring, or a heterocyclic ring, R$_1$ and R$_3$ are, independently each other, hydrogen or halogen, R$_2$ and R$_4$ are, independently each other, hydrogen; halogen; a C$_1$~C$_5$ alkyl group optionally substituted with one or more halogens; a C$_1$~C$_5$ alkoxy group; an aryl group; a heteroaryl group; or a heterocyclic group, when R$_2$ and R$_4$ are, independently each other, an aryl group, a heteroaryl group or a heterocyclic group, the aryl group, the heteroaryl group or the heterocyclic group is optionally substituted with one or more substituents selected from the group consisting of halogen; hydroxyl; cyano; azido; C$_1$~C$_5$ alkyl optionally substituted with one or more substituents selected from the group consisting of halogen, hydroxy, and hydroxyimino; C$_2$~C$_6$ alkenyl; C$_2$~C$_6$ alkynyl; C$_3$~C$_6$ cycloalkyl; aryl; heteroaryl; heterocyclic; —SO$_3$H; —SO$_2$R; —SOR; —SR;

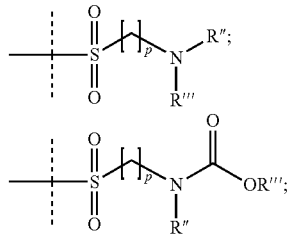

—OR; —COR; —CO$_2$R; —OC(=O)R; —OCO$_2$R; —OC(=O)NRR'; —NR"C(=O)R'''; —NR"C(=O)OR'''; —NR"SO$_2$R'''; —CONR"R'''; and —NR"R''', R and R' are, independently each other, hydrogen; a C$_1$~C$_5$ alkyl group optionally substituted with one or more substituents selected from the group consisting of halogen, hydroxy and C$_3$~C$_6$ cycloalkyl; a C$_3$~C$_6$ cycloalkyl group; an aryl group optionally substituted with one or more halogens; an aralkyl group; a heteroaryl group; or a heterocyclic group, R" and R''' are, independently each other, hydrogen; a C$_1$~C$_5$ alkyl group optionally substituted with one or more substituents selected from the group consisting of halogen and hydroxy; a C$_3$~C$_6$ cycloalkyl group; or an aryl group, p is 0, 1, 2, 3, 4, or 5, and R$_5$ is CF$_2$CF$_3$ or C(CF$_3$)$_2$OH.

In an embodiment of the present invention, Ring Y may be benzene. In said embodiment, the compound according to the present invention has the following Formula 1a:

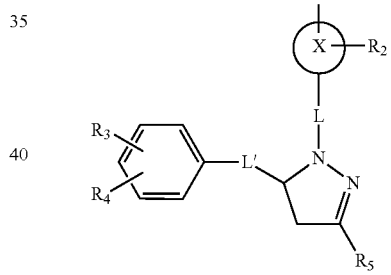

<Formula 1a> wherein, Ring X, L, L', R$_1$, R$_2$, R$_3$, R$_4$, and R$_5$ are the same as defined in the above.

In another embodiment of the present invention, Ring Y may be pyridine. In said embodiment, the compound according to the present invention has the following Formula 1 b:

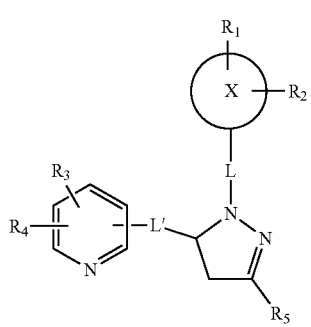

<Formula 1b> wherein, Ring X, L, L', $R_1$, $R_2$, $R_3$, $R_4$, and $R_5$ are the same as defined in the above.

In still another embodiment of the present invention, Ring Y may be thiophene. In said embodiment, the compound according to the present invention has the following Formula 1c:

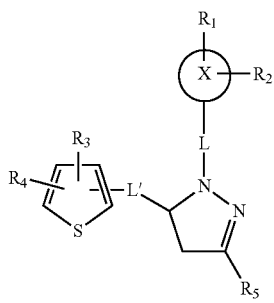

<Formula 1c> wherein, Ring X, L, L', $R_1$, $R_2$, $R_3$, $R_4$, and $R_5$ are the same as defined in the above for the Formula 1.

In still another embodiment of the present invention, $R_5$ may be $CF_2CF_3$. In said embodiment, the compound according to the present invention has the following Formula 1d:

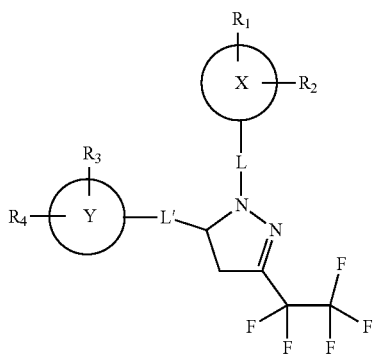

<Formula 1d> wherein, Ring X, Ring Y, L, L', $R_1$, $R_2$, $R_3$, and $R_4$ are the same as defined in the above.

In the compound of Formula 1d or its pharmaceutically acceptable salt, preferably L is —$(CH_2)_n$—, n is 0 or 1, L' is —$(CH_2)_n$—, n is 0, Ring X is a $C_3$~$C_6$ cycloalkyl ring; benzene; pyridine; or pyridazine, Ring Y is benzene; pyridine; or thiophene, $R_1$ and $R_3$ are, independently each other, hydrogen or halogen, $R_2$ is hydrogen; halogen; a $C_1$~$C_5$ alkyl group optionally substituted with one or more halogens; a $C_1$~$C_5$ alkoxy group; a phenyl group; a pyridinyl group; a 1,2,3,6-tetrahydropyridinyl group; or a piperazinyl group, when $R_2$ is a phenyl group, a pyridinyl group, a 1,2,3,6-tetrahydropyridinyl group, or a piperazinyl group, the phenyl group, the pyridinyl group, the 1,2,3,6-tetrahydropyridinyl group, or the piperazinyl group is optionally substituted with one or more substituents selected from the group consisting of $C_1$~$C_5$ alkylthio; $C_1$~$C_5$ alkylsulfonyl; $C_3$~$C_6$ cycloalkylsulfonyl; $C_1$~$C_5$ alkoxycarbonyl;

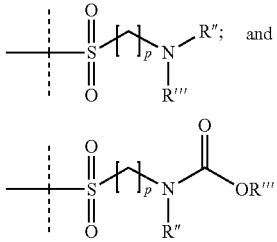

(wherein, R" and R'" are, independently each other, hydrogen; or a $C_1$~$C_5$ alkyl group optionally substituted with hydroxy, and p is 0, 1, 2, or 3), $R_4$ is halogen; a phenyl group; a heteroaryl group selected from the group consisting of pyrazolyl, pyridinyl, pyrimidinyl, and quinolinyl; or a heterocyclic group selected from the group consisting of pyrrolidinyl, 2-oxo-pyrrolidinyl, 1,2,3,6-tetrahydropyridinyl, piperidinyl, piperazinyl, morpholinyl, and homopiperazinyl, when $R_4$ is a phenyl group, the phenyl group is optionally substituted with one or more substituents selected from the group consisting of halogen; hydroxy; cyano; $C_1$~$C_5$ alkyl optionally substituted with one or more substituents selected from the group consisting of halogen, hydroxy, and hydroxyimino; $C_1$~$C_5$ alkoxy; $C_1$~$C_5$ alkylthio; $C_1$~$C_5$ alkylsulfonyl; $C_1$~$C_5$ alkylsulfinyl; $C_1$~$C_5$ alkylcarbonyl; triazolyl; tetrazolyl; —NR"R'"; —NR"SO$_2$R'";

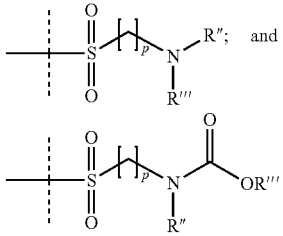

(wherein, p, R" and R'" are the same as defined in the above), when $R_4$ is a heteroaryl group or a heterocyclic group, the heteroaryl group or the heterocyclic group is optionally substituted with one or more substituents selected from the group consisting of halogen; cyano; hydroxy; $C_1$~$C_5$ alkyl optionally substituted with one or more substituents selected from the group consisting of halogen and hydroxy; $C_1$~$C_5$ alkoxy; formyl; $C_1$~$C_5$ alkylthio; $C_1$~$C_5$ alkylsulfonyl optionally substituted with trifluoromethyl; $C_3$~$C_6$ cycloalkylsulfonyl; mono or di-$C_1$~$C_5$ alkylaminosulfonyl; $C_1$~$C_5$ alkylcarbonyl; $C_1$~$C_5$ alkoxycarbonyl; mono or di-$C_1$~$C_5$ alkylaminocarbonyl; amino; $C_1$~$C_5$ alkylsulfonylamino; $C_3$-$C_6$ cycloalkylsulfonylamino; and $C_1$~$C_5$ alkoxycarbonylamino.

In the compound of Formula 1 d or its pharmaceutically acceptable salt, $R_3$ may be hydrogen. At this time, the compound according to the present invention has the following Formula 1e:

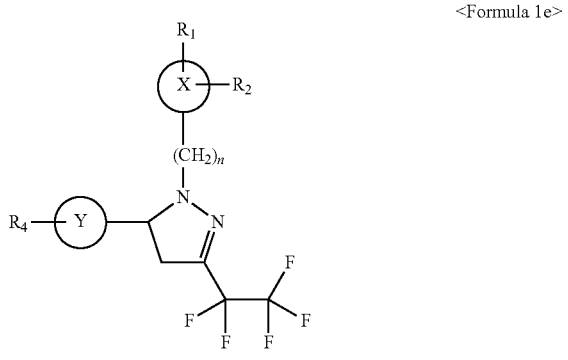

<Formula 1e> wherein, Ring X, Ring Y, $R_1$, $R_2$, and $R_4$ are the same as defined in the above, and n is 0 or 1.

In the compound of Formula 1 d or its pharmaceutically acceptable salt, $R_3$ may be halogen; and Ring X and Ring Y may be benzene. At this time, the compound according to the present invention has the following Formula 1f:

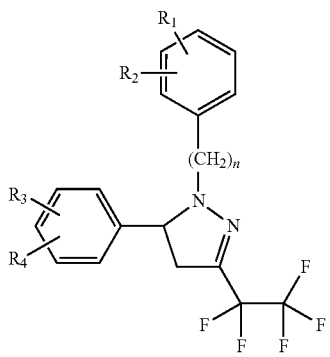

<Formula 1f> wherein, $R_1$, $R_2$, and $R_4$ are the same as defined in the above, $R_3$ is halogen, and n is 0 or 1.

In the compound of Formula 1d or its pharmaceutically acceptable salt, $R_3$ and $R_4$ may be halogen; Ring X and Ring Y may be benzene; $R_2$ may be a phenyl group, a pyridinyl group, a 1,2,3,6-tetrahydropyridinyl group, or a piperazinyl group [where the phenyl group, the pyridinyl group, the 1,2,3,6-tetrahydropyridinyl group, or the piperazinyl group may be optionally substituted with one or more substituents selected from the group consisting of $C_1$~$C_5$ alkylthio; $C_1$~$C_5$ alkylsulfonyl; $C_3$~$C_6$ cycloalkylsulfonyl; $C_1$~$C_5$ alkoxycarbonyl;

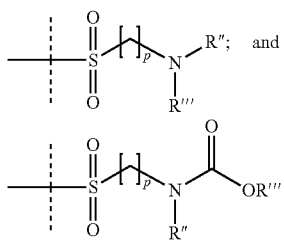

(wherein, R" and R'" are, independently each other, hydrogen; or $C_1$~$C_5$ alkyl optionally substituted with hydroxy, and p is 0, 1, 2, or 3)].

In still another embodiment of the present invention, $R_5$ may be $C(CF_3)_2OH$. In said embodiment, the compound according to the present invention has the following Formula 1g:

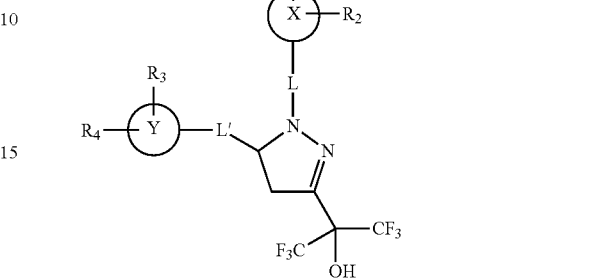

<Formula 1g> wherein, Ring X, Ring Y, L, L', $R_1$, $R_2$, $R_3$, and $R_4$ are the same as defined in the above for the Formula 1.

In the compound of Formula 1g or its pharmaceutically acceptable salt, preferably n is 0, Ring X is benzene, Ring Y is benzene; pyridine; or thiophene, $R_1$ and $R_3$ are, independently each other, hydrogen or halogen, $R_2$ is halogen; a phenyl group; a pyridinyl group; a 1,2,3,6-tetrahydropyridinyl group; or a piperazinyl group, when $R_2$ is a phenyl group, a pyridinyl group, a 1,2,3,6-tetrahydropyridinyl group, or a piperazinyl group, the phenyl group, the pyridinyl group, the 1,2,3,6-tetrahydropyridinyl group, or the piperazinyl group is optionally substituted with one or more substituents selected from the group consisting of $C_1$~$C_5$ alkylthio; $C_1$~$C_5$ alkylsulfonyl; $C_3$~$C_6$ cycloalkylsulfonyl; and $C_1$~$C_5$ alkoxycarbonyl, $R_4$ is halogen; a phenyl group; a heteroaryl group selected from the group consisting of furanyl, pyridinyl, pyrimidinyl, indolyl, benzofuranyl, benzothienyl, and quinolinyl; or a heterocyclic group selected from the group consisting of 1,2,3,6-tetrahydropyridinyl, piperidinyl, piperazinyl, 1,1-dioxothiomorpholinyl, and homopiperazinyl, when $R_4$ is a phenyl group, the phenyl group is optionally substituted with one or more substituents selected from the group consisting of halogen; hydroxy; cyano; $C_1$~$C_5$ alkyl optionally substituted with one or more substituents selected from the group consisting of halogen and hydroxy; $C_1$~$C_5$ alkoxy optionally substituted with one or more halogens; $C_1$~$C_5$ alkylthio; $C_1$~$C_5$ alkylsulfonyl; $C_1$~$C_5$ alkylsulfinyl; $C_1$~$C_5$ alkylcarbonyl; hydroxycarbonyl; triazolyl; tetrazolyl; —NR"R'"; —NR"SO$_2$R'"; —NR"C(=O)R'";

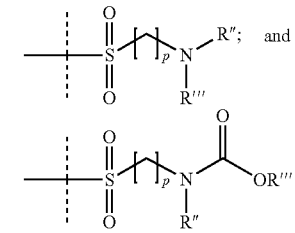

(wherein, R" and R'" are, independently each other, hydrogen, $C_1 \sim C_5$ alkyl optionally substituted with hydroxy, or $C_3 \sim C_6$ cycloalkyl, and p is 0, 1, 2, or 3), when $R_4$ is a heteroaryl group or a heterocyclic group, the heteroaryl group or the heterocyclic group is optionally substituted with one or more substituents selected from the group consisting of halogen; cyano; $C_1 \sim C_5$ alkyl optionally substituted with one or more halogens; $C_1 \sim C_5$ alkoxy; formyl; $C_1 \sim C_5$ alkylthio; $C_1 \sim C_5$ alkylsulfonyl alkyl optionally substituted with one or more halogens; $C_3 \sim C_6$ cycloalkylsulfonyl; benzenesulfonyl; pyrrolidin-1-yl-sulfonyl; mono or di-$C_1 \sim C_5$ alkylaminosulfonyl; $C_1 \sim C_5$ alkylcarbonyl optionally substituted with hydroxy; $C_3 \sim C_6$ cycloalkylcarbonyl; $C_3 \sim C_6$ cycloalkyl-$C_1 \sim C_5$ alkylcarbonyl; benzoyl optionally substituted with halogen; benzylcarbonyl; thiophenecarbonyl; $C_1 \sim C_5$ alkoxycarbonyl; hydroxycarbonyl; mono or di-$C_1 \sim C_5$ alkylaminocarbonyl; amino; $C_3 \sim C_6$ cycloalkylsulfonylamino; $C_1 \sim C_5$ alkoxycarbonylamino; and tetrazolyl.

In the compound of Formula 1g or its pharmaceutically acceptable salt, $R_3$ may be hydrogen. At this time, the compound according to the present invention has the following Formula 1h:

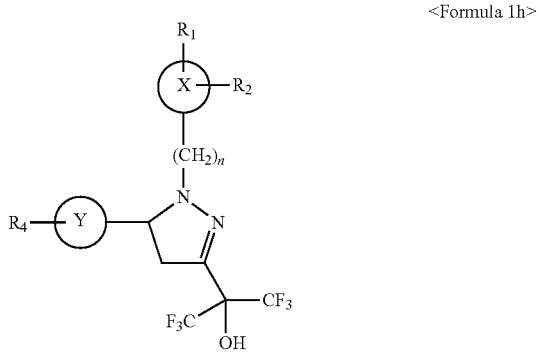

<Formula 1h> wherein, Ring X, Ring Y, $R_1$, $R_2$, and $R_4$ are the same as defined in the above, and n is 0.

In the compound of Formula 1g or its pharmaceutically acceptable salt, $R_3$ may be halogen; and Ring X and Ring Y may be benzene. At this time, the compound according to the present invention has the following Formula 1i.

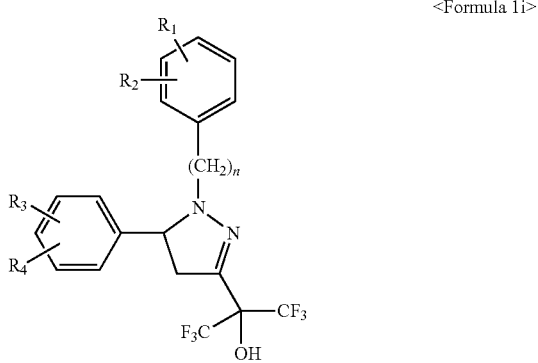

<Formula 1i> wherein, $R_1$, $R_2$, and $R_4$ are the same as defined in the above, $R_3$ is halogen, and n is 0.

In the compound of Formula 1g or its pharmaceutically acceptable salt, $R_3$ may be hydrogen; $R_4$ may be halogen; Ring X and Ring Y may be benzene; $R_2$ may be a phenyl group, a pyridinyl group, a 1,2,3,6-tetrahydropyridinyl group, or a piperazinyl group (where the phenyl group, the pyridinyl group, the 1,2,3,6-tetrahydropyridinyl, or the piperazinyl group is optionally substituted with one or more substituents selected from the group consisting of $C_1 \sim C_5$ alkylthio; $C_1 \sim C_5$ alkylsulfonyl; $C_3 \sim C_6$ cycloalkylsulfonyl; and $C_1 \sim C_5$ alkoxycarbonyl).

The compound of Formula 1 or its pharmaceutically acceptable salt may have substituents containing asymmetric carbon and therefore be in the form of racemic mixture (RS) or in forms of optical isomers, such as (R) or (S) isomer. The compound of Formula 1 or its pharmaceutically acceptable salt comprises both racemic mixture (RS) and optical isomers such as (R) or (S) isomer.

The compound of Formula 1 of the present invention may be in a pharmaceutically acceptable salt form. The salt may be a conventional acid addition salt form, which includes e.g., salts derived from an inorganic acid such as hydrochloric acid, hydrobromic acid, sulfuric acid, or phosphoric acid; and salts derived from an organic acid such as citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, glutamic acid, or aspartic acid. And also, the salt includes a conventional metal salt form, e.g., salts derived from an alkali metal such as lithium, sodium, or potassium; salts derived from an alkaline earth metal such as calcium or magnesium; or a chromium salt.

The compound of Formula 1 or its pharmaceutically acceptable salt of the present invention may be prepared according to the following exemplary reaction schemes. In the following reaction schemes, it will be apparent to those skilled in the art that the reaction steps are changeable according to the procedures for introducing Ring X, Ring Y, $R_1$, $R_2$, $R_3$, and $R_4$.

The compound of Formula 1 or its pharmaceutically acceptable salt of the present invention may be prepared according to the following Reaction Scheme 1.

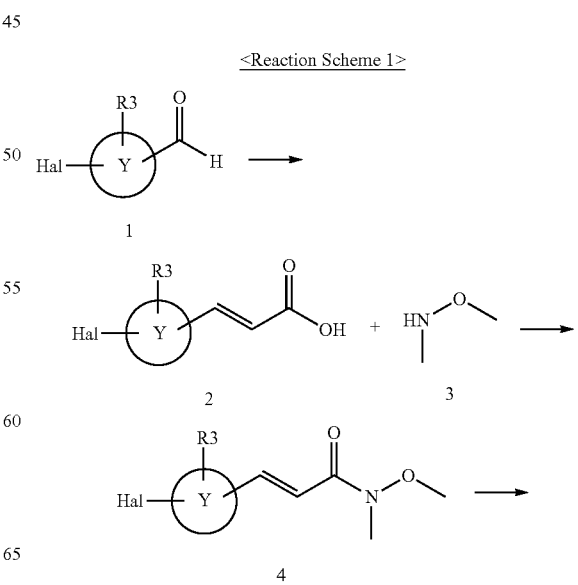

<Reaction Scheme 1>

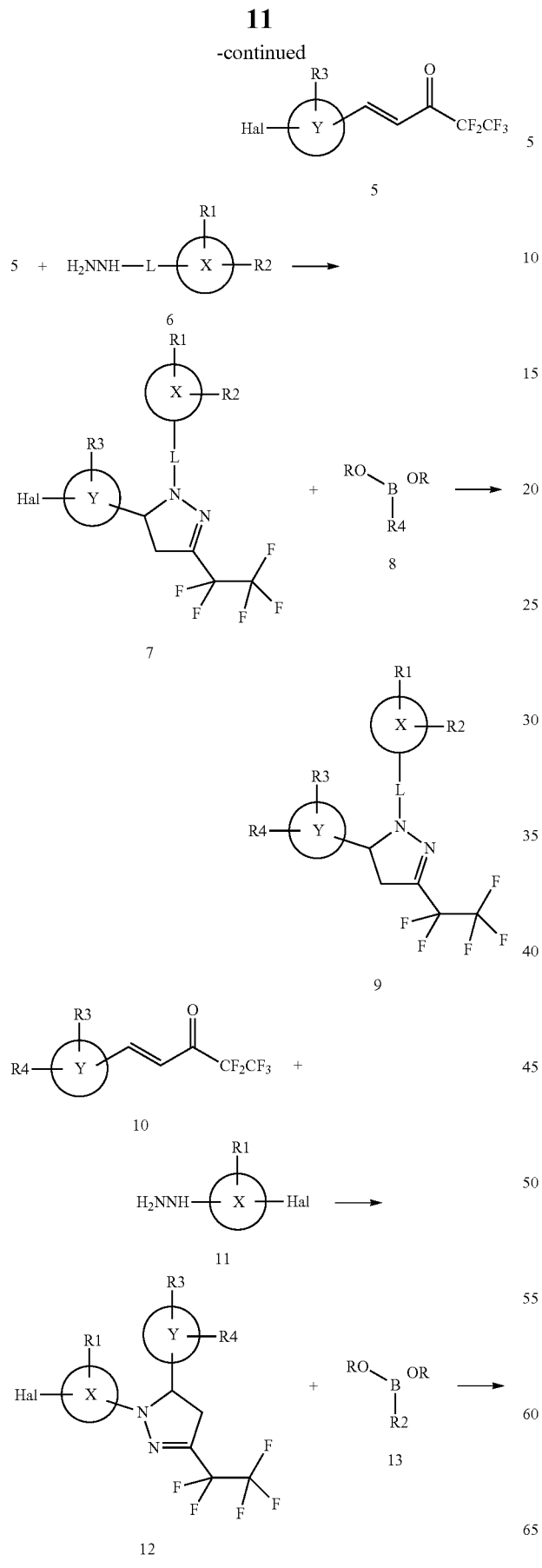

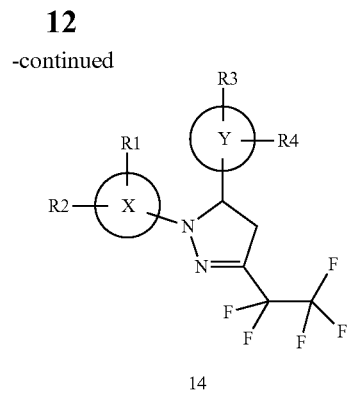

In the above reaction scheme, Ring X, Ring Y, L, $R_1$, $R_2$, $R_3$, and $R_4$ are the same as defined in the above; Hal is halogen; and R is hydrogen or $C_1$~$C_5$ alkyl or may be cyclized each other to form a pentagonal or hexagonal ring comprising boron and oxygen, wherein the ring may be substituted with $C_1$~$C_5$ alkyl.

The compound 1, i.e., an aldehyde derivative, is commercially available. The compound 1 may be reacted with malonic acid to convert to a compound 2. The reaction between the compound 1 and malonic acid may be carried out according to known methods (Szymanski, Wiktor; Wu, Bian; Janssen, Dick B.; Weiner, Barbara; Feringa, Ben L.; De Wildeman, Stefaan; *Journal of Organic Chemistry*, 74, 9152-9157, 2009).

The compound 2 may be converted to a compound 4 by coupling the cinnamic acid derivative thereof with N,O-dimethylhydroxylamine hydrochloride of the compound 3. The coupling, i.e., an amide-coupling, may be carried out according to conventional methods, for example, an acyl halide method, an azide method, a carboxylic acid anhydride method, a carbodiimide method, an active ester method, or a carbonyldiimidazole method (see Miklos Bodanszky, *Principles of Peptide Synthesis*, 2nd Ed., 1993). Preferably, the carbodiimide method or the acyl halide method may be used.

The coupling reaction may be carried out using dicyclohexylcarbodiimide (DCC), diisopropylcarbodiimide, or soluble N-(3-dimethylaminopropyl)-N'-ethylcarbodiimide (EDAC). If necessary, the reaction may be facilitated by the addition of 1-hydroxybenzotriazole (HOBT). The coupling reaction may be carried out in an inert solvent such as dichloromethane, acetonitrile or N,N-dimethylformamide, in the presence of an organic base such as triethylamine, diisopropylethylamine, N-methylmorpholine, N,N-dimethylaminopyridine or N-methylpyrrolidine, at a temperature ranging from room temperature to 50° C.

The coupling reaction according to the acyl halide method may be carried out by reacting the compound 2 with thionyl chloride or oxalyl chloride to convert the carboxylic acid of the compound 2 to an acyl halide and then reacting the resulting acyl halide with the compound 3 in the presence of an organic base such as pyridine, triethylamine, diisopropyl ethylamine, N-methylmorpholine, N, N-dimethylaminopyridine or N-methylpyrrolidine. The coupling reaction may be carried out in a solvent such as dichloromethane or pyridine, at a temperature ranging from room temperature to 100° C.

The compound 4 may be converted to a compound 5 or a compound 10 through pentafluoroethyl-substitution. The pentafluoroethyl-substitution may be performed according to known methods (Kokotos, Christoforos G.; Baskakis, Constantinos; Kokotos, George; *Journal of Organic Chemistry*, 73, 8623-8626, 2008).

The compound 5 or the compound 10 may be converted to a compound 7 or a compound 12 by condensing with a hydrazine derivative of the compound 6 or 11. The compound 6 and the compound 11 are commercially available. The condensation may be performed according to known methods (Chimenti, F.; Bizzarri, B.; Manna, F.; Bolasco, A.; Secci, D.; Chimenti, P.; Granese, A.; Rivanera, D.; Lilli, D.; Scaltrito, M. M.; Brenciaglia, M. I.; *Bioorganic & Medicinal Chemistry Letters*, 15, 603-608, 2005).

The compound 7 or the compound 12 may be converted to a compound 9 or a compound 14 by reacting with a boronic acid derivative of the compound 8 or 13. The reaction may be performed according to an arylation reaction (e.g., a Suzuki coupling reaction) and a Buchwald-Hartwig cross-coupling reaction (Barbara Czako and Laszlo Kurti; *STRATEGIC APPLICATIONS of NAMED REACTIONS in ORGANIC SYNTHESIS*, 2005).

If necessary, the compound 9 or the compound 14 may be used as an intermediate for preparing other compounds according to the present invention. For example, the compound 9 or the compound 14 may be subject to oxidation, reduction, addition, protection, deprotection, amide coupling, etc., so as to prepare other compounds according to the present invention having a moiety such as sulfinyl, sulfonyl, amine, alcohol, carboxylic acid, carboxamide, sulfonamide, oxime, etc.

The compound of Formula 1 or its pharmaceutically acceptable salt of the present invention may be also prepared according to the following Reaction Scheme 2.

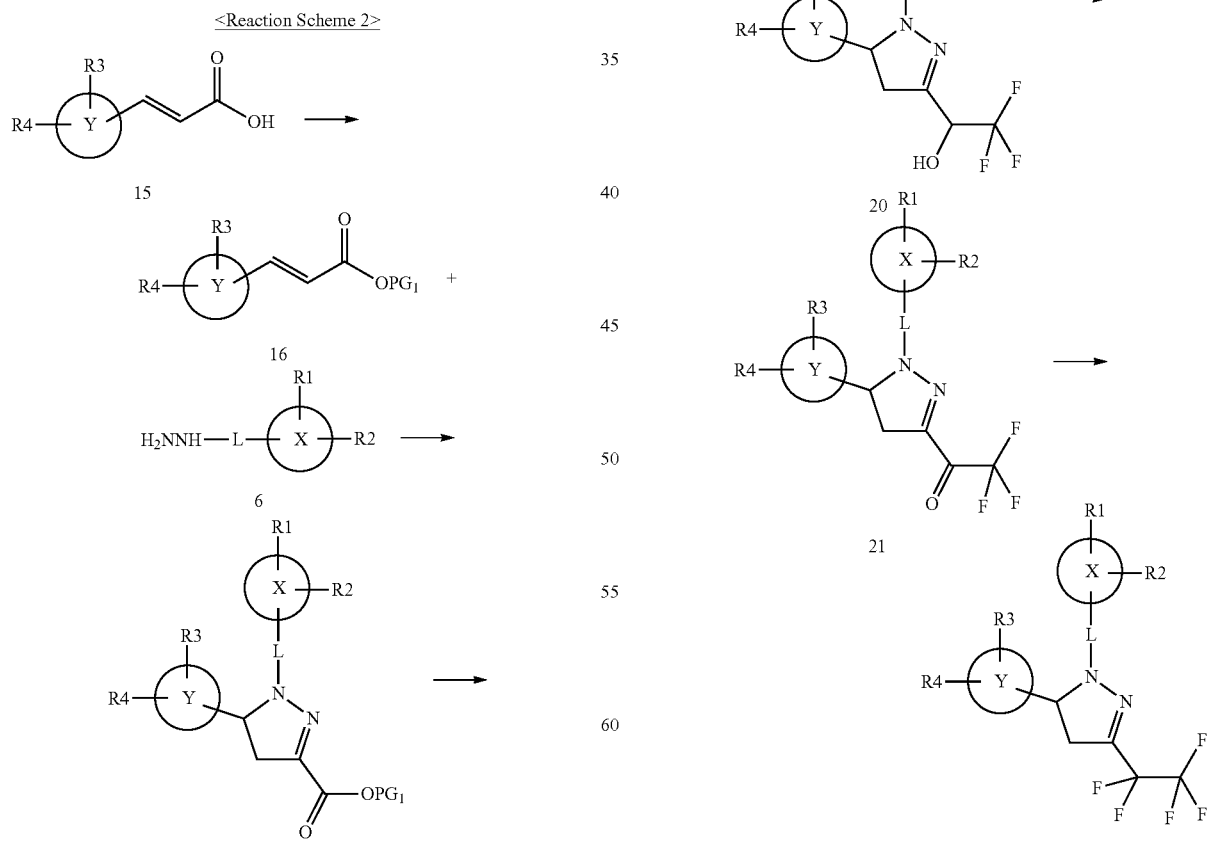

In the above reaction scheme, Ring X, Ring Y, L, $R_1$, $R_2$, $R_3$, and $R_4$ are the same as defined in the above; and $PG_1$ is a carboxyl-protecting group.

A cinnamic acid derivative of the compound 15 is commercially available. The compound 15 may be converted to an ester derivative of compound 16 by reacting with alkyl alcohol in the presence of an acid. The available carboxyl-protecting group ($PG_1$) is preferably a $C_1$~$C_6$ alkyl group, such as methyl, ethyl, isobutyl, tert-butyl, etc.

The compound 16 may be converted to a compound 17 by condensing with a hydrazine derivative of the compound 6. The compound 6 is commercially available. The condensation may be performed according to known methods (Chimenti, F.; Bizzarri, B.; Manna, F.; Bolasco, A.; Secci, D.; Chimenti, P.; Granese, A.; Rivanera, D.; Lilli, D.; Scaltrito, M. M.; Brenciaglia, M. I.; *Bioorganic & Medicinal Chemistry Letters*, 15, 603-608, 2005).

The compound 17 may be converted to a 4,5-dihydro-1H-pyrazole methylalcohol derivative of the compound 18 through reduction using sodium borohydride. The reduction may be performed according to known methods (Boechat, Nubia; Costa, Jorge Carlos Santos da; Mendonca, Jorge de Souza; Oliveira, Pedro Santos Mello de; Souza, Marcus Vinicius Nora De; *Tetrahedron Letters*, 45, 6021-6022, 2004).

The compound 18 may be converted to a 4,5-dihydro-1H-pyrazole aldehyde derivative of the compound 19 through oxidation using magnesium peroxide ($MnO_2$). The oxidation may be performed according to known methods (Kikuchi, Kouichi; Hibi, Shigeki; Yoshimura, Hiroyuki; Tai, Kenji; Hida, Takayuki; Tokuhara, Naoki; Yamauchi, Toshihiko; Nagai, Mitsuo; *Bioorganic & Medicinal Chemistry Letters*, 10, 619-622, 2000).

The compound 19 may be converted to a compound 20 through mono-$CF_3$ addition using $CF_3TMS$. The mono-$CF_3$ addition may be performed according to known methods (Santos Fustero; Raquel Romaan; Juan F. Sanz-Cervera; Antonio Simon-Fuentes; Jorge Bueno; Salvador Villanova; *Journal of Organic Chemistry*, 73, 8545-8552, 2008).

The compound 20 may be converted to a compound 21 through oxidation using Dess-Martin Periodinane (DMP). The oxidation may be performed according to known methods (Kobayashi, Kensuke; Tsujita, Tomohiro; Ito, Hirokatsu; Ozaki, Satoshi; Tani, Takeshi; Ishii, Yasuyuki; Okuda, Shoki; Tadano, Kiyoshi; Fukuroda, Takahiro; Ohta, Hisashi; Okamoto, Osamu; *Bioorganic & Medicinal Chemistry Letters*, 19, 4729-4732, 2009).

The compound 21 may be converted to a compound 22 through fluorination using bis(2-methoxyethyl)aminosulfur trifluoride (BAST). The fluorination may be performed according to known methods (Alexandre L'Heureux; Francis Beaulieu; Christopher Bennett; David R. Bill; Simon Clayton; Franc-ois LaFlamme; Mahmoud Mirmehrabi; Sam Tadayon; David Tovell; Michel Couturier; *Journal of Organic Chemistry*, 75, 3401-3411, 2010).

If necessary, the compound 22 may be used as an intermediate for preparing other compounds according to the present invention. For example, the compound 22 may be subject to Suzuki coupling (as mentioned in the above Scheme 1), Buchwald-Hartwig cross-coupling, oxidation, reduction, addition, protection, deprotection, amide coupling, arylation, C—N coupling, etc., so as to prepare other compounds according to the present invention having a moiety such as sulfinyl, sulfonyl, amine, alcohol, carboxylic acid, carboxamide, sulfonamide, oxime, etc.

The compound of Formula 1 or its pharmaceutically acceptable salt of the present invention may be also prepared according to the following Reaction Scheme 3.

<Reaction Scheme 3>

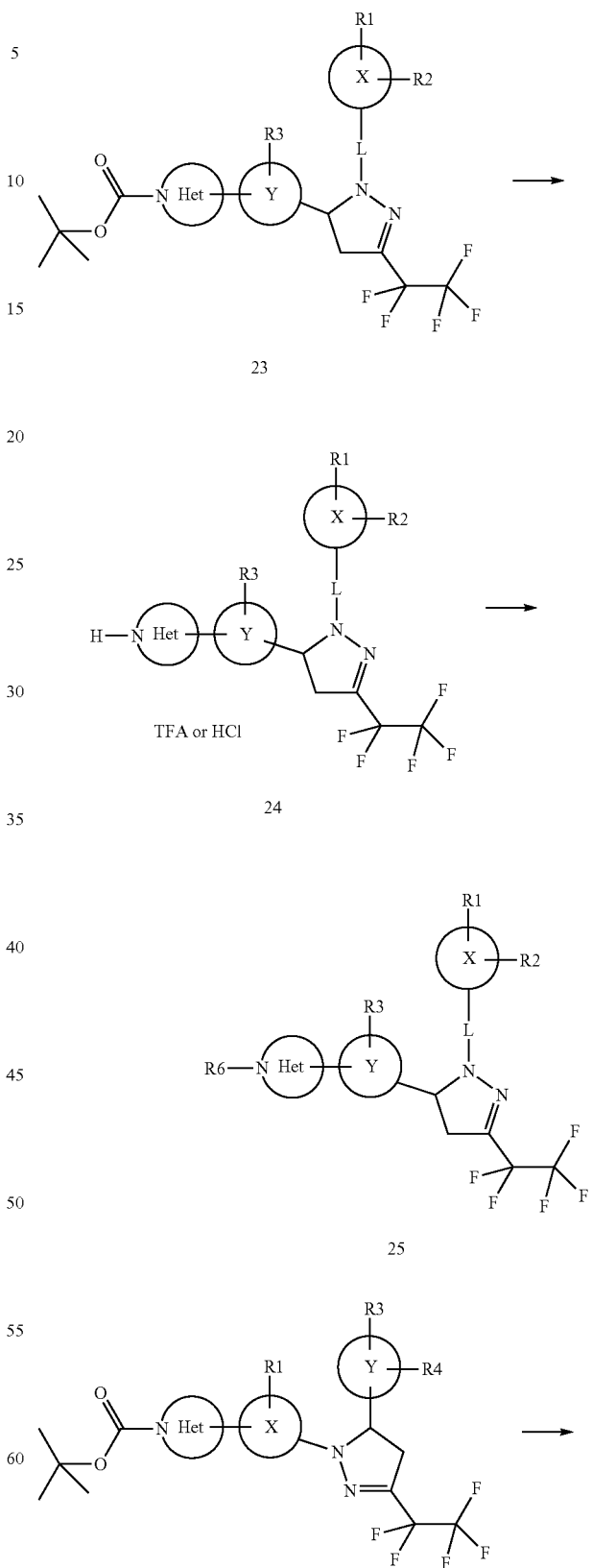

17

-continued

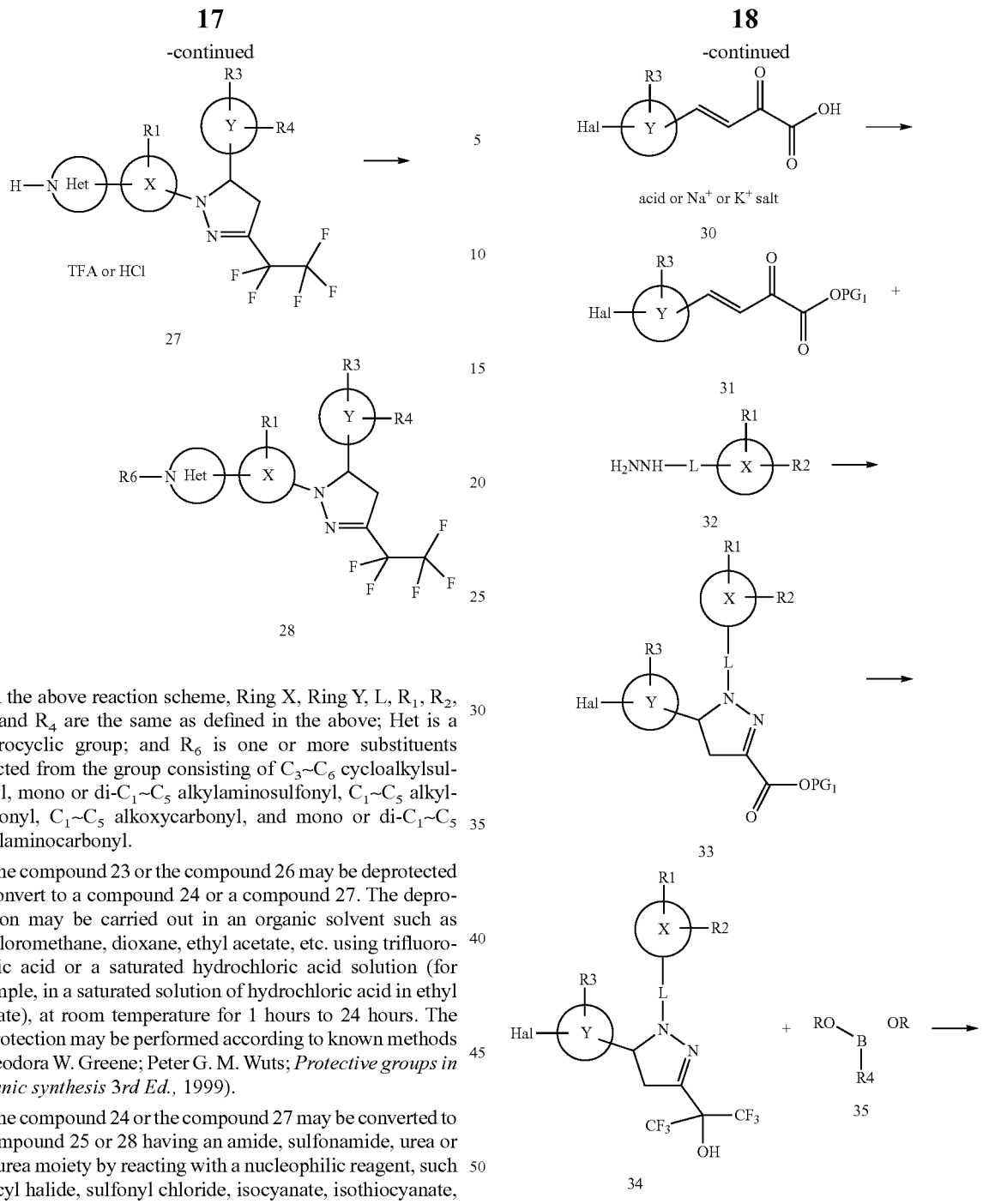

In the above reaction scheme, Ring X, Ring Y, L, $R_1$, $R_2$, $R_3$, and $R_4$ are the same as defined in the above; Het is a heterocyclic group; and $R_6$ is one or more substituents selected from the group consisting of $C_3$~$C_6$ cycloalkylsulfonyl, mono or di-$C_1$~$C_5$ alkylaminosulfonyl, $C_1$~$C_5$ alkylcarbonyl, $C_1$~$C_5$ alkoxycarbonyl, and mono or di-$C_1$~$C_5$ alkylaminocarbonyl.

The compound 23 or the compound 26 may be deprotected to convert to a compound 24 or a compound 27. The deprotection may be carried out in an organic solvent such as dichloromethane, dioxane, ethyl acetate, etc. using trifluoroacetic acid or a saturated hydrochloric acid solution (for example, in a saturated solution of hydrochloric acid in ethyl acetate), at room temperature for 1 hours to 24 hours. The deprotection may be performed according to known methods (Theodora W. Greene; Peter G. M. Wuts; *Protective groups in organic synthesis* 3*rd Ed.*, 1999).

The compound 24 or the compound 27 may be converted to a compound 25 or 28 having an amide, sulfonamide, urea or thiourea moiety by reacting with a nucleophilic reagent, such as acyl halide, sulfonyl chloride, isocyanate, isothiocyanate, etc., in an organic solvent such as dichloromethane, tetrahydrofuran, N,N-dimethylformamide, etc.

The compound of Formula 1 or its pharmaceutically acceptable salt of the present invention may be also prepared according to the following Reaction Scheme 4.

<Reaction Scheme 4>

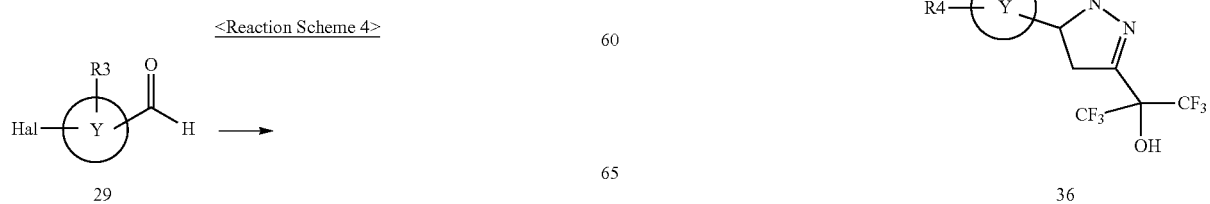

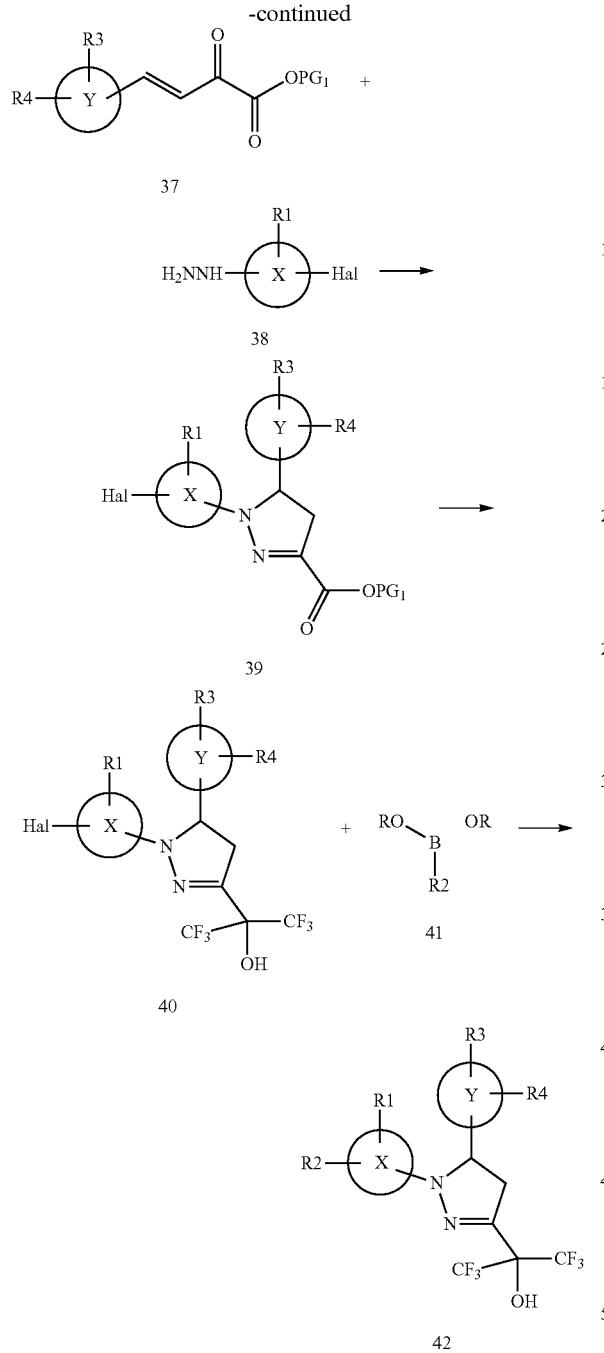

In the above reaction scheme, Ring X, Ring Y, L, $R_1$, $R_2$, $R_3$, and $R_4$ are the same as defined in the above; Hal is halogen; $PG_1$ is a carboxyl-protecting group; and R is hydrogen or $C_1$~$C_5$ alkyl or may be cyclized each other to form a pentagonal or hexagonal ring comprising boron and oxygen, wherein the ring may be substituted with $C_1$~$C_5$ alkyl.

An aldehyde derivative of the compound 29 is commercially available. The compound 29 may be reacted with pyruvic add to convert to a compound 30 (i.e., acid, or sodium salt or potassium salt). The reaction between the compound 29 and pyruvic acid may be performed according to known methods (Meng, Qinghua; Zhu, Lufeng; Zhang, Zhaoguo; *Journal of Organic Chemistry,* 73, 7209-7212, 2008).

The compound 30 may be reacted with alkyl alcohol or alkyl halide in the presence of add or base to convert to an ester derivative of compound 31. The carboxyl-protecting group may be preferably a $C_1$~$C_6$ alkyl group, such as methyl, ethyl, isobutyl, tert-butyl, etc.

The compound 31 or the compound 37 may be converted to a compound 33 or a compound 39 by condensing with a hydrazine derivative of the compound 32 or 38. The hydrazine derivative of compound 32 or 38 is commercially available. The condensation may be performed according to known methods (Srivastava, Brijesh Kumar; Joharapurkar, Amit; Raval, Saurin; Patel, Jayendra Z.; Soni, Rina; Ravel, Preeti; Gite, Archana; Amitgiri; Sadhwani, Nisha; Gandhi, Neha; Patel, Harilal; et al.; *Journal of Medicinal Chemistry,* 50, 5951-5966, 2007).

The compound 33 or the compound 39 may be converted to a compound 34 or compound 40 through mono and di-$CF_3$ addition using the commercially available $CF_3$TMS. The addition may be performed according to known methods (Yoshikazu Kawano; Nobuya Kaneko; Teruaki Mukaiyama; *Bull. Chem. Soc. Jpn.,* 79, 1133-1145, 2006).

The compound 34 or the compound 40 is reacted with a boronic acid derivative of compound 35 or compound 41 to convert to a compound 36 or a compound 42. The reaction may be performed according to an arylation reaction (e.g., a Suzuki coupling reaction) and a Buchwald-Hartwig cross-coupling reaction using an amine (Barbara Czako and Laszlo Kurti; *STRATEGIC APPLICATIONS of NAMED REACTIONS in ORGANIC SYNTHESIS,* 2005).

If necessary, the compound 36 or the compound 42 may be used as an intermediate for preparing other compounds according to the present invention. For example, the compound 36 or the compound 42 may be subject to oxidation, reduction, addition, protection, deprotection, amide coupling, etc., so as to prepare other compounds according to the present invention having a moiety such as sulfinyl, sulfonyl, amine, alcohol, carboxylic acid, carboxamide, sulfonamide, oxime, etc.

The compound of Formula 1 or its pharmaceutically acceptable salt of the present invention may be also prepared according to the following Reaction Scheme 5.

<Reaction Scheme 5>

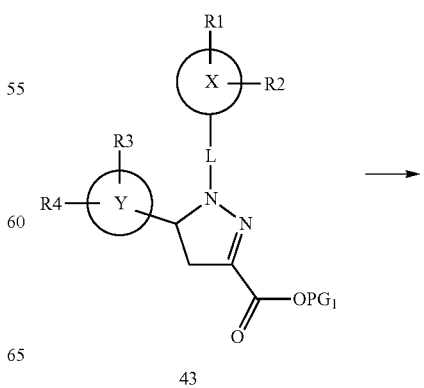

43

-continued

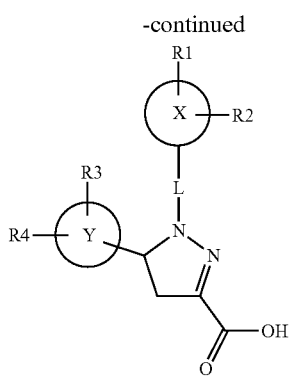
44

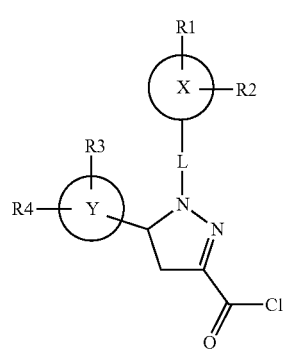
45

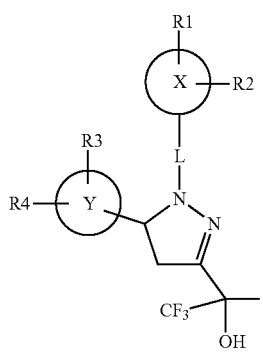
46

In the above reaction scheme, Ring X, Ring Y, L, $R_1$, $R_2$, $R_3$, and $R_4$ are the same as defined in the above; and $PG_1$ is a carboxyl-protecting group.

The compound 43 may be deprotected to convert to a compound 44. The deprotection may be carried out, using an inorganic base such as sodium hydroxide, lithium hydroxide or potassium hydroxide, in distilled water or tetrahydrofuran or in a mixed solvent of water and a polar solvent (e.g., alcohol). And also, the deprotection may be carried out e.g., at a temperature ranging from room temperature to 80° C.

The compound 44 may be reacted with thionyl chloride to convert to an acyl halide derivative of the compound 45. And also, the compound 45 may be converted to a compound 46 through di-$CF_3$ addition using $CF_3TMS$. The addition may be performed according to known methods (Babadzhanova, L. A.; Kirij, N. V.; Yagupolskii, Yu. L.; Tyrra, W.; Naumann, D.; *Tetrahedron*, 61, 1813-1820, 2005).

If necessary, the compound 46 may be used as an intermediate for preparing other compounds according to the present invention. For example, the compound 46 may be subject to Suzuki coupling (as mentioned in the above Scheme 4), Buchwald-Hartwig cross-coupling, oxidation, reduction, addition, protection, deprotection, amide coupling, arylation, C—N coupling, etc., so as to prepare other compounds according to the present invention having a moiety such as sulfinyl, sulfonyl, amine, alcohol, carboxylic acid, carboxamide, sulfonamide, oxime, etc.

The compound of Formula 1 or its pharmaceutically acceptable salt of the present invention may be also prepared according to the following Reaction Scheme 6.

<Reaction Scheme 6>

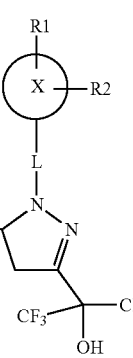

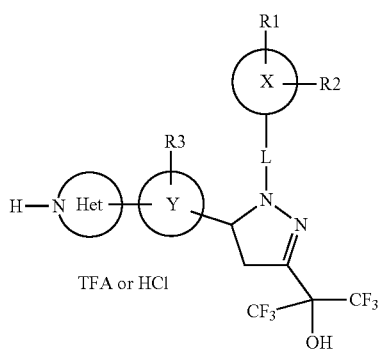
47

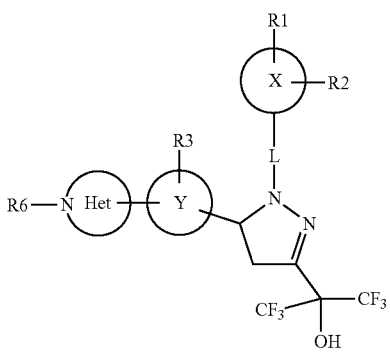
48
TFA or HCl

49

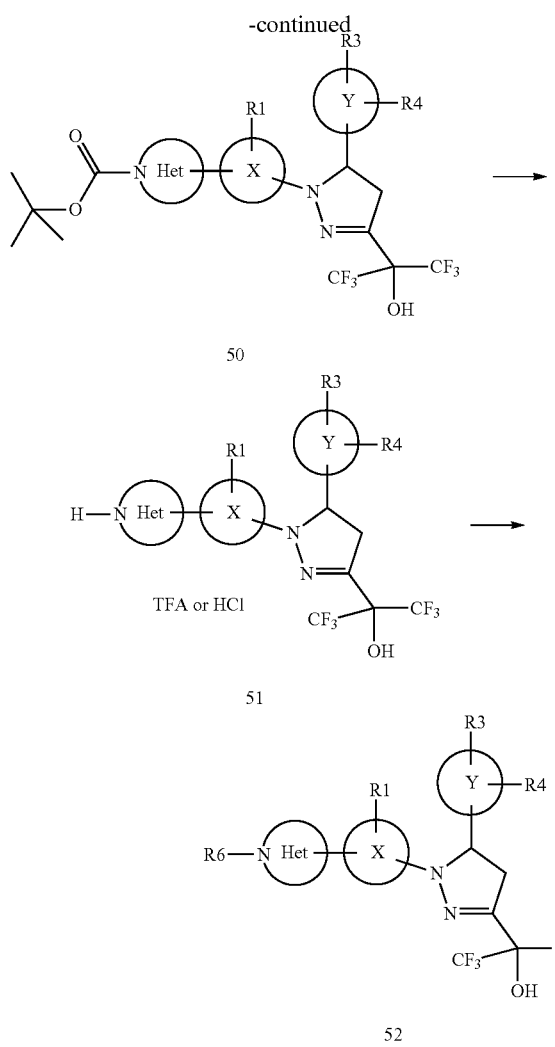

In the above reaction scheme, Ring X, Ring Y, L, $R_1$, $R_2$, $R_3$, and $R_4$ are the same as defined in the above; Het is a heterocyclic group; and $R_6$ is one or more substituents selected from the group consisting of $C_3$~$C_6$ cycloalkylsulfonyl, mono or di-$C_1$~$C_5$ alkylaminosulfonyl, $C_1$~$C_5$ alkylcarbonyl, $C_1$~$C_5$ alkoxycarbonyl, and mono or di-$C_1$~$C_5$ alkylaminocarbonyl.

The compound 47 or the compound 50 may be deprotected to convert to a compound 48 or a compound 51. The deprotection may be carried out in an organic solvent such as dichloromethane, dioxane, ethyl acetate, etc. using trifluoroacetic acid or a saturated hydrochloric acid solution (for example, in a saturated solution of hydrochloric acid in ethyl acetate), at room temperature for 1 hours to 24 hours. The deprotection may be performed according to known methods (Theodora W. Greene; Peter G. M. Wuts; *Protective groups in organic synthesis* 3rd Ed., 1999).

The compound 48 or the compound 51 may be converted to a compound 49 or 52 having an amide, sulfonamide, urea or thiourea moiety by reacting with a nucleophilic reagent, such as acyl halide, sulfonyl chloride, isocyanate, isothiocyanate, etc., in an organic solvent such as dichloromethane, tetrahydrofuran, N,N-dimethylformamide, etc.

The present invention provides a pharmaceutical composition for preventing or treating a dysfunction in cholesterol metabolism comprising a therapeutically effective amount of the compound of Formula 1 or its pharmaceutically acceptable salt as an active ingredient. The dysfunction in cholesterol metabolism includes cholesterol gallstone, hyperlipidemia, or coronary atherosclerosis, but not limited thereto.

The pharmaceutical composition may comprise a pharmaceutically acceptable carrier, such as diluents, disintegrants, sweeteners, lubricants, or flavoring agents. The pharmaceutical composition may be formulated to an oral dosage form such as tablets, capsules, powders, granules, suspensions, emulsions, or syrups; or a parenteral dosage form such as injection. The dosage form may be various forms, e.g., dosage forms for single administration or for multiple administrations.

The pharmaceutical composition of the present invention may comprise, for example, a diluent (e.g., lactose, corn starch, etc); a lubricant (e.g., magnesium stearate); an emulsifying agent; a suspending agent; a stabilizer; and/or an isotonic agent. If necessary, the composition further comprises sweeteners and/or flavoring agents.

The composition of the present invention may be administered orally or parenterally, including intravenous, intraperitoneal, subcutaneous, rectal and topical routes of administration. Therefore, the composition of the present invention may be formulated into various forms such as tablets, capsules, aqueous solutions or suspensions. In the case of tablets for oral administration, carriers such as lactose, corn starch, and lubricating agents, e.g. magnesium stearate, are conventionally used. In the case of capsules for oral administration, lactose and/or dried corn starch can be used as a diluent. When an aqueous suspension is required for oral administration, the active ingredient may be combined with emulsifying and/or suspending agents. If desired, certain sweetening and/or flavoring agents may be used. For intramuscular, intraperitoneal, subcutaneous and intravenous administration, sterile solutions of the active ingredient are usually prepared, and the pH of the solutions should be suitably adjusted and buffered. For intravenous administration, the total concentration of solutes should be controlled in order to render the preparation isotonic. The composition of the present invention may be in the form of an aqueous solution containing pharmaceutically acceptable carriers, e.g., saline having a pH level of 7.4. The solutions may be introduced into a patient's intramuscular blood-stream by local bolus injection.

The pharmaceutical composition according to the present invention may be administered in a therapeutically effective amount. Therefore, the compound of Formula 1 or its pharmaceutically acceptable salt may be administered in a therapeutically effective amount ranging from about 50 mg/kg to about 500 mg/kg per day to a subject patient. Of course, the dosage may be changed according to the patient's age, weight, susceptibility, symptom, or activity of the compound.

The present invention also provides a use of the compound or its pharmaceutically acceptable salt for the manufacture of a medicament for preventing or treating a dysfunction in cholesterol metabolism. The dysfunction in cholesterol metabolism includes cholesterol gallstone, hyperlipidemia, or coronary atherosclerosis, but not limited thereto.

The present invention also provides a method for treating a dysfunction in cholesterol metabolism in a patient, which comprises administering a therapeutically effective amount of the compound of Formula 1 or its pharmaceutically acceptable salt to the patient in need thereof. The dysfunction in cholesterol metabolism includes cholesterol gallstone, hyperlipidemia, or coronary atherosclerosis, but not limited thereto.

The following examples and experimental examples are provided for illustration purposes only, and are not intended to limit the scope of the invention.

The analyses of the compounds prepared in the following Preparations and Examples were carried out as follows: Nuclear magnetic resonance (NMR) spectrum analysis was carried out using Bruker 400 MHz spectrometer and chemical shifts thereof were analyzed in ppm. Column chromatography was carried out on silica gel (Merck, 70-230 mesh or ZEOCHEM, ZEOprep 60-200 μm) (W. C. Still, *J. Org. Chem.*, 1978 (43), 2923-2925). The abbreviations used in the following Preparations and Examples are as follows: 'methyl' is abbreviated to 'Me'; 'ethyl' is abbreviated to 'Et'; 'phenyl' is abbreviated to 'Ph'; 'tert-butyloxycarbonyl' is abbreviated to 'BOC'; 'N-(3-dimethylaminopropyl)-N'-ethylcarbodiimide' is abbreviated to 'EDAC'; '1-hydroxybenzotriazole' is abbreviated to 'HOBT; '(trifluoromethyl)trimethylsilane' is abbreviated to 'CF$_3$TMS'; 'tetrabutylammonium fluoride' is abbreviated to 'TBAF'; 'Dess-Martin Periodinane' is abbreviated to 'DMP'; 'bis(2-methoxyethyl)aminosulfur trifluoride' is abbreviated to 'BAST'. The starting materials in each Example are known compounds, which were synthesized according literatures or obtained from Sigma-Aldrich or TCI.

Preparation 1. 5-(4-bromo-phenyl)-1-(2-chloro-phenyl)-3-pentafluoroethyl-4,5-dihydro-1H-pyrazole Step 1:
3-(4-bromo-phenyl)-N-methoxy-N-methyl-acrylamide 4-Bromocinnamic acid (28.3 g, 124.6 mmol), N,O-dimethylhydroxylamine hydrochloride (14.6 g, 149.6 mmol), HOBT (33.7 g, 249.3 mmol), EDAC (47.8 g, 249.3 mmol) and triethylamine (34.7 mL, 249.3 mmol) were added to dichloromethane (800.0 mL). The reaction mixture was stirred at room temperature for 16 hours, quenched with a saturated solution of ammonium chloride, and then extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/2) to give 26.8 g of the titled compound as a white solid.
$^1$H NMR (400 MHz, CDCl$_3$) 7.66 (d, 1H), 7.51 (d, 2H), 7.43 (d, 2H), 7.02 (d, 1H), 3.77 (s, 3H), 3.31 (s, 3H)

Step 2: 1-(4-bromo-phenyl)-4,4,5,5,5-pentafluoro-pent-1-en-3-one

To a saturated solution of pentafluoroiodoethane (0.84 M, in diethyl ether) (198.3 mL, 166.6 mmol), was slowly added a solution of methyllithium/lithium bromide (1.5 M, in diethyl ether) (111.1 mL, 166.6 mmol) under nitrogen atmosphere at −78° C. The reaction mixture was stirred for 20 minutes and then a solution of 3-(4-bromo-phenyl)-N-methoxy-N-methyl-acrylamide (15.0 g, 55.5 mmol, in diethyl ether 20.0 mL) prepared in Step 1 was slowly added thereto at −78° C. The reaction mixture was stirred at room temperature, quenched with distilled water, acidified by a 10% potassium hydrogen sulfate solution (pH=5), and then extracted with diethyl ether three times. The combined extract was washed with a saturated solution of sodium hydrogen carbonate, dried on anhydrous magnesium sulfate, and then concentrated under reduced pressure to give a yellow liquid residue. The resulting residue was purified by silica gel column chromatography (eluent: ethyl acetate/n-hexane=1/60) to give 9.0 g of the titled compound as a yellow solid.
$^1$H NMR (400 MHz, CDCl$_3$) 7.92 (d, 1H), 7.60 (d, 2H), 7.52 (d, 2H), 7.11 (d, 1H)

Step 3: 5-(4-bromo-phenyl)-1-(2-chloro-phenyl)-3-pentafluoroethyl-4,5-dihydro-1H-pyrazole 1-(4-Bromo-phenyl)-4,4,5,5,5-pentafluoro-pent-1-en-3-one (8.0 g, 24.3 mmol) prepared in Step 2 and 2-chlorophenylhydrazine hydrochloride (5.7 g, 31.6 mmol) were added to acetic acid (116.0 mL). The reaction mixture was stirred at 125° C. for 4 hours, concentrated under reduced pressure, and then ethyl acetate was added thereto. The mixture was washed with a saturated solution of sodium hydrogen carbonate, dried on anhydrous magnesium sulfate, and then concentrated under reduced pressure to give a yellow liquid residue. The resulting residue was purified by silica gel column chromatography (eluent: ethyl acetate/n-hexane=1/60) to give 8.5 g of the titled compound as a yellow liquid.
$^1$H NMR (400 MHz, CDCl$_3$) 7.33 (d, 2H), 7.22 (d, 2H), 7.10 (t, 1H), 7.02-6.95 (m, 3H), 5.87 (dd, 1H), 3.70 (dd, 1H), 3.20 (dd, 1H)

Preparation 2. 4,4,5,5,5-pentafluoro-1-(3'-methylsulfanyl-biphenyl-4-yl)-pent-1-en-3-one Step 1: N-methoxy-N-methyl-3-(3'-methylsulfanyl-biphenyl-4-yl)-acrylamide 3-(4-Bromo-phenyl)-N-methoxy-N-methyl-acrylamide (11.7 g, 43.2 mmol) prepared in Step 1 of Preparation 1, 3-(methylthio)phenylboronic acid (14.5 g, 86.4 mmol), Pd(PPh$_3$)$_4$ (2.5 g, 2.2 mmol) and sodium carbonate (13.7 g, 129.6 mmol) were added to a mixed solvent of N,N-dimethylformamide (200.0 mL) and distilled water (50.0 mL). The reaction mixture was stirred at 80° C. for 7 hours and then extracted with ethyl acetate. The extract was washed with a saturated solution of ammonium chloride, dried on anhydrous magnesium sulfate, and then concentrated under reduced pressure to give a yellow liquid residue. The resulting residue was purified by silica gel column chromatography (eluent: ethyl acetate/n-hexane=1/5) to give 17.0 g of the titled compound as a yellow solid.
$^1$H NMR (400 MHz, CDCl$_3$) 7.77 (d, 1H), 7.65 (d, 2H), 7.60 (d, 2H), 7.48 (s, 1H), 7.38-7.36 (m, 2H), 7.26 (m, 1H), 7.08 (d, 1H), 3.79 (s, 3H), 3.33 (s, 3H), 2.54 (s, 3H)

Step 2: 4,4,5,5,5-pentafluoro-1-(3'-methylsulfanyl-biphenyl-4-yl)-pent-1-en-3-one To a saturated solution of pentafluoroiodoethane (0.84 M, in diethyl ether) (203.5 mL, 162.8 mmol), was slowly added methyllithium/lithium bromide (1.5 M, in diethyl ether) (108.6 mL, 162.8 mmol) under nitrogen atmosphere at −78° C. The reaction mixture was stirred for 20 minutes and then a solution of N-methoxy-N-methyl-3-(3'-methylsulfanyl-biphenyl-4-yl)-acrylamide (17.0 g, 54.3 mmol, in tetrahydrofuran 20.0 mL) prepared in Step 1 was slowly added thereto at −78° C. The reaction mixture was stirred at room temperature, quenched with distilled water, acidified by a 10% potassium hydrogen sulfate solution (pH=5), and then extracted with diethyl ether three times. The combined extract was washed with a saturated solution of sodium hydrogen carbonate, dried on anhydrous magnesium sulfate, and then concentrated under reduced pressure to give a yellow liquid residue. The resulting residue was purified by silica gel column chromatography (eluent: ethyl acetate/n-hexane=1/30) to give 15.4 g of the titled compound as a yellow liquid.

$^1$H NMR (400 MHz, CDCl$_3$) 8.03 (d, 1H), 7.73 (d, 2H), 7.66 (d, 2H), 7.49 (s, 1H), 7.42-7.38 (m, 2H), 7.35-7.28 (m, 1H), 7.15 (d, 1H), 2.55 (s, 3H)

Preparation 3. 5-(3-bromo-pyridin-6-yl)-1-(2-chloro-phenyl)-3-pentafluoroethyl-4,5-dihydro-1H-pyrazole Step 1: 3-(5-bromo-pyridin-2-yl)-acrylic acid 5-Bromo-pyridin-2-carbaldehyde (2.0 g, 10.6 mmol), malonic acid (2.5 g, 24.2 mmol), and piperidine (0.9 mL, 9.0 mmol) were added to pyridine (6.5 mL). The reaction mixture was stirred at 100° C. for 1 hour and then concentrated under reduced pressure. Distilled water was added to the reaction mixture, which was then filtered. The resulting solid was dried under reduced pressure to give 1.3 g of the titled compound as a brown solid.

$^1$H NMR (400 MHz, CDCl$_3$) 8.69 (d, 1H), 8.02 (dd, 1H), 7.62 (d, 1H), 7.56 (d, 1H), 6.89 (d, 1H)

Step 2: 3-(5-bromo-pyridin-2-yl)-N-methoxy-N-methyl-acrylamide 3-(5-Bromo-pyridin-2-yl)-acrylic acid (1.3 g, 5.7 mmol) prepared in Step 1, N,O-dimethylhydroxylamine hydrochloride (0.7 g, 6.8 mmol), HOBT (1.5 g, 11.4 mmol), EDAC (2.2 g, 11.4 mmol) and triethylamine (1.6 mL, 11.4 mmol) were added to dichloromethane (42.0 mL). The reaction mixture was stirred at room temperature for 18 hours, quenched with a saturated solution of ammonium chloride, and then extracted with dichloromethane. The extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/9) to give 1.3 g of the titled compound as a white solid.

$^1$H NMR (400 MHz, CDCl$_3$) 8.69 (s, 1H), 7.83 (dd, 1H), 7.65 (d, 1H), 7.54 (d, 1H), 7.29 (d, 1H), 3.79 (s, 3H), 3.32 (s, 3H)

Step 3: 1-(5-bromo-pyridin-2-yl)-4,4,5,5,5-pentafluoro-pent-1-en-3-one

To a saturated solution of pentafluoroiodoethane (0.84 M, in diethyl ether) (17.1 mL, 14.3 mmol), was slowly added a solution of methyllithium/lithium bromide (1.5 M, in diethyl ether) (9.6 mL, 14.3 mmol) under nitrogen atmosphere at −78° C. The reaction mixture was stirred for 20 minutes and then a solution of 3-(5-bromo-pyridin-2-yl)-N-methoxy-N-methyl-acrylamide (1.3 g, 4.8 mmol, in tetrahydrofuran 12.0 mL) prepared in Step 2 was slowly added thereto at −78° C. The reaction mixture was stirred at room temperature for 2 hours, quenched with distilled water, acidified by a 10% potassium hydrogen sulfate solution (pH=5), and then extracted with ethyl acetate. The extract was washed with a saturated solution of sodium hydrogen carbonate, dried on anhydrous magnesium sulfate, and then concentrated under reduced pressure to give a yellow liquid residue. The resulting residue was purified by silica gel column chromatography (eluent: ethyl acetate/n-hexane=1/10) to give 0.9 g of the titled compound as a yellow liquid.

$^1$H NMR (400 MHz, CDCl$_3$) 8.76 (s, 1H), 7.91 (dd, 1H), 7.85 (d, 1H), 7.67 (d, 1H), 7.40 (d, 1H)

Step 4: 5-(3-bromo-pyridin-6-yl)-1-(2-chloro-phenyl)-3-pentafluoroethyl-4,5-dihydro-1H-pyrazole 1-(5-Bromo-pyridin-2-yl)-4,4,5,5,5-pentafluoro-pent-1-en-3-one (936.0 mg, 2.8 mmol) prepared in Step 3, 2-chlorophenylhydrazine hydrochloride (508.0 mg, 2.8 mmol), and piperidine (560.0 uL, 5.7 mmol) were added to ethanol (28.4 mL). The reaction mixture was stirred at 60° C. for 2 hours, concentrated under reduced pressure, and then ethyl acetate was added thereto. The mixture was washed with distilled water, dried on anhydrous magnesium sulfate, and then concentrated under reduced pressure to give a yellow liquid residue. The resulting residue was purified by silica gel column chromatography (eluent: ethyl acetate/n-hexane=1/10) to give 450.0 mg of the titled compound as a yellow liquid.

$^1$H NMR (400 MHz, CDCl$_3$) 8.54 (dd, 1H), 7.61 (dd, 1H), 7.22 (dd, 2H), 7.09 (t, 1H), 6.99-6.95 (m, 2H), 5.92 (dd, 1H), 3.62 (m, 1H), 3.42 (m, 1H)

Preparation 4. 4,4,5,5,5-pentafluoro-1-(4'-methylsulfanyl-biphenyl-3-yl)-pent-1-en-3-one Step 1: 3-(3-bromo-phenyl)-N-methoxy-N-methylacrylamide 3-Bromocinnamic acid (15.3 g, 67.3 mmol), N,O-dimethylhydroxylamine hydrochloride (7.9 g, 80.8 mmol), HOBT (18.2 g, 134.7 mmol), EDAC (25.8 g, 134.7 mmol) and triethylamine (18.7 mL, 134.68 mmol) were added to dichloromethane (500.0 mL). The reaction mixture was stirred at room temperature for 16 hours, quenched with a saturated solution of ammonium chloride, and then extracted with dichloromethane three times. The combined extract was dried on anhydrous magnesium sulfate and then concentrated under reduced pressure to give a yellow liquid residue. The resulting residue was purified by silica gel column chromatography (eluent: ethyl acetate/n-hexane=1/3) to give 14.8 g of the titled compound as a yellow liquid.

$^1$H NMR (400 MHz, CDCl$_3$) 7.72 (s, 1H), 7.65 (d, 1H), 7.49 (d, 1H), 7.47 (d, 1H), 7.26 (t, 1H), 7.02 (d, 1H), 3.78 (s, 3H), 3.32 (s, 3H)

Step 2: N-methoxy-N-methyl-3-(4'-methylsulfanyl-biphenyl-3-yl)-acrylamide 3-(3-Bromo-phenyl)-N-methoxy-N-methylacrylamide (14.5 g, 53.7 mmol) prepared in Step 1, 4-(methylthio)phenylboronic acid (18.0 g, 107.4 mmol), Pd(PPh$_3$)$_4$ (3.1 g, 2.7 mmol) and sodium carbonate (17.1 g, 161.1 mmol) were added to a mixed solvent of N,N-dimethylformamide (100.0 mL) and distilled water (10.0 mL). The reaction mixture was stirred at 80° C. for 20 hours, quenched with a saturated solution of ammonium chloride, and then extracted with diethyl ether three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/3) to give 17.6 g of the titled compound as a yellow solid.

$^1$H NMR (400 MHz, CDCl$_3$) 7.80 (d, 1H), 7.73 (s, 1H), 7.58-7.51 (m, 2H), 7.54 (d, 2H), 7.49-7.44 (m, 1H), 7.35 (d, 2H), 7.09 (d, 1H), 3.78 (s, 3H), 3.33 (s, 3H), 2.54 (s, 3H)

Step 3: 4,4,5,5,5-pentafluoro-1-(4'-methylsulfanyl-biphenyl-3-yl)-pent-1-en-3-one To a saturated solution of pentafluoroiodoethane (0.84 M, in diethyl ether) (200.9 mL, 168.8 mmol), was slowly added a solution of methyllithium/lithium bromide (1.5 M, in diethyl ether) (112.5 mL, 168.8 mmol) under nitrogen atmosphere at −78° C. The reaction mixture was stirred for 20 minutes and then a solution of N-methoxy-N-methyl-3-(4'-methylsulfanyl-biphenyl-3-yl)-acrylamide (17.6 g, 56.3 mmol, in tetrahydrofuran 20.0 mL) prepared in Step 2 was slowly added thereto at −78° C. The reaction mixture was stirred at room temperature, quenched with distilled water, acidified by a 10% potassium hydrogen sulfate solution (pH=5), and then extracted with diethyl ether three times. The combined extract was washed with a saturated solution of sodium hydrogen carbonate, dried on anhydrous magnesium sulfate, and then concentrated under reduced pressure to give a yellow liquid residue. The resulting residue was purified by silica gel column chromatography (eluent: ethyl acetate/n-hexane=1/30) to give 16.4 g of the titled compound as a yellow solid.

$^1$H NMR (400 MHz, CDCl$_3$) 8.04 (d, 1H), 7.80 (s, 1H), 7.69 (d, 1H), 7.62 (d, 1H), 7.54-7.45 (m, 1H), 7.50 (d, 2H), 7.35 (d, 2H), 7.16 (d, 1H), 2.54 (s, 3H)

Preparation 5. 5-(3-bromo-phenyl)-1-(2,4-difluoro-phenyl)-3-pentafluoroethyl-4,5-dihydro-1H-pyrazole Step 1: 1-(3-bromo-phenyl)-4,4,5,5,5-pentafluoro-pent-1-en-3-one To a saturated solution of pentafluoroiodoethane (0.84 M, in diethyl ether) (102.0 mL, 85.5 mmol), was slowly added a solution of methyllithium/lithium bromide (1.5 M, in diethyl ether) (57.0 mL, 85.5 mmol) under nitrogen atmosphere at −78° C. The reaction mixture was stirred for 20 minutes and then a solution of 3-(3-bromo-phenyl)-N-methoxy-N-methylacrylamide (7.7 g, 28.5 mmol, in diethyl ether 50.0 mL) prepared in Step 1 of Preparation 4 was slowly added thereto at −78° C. The reaction mixture was stirred at room temperature for 1 hour, quenched with distilled water, acidified by a 10% potassium hydrogen sulfate solution (pH=5), and then extracted with diethyl ether. The extract was washed with a saturated solution of sodium hydrogen carbonate, dried on anhydrous magnesium sulfate, and then concentrated under reduced pressure to give a yellow liquid residue. The resulting residue was purified by silica gel column chromatography (eluent: ethyl acetate/n-hexane=1/30) to give 8.0 g of the titled compound as a yellow liquid.

$^1$H NMR (400 MHz, CDCl$_3$) 7.88 (d, 1H), 7.79 (s, 1H), 7.62 (d, 1H), 7.56 (d, 1H), 7.33 (dd, 1H), 7.10 (d, 1H)

Step 2: 5-(3-bromo-phenyl)-1-(2,4-difluoro-phenyl)-3-pentafluoroethyl-4,5-dihydro-1H-pyrazole 1-(3-Bromo-phenyl)-4,4,5,5,5-pentafluoro-pent-1-en-3-one (1.8 g, 5.3 mmol) prepared in Step 1, 2,4-difluorophenyl-hydrazine hydrochloride (1.2 g, 6.4 mmol) and conc. hydrochloric acid (100.0 uL) were added to ethanol (15.0 mL). The reaction mixture was stirred at 100° C. for 8 hours, quenched with a saturated solution of sodium hydrogen carbonate, and then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/60) to give 2.3 g of the titled compound as a yellow liquid.

$^1$H NMR (400 MHz, CDCl$_3$) 7.38-7.33 (m, 2H), 7.31 (s, 1H), 7.14 (t, 1H), 7.05 (d, 1H), 6.77 (t, 1H), 6.70 (t, 1H), 5.53 (dd, 1H), 3.64 (dd, 1H), 3.12 (dd, 1H)

Preparation 6. 5-(3-bromo-phenyl)-1-(2-chloro-phenyl)-3-pentafluoroethyl-4,5-dihydro-1H-pyrazole Step 1: 5-(3-bromo-phenyl)-1-(2-chloro-phenyl)-3-pentafluoroethyl-4,5-dihydro-1H-pyrazole 1-(3-Bromo-phenyl)-4,4,5,5,5-pentafluoro-pent-1-en-3-one (1.4 g, 4.3 mmol) prepared in Step 1 of Preparation 5 and 2-chlorophenylhydrazine hydrochloride (0.8 g, 4.3 mmol) were added to acetic acid (30.0 mL). The reaction mixture was stirred at 100° C. for 12 hours, concentrated under reduced pressure, and then ethyl acetate was added thereto. The mixture was washed with a saturated solution of sodium hydrogen carbonate, dried on anhydrous magnesium sulfate, and then concentrated under reduced pressure to give a yellow liquid residue. The resulting residue was purified by silica gel column chromatography (eluent: diethyl ether/n-hexane=1/9) to give 1.1 g of the titled compound as a brown liquid.

$^1$H NMR (400 MHz, CDCl$_3$) 7.38-7.21 (m, 4H), 7.16-7.05 (m, 3H), 6.98 (dd, 1H), 5.82 (dd, 1H), 3.68 (dd, 1H), 3.21 (dd, 1H)

Preparation 7. 5-(3-bromo-4-fluoro-phenyl)-1-(2,4-difluoro-phenyl)-3-pentafluoroethyl-4,5-dihydro-1H-pyrazole Step 1: 3-(3-bromo-4-fluoro-phenyl)-acrylic acid 3-Bromo-4-fluoro-benzaldehyde (5.0 g, 24.6 mmol), malonic acid (5.6 g, 53.7 mmol), and piperidine (0.5 mL, 4.9 mmol) were added to pyridine (11.4 mL). The reaction mixture was stirred at 100° C. for 3 hours and then concentrated under reduced pressure. Distilled water was added to the reaction mixture, which was then filtered. The resulting solid was recrystallized from ethanol to give 3.3 g of the titled compound as a white solid.

$^1$H NMR (400 MHz, CD$_3$OD) 7.93 (d, 1H), 7.64-7.60 (m, 2H), 7.27 (t, 1H), 6.49 (d, 1H)

Step 2: 3-(3-bromo-4-fluoro-phenyl)-acryloyl chloride 3-(3-Bromo-4-fluoro-phenyl)-acrylic acid (3.3 g, 13.3 mmol) prepared in Step 1 was added to thionyl chloride (10.0 mL). The reaction mixture was stirred at 100° C. for 2 hours, concentrated under reduced pressure. The resulting residue was concentrated under reduced pressure three times, along with using toluene, to give 3.5 g of the titled compound as an unpurified dark brown liquid.

$^1$H NMR (400 MHz, CDCl$_3$) 7.93 (d, 1H), 7.66-7.62 (m, 2H), 7.27 (t, 1H), 6.54 (d, 1H)

Step 3: 3-(3-bromo-4-fluoro-phenyl)-N-methoxy-N-methylacrylamide

The unpurified 3-(3-bromo-4-fluoro-phenyl)-acryloyl chloride (3.5 g, 13.3 mmol) prepared in Step 2, N,O-dimethylhydroxylamine hydrochloride (1.4 g, 14.0 mmol), and pyridine (2.4 mL, 29.4 mmol) were added at 0° C. to dichloromethane (20.0 mL). The reaction mixture was stirred at room temperature for 12 hours, quenched with a 1N hydrochloric acid solution, and then extracted with diethyl ether two times. The combined extract was washed with a saturated solution of sodium hydrogen carbonate and brine, dried on anhydrous magnesium sulfate, and then concentrated under reduced pressure to give a yellow liquid residue. The resulting residue was recrystallized from diethyl ether and n-hexane to give 3.2 g of the titled compound as a white solid.

$^1$H NMR (400 MHz, CDCl$_3$) 7.77 (d, 1H), 7.62 (d, 1H), 7.46 (br, 1H), 7.13 (t, 1H), 6.95 (d, 1H), 3.78 (s, 3H), 3.31 (s, 3H)

Step 4: 1-(3-bromo-4-fluoro-phenyl)-4,4,5,5,5-pentafluoro-pent-1-en-3-one

To a saturated solution of pentafluoroiodoethane (0.84 M, in diethyl ether) (37.7 mL, 32.9 mmol), was slowly added a solution of methyllithium/lithium bromide (1.5 M, in diethyl ether) (21.9 mL, 32.9 mmol) under nitrogen atmosphere at −78° C. The reaction mixture was stirred for 20 minutes and then a solution of 3-(3-bromo-4-fluoro-phenyl)-N-methoxy-N-methylacrylamide (3.2 g, 11.0 mmol, in tetrahydrofuran 10.0 mL) prepared in Step 3 was slowly added thereto at −78° C. The reaction mixture was stirred at room temperature, quenched with distilled water, acidified by a 10% potassium hydrogen sulfate solution (pH=5), and then extracted with ethyl acetate. The extract was washed with a saturated solution of sodium hydrogen carbonate, dried on anhydrous magnesium sulfate, and then concentrated under reduced pressure to give a yellow liquid residue. The resulting residue was purified by silica gel column chromatography (eluent: ethyl acetate/n-hexane=1/10) to give 2.5 g of the titled compound as a yellow liquid.

$^1$H NMR (400 MHz, CDCl$_3$) 7.76 (d, 1H), 7.66 (d, 1H), 7.46 (t, 1H), 7.16 (t, 1H), 6.38 (d, 1H)

Step 5: 5-(3-bromo-4-fluoro-phenyl)-1-(2,4-difluoro-phenyl)-3-pentafluoroethyl-4,5-dihydro-1H-pyrazole 1-(3-Bromo-4-fluoro-phenyl)-4,4,5,5,5-pentafluoro-pent-1-en-3-one (2.5 g, 7.1 mmol) prepared in Step 4 and 2,4-difluorophenylhydrazine hydrochloride (1.4 g, 7.8 mmol) were added to acetic acid (35.0 mL). The reaction mixture was stirred at 125° C. for 2 hours, concentrated under reduced pressure, and then ethyl acetate was added thereto. The mixture was washed with a saturated solution of sodium hydrogen carbonate, dried on anhydrous magnesium sulfate, and then concentrated under reduced pressure to give a yellow liquid residue. The resulting residue was purified by silica gel column chromatography (eluent: ethyl acetate/n-hexane=1/30) to give 2.1 g of the titled compound as a yellow liquid.

$^1$H NMR (400 MHz, CDCl$_3$) 7.57 (m, 2H), 7.03 (m, 2H), 6.77 (t, 1H), 7.70 (t, 1H), 5.51 (dd, 1H), 3.64 (dd, 1H), 3.10 (dd, 1H)

Preparation 8. 5-(5-bromo-2-fluoro-phenyl)-1-(2,4-difluoro-phenyl)-3-pentafluoroethyl-4,5-dihydro-1H-pyrazole

Step 1: 3-(5-bromo-2-fluoro-phenyl)-acrylic acid

5-Bromo-2-fluoro-benzaldehyde (5.0 g, 24.6 mmol), malonic acid (5.6 g, 53.7 mmol), and piperidine (0.5 mL, 4.9 mmol) were added to pyridine (11.4 mL). The reaction mixture was stirred at 100° C. for 3 hours and then concentrated under reduced pressure. Distilled water was added to the reaction mixture, which was then filtered. The resulting solid was recrystallized from ethanol to give 1.3 g of the titled compound as a white solid.

$^1$H NMR (400 MHz, CD$_3$OD) 7.89 (d, 1H), 7.74-7.70 (m, 2H), 7.15 (t, 1H), 6.62 (d, 1H)

Step 2: 3-(5-bromo-2-fluoro-phenyl)-acryloyl chloride 3-(5-Bromo-2-fluoro-phenyl)-acrylic acid (1.3 g, 5.0 mmol) prepared in Step 1 was added to thionyl chloride (10.0 mL). The reaction mixture was stirred at 100° C. for 2 hours and then concentrated under reduced pressure. The resulting residue was concentrated under reduced pressure three times, along with using toluene, to give 1.4 g of the titled compound as an unpurified dark brown liquid.

$^1$H NMR (400 MHz, CDCl$_3$) 7.86 (d, 1H), 7.70 (d, 1H), 7.56 (t, 1H), 7.07 (t, 1H), 6.75 (d, 1H)

Step 3: 3-(5-bromo-2-fluoro-phenyl)-N-methoxy-N-methylacrylamide

The unpurified 3-(5-bromo-2-fluoro-phenyl)-acryloyl chloride (1.4 g, 5.0 mmol) prepared in Step 2, N,O-dimethylhydroxylamine hydrochloride (0.52 g, 5.3 mmol), and pyridine (0.9 mL, 11.1 mmol) were added at 0° C. to dichloromethane (10.0 mL). The reaction mixture was stirred at room temperature for 12 hours, quenched with a 1N hydrochloric acid solution, and then extracted with diethyl ether two times. The combined extract was washed with a saturated solution of sodium hydrogen carbonate and brine, dried on anhydrous magnesium sulfate, and then concentrated under reduced pressure to give a yellow liquid residue. The resulting residue was recrystallized from diethyl ether and n-hexane to give 1.3 g of the titled compound as a white solid.

$^1$H NMR (400 MHz, CDCl$_3$) 7.74 (d, 1H), 7.68 (d, 1H), 7.42 (br, 1H), 7.10 (d, 1H), 6.99 (t, 1H), 3.78 (s, 3H), 3.32 (s, 3H)

Step 4: 1-(5-bromo-2-fluoro-phenyl)-4,4,5,5,5-pentafluoro-pent-1-en-3-one

To a saturated solution of pentafluoroiodoethane (0.84 M, in diethyl ether) (15.3 mL, 13.3 mmol), was slowly added a solution of methyllithium/lithium bromide (1.5 M, in diethyl ether) (8.9 mL, 13.3 mmol) under nitrogen atmosphere at −78° C. The reaction mixture was stirred for 20 minutes and then 3-(5-bromo-2-fluoro-phenyl)-N-methoxy-N-methylacrylamide (1.3 g, 4.4 mmol, in tetrahydrofuran 10.0 mL) prepared in Step 3 was slowly added thereto at −78° C. The reaction mixture was stirred at room temperature, quenched with distilled water, acidified by a 10% potassium hydrogen sulfate solution (pH=5), and then extracted with ethyl acetate. The extract was washed with a saturated solution of sodium hydrogen carbonate, dried on anhydrous magnesium sulfate, and then concentrated under reduced pressure to give a yellow liquid residue. The resulting residue was purified by silica gel column chromatography (eluent: ethyl acetate/n-hexane=1/10) to give 620.0 mg of the titled compound as a yellow liquid.

$^1$H NMR (400 MHz, CDCl$_3$) 7.98 (d, 1H), 7.75 (d, 1H), 7.56 (t, 1H), 7.21 (d, 1H), 7.07 (t, 1H)

Step 5: 5-(5-bromo-2-fluoro-phenyl)-1-(2,4-difluoro-phenyl)-3-pentafluoroethyl-4,5-dihydro-1H-pyrazole 1-(5-Bromo-2-fluoro-phenyl)-4,4,5,5,5-pentafluoro-pent-1-en-3-one (620.0 mg, 1.8 mmol) prepared in Step 4 and 2,4-difluorophenylhydrazine hydrochloride (390.0 mg, 2.1 mmol) were added to acetic acid (30.0 mL). The reaction mixture was stirred at 125° C. for 2 hours, concentrated under reduced pressure, and then ethyl acetate was added thereto. The mixture was washed with a saturated solution of sodium hydrogen carbonate, dried on anhydrous magnesium sulfate, and then concentrated under reduced pressure to give a yellow liquid residue. The resulting residue was purified by silica gel column chromatography (eluent: ethyl acetate/n-hexane=1/30) to give 250.0 mg of the titled compound as a yellow liquid.

$^1$H NMR (400 MHz, CDCl$_3$) 7.34 (d, 2H), 7.28 (d, 1H), 6.89 (t, 1H), 6.77 (t, 1H), 6.70 (t, 1H), 5.73 (dd, 1H), 3.64 (dd, 1H), 3.12 (dd, 1H)

Preparation 9. 5-(2-bromo-pyridin-6-yl)-1-(2-chloro-phenyl)-3-pentafluoroethyl-4,5-dihydro-1H-pyrazole Step 1: 3-(6-bromo-pyridin-2-yl)-acrylic acid 6-Bromo-pyridin-2-carbaldehyde (5.0 g, 26.9 mmol), malonic acid (6.3 g, 60.5 mmol), and piperidine (2.2 mL, 22.4 mmol) were added to pyridine (16.3 mL). The reaction mixture was stirred at 100° C. for 1 hour, concentrated under reduced pressure, and then distilled water was added thereto. The mixture was filtered and then the resulting solid was dried under reduced pressure to give 4.5 g of the titled compound as a brown solid.

$^1$H NMR (400 MHz, CD$_3$OD) 7.71 (t, 1H), 7.57 (m, 3H), 6.87 (d, 1H)

Step 2: 3-(6-bromo-pyridin-2-yl)-N-methoxy-N-methyl-acrylamide 3-(6-Bromo-pyridin-2-yl)-acrylic acid (4.5 g, 19.5 mmol) prepared in Step 1, N,O-dimethylhydroxylamine hydrochloride (2.3 g, 23.4 mmol), HOBT (5.3 g, 39.1 mmol), EDAC (7.5 g, 39.1 mmol) and triethylamine (5.4 mL, 39.1 mmol) were added to dichloromethane (100.0 mL). The reaction mixture was stirred at room temperature for 18 hours, quenched with a saturated solution of ammonium chloride, and then extracted with dichloromethane. The extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/9) to give 3.2 g of the titled compound as a white solid.

$^1$H NMR (400 MHz, CDCl$_3$) 7.63-7.53 (m, 3H), 7.43 (d, 1H), 7.33 (d, 1H), 3.80 (s, 3H), 3.32 (s, 3H)

Step 3: 1-(6-bromo-pyridin-2-yl)-4,4,5,5,5-pentafluoro-pent-1-en-3-one

To a saturated solution of pentafluoroiodoethane (0.84 M, in diethyl ether) (42.1 mL, 35.3 mmol), was slowly added a solution of methyllithium/lithium bromide (1.5 M, in diethyl ether) (23.6 mL, 35.3 mmol) under nitrogen atmosphere at −78° C. The reaction mixture was stirred for 20 minutes and then a solution of 3-(6-bromo-pyridin-2-yl)-N-methoxy-N-methyl-acrylamide (3.2 g, 11.8 mmol, in tetrahydrofuran 30.0 mL) prepared in Step 2 was slowly added at −78° C. The reaction mixture was stirred at room temperature, quenched with distilled water, acidified by a 10% potassium hydrogen sulfate solution (pH=5), and then extracted with ethyl acetate. The extract was washed with a saturated solution of sodium hydrogen carbonate, dried on anhydrous magnesium sulfate, concentrated under reduced pressure to give a yellow liquid residue. The resulting residue was purified by silica gel column chromatography (eluent: ethyl acetate/n-hexane=1/10) to give 2.4 g of the titled compound as a yellow liquid.

$^1$H NMR (400 MHz, CDCl$_3$) 7.81 (d, 1H), 7.67 (d, 1H), 7.64 (t, 1H), 7.55 (d, 1H), 7.46 (d, 1H)

Step 4: 5-(2-bromo-pyridin-6-yl)-1-(2-chloro-phenyl)-3-pentafluoroethyl-4,5-dihydro-1H-pyrazole 1-(6-Bromo-pyridin-2-yl)-4,4,5,5,5-pentafluoro-pent-1-en-3-one (100.0 mg, 0.3 mmol) prepared in Step 3, 2-chlorophenylhydrazine hydrochloride (55.0 mg, 0.3 mmol), and piperidine (60.0 uL, 0.6 mmol) were added to ethanol (3.0 mL). The reaction mixture was stirred at 60° C. for 2 hours, concentrated under reduced pressure, and then ethyl acetate was added thereto. The mixture was washed with distilled water, dried on anhydrous magnesium sulfate, and concentrated under reduced pressure to give a yellow liquid residue. The resulting residue was purified by silica gel column chromatography (eluent: ethyl acetate/n-hexane=1/10) to give 15.0 mg of the titled compound as a yellow liquid.

$^1$H NMR (400 MHz, CDCl$_3$) 7.34 (t, 1H), 7.28 (d, 1H), 7.23 (dd, 1H), 7.11 (dt, 1H), 7.03 (d, 1H), 6.98 (dt, 1H), 5.90 (dd, 1H), 3.64 (m, 1H), 3.40 (m, 1H)

Preparation 10. 5-(3-bromo-pyridin-5-yl)-1-(2,4-difluoro-phenyl)-3-pentafluoroethyl-4,5-dihydro-1H-pyrazole Step 1: 3-(5-bromo-pyridin-3-yl)-acrylic acid 5-Bromo-pyridin-3-carbaldehyde (15.0 g, 80.6 mmol), malonic acid (18.9 g, 181.4 mmol), and piperidine (6.6 mL, 66.9 mmol) were added to pyridine (48.9 mL). The reaction mixture was stirred at 100° C. for 1 hour, concentrated under reduced pressure, and then distilled water was added thereto. The mixture was filtered and then the resulting solid was dried under reduced pressure to give 28.4 g of the titled compound as a white solid.

$^1$H NMR (400 MHz, CD$_3$OD) 8.70 (s, 1H), 8.64 (s, 1H), 8.32 (s, 1H), 7.62 (d, 1H), 6.87 (d, 1H)

Step 2: 3-(5-bromo-pyridin-3-yl)-N-methoxy-N-methyl-acrylamide 3-(5-Bromo-pyridin-3-yl)-acrylic acid (26.2 g, 114.7 mmol) prepared in Step 1 was added to thionyl chloride (100.0 mL). The reaction mixture was stirred at 100° C. for 2 hours and then concentrated under reduced pressure. The resulting residue was concentrated under reduced pressure three times, along with using toluene, to give 3-(5-bromo-pyridin-3-yl)-acryloyl chloride as an unpurified dark brown liquid.

The 3-(5-bromo-pyridin-3-yl)-acryloyl chloride in the form of unpurified dark brown liquid, N,O-dimethylhydroxylamine hydrochloride (11.6 g, 119.3 mmol), and pyridine (20.4 mL, 252.4 mmol) were added at 0° C. to dichloromethane (150.0 mL). The reaction mixture was stirred at room temperature for 3 hours, quenched with distilled water, and then extracted with dichloromethane. The extract was washed with a 1N hydrochloric acid solution and brine, dried on anhydrous magnesium sulfate, and then concentrated under reduced pressure to give a yellow liquid residue. The resulting residue was recrystallized from diethyl ether and n-hexane to give 8.2 g of the titled compound as a yellow solid.

$^1$H NMR (400 MHz, CDCl$_3$) 8.66 (d, 2H), 8.01 (s, 1H), 7.65 (d, 1H), 7.10 (d, 1H), 3.79 (s, 3H), 3.33 (s, 3H)

Step 3: 1-(5-bromo-pyridin-3-yl)-4,4,5,5,5-pentafluoro-pent-1-en-3-one

To a saturated solution of pentafluoroiodoethane (0.84 M, in diethyl ether) (108.0 mL, 91.0 mmol), was slowly added a solution of methyllithium/lithium bromide (1.5 M, in diethyl ether) (61.0 mL, 91.0 mmol) under nitrogen atmosphere at −78° C. The reaction mixture was stirred for 20 minutes and then a solution of 3-(5-bromo-pyridin-3-yl)-N-methoxy-N-methyl-acrylamide (8.2 g, 30.3 mmol, in diethyl ether/tetrahydrofuran 50.0 mL/150.0 mL) prepared in Step 2 was slowly added thereto at −78° C. The reaction mixture was stirred at room temperature for 2 hours, quenched with distilled water, acidified by a 10% potassium hydrogen sulfate solution (pH=5), and then extracted with ethyl acetate. The extract was washed with a saturated solution of sodium hydrogen carbonate, dried on anhydrous magnesium sulfate, and then concentrated under reduced pressure to give a yellow liquid residue. The resulting residue was purified by silica gel column chromatography (eluent: ethyl acetate/n-hexane=1/5) to give 2.9 g of the titled compound as a yellow solid.

$^1$H NMR (400 MHz, CDCl$_3$) 8.76 (s, 2H), 8.11 (s, 1H), 7.90 (d, 1H), 7.17 (d, 1H)

Step 4: 5-(3-bromo-pyridin-5-yl)-1-(2,4-difluoro-phenyl)-3-pentafluoroethyl-4,5-dihydro-1H-pyrazole 1-(5-Bromo-pyridin-3-yl)-4,4,5,5,5-pentafluoro-pent-1-en-3-one (2.9 g, 8.6 mmol) prepared in Step 3, 2,4-difluorophenylhydrazine hydrochloride (2.4 g, 8.6 mmol), and piperidine (1.7 mL, 17.3 mmol) were added to ethanol (86.4 mL). The reaction mixture was stirred at 90° C. for 18 hours, concentrated under reduced pressure, and then ethyl acetate was added thereto. The mixture was washed with distilled water, dried on anhydrous magnesium sulfate, and then concentrated under reduced pressure to give a yellow liquid residue. The resulting residue was purified by silica gel column chromatography (eluent: ethyl acetate/n-hexane=1/9) to give 2.4 g of the titled compound as a yellow solid.

$^1$H NMR (400 MHz, CDCl$_3$) 8.58 (s, 1H), 8.35 (s, 1H), 7.63 (s, 1H), 7.37 (q, 1H), 6.80 (t, 1H), 6.72 (t, 1H), 5.56 (dd, 1H), 3.70 (t, 1H), 3.14 (dd, 1H)

Preparation 11. 5-(4-bromo-pyridin-2-yl)-1-(2,4-difluoro-phenyl)-3-pentafluoroethyl-4,5-dihydro-1H-pyrazole

Step 1: 3-(4-bromo-pyridin-2-yl)-acrylic acid

4-Bromo-pyridin-2-carbaldehyde (10.0 g, 53.5 mmol), malonic acid (12.5 g, 120.5 mmol), and piperidine (4.4 mL, 44.4 mmol) were added to pyridine (32.5 mL). The reaction mixture was stirred at 100° C. for 1 hour, concentrated under reduced pressure, and then distilled water was added thereto. The mixture was filtered and then the resulting solid was dried under reduced pressure to give 6.3 g of the titled compound as a white solid.

$^1$H NMR (400 MHz, CD$_3$OD) 8.44 (d, 1H), 7.88 (s, 1H), 7.63-7.59 (m, 2H), 6.89 (d, 1H)

Step 2: 3-(4-bromo-pyridin-2-yl)-N-methoxy-N-methyl-acrylamide 3-(4-Bromo-pyridin-2-yl)-acrylic acid (6.3 g, 27.6 mmol) prepared in Step 1, N,O-dimethylhydroxylamine hydrochloride (3.0 g, 30.4 mmol), HOBT (7.5 g, 55.3 mmol), EDAC (10.6 g, 55.3 mmol) and triethylamine (11.5 mL, 82.9 mmol) were added to N,N-dimethylformamide (100.0 mL). The reaction mixture was stirred at room temperature for 18 hours, quenched with a saturated solution of ammonium chloride, and then extracted with ethyl acetate. The extract was washed with brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 2.4 g of the titled compound as a pale yellow solid.

$^1$H NMR (400 MHz, CDCl$_3$) 8.46 (d, 1H), 7.66-7.53 (m, 3H), 7.42 (d, 1H), 3.79 (s, 3H), 3.33 (s, 3H)

Step 3: 1-(4-bromo-pyridin-2-yl)-4,4,5,5,5-pentafluoro-pent-1-en-3-one

To a saturated solution of pentafluoroiodoethane (0.84 M, in diethyl ether) (31.6 mL, 26.6 mmol), was slowly added a solution of methyllithium/lithium bromide (1.5 M, in diethyl ether) (17.7 mL, 26.6 mmol) under nitrogen atmosphere at −78° C. The reaction mixture was stirred for 20 minutes and then a solution of 3-(4-bromo-pyridin-2-yl)-N-methoxy-N-methyl-acrylamide (2.4 g, 8.9 mmol, in diethyl ether/tetrahydrofuran 20.0 mL/20.0 mL) prepared in Step 2 solution was slowly added thereto at −78° C. The reaction mixture was stirred at −78° C. for 1 hour, quenched with distilled water at room temperature, acidified by a 10% potassium hydrogen sulfate solution (pH=5), and then extracted with ethyl acetate. The extract was washed with a saturated solution of sodium hydrogen carbonate, dried on anhydrous magnesium sulfate, and then concentrated under reduced pressure to give a yellow liquid residue. The resulting residue was purified by silica gel column chromatography (eluent: ethyl acetate/n-hexane=1/5) to give 2.2 g of the titled compound as a yellow solid.

$^1$H NMR (400 MHz, CDCl$_3$) 8.52 (d, 1H), 7.83 (d, 1H), 7.71-7.66 (m, 2H), 7.54 (d, 1H)

Step 4: 5-(4-bromo-pyridin-2-yl)-1-(2,4-difluoro-phenyl)-3-pentafluoroethyl-4,5-dihydro-1H-pyrazole 1-(4-Bromo-pyridin-2-yl)-4,4,5,5,5-pentafluoro-pent-1-en-3-one (2.2 g, 6.6 mmol) prepared in Step 3, 2,4-difluorophenylhydrazine hydrochloride (1.8 g, 6.6 mmol), and piperidine (1.3 mL, 13.2 mmol) were added to ethanol (66.1 mL). The reaction mixture was stirred at 90° C. for 2 hours, concentrated under reduced pressure, and then ethyl acetate was added thereto. The mixture was washed with distilled water, dried on anhydrous magnesium sulfate, and then concentrated under reduced pressure to give a yellow liquid residue. The resulting residue was purified by silica gel column chromatography (eluent: ethyl acetate/n-hexane=1/3) to give 2.1 g of the titled compound as a yellow liquid.

$^1$H NMR (400 MHz, CDCl$_3$) 8.33 (d, 1H), 7.56-7.27 (m, 3H), 6.86-6.69 (m, 2H), 5.68-5.53 (dd, 1H), 3.70-3.60 (dd, 1H), 3.38-3.23 (dd, 1H)

Preparation 12. 5-(2-bromo-pyridin-4-yl)-1-(2,4-difluoro-phenyl)-3-pentafluoroethyl-4,5-dihydro-1H-pyrazole

Step 1: 3-(2-bromo-pyridin-4-yl)-acrylic acid

2-Bromo-pyridin-4-carbaldehyde (20.0 g, 107.5 mmol), malonic acid (25.2 g, 241.9 mmol), and piperidine (8.8 mL, 89.2 mmol) were added to pyridine (65.2 mL). The reaction mixture was stirred at 100° C. for 1 hour, concentrated under reduced pressure, and then distilled water was added thereto.

The mixture was filtered and then the resulting solid dried under reduced pressure to give 18.2 g of the titled compound as a white solid.

$^1$H NMR (400 MHz, CD$_3$OD) 8.36 (d, 1H), 7.82 (s, 1H), 7.67-7.45 (m, 2H), 6.75 (d, 1H)

Step 2: 3-(2-bromo-pyridin-4-yl)-N-methoxy-N-methyl-acrylamide 3-(2-Bromo-pyridin-4-yl)-acrylic acid (5.0 g, 21.9 mmol) prepared in Step 1, N,O-dimethylhydroxylamine hydrochloride (2.4 g, 24.1 mmol), HOBT (5.9 g, 43.9 mmol), EDAC (8.4 g, 43.9 mmol) and triethylamine (9.1 mL, 65.8 mmol) were added to N,N-dimethylformamide (100.0 mL). The reaction mixture was stirred at room temperature for 18 hours, quenched with a saturated solution of ammonium chloride, and then extracted with ethyl acetate. The extract was washed with brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 5.6 g of the titled compound as a white solid.

$^1$H NMR (400 MHz, CDCl$_3$) 8.39 (d, 1H), 7.61-7.55 (m, 2H), 7.35 (d, 1H), 7.17 (d, 1H), 3.74 (s, 3H), 3.33 (s, 3H)

Step 3: 1-(2-bromo-pyridin-4-yl)-4,4,5,5,5-pentafluoro-pent-1-en-3-one

To a saturated solution of pentafluoroiodoethane (0.84 M, in diethyl ether) (73.8 mL, 62.0 mmol), was slowly added a solution of methyllithium/lithium bromide (1.5 M, in diethyl ether) (41.3 mL, 62.0 mmol) under nitrogen atmosphere at −78° C. The reaction mixture was stirred for 20 minutes and then 3-(2-bromo-pyridin-4-yl)-N-methoxy-N-methyl-acrylamide (5.6 g, 20.7 mmol, in diethyl ether/tetrahydrofuran 30.0 mL/30.0 mL) prepared in Step 2 was added thereto at −78° C. The reaction mixture was stirred at −78° C. for 1 hour, quenched with distilled water at room temperature, acidified by a 10% potassium hydrogen sulfate solution (pH=5), and then extracted with ethyl acetate. The extract was washed with a saturated solution of sodium hydrogen carbonate, dried on anhydrous magnesium sulfate, and then concentrated under reduced pressure to give a yellow liquid residue. The resulting residue was purified by silica gel column chromatography (eluent: ethyl acetate/n-hexane=1/5) to give 2.9 g of the titled compound as a white solid.

$^1$H NMR (400 MHz, CDCl$_3$) 8.50 (d, 1H), 7.79 (d, 1H), 7.67 (s, 1H), 7.43 (d, 1H), 7.22 (d, 1H)

Step 4: 5-(2-bromo-pyridin-4-yl)-1-(2,4-difluoro-phenyl)-3-pentafluoroethyl-4,5-dihydro-1H-pyrazole 1-(2-Bromo-pyridin-4-yl)-4,4,5,5,5-pentafluoro-pent-1-en-3-one (2.9 g, 8.9 mmol) prepared in Step 3, 2,4-difluorophenylhydrazine hydrochloride (2.4 g, 8.9 mmol), and piperidine (1.8 mL, 17.8 mmol) were added to ethanol (88.8 mL). The reaction mixture was stirred at 90° C. for 2 hours, concentrated under reduced pressure, and then ethyl acetate was added thereto. The mixture was washed with distilled water, dried on anhydrous magnesium sulfate, and then concentrated under reduced pressure to give a yellow liquid residue. The resulting residue was purified by silica gel column chromatography (eluent: ethyl acetate/n-hexane=1/3) to give 1.8 g of the titled compound as a yellow liquid.

$^1$H NMR (400 MHz, CDCl$_3$) 8.30 (d, 1H), 7.41-7.35 (m, 1H), 7.30 (s, 1H), 7.01 (dd, 1H), 6.84-6.70 (m, 2H), 5.52 (dd, 1H), 3.69 (dd, 1H), 3.09 (dd, 1H)

Preparation 13. 5-(5-bromo-thiophen-2-yl)-1-(2,4-difluoro-phenyl)-3-pentafluoroethyl-4,5-dihydro-1H-pyrazole

Step 1: 4-(5-bromo-thiophen-2-yl)-2-oxo-3-butenoic acid

A solution of pyruvic acid (12.1 mL, 174.4 mmol) in ethanol (15.0 mL) was added to a 0.5 M sodium hydroxide solution (476.2 mL). The reaction mixture was stirred at room temperature for 20 minutes. A solution of 5-bromo-thiophen-2-carbaldehyde (30.3 g, 158.6 mmol) in ethanol (140.0 mL) was slowly added to the reaction mixture at room temperature for 1 hour. The reaction mixture was stirred at room temperature for 18 hours and then the precipitate solid was filtered. The resulting solid was washed with diethyl ether, acidified by a 3N hydrochloric acid solution, and then extracted with ethyl acetate. The extract was washed with distilled water and brine, dried on anhydrous magnesium sulfate, and then concentrated under reduced pressure to give 39.6 g of the titled compound as a yellow solid.

$^1$H NMR (400 MHz, CDCl$_3$) 8.14 (d, 1H), 7.26 (s, 1H), 7.23 (d, 1H), 7.13 (s, 1H)

Step 2: 4-(5-bromo-thiophen-2-yl)-2-oxo-3-butenoic acid methyl ester

Acetyl chloride (36.4 mL, 515.7 mmol) was slowly added at 0° C. to methanol (200.0 mL) under stirring. A solution of 4-(5-bromo-thiophen-2-yl)-2-oxo-3-butenoic acid (39.6 g, 151.7 mmol) prepared in Step 1 in methanol (20.0 mL) was added to the reaction mixture at room temperature. The reaction mixture was stirred at 80° C. for 18 hours and then filtered to give 34.0 g of the titled compound as a yellow solid.

$^1$H NMR (400 MHz, CDCl$_3$) 7.86 (d, 1H), 7.17-7.16 (m, 1H), 7.09-7.04 (m, 2H), 3.93 (s, 3H)

Step 3: 5-(5-bromo-thiophen-2-yl)-1-(2,4-difluoro-phenyl)-4,5-dihydro-1H-pyrazole-3-carboxylic acid methyl ester 4-(5-Bromo-thiophen-2-yl)-2-oxo-3-butenoic acid methyl ester (17.0 g, 61.8 mmol) prepared in Step 2 and 2,4-difluorophenylhydrazine hydrochloride (12.3 g, 68.0 mmol) were added to acetic acid (200.0 mL). The reaction mixture was stirred at 125° C. for 2 hours, concentrated under reduced pressure, and then ethyl acetate was added thereto. The mixture was washed with a saturated solution of sodium hydrogen carbonate, dried on anhydrous magnesium sulfate, and then concentrated under reduced pressure to give a yellow liquid residue. The resulting residue was purified by silica gel column chromatography (eluent: ethyl acetate/n-hexane=1/20) to give 15.1 g of the titled compound as a yellow solid.

$^1$H NMR (400 MHz, CDCl$_3$) 7.43-7.37 (m, 1H), 6.79-6.63 (m, 3H), 6.62 (s, 1H), 5.81-5.77 (m, 1H), 3.90 (s, 3H), 3.62 (dd, 1H), 3.33 (dd, 1H)

Step 4: [5-(5-bromo-thiophen-2-yl)-1-(2,4-difluoro-phenyl)-4,5-dihydro-1H-pyrazol-3-yl]-methanol To a solution of 5-(5-bromo-thiophen-2-yl)-1-(2,4-difluoro-phenyl)-4,5-dihydro-1H-pyrazole-3-carboxylic acid methyl ester (15.1 g, 37.6 mmol) prepared in Step 3 in methanol (125.3 mL), was slowly added sodium borohydride (6.4 g, 169.2 mmol) at 0° C. The reaction mixture was stirred at 80° C. for 18 hours, concentrated under reduced pressure, acidified by a 1N hydrochloric acid solution, and then extracted with dichloromethane. The extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/2) to give 12.9 g of the titled compound as a yellow liquid.

$^1$H NMR (400 MHz, CDCl$_3$) 7.34-7.26 (m, 1H), 6.74-6.71 (m, 3H), 6.60 (d, 1H), 5.57 (dd, 1H), 4.51 (s, 2H), 3.41 (dd, 1H), 3.06 (dd, 1H), 2.14 (s, 1H)

Step 5: 5-(5-bromo-thiophen-2-yl)-1-(2,4-difluoro-phenyl)-4,5-dihydro-1H-pyrazole-3-carbaldehyde

[5-(5-Bromo-thiophen-2-yl)-1-(2,4-difluoro-phenyl)-4,5-dihydro-1H-pyrazol-3-yl]-methanol (12.9 g, 34.5 mmol) prepared in Step 4 and magnesium dioxide (MnO$_2$) (30.0 g, 344.6 mmol) were added to dichloromethane (115.0 mL). The reaction mixture was stirred at room temperature for 3 days and then filtered to obtain a yellow filtrate. The filtrate was concentrated under reduced pressure. The resulting residue was purified by silica gel column chromatography (eluent: n-hexane) to give 9.1 g of the titled compound as a yellow liquid.

$^1$H NMR (400 MHz, CDCl$_3$) 9.85 (s, 1H), 7.47-7.37 (m, 1H), 6.90-6.75 (m, 3H), 6.65-6.62 (m, 1H), 5.88 (dd, 1H), 3.55 (dd, 1H), 3.30 (dd, 1H)

Step 6: 1-[5-(5-bromo-thiophen-2-yl)-1-(2,4-difluoro-phenyl)-4,5-dihydro-1H-pyrazol-3-yl]-2,2,2-trifluoro-ethanol To a solution of 5-(5-bromo-thiophen-2-yl)-1-(2,4-difluoro-phenyl)-4,5-dihydro-1H-pyrazole-3-carbaldehyde (9.1 g, 22.4 mmol) prepared in Step 5 and CF$_3$TMS (5.7 mL, 38.1 mmol) in tetrahydrofuran (100.0 mL), was slowly added a solution of TBAF (1.0 M, in tetrahydrofuran 0.5 mL, 0.5 mmol) at 0° C. The reaction mixture was stirred at room temperature for 1 hour and then a 6N hydrochloric acid solution was added thereto. The reaction mixture was stirred at room temperature for 1 hour and then extracted with ethyl acetate. The extract was washed distilled water and brine, dried on anhydrous magnesium sulfate, and then concentrated under reduced pressure to give 9.9 g of the titled compound as a yellow liquid.

$^1$H NMR (400 MHz, CDCl$_3$) 7.30-7.20 (m, 1H), 6.80-6.70 (m, 3H), 6.62-6.58 (m, 1H), 5.68-5.63 (m, 1H), 5.00-4.90 (m, 1H), 3.58-3.40 (m, 2H), 3.30-3.08 (m, 1H)

Step 7: 1-[5-(5-bromo-thiophen-2-yl)-1-(2,4-difluoro-phenyl)-4,5-dihydro-1H-pyrazol-3-yl]-2,2,2-trifluoro-ethanone To a solution of 1-[5-(5-bromo-thiophen-2-yl)-1-(2,4-difluoro-phenyl)-4,5-dihydro-1H-pyrazol-3-yl]-2,2,2-trifluoro-ethanol (9.9 g, 22.4 mmol) prepared in Step 6 in dichloromethane (100.0 mL), was slowly added DMP (10.5 g, 24.7 mmol) at 0° C. The reaction mixture was stirred at room temperature for 1 hour, quenched with a saturated sodium thiosulfate solution, and then extracted with diethyl ether. The extract was washed with a saturated solution of sodium hydrogen carbonate, dried on anhydrous magnesium sulfate, and then concentrated under reduced pressure to give a yellow liquid residue. The resulting residue was purified by silica gel column chromatography (eluent: dichloromethane/n-hexane=2/5) to give 8.5 g of the titled compound as a yellow solid.

$^1$H NMR (400 MHz, CDCl$_3$) 7.48-7.42 (m, 1H), 6.90-6.78 (m, 3H), 6.69 (d, 1H), 5.94 (dd, 1H), 3.66 (dd, 1H), 3.40 (dd, 1H)

Step 8: 5-(5-bromo-thiophen-2-yl)-1-(2,4-difluoro-phenyl)-3-pentafluoroethyl-4,5-dihydro-1H-pyrazole 1-[5-(5-Bromo-thiophen-2-yl)-1-(2,4-difluoro-phenyl)-4,5-dihydro-1H-pyrazol-3-yl]-2,2,2-trifluoro-ethanone (3.0 g, 7.8 mmol) prepared in Step 7 and BAST (4.1 mL, 23.4 mmol) were added to dimethoxyethane (24.0 mL). The reaction mixture was stirred in a microwave reactor (Anton Paar-Synthos 3000) for 30 minutes, slowly quenched with a saturated solution of sodium hydrogen carbonate at 0° C., extracted with ethyl acetate. The extract was washed with a saturated solution of sodium hydrogen carbonate, dried on anhydrous magnesium sulfate, and then concentrated under reduced pressure to give 2.0 g of the titled compound as a yellow liquid.

$^1$H NMR (400 MHz, CDCl$_3$) 7.33-7.27 (m, 1H), 6.78-6.75 (m, 2H), 6.62 (s, 1H), 5.78-5.73 (m, 1H), 3.58 (dd, 1H), 3.25 (dd, 1H)

Preparation 14. 1-(3-bromo-phenyl)-5-(2,4-difluoro-phenyl)-3-pentafluoroethyl-4,5-dihydro-1H-pyrazole Step 1: 3-(2,4-difluoro-phenyl)-acrylic acid 2,4-Difluoro-benzaldehyde (10.0 g, 70.4 mmol), malonic acid (16.5 g, 158.3 mmol), and piperidine (5.8 mL, 58.4 mmol) were added to pyridine (42.7 mL). The reaction mixture was stirred at 100° C. for 2 hours, concentrated under reduced pressure, and then distilled water was added thereto. The mixture was filtered and then the resulting solid was dried under reduced pressure to give 9.5 g of the titled compound as a yellow solid.

$^1$H NMR (400 MHz, CD$_3$OD) 7.76-7.71 (m, 2H), 7.07-7.02 (m, 2H), 6.52 (d, 1H)

Step 2: 3-(2,4-difluoro-phenyl)-N-methoxy-N-methyl-acrylamide 3-(2,4-Difluoro-phenyl)-acrylic acid (9.5 g, 51.4 mmol) prepared in Step 1, N,O-dimethylhydroxylamine hydrochloride (6.5 g, 66.8 mmol), HOBT (7.6 g, 56.5 mmol), EDAC (10.8 g, 56.5 mmol) and diisopropylethylamine (9.8 mL, 56.5 mmol) were added to dichloromethane (250.0 mL). The reaction mixture stirred at room temperature for 24 hours, quenched with a saturated solution of ammonium chloride, and then extracted with dichloromethane. The extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/3) to give 10.1 g of the titled compound as a yellow liquid.

$^1$H NMR (400 MHz, CDCl$_3$) 7.76 (d, 1H), 7.58-7.52 (m, 1H), 7.08 (d, 1H), 6.93-6.83 (m, 2H), 3.81 (s, 3H), 3.31 (s, 3H)

Step 3: 1-(2,4-difluoro-phenyl)-4,4,5,5,5-pentafluoro-pent-1-en-3-one

To a saturated solution of pentafluoroiodoethane (0.84 M, in diethyl ether) (79.0 mL, 66.0 mmol), was slowly added a solution of methyllithium/lithium bromide (1.5 M, in diethyl ether) (44.0 mL, 66.0 mmol) under nitrogen atmosphere at −78° C. The reaction mixture was stirred for 20 minutes and then a solution of 3-(2,4-difluoro-phenyl)-N-methoxy-N-methyl-acrylamide (5.0 g, 22.0 mmol, in diethyl ether 30.0 mL) prepared in Step 2 was slowly added thereto at −78° C. The reaction mixture was stirred at −78° C. for 30 minutes, quenched with distilled water, acidified by a 10% potassium hydrogen sulfate solution (pH=5), and then extracted with ethyl acetate. The extract was washed with a saturated solution of sodium hydrogen carbonate, dried on anhydrous magnesium sulfate, and then concentrated under reduced pressure to give a yellow liquid residue. The resulting residue was purified by silica gel column chromatography (eluent: ethyl acetate/n-hexane=1/10) to give 6.2 g of the titled compound as a yellow liquid.
$^1$H NMR (400 MHz, CDCl$_3$) 8.02 (d, 1H), 7.69-7.62 (m, 1H), 7.17 (d, 1H), 7.01-6.90 (m, 2H)

Step 4: 1-(3-bromo-phenyl)-5-(2,4-difluoro-phenyl)-3-pentafluoroethyl-4,5-dihydro-1H-pyrazole 1-(2,4-Difluoro-phenyl)-4,4,5,5,5-pentafluoro-pent-1-en-3-one (4.8 g, 16.9 mmol) prepared in Step 3 and 3-bromophenylhydrazine hydrochloride (4.2 g, 18.6 mmol) were added to acetic acid (50.0 mL). The reaction mixture was stirred at 95° C. for 5 hours, concentrated under reduced pressure, and then ethyl acetate was added thereto. The mixture was washed with a saturated solution of sodium hydrogen carbonate, dried on anhydrous magnesium sulfate, and then concentrated under reduced pressure to give a yellow liquid residue. The resulting residue was purified by silica gel column chromatography (eluent: n-hexane) to give 2.7 g of the titled compound as a yellow liquid.
$^1$H NMR (400 MHz, CDCl$_3$) 7.25 (d, 1H), 7.12-7.01 (m, 3H), 6.96-6.74 (m, 3H), 5.61 (dd, 1H), 3.73 (dd, 1H), 2.97 (dd, 1H)

Preparation 15. 1-(4-bromo-phenyl)-5-(2,4-difluoro-phenyl)-3-pentafluoroethyl-4,5-dihydro-1H-pyrazole 1-(2,4-Difluoro-phenyl)-4,4,5,5,5-pentafluoro-pent-1-en-3-one (3.8 g, 13.3 mmol) prepared in Step 3 of Preparation 14, 4-bromophenylhydrazine hydrochloride (3.3 g, 13.5 mmol), acetic acid (15.0 mL) and conc. hydrochloric acid (20.0 mL) were added to ethanol (35.0 mL). The reaction mixture was stirred at 100° C. for 18 hours, quenched with a saturated solution of sodium hydrogen carbonate, and then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/10) to give 5.4 g of the titled compound as a yellow liquid.
$^1$H NMR (400 MHz, CDCl$_3$) 7.30 (d, 2H), 7.09 (dd, 1H), 6.92-6.08 (m, 4H), 5.60 (dd, 1H), 3.73 (dd, 1H), 2.97 (dd, 1H)

Preparation 16. 5-(3-bromo-phenyl)-1-(2-chloro-phenyl)-3-[di-(trifluoromethyl)-hydroxy-methyl]-4,5-dihydro-1H-pyrazole Step 1: 4-(3-bromo-phenyl)-2-oxo-3-butenoic acid potassium salt To a mixture of 3-Bromobenzaldehyde (22.0 mL, 189.0 mmol) and pyruvic acid (15.8 mL, 227.0 mmol) in methanol (100.0 mL), was slowly added a solution of potassium hydroxide (19.0 g, 340.0 mmol) in methanol (100.0 mL) at 0° C. The reaction mixture was stirred at room temperature for 16 hours and then filtered. The resulting solid was washed with diethyl ether to give 47.0 g of the titled compound as a yellow solid.
$^1$H NMR (400 MHz, DMSO-d$_6$) 7.87 (s, 1H), 7.66 (d, 1H), 7.58 (d, 1H), 7.40-7.34 (m, 2H), 6.82 (d, 1H)

Step 2: 4-(3-bromo-phenyl)-2-oxo-3-butenoic acid methyl ester 4-(3-Bromo-phenyl)-2-oxo-3-butenoic acid potassium salt (41.0 g, 140.0 mmol) prepared in Step 1 and methyl iodide (15.0 mL, 238.0 mmol) were added to N,N-dimethylformamide (200.0 mL). The reaction mixture was stirred at 75° C. for 4 hours and then distilled water was added thereto. The reaction mixture was extracted with ethyl acetate. The extract was washed with a saturated solution of sodium hydrogen carbonate and brine, dried on anhydrous magnesium sulfate, and then concentrated under reduced pressure to give a yellow liquid residue. The resulting residue was purified by silica gel column chromatography (eluent: ethyl acetate/n-hexane=1/8) to give 10.0 g of the titled compound as a pale yellow solid.
$^1$H NMR (400 MHz, CDCl$_3$) 7.82-7.77 (m, 2H), 7.60-7.54 (m, 2H), 7.37 (d, 1H), 7.31 (t, 1H), 3.95 (s, 3H)

Step 3: 5-(3-bromo-phenyl)-1-(2-chloro-phenyl)-4,5-dihydro-1H-pyrazole-3-carboxylic acid methyl ester 4-(3-Bromo-phenyl)-2-oxo-3-butenoic acid methyl ester (10.0 g, 37.2 mmol) prepared in Step 2 and 2-chlorophenylhydrazine hydrochloride (7.3 g, 40.9 mmol) were added to acetic acid (150.0 mL). The reaction mixture was stirred at 125° C. for 4 hours, concentrated under reduced pressure, and then ethyl acetate was added thereto. The reaction mixture was washed with a saturated solution of sodium hydrogen carbonate, dried on anhydrous magnesium sulfate, and then concentrated under reduced pressure to give a yellow liquid residue. The resulting residue was purified by silica gel column chromatography (eluent: ethyl acetate/n-hexane=1/5) to give 11.0 g of the titled compound as a yellow liquid.
$^1$H NMR (400 MHz, CDCl$_3$) 7.33-7.23 (m, 4H), 7.13-7.05 (m, 3H), 6.99 (t, 1H), 5.84 (dd, 1H), 3.90 (s, 3H), 3.70 (dd, 1H), 3.27 (dd, 1H)

Step 4: 5-(3-bromo-phenyl)-1-(2-chloro-phenyl)-3-[di-(trifluoromethyl)-hydroxy-methyl]-4,5-dihydro-1H-pyrazole 5-(3-Bromo-phenyl)-1-(2-chloro-phenyl)-4,5-dihydro-1H-pyrazole-3-carboxylic acid methyl ester (210.0 mg, 0.53 mmol) prepared in Step 3, CF$_3$TMS (316.0 uL, 2.13 mmol), and molecular sieve (4, 100.0 mg) were added to toluene (4.0 mL) under nitrogen atmosphere. TBAF (1.0 M, in tetrahydrofuran 106.0 uL, 0.11 mmol) was slowly added to the reaction mixture, which was then stirred at room temperature for 2 hours. Since the reaction was not completed, CF$_3$TMS (158.0 uL, 1.06 mmol) and TBAF (1.0 M, in tetrahydrofuran 30.0 uL, 0.03 mmol) were added at room temperature to the reaction mixture, which was then stirred at at 45° C. for 48 hours. The reaction mixture was filtered through celite pad. Dichloromethane was added to the filtrate, which was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/5) to give 130.0 mg of the titled compound as a brown liquid.

¹H NMR (400 MHz, CDCl₃) 7.34-7.26 (m, 3H), 7.17-7.06 (m, 4H), 7.00 (t, 1H), 5.81 (dd, 1H), 4.90 (s, 1H), 3.63 (dd, 1H), 3.18 (dd, 1H)

Preparation 17. 5-(4-bromo-phenyl)-1-(2-chloro-phenyl)-3-[di-(trifluoromethyl)-hydroxy-methyl]-4,5-dihydro-1H-pyrazole Step 1: 4-(4-bromo-phenyl)-2-oxo-3-butenoic acid potassium salt To a mixture of 4-bromobenzaldehyde (35.0 g, 189.0 mmol) and pyruvic acid (15.8 mL, 227.0 mmol) in methanol (100.0 mL), was slowly added a solution of potassium hydroxide (19.0 g, 340.0 mmol) in methanol (100.0 mL) at 0° C. The reaction mixture was stirred at room temperature for 16 hours and then filtered. The resulting solid was washed with diethyl ether to give 48.0 g of the titled compound as a pale yellow solid.
¹H NMR (400 MHz, DMSO-d₆) 7.61-7.58 (m, 4H), 7.37 (d, 1H), 6.75 (d, 1H)

Step 2: 4-(4-bromo-phenyl)-2-oxo-3-butenoic acid methyl ester

A mixture of 4-(4-bromo-phenyl)-2-oxo-3-butenoic acid potassium salt (48.0 g, 164.0 mmol) prepared in Step 1 and methyl iodide (20.0 mL, 327.0 mmol) in N,N-dimethylformamide (250.0 mL) was stirred at 75° C. for 4 hours and then distilled water was added thereto. The reaction mixture was extracted with ethyl acetate. The extract was washed with a sodium hydrogen carbonate solution and brine, dried on anhydrous magnesium sulfate, and then concentrated under reduced pressure to give a yellow liquid residue. The resulting residue was purified by silica gel column chromatography (eluent: ethyl acetate/n-hexane=1/5) to give 13.5 g of the titled compound as a pale yellow solid.
¹H NMR (400 MHz, CDCl₃) 7.81 (d, 1H), 7.57 (d, 2H), 7.50 (d, 2H), 7.37 (d, 1H), 3.94 (s, 3H)

Step 3: 5-(4-bromo-phenyl)-1-(2-chloro-phenyl)-4,5-dihydro-1H-pyrazole-3-carboxylic acid methyl ester 4-(4-Bromo-phenyl)-2-oxo-3-butenoic acid methyl ester (13.5 g, 50.2 mmol) prepared in Step 2 and 2-chlorophenyl-hydrazine hydrochloride (9.9 g, 55.2 mmol) were added to acetic acid (200.0 mL). The reaction mixture was stirred at 125° C. for 4 hours, concentrated under reduced pressure, and then ethyl acetate was added thereto. The reaction mixture was washed with a saturated solution of sodium hydrogen carbonate, dried on anhydrous magnesium sulfate, and then concentrated under reduced pressure to give a yellow liquid residue. The resulting residue was purified by silica gel column chromatography (eluent: ethyl acetate/n-hexane=1/5) to give 18.9 g of the titled compound as a brown liquid.
¹H NMR (400 MHz, CDCl₃) 7.33-7.26 (m, 3H), 7.21 (d, 1H), 7.09 (t, 1H), 7.03 (d, 2H), 6.96 (t, 1H), 5.87 (dd, 1H), 3.89 (s, 3H), 3.70 (dd, 1H), 3.25 (dd, 1H)

Step 4: 5-(4-bromo-phenyl)-1-(2-chloro-phenyl)-3-[di-(trifluoromethyl)-hydroxy-methyl]-4,5-dihydro-1H-pyrazole 5-(4-Bromo-phenyl)-1-(2-chloro-phenyl)-4,5-dihydro-1H-pyrazole-3-carboxylic acid methyl ester (3.0 g, 7.6 mmol) prepared in Step 3, CF₃TMS (4.5 mL, 30.5 mmol), and molecular sieve (4, 1.0 g) were slowly added to toluene (50.0 mL) under nitrogen atmosphere. TBAF (1.0 M, in tetrahydrofuran 1.5 mL, 30.5 mmol) was slowly added to the reaction mixture, which was then stirred at room temperature for 2 hours. Since the reaction was not completed, CF₃TMS (2.3 mL, 15.3 mmol) and TBAF (1.0 M, in tetrahydrofuran 0.38 mL, 0.38 mmol) were added at room temperature to the reaction mixture, which was then stirred at at 45° C. for 16 hours. The reaction mixture was filtered through celite pad. Dichloromethane was added to the filtrate, which was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/8) to give 890.0 mg of the titled compound as a brown liquid.
¹H NMR (400 MHz, CDCl₃) 7.35 (d, 2H), 7.25 (d, 1H), 7.16-7.08 (m, 2H), 7.03-6.97 (m, 3H), 5.84 (dd, 1H), 4.88 (s, 1H), 3.63 (dd, 1H), 3.16 (dd, 1H)

Preparation 18. 4-(3'-ethoxy-biphenyl-4-yl)-2-oxo-3-butenoic acid methyl ester

Step 1: 3'-ethoxy-biphenyl-4-carbaldehyde

4-Bromobenzaldehyde (4.0 g, 21.6 mmol), 3-ethoxyphenylboronic acid (4.0 g, 21.6 mmol), a 2N sodium carbonate solution (216.0 mL, 216.0 mmol), and Pd(dppf)Cl₂ (1.6 g, 2.2 mmol) were added to N,N-dimethylformamide (216.0 mL). The reaction mixture was stirred at 80° C. for 3 hours and then filtered through celite pad. Distilled water was added to the filtrate, which was then extracted with ethyl acetate. The extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/5) to give 4.6 g of the titled compound as a pale yellow liquid.
¹H NMR (400 MHz, CDCl₃) 10.05 (s, 1H), 7.94 (d, 2H), 7.74 (d, 2H), 7.38 (t, 1H), 7.20 (d, 1H), 7.16 (s, 1H), 6.95 (d, 1H), 4.10 (q, 2H), 1.45 (t, 3H)

Step 2: 4-(3'-ethoxy-biphenyl-4-yl)-2-oxo-3-butenoic acid

To a mixture of 3'-ethoxy-biphenyl-4-carbaldehyde (4.6 g, 20.1 mmol) prepared in Step 1 and pyruvic acid (1.7 mL, 24.1 mmol) in methanol (15.0 mL), was slowly added a solution of potassium hydroxide (2.0 g, 36.2 mmol) in methanol (15.0 mL) at 0° C. The reaction mixture was stirred at room temperature for 7 hours and then filtered. The resulting solid was diluted with a 1N hydrochloric acid solution and then extracted with ethyl acetate. The extract was washed with distilled water and brine, dried on anhydrous magnesium sulfate, and then concentrated under reduced pressure to give 2.5 g of the titled compound as a brown liquid.
¹H NMR (400 MHz, CDCl₃) 8.19 (d, 1H), 7.76 (d, 2H), 7.70-7.62 (m, 3H), 7.36 (d, 1H), 7.21 (d, 1H), 7.16 (s, 1H), 6.94 (d, 1H), 4.12 (q, 2H), 1.46 (t, 3H)

Step 3: 4-(3'-ethoxy-biphenyl-4-yl)-2-oxo-3-butenoic acid methyl ester

Acetyl chloride (2.0 mL, 28.7 mmol) was slowly added to methanol (10.0 mL) at 0° C. under stirring. A solution of 4-(3'-ethoxy-biphenyl-4-yl)-2-oxo-3-butenoic acid (2.5 g, 8.4 mmol) prepared in Step 2 in methanol (10.0 mL) was added to the reaction mixture at room temperature. The reaction mixture was stirred at room temperature for 1 hour, additionally at 80° C. for 16 hours, and then filtered at room temperature to give 1.0 g of the titled compound as a yellow solid.

$^1$H NMR (400 MHz, CDCl$_3$) 7.92 (d, 1H), 7.72-7.64 (m, 4H), 7.44-7.35 (m, 2H), 7.20 (d, 1H), 7.15 (s, 1H), 6.93 (d, 1H), 4.11 (q, 2H), 3.95 (s, 3H), 1.45 (t, 3H)

Preparation 19. 5-(4-bromo-2-fluoro-phenyl)-1-(2-chloro-phenyl)-3-[di-(trifluoromethyl)-hydroxy-methyl]-4,5-dihydro-1H-pyrazole Step 1: 4-(4-bromo-2-fluoro-phenyl)-2-oxo-3-butenoic acid A solution of pyruvic acid (1.9 mL, 27.1 mmol) in ethanol (2.5 mL) was added to a 0.5 M sodium hydroxide solution (74.0 mL). The reaction mixture was stirred at room temperature for 10 minutes and then a solution of 4-bromo-2-fluorobenzaldehyde (5.0 g, 24.6 mmol) in ethanol (22.5 mL) was slowly added thereto at room temperature for 1 hour. The reaction mixture was stirred at room temperature for 18 hours and then filtered. The resulting solid was washed with ethyl acetate, diluted with a 1N hydrochloric acid solution and then extracted with ethyl acetate. The extract was washed with distilled water and brine, dried on anhydrous magnesium sulfate, and then concentrated under reduced pressure to give 5.5 g of the titled compound as a yellow solid.

$^1$H NMR (400 MHz, CD$_3$OD) 7.90 (d, 1H), 7.76 (t, 1H), 7.53-7.47 (m, 3H)

Step 2: 4-(4-bromo-2-fluoro-phenyl)-2-oxo-3-butenoic acid methyl ester

Acetyl chloride (4.8 mL, 68.5 mmol) was slowly added at 0° C. to methanol (28.0 mL) under stirring. A solution of 4-(4-bromo-2-fluoro-phenyl)-2-oxo-3-butenoic acid (5.5 g, 20.1 mmol) prepared in Step 1 in methanol (5.0 mL) was added to the reaction mixture at room temperature. The reaction mixture was stirred at room temperature for 1 hour, additionally at 80° C. for 16 hours, and then filtered at room temperature to give 4.7 g of the titled compound as a yellow solid.

$^1$H NMR (400 MHz, CDCl$_3$) 7.93 (d, 1H), 7.52 (t, 1H), 7.44 (s, 1H), 7.35 (m, 2H), 3.94 (s, 3H)

Step 3: 5-(4-bromo-2-fluoro-phenyl)-1-(2-chloro-phenyl)-4,5-dihydro-1H-pyrazole-3-carboxylic acid methyl ester 4-(4-Bromo-2-fluoro-phenyl)-2-oxo-3-butenoic acid methyl ester (2.0 g, 7.0 mmol) prepared in Step 2 and 2-chlorophenylhydrazine hydrochloride (1.4 g, 7.7 mmol) were added to acetic acid (25.0 mL). The reaction mixture was stirred at 80° C. for 2 hours, concentrated under reduced pressure, and then ethyl acetate was added thereto. The mixture was washed with a saturated solution of sodium hydrogen carbonate, dried on anhydrous magnesium sulfate, and then concentrated under reduced pressure to give 3.0 g of the titled compound as a black liquid.

$^1$H NMR (400 MHz, CDCl$_3$) 7.36 (d, 1H), 7.25 (d, 1H), 7.12-7.09 (m, 3H), 6.99 (t, 1H), 3.95 (s, 3H), 3.63 (dd, 1H), 3.22 (dd, 1H)

Step 4: 5-(4-bromo-2-fluoro-phenyl)-1-(2-chloro-phenyl)-4,5-dihydro-1H-pyrazole-3-carboxylic acid 5-(4-Bromo-2-fluoro-phenyl)-1-(2-chloro-phenyl)-4,5-dihydro-1H-pyrazole-3-carboxylic acid methyl ester (3.0 g, 7.0 mmol) prepared in Step 3 and a solution of potassium hydroxide (790.9 mg, 14.1 mmol) in distilled water (47.0 mL) were added to methanol (47.0 mL). The reaction mixture was stirred at 70° C. for 2 hours and then concentrated under reduced pressure to discard methanol. The resulting residue was washed with diethyl ether, acidified by a 1N hydrochloric acid solution, and then extracted with ethyl acetate. The extract was washed with distilled water and brine, dried on anhydrous magnesium sulfate, and then concentrated under reduced pressure to give 2.5 g of the titled compound as a white solid.

$^1$H NMR (400 MHz, CD$_3$OD) 7.37 (d, 1H), 7.26-7.14 (m, 5H), 7.03 (t, 1H), 3.68 (dd, 1H), 3.20 (dd, 1H)

Step 5: 5-(4-bromo-2-fluoro-phenyl)-1-(2-chloro-phenyl)-3-[di-(trifluoromethyl)-hydroxy-methyl]-4,5-dihydro-1H-pyrazole 5-(4-Bromo-2-fluoro-phenyl)-1-(2-chloro-phenyl)-4,5-dihydro-1H-pyrazole-3-carboxylic acid (2.5 g, 6.3 mmol) prepared in Step 4 was added to thionyl chloride (30.0 mL). The reaction mixture was stirred at 100° C. for 2 hours and then concentrated under reduced pressure. The resulting residue was concentrated under reduced pressure three times, along with toluene, to give 5-(4-bromo-2-fluoro-phenyl)-1-(2-chloro-phenyl)-4,5-dihydro-1H-pyrazole-3-carbonyl chloride as a dark brown liquid.

To a mixture of 5-(4-bromo-2-fluoro-phenyl)-1-(2-chloro-phenyl)-4,5-dihydro-1H-pyrazole-3-carbonyl chloride in the form of a dark brown liquid and TMAF (1.3 g, 13.7 mmol) in 1,2-dimethoxyethane (100.0 mL), was slowly added CF$_3$TMS (2.0 mL, 13.7 mmol) under nitrogen atmosphere at −78° C. The reaction mixture was stirred at −50° C. for 2 hours, quenched with a 1N hydrochloric acid solution, and then extracted with ethyl acetate. The extract was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/5) to give 2.5 g of the titled compound as a yellow liquid.

$^1$H NMR (400 MHz, CDCl$_3$) 7.37-7.28 (m, 2H), 7.25-7.12 (m, 4H), 7.02 (t, 1H), 6.06 (dd, 1H), 4.86 (s, 1H), 3.62 (dd, 1H), 3.13 (dd, 1H)

Preparation 20. 5-(6-bromo-pyridin-3-yl)-1-(2-chloro-phenyl)-3-[di-(trifluoromethyl)-hydroxy-methyl]-4,5-dihydro-1H-pyrazole Step 1: 4-(6-bromo-pyridin-3-yl)-2-oxo-3-butenoic acid methyl ester A solution of pyruvic acid (412.0 uL, 5.9 mmol) in ethanol (0.6 mL) was added to a 0.5 M sodium hydroxide solution (16.1 mL). The reaction mixture was stirred at room temperature for 10 minutes and then a solution of 6-bromo-3-pyridinecarbaldehyde (1.0 g, 5.4 mmol) in ethanol (5.4 mL) was slowly added thereto at room temperature for 1 hour. The reaction mixture was stirred at room temperature for 18 hours and then filtered. The resulting solid was washed with diethyl ether to give 1.3 g of 4-(6-bromo-pyridin-3-yl)-2-oxo-3-butenoic acid sodium salt as a pale yellow solid.

A mixture of the 4-(6-bromo-pyridin-3-yl)-2-oxo-3-butenoic acid sodium salt (900.0 mg, 3.2 mmol) in the form of a pale yellow solid, methyl iodide (400.0 mL, 6.47 mmol) in N,N-dimethylformamide (20.0 mL) was stirred at 75° C. for 3 hours. Distilled water was added to the reaction mixture, which was then extracted with ethyl acetate. The extract was washed with a saturated solution of sodium hydrogen carbonate and brine, dried on anhydrous magnesium sulfate, and then concentrated under reduced pressure to give 615.0 mg of the titled compound as a pale yellow solid.

$^1$H NMR (400 MHz, CDCl$_3$) 8.58 (s, 1H), 7.82 (d, 2H), 7.57 (d, 1H), 7.45 (d, 1H), 3.96 (s, 3H)

Step 2: 5-(6-bromo-pyridin-3-yl)-1-(2-chloro-phenyl)-4,5-dihydro-1H-pyrazole-3-carboxylic acid methyl ester 4-(6-bromo-pyridin-3-yl)-2-oxo-3-butenoic acid methyl ester (615.0 mg, 2.3 mmol) prepared in Step 1 and 2-chlorophenylhydrazine hydrochloride (450.0 mg, 2.5 mmol) were added to acetic acid (10.0 mL). The reaction mixture was stirred at 125° C. for 3 hours, concentrated under reduced pressure, and then ethyl acetate was added thereto. The reaction mixture was washed with a saturated solution of sodium hydrogen carbonate, dried on anhydrous magnesium sulfate, and then concentrated under reduced pressure to give a yellow liquid residue. The resulting residue was purified by silica gel column chromatography (eluent: ethyl acetate/n-hexane=1/2) to give 650.0 mg of the titled compound as a pale yellow liquid.

$^1$H NMR (400 MHz, CDCl$_3$) 8.21 (s, 1H), 7.46 (d, 1H), 7.32 (d, 1H), 7.25 (d, 1H), 7.19 (d, 1H), 7.13 (t, 1H), 7.02 (t, 1H), 5.92 (dd, 1H), 3.91 (s, 3H), 3.75 (dd, 1H), 3.26 (dd, 1H)

Step 3: 5-(6-bromo-pyridin-3-yl)-1-(2-chloro-phenyl)-4,5-dihydro-1H-pyrazole-3-carboxylic acid 5-(6-bromo-pyridin-3-yl)-1-(2-chloro-phenyl)-4,5-dihydro-1H-pyrazole-3-carboxylic acid methyl ester (650.0 mg, 1.7 mmol) prepared in Step 2 and a solution of potassium hydroxide (185.0 mg, 3.3 mmol) in distilled water (10.0 mL) were added to methanol (10.0 mL). The reaction mixture was stirred at 70° C. for 2 hours and then concentrated under reduced pressure to discard methanol. The resulting residue was washed with diethyl ether, acidified by a 1N hydrochloric acid solution, and then extracted with ethyl acetate. The extract was washed with distilled water and brine, dried on anhydrous magnesium sulfate, and then concentrated under reduced pressure to give 455.0 g of the titled compound as a pale yellow solid.

$^1$H NMR (400 MHz, CD$_3$OD) 8.22 (s, 1H), 7.48 (d, 1H), 7.29-7.20 (m, 3H), 7.15 (t, 1H), 7.06 (t, 1H), 6.00 (dd, 1H), 3.77 (dd, 1H), 3.27 (dd, 1H)

Step 4: 5-(6-bromo-pyridin-3-yl)-1-(2-chloro-phenyl)-3-[di-(trifluoromethyl)-hydroxy-methyl]-4,5-dihydro-1H-pyrazole 5-(6-Bromo-pyridin-3-yl)-1-(2-chloro-phenyl)-4,5-dihydro-1H-pyrazole-3-carboxylic acid (450.0 mg, 1.2 mmol) prepared in Step 3 was added to thionyl chloride (5.0 mL). The reaction mixture was stirred at 100° C. for 2 hours and then concentrated under reduced pressure. The resulting residue was concentrated under reduced pressure three times, along with using toluene, to give 5-(6-bromo-pyridin-3-yl)-1-(2-chloro-phenyl)-4,5-dihydro-1H-pyrazole-3-carbonyl chloride as a dark brown liquid.

To the mixture of the 5-(6-bromo-pyridin-3-yl)-1-(2-chloro-phenyl)-4,5-dihydro-1H-pyrazole-3-carbonyl chloride in the form of a dark brown liquid and TMAF (242.0 mg, 2.6 mmol) in 1,2-dimethoxyethane (10.0 mL), was slowly added CF$_3$TMS (385.0 uL, 2.6 mmol) under nitrogen atmosphere at −78° C. The reaction mixture was stirred at −50° C. for 1 hour, quenched with a 1N hydrochloric acid solution, and then extracted with ethyl acetate. The extract was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/2) to give 500.0 mg of the titled compound as a pale yellow liquid.

$^1$H NMR (400 MHz, CDCl$_3$) 8.21 (s, 1H), 7.43 (d, 1H), 7.27 (d, 1H), 7.21-7.11 (m, 3H), 7.02 (t, 1H), 5.90 (dd, 1H), 4.97 (s, 1H), 3.68 (dd, 1H), 3.17 (dd, 1H)

Preparation 21. 5-(4-bromo-3-fluoro-phenyl)-1-(2-chloro-phenyl)-3-[di-(trifluoromethyl)-hydroxy-methyl]-4,5-dihydro-1H-pyrazole

Step 1: 4-(4-bromo-3-fluoro-phenyl)-2-oxo-3-butenoic acid

A solution of pyruvic acid (1.9 mL, 27.1 mmol) in ethanol (6.0 mL) was added to a 0.5 M sodium hydroxide solution (74.0 mL). The reaction mixture was stirred at room temperature for 5 minutes and then a solution of 4-bromo-3-fluorobenzaldehyde (5.0 g, 24.6 mmol) in ethanol (20.0 mL) was slowly added thereto at room temperature for 1 hour. The reaction mixture was stirred at room temperature for 18 hours and then filtered. The resulting solid washed with ethyl acetate, diluted with a 1N hydrochloric acid solution and then extracted with ethyl acetate. The extract was washed with distilled water and brine, dried on anhydrous magnesium sulfate, and then concentrated under reduced pressure to give 3.2 g of the titled compound as a yellow solid.

$^1$H NMR (400 MHz, CDCl$_3$) 8.02 (d, 1H), 7.65 (t, 1H), 7.57 (d, 1H), 7.43 (d, 1H), 7.34 (d, 1H)

Step 2: 4-(4-bromo-3-fluoro-phenyl)-2-oxo-3-butenoic acid methyl ester

Acetyl chloride (2.9 mL, 41.0 mmol) was slowly added at 0° C. to methanol (15.0 mL) under stirring. A solution of 4-(4-bromo-3-fluoro-phenyl)-2-oxo-3-butenoic acid (3.2 g, 11.7 mmol) prepared in Step 1 in methanol (5.0 mL) was added to the reaction mixture at room temperature. The reaction mixture was stirred at room temperature for 1 hour, additionally at 80° C. for 16 hours, and then filtered at room temperature to give 1.1 g of the titled compound as a pale yellow solid.

$^1$H NMR (400 MHz, CDCl$_3$) 7.77 (d, 1H), 7.62 (t, 1H), 7.39 (s, 1H), 7.36 (d, 1H), 7.29 (d, 1H), 3.95 (s, 3H)

Step 3: 5-(4-bromo-3-fluoro-phenyl)-1-(2-chloro-phenyl)-4,5-dihydro-1H-pyrazole-3-carboxylic acid methyl ester 4-(4-bromo-3-fluoro-phenyl)-2-oxo-3-butenoic acid methyl ester (665.0 mg, 2.3 mmol) prepared in Step 2 and 2-chlorophenylhydrazine hydrochloride (455.0 mg, 2.6 mmol) were added to acetic acid (10.0 mL). The reaction mixture was stirred at 125° C. for 3 hours, concentrated under reduced pressure, and then ethyl acetate was added thereto. The reaction mixture was washed with a saturated solution of sodium hydrogen carbonate, dried on anhydrous magnesium sulfate, and then concentrated under reduced pressure to give a yellow liquid residue. The resulting residue was purified by silica gel column chromatography (eluent: ethyl acetate/n-hexane=1/2) to give 835.0 mg of the titled compound as a pale yellow liquid.

$^1$H NMR (400 MHz, CDCl$_3$) 7.38 (t, 1H), 7.32 (d, 1H), 7.24 (d, 1H), 7.12 (t, 1H), 7.00 (t, 1H), 6.94 (d, 1H), 6.84 (d, 1H), 5.86 (dd, 1H), 3.90 (s, 3H), 3.71 (dd, 1H), 3.25 (dd, 1H)

Step 4: 5-(4-bromo-3-fluoro-phenyl)-1-(2-chloro-phenyl)-4,5-dihydro-1H-pyrazole-3-carboxylic acid 5-(4-Bromo-3-fluoro-phenyl)-1-(2-chloro-phenyl)-4,5-dihydro-1H-pyrazole-3-carboxylic acid methyl ester (830.0 mg, 2.0 mmol) prepared in Step 3 and a solution of potassium hydroxide (226.0 mg, 4.0 mmol) in distilled water (10.0 mL) were added to methanol (10.0 mL). The reaction mixture was stirred at 70° C. for 4 hours and then concentrated under reduced pressure to discard methanol. The resulting residue was washed with diethyl ether, acidified by a 1N hydrochloric acid solution, and then extracted with ethyl acetate. The extract was washed with distilled water and brine, dried on anhydrous magnesium sulfate, and then concentrated under reduced pressure to give 820.0 mg of the titled compound as a pale yellow solid.

$^1$H NMR (400 MHz, CDCl$_3$) 7.41 (t, 1H), 7.29-7.26 (m, 2H), 7.15 (t, 1H), 7.05 (t, 1H), 6.95 (d, 1H), 6.86 (d, 1H), 5.94 (dd, 1H), 3.74 (dd, 1H), 3.28 (dd, 1H)

Step 5: 5-(4-bromo-3-fluoro-phenyl)-1-(2-chloro-phenyl)-3-[di-(trifluoromethyl)-hydroxy-methyl]-4,5-dihydro-1H-pyrazole 5-(4-Bromo-3-fluoro-phenyl)-1-(2-chloro-phenyl)-4,5-dihydro-1H-pyrazole-3-carboxylic acid (820.0 mg, 2.1 mmol) prepared in Step 4 was added to thionyl chloride (7.0 mL). The reaction mixture was stirred at 100° C. for 2 hours and then concentrated under reduced pressure. The resulting residue was concentrated under reduced pressure three times, along with using toluene, to give 5-(4-bromo-3-fluoro-phenyl)-1-(2-chloro-phenyl)-4,5-dihydro-1H-pyrazole-3-carbonyl chloride as a dark brown liquid.

To a mixture of the 5-(4-bromo-3-fluoro-phenyl)-1-(2-chloro-phenyl)-4,5-dihydro-1H-pyrazole-3-carbonyl chloride in the form of a dark brown liquid and TMAF (420.0 mg, 4.5 mmol) in 1,2-dimethoxyethane (10.0 mL), was slowly added CF$_3$TMS (670.0 uL, 4.5 mmol) under nitrogen atmosphere at −78° C. The reaction mixture was stirred at −40° C. for 2 hours, quenched with a 1N hydrochloric acid solution, and then extracted with ethyl acetate. The extract was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/5) to give 940.0 mg of the titled compound as a yellow liquid.

$^1$H NMR (400 MHz, CDCl$_3$) 7.40 (t, 1H), 7.28 (d, 1H), 7.19-7.10 (m, 2H), 7.04-7.00 (m, 1H), 6.93 (d, 1H), 6.83 (d, 1H), 5.83 (dd, 1H), 4.84 (s, 1H), 3.65 (dd, 1H), 3.16 (dd, 1H)

Preparation 22. 5-(4-bromo-phenyl)-1-(2,4-difluoro-phenyl)-3-[di-(trifluoromethyl)-hydroxy-methyl]-4,5-dihydro-1H-pyrazole Step 1: 5-(4-bromo-phenyl)-1-(2,4-difluoro-phenyl)-4,5-dihydro-1H-pyrazole-3-carboxylic acid 4-(4-Bromo-phenyl)-2-oxo-3-butenoic acid methyl ester (50.0 g, 185.8 mmol) prepared in Step 2 of Preparation 17 and 2,4-difluorophenylhydrazine hydrochloride (36.9 g, 204.4 mmol) were added to acetic acid (600.0 mL). The reaction mixture was stirred at 125° C. for 3 hours, concentrated under reduced pressure, and then ethyl acetate was added thereto. The reaction mixture was washed with a saturated solution of sodium hydrogen carbonate, dried on anhydrous magnesium sulfate, and then concentrated under reduced pressure to give 73.4 g of 5-(4-bromo-phenyl)-1-(2,4-difluoro-phenyl)-4,5-dihydro-1H-pyrazole-3-carboxylic acid methyl ester as a yellow liquid.

The 5-(4-bromo-phenyl)-1-(2,4-difluoro-phenyl)-4,5-dihydro-1H-pyrazole-3-carboxylic acid methyl ester in the form of a yellow liquid (73.4 g, 185.8 mmol) and a solution of potassium hydroxide (20.9 g, 371.6 mmol) in distilled water (400.0 mL) were added to methanol (400.0 mL). The reaction mixture was stirred at 70° C. for 4 hours and then concentrated under reduced pressure to discard methanol. The resulting residue was washed with diethyl ether, acidified by a 1N hydrochloric acid solution, and then extracted with ethyl acetate. The extract was washed with distilled water and brine, dried on anhydrous magnesium sulfate, and then concentrated under reduced pressure to give 70.0 g of the titled compound as a yellow solid.

$^1$H NMR (400 MHz, CDCl$_3$) 7.46-7.38 (m, 3H), 7.03 (d, 2H), 6.79-6.66 (m, 2H), 5.65 (dd, 1H), 3.69 (dd, 1H), 3.19 (dd, 1H)

Step 2: 5-(4-bromo-phenyl)-1-(2,4-difluoro-phenyl)-3-[di-(trifluoromethyl)-hydroxy-methyl]-4,5-dihydro-1H-pyrazole 5-(4-bromo-phenyl)-1-(2,4-difluoro-phenyl)-4,5-dihydro-1H-pyrazole-3-carboxylic acid (10.0 g, 26.2 mmol) prepared in Step 1 was added to thionyl chloride (100.0 mL). The reaction was stirred at 100° C. for 2 hours and then concentrated under reduced pressure. The resulting residue was concentrated under reduced pressure three times, along with using toluene, to give 5-(4-bromo-phenyl)-1-(2,4-difluoro-phenyl)-4,5-dihydro-1H-pyrazole-3-carbonyl chloride as a dark brown liquid.

The 5-(4-bromo-phenyl)-1-(2,4-difluoro-phenyl)-4,5-dihydro-1H-pyrazole-3-carbonyl chloride in the form of a dark brown liquid and TMAF (5.4 g, 57.7 mmol) were diluted with 1,2-dimethoxyethane (80.0 mL). CF$_3$TMS (8.5 mL, 57.7 mmol) was slowly added to the reaction mixture under nitrogen atmosphere at −78° C. The reaction mixture was stirred at −50° C. for 2 hours, quenched with a 1N hydrochloric acid solution, and then extracted with ethyl acetate. The extract was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/10) to give 7.0 g of the titled compound as a yellow liquid.

$^1$H NMR (400 MHz, CDCl$_3$) 7.42 (d, 2H), 7.22 (q, 1H), 7.01 (d, 2H), 6.77-6.68 (m, 2H), 5.52 (dd, 1H), 4.81 (s, 1H), 3.61 (dd, 1H), 3.10 (dd, 1H)

Preparation 23. 5-(5-bromo-thiophen-2-yl)-1-(2-chloro-phenyl)-3-[di-(trifluoromethyl)-hydroxy-methyl]-4,5-dihydro-1H-pyrazole Step 1: 4-(5-bromo-thiophen-2-yl)-2-oxo-3-butenoic acid A solution of pyruvic acid (10.0 mL, 143.9 mmol) in ethanol (13.0 mL) was added to a 0.5 M sodium hydroxide solution (393.0 mL). The reaction mixture was stirred at room temperature for 5 minutes and then a solution of 5-bromo-thiophen-2-carbaldehyde (25.0 g, 130.9 mmol) in ethanol (112.0 mL) was slowly added thereto at room temperature for 1 hour. The reaction mixture was stirred at room temperature for 18 hours and then filtered. The resulting solid was washed with ethyl acetate, diluted with a 3N hydrochloric acid solution and then extracted with ethyl acetate. The extract was washed with distilled water and brine, dried on anhydrous magnesium sulfate, and then concentrated under reduced pressure to give 25.0 g of the titled compound as a yellow solid.

$^1$H NMR (400 MHz, CD$_3$OD) 7.89 (d, 1H), 7.33 (s, 1H), 7.19 (s, 1H), 7.05 (d, 1H)

Step 2: 4-(5-bromo-thiophen-2-yl)-2-oxo-3-butenoic acid methyl ester

Acetyl chloride (23.0 mL, 325.6 mmol) was slowly added at 0° C. to methanol (100.0 mL) under stirring. A solution of 4-(5-bromo-thiophen-2-yl)-2-oxo-3-butenoic acid (25.0 g, 95.8 mmol) prepared in Step 1 in methanol (25.0 mL) was added at 0° C. to the reaction mixture. The reaction mixture was stirred at room temperature for 1 hour, additionally at 80° C. for 3 hours, and then filtered at room temperature to give 23.6 g of the titled compound as a yellow solid.

$^1$H NMR (400 MHz, CDCl$_3$) 7.86 (d, 1H), 7.26 (s, 1H), 7.17 (s, 1H), 7.06 (d, 1H), 3.93 (s, 3H)

Step 3: 5-(5-bromo-thiophen-2-yl)-1-(2-chloro-phenyl)-4,5-dihydro-1H-pyrazole-3-carboxylic acid methyl ester 4-(5-Bromo-thiophen-2-yl)-2-oxo-3-butenoic acid methyl ester (19.9 mg, 72.2 mmol) prepared in Step 2 and 2-chlorophenylhydrazine hydrochloride (14.2 g, 79.4 mmol) were added to acetic acid (250.0 mL). The reaction mixture was stirred at 125° C. for 3 hours, concentrated under reduced pressure, and then ethyl acetate was added thereto. The reaction mixture was washed with a saturated solution of sodium hydrogen carbonate, dried on anhydrous magnesium sulfate, and then concentrated under reduced pressure to give a yellow liquid residue. The resulting residue was purified by silica gel column chromatography (eluent: ethyl acetate/n-hexane=1/6) to give 18.9 g of the titled compound as a pale yellow liquid.

$^1$H NMR (400 MHz, CDCl$_3$) 7.40-7.22 (m, 2H), 7.20-7.00 (m, 2H), 6.72 (s, 1H), 6.57 (s, 1H), 6.10 (dd, 1H), 3.91 (s, 3H), 3.65 (dd, 1H), 3.44 (dd, 1H)

Step 4: 5-(5-bromo-thiophen-2-yl)-1-(2-chloro-phenyl)-4,5-dihydro-1H-pyrazole-3-carboxylic acid 5-(5-Bromo-thiophen-2-yl)-1-(2-chloro-phenyl)-4,5-dihydro-1H-pyrazole-3-carboxylic acid methyl ester (18.9 g, 47.3 mmol) prepared in Step 3 and a solution of potassium hydroxide (5.3 g, 94.6 mmol) in distilled water (200.0 mL) were added to methanol (200.0 mL). The reaction mixture was stirred at 80° C. for 12 hours and then concentrated under reduced pressure to discard methanol. The resulting residue was washed with diethyl ether, acidified by a 1N hydrochloric acid solution, and then extracted with ethyl acetate. The extract was washed with distilled water and brine, dried on anhydrous magnesium sulfate, and then concentrated under reduced pressure to give 18.1 g of the titled compound as a pale yellow solid.

$^1$H NMR (400 MHz, CDCl$_3$) 7.38-7.22 (m, 2H), 7.20-7.00 (m, 2H), 6.72 (s, 1H), 6.60 (s, 1H), 6.16 (dd, 1H), 3.68 (dd, 1H), 3.42 (dd, 1H)

Step 5: 5-(5-bromo-thiophen-2-yl)-1-(2-chloro-phenyl)-3-[di-(trifluoromethyl)-hydroxy-methyl]-4,5-dihydro-1H-pyrazole 5-(5-Bromo-thiophen-2-yl)-1-(2-chloro-phenyl)-4,5-dihydro-1H-pyrazole-3-carboxylic acid (18.1 g, 46.9 mmol) prepared in Step 4 was added to thionyl chloride (200.0 mL). The reaction mixture was stitted at 100° C. for 2 hours and then concentrated under reduced pressure. The resulting residue was concentrated under reduced pressure three times, along with using toluene, to give 5-(5-bromo-thiophen-2-yl)-1-(2-chloro-phenyl)-4,5-dihydro-1H-pyrazole-3-carbonyl chloride as a dark brown liquid.

The 5-(5-bromo-thiophen-2-yl)-1-(2-chloro-phenyl)-4,5-dihydro-1H-pyrazole-3-carbonyl chloride in the form of a dark brown liquid and TMAF (9.6 g, 103.1 mmol) were diluted with 1,2-dimethoxyethane (200.0 mL). CF$_3$TMS (15.3 mL, 103.1 mmol) was slowly added to the reaction mixture under nitrogen atmosphere at −78° C. The reaction mixture was stirred at −50° C. for 3 hours, quenched with a 1N hydrochloric acid solution, and then extracted with ethyl acetate. The extract was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/8) to give 19.0 g of the titled compound as a brown liquid.

$^1$H NMR (400 MHz, CDCl$_3$) 7.30 (dd, 1H), 7.22-7.00 (m, 3H), 6.70 (s, 1H), 6.57 (s, 1H), 6.13 (dd, 1H), 4.84 (s, 1H), 3.60 (dd, 1H), 3.30 (dd, 1H)

Preparation 24. 1-(4-bromo-phenyl)-5-(2-chloro-phenyl)-3-[di-(trifluoromethyl)-hydroxy-methyl]-4,5-dihydro-1H-pyrazole Step 1: 4-(2-chloro-phenyl)-2-oxo-3-butenoic acid A solution of pyruvic acid (13.6 mL, 195.3 mmol) in ethanol (20.0 mL) was added to a 0.5 M sodium hydroxide solution (533.0 mL). The reaction mixture was stirred at room temperature for 5 minutes and then a solution of 2-chlorobenzaldehyde (20.0 mL, 177.6 mmol) in ethanol (155.0 mL) was slowly added thereto at room temperature for 1 hour. The reaction mixture was stirred at room temperature for 18 hours and then filtered. The resulting solid was washed with ethyl acetate, diluted with a 6N hydrochloric acid solution and then extracted with ethyl acetate. The extract was washed with distilled water and brine, dried on anhydrous magnesium sulfate, and then concentrated under reduced pressure to give 34.5 g of the titled compound as a yellow liquid.

$^1$H NMR (400 MHz, CDCl$_3$) 8.53 (d, 1H), 7.81 (d, 1H), 7.59 (d, 1H), 7.47 (d, 1H), 7.42 (dd, 1H), 7.35 (dd, 1H)

Step 2: 4-(2-chloro-phenyl)-2-oxo-3-butenoic acid methyl ester

Acetyl chloride (19.4 mL, 274.4 mmol) was slowly added at 0° C. to methanol (120.0 mL) under stirring. A solution of 4-(2-chloro-phenyl)-2-oxo-3-butenoic acid (17.0 g, 80.7 mmol) prepared in Step 1 in methanol (80.0 mL) was added to the reaction mixture at room temperature. The reaction mixture was stirred at room temperature for 1 hour, additionally at 80° C. for 16 hours. The reaction mixture was concentrated under reduced pressure and then ethyl acetate was added thereto. The reaction mixture was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/8) to give 7.2 g of the titled compound as a yellow solid.

$^1$H NMR (400 MHz, CDCl$_3$) 8.32 (d, 1H), 7.76 (d, 1H), 7.46 (d, 1H), 7.40-7.30 (m, 3H), 3.95 (s, 3H)

Step 3: 1-(4-bromo-phenyl)-5-(2-chloro-phenyl)-4,5-dihydro-1H-pyrazole-3-carboxylic acid methyl ester 4-(2-Chloro-phenyl)-2-oxo-3-butenoic acid methyl ester (4.9 g, 21.9 mmol) prepared in Step 2 and 4-bromophenylhydrazine hydrochloride (5.0 g, 22.4 mmol) was added to acetic acid (50.0 mL). The reaction mixture was stirred at 125° C. for 3 hours, concentrated under reduced pressure, and then ethyl acetate was added thereto. The reaction mixture was washed with a saturated solution of sodium hydrogen carbonate, dried on anhydrous magnesium sulfate, and then concentrated under reduced pressure to give a yellow liquid residue. The resulting yellow liquid residue was crystallized from diethyl ether to give 5.3 g of the titled compound as a white solid.

$^1$H NMR (400 MHz, CDCl$_3$) 7.44 (d, 1H), 7.31 (d, 2H), 7.23 (dd, 1H), 7.16 (dd, 1H), 7.01 (d, 1H), 6.91 (d, 2H), 5.76 (dd, 1H), 3.87 (s, 3H), 3.82 (dd, 1H), 2.99 (dd, 1H)

Step 4: 1-(4-bromo-phenyl)-5-(2-chloro-phenyl)-4,5-dihydro-1H-pyrazole-3-carboxylic acid 1-(4-Bromo-phenyl)-5-(2-chloro-phenyl)-4,5-dihydro-1H-pyrazole-3-carboxylic acid methyl ester (5.3 g, 13.5 mmol) prepared in Step 3 and a solution of potassium hydroxide (2.0 g, 35.6 mmol) in distilled water (25.0 mL) were added to methanol (25.0 mL). The reaction mixture was stirred at 100° C. for 12 hours and then concentrated under reduced pressure to discard methanol. The resulting residue was washed with diethyl ether, acidified by a 1N hydrochloric acid solution, and then extracted with ethyl acetate. The extract was washed with distilled water and brine, dried on anhydrous magnesium sulfate, and then concentrated under reduced pressure to give 5.4 g of the titled compound as a white solid.

$^1$H NMR (400 MHz, CDCl$_3$) 7.20-6.98 (m, 3H), 6.97-6.60 (m, 5H), 5.40-5.20 (m, 1H), 3.70-3.45 (m, 1H), 2.80-2.55 (m, 1H)

Step 5: 1-(4-bromo-phenyl)-5-(2-chloro-phenyl)-3-[di-(trifluoromethyl)-hydroxy-methyl]-4,5-dihydro-1H-pyrazole 1-(4-Bromo-phenyl)-5-(2-chloro-phenyl)-4,5-dihydro-1H-pyrazole-3-carboxylic acid (5.4 g, 14.3 mmol) prepared in Step 4 was added to thionyl chloride (50.0 mL). The reaction mixture was stirred at 100° C. for 2 hours and then concentrated under reduced pressure. The resulting residue was concentrated under reduced pressure three times, along with using toluene, to give 1-(4-bromo-phenyl)-5-(2-chloro-phenyl)-4,5-dihydro-1H-pyrazole-3-carbonyl chloride as a dark brown liquid.

The 1-(4-bromo-phenyl)-5-(2-chloro-phenyl)-4,5-dihydro-1H-pyrazole-3-carbonyl chloride in the form of a dark brown liquid and TMAF (2.9 g, 31.4 mmol) were diluted with 1,2-dimethoxyethane (70.0 mL). CF$_3$TMS (4.7 mL, 31.4 mmol) was slowly added to the reaction mixture under nitrogen atmosphere at −78° C. The reaction mixture was stirred at −50° C. for 2 hours, quenched with a 1N hydrochloric acid solution, and then extracted with ethyl acetate. The extract was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/10) to give 5.5 g of the titled compound as a yellow solid.

$^1$H NMR (400 MHz, CDCl$_3$) 7.45 (d, 1H), 7.32-7.18 (m, 4H), 7.07 (d, 1H), 6.77 (d, 2H), 5.81 (dd, 1H), 4.76 (s, 1H), 3.77 (dd, 1H), 2.91 (dd, 1H)

Preparation 25. 1-(3-bromo-phenyl)-5-(2-chloro-phenyl)-3-[di-(trifluoromethyl)-hydroxy-methyl]-4,5-dihydro-1H-pyrazole Step 1: 1-(3-bromo-phenyl)-5-(2-chloro-phenyl)-4,5-dihydro-1H-pyrazole-3-carboxylic acid methyl ester 4-(2-Chloro-phenyl)-2-oxo-3-butenoic acid methyl ester (1.4 g, 6.0 mmol) prepared in Step 2 of Preparation 24 and 3-bromophenylhydrazine hydrochloride (1.4 g, 6.1 mmol) were added to acetic acid (20.0 mL). The reaction mixture was stirred at 125° C. for 3 hours, concentrated under reduced pressure, and then ethyl acetate was added thereto. The reaction mixture was washed with a saturated solution of sodium hydrogen carbonate, dried on anhydrous magnesium sulfate, and then concentrated under reduced pressure to give a yellow liquid residue. The resulting yellow liquid residue was crystallized from methanol to give 1.2 g of the titled compound as a pale yellow solid.

$^1$H NMR (400 MHz, CDCl$_3$) 7.46-7.40 (m, 2H), 7.26-7.15 (m, 2H), 7.05-7.01 (m, 3H), 6.77-63.73 (m, 1H), 5.76 (dd, 1H), 3.88 (s, 3H), 3.82 (dd, 1H), 2.99 (dd, 1H)

Step 2: 1-(3-bromo-phenyl)-5-(2-chloro-phenyl)-3-[di-(trifluoromethyl)-hydroxy-methyl]-4,5-dihydro-1H-pyrazole 1-(3-Bromo-phenyl)-5-(2-chloro-phenyl)-4,5-dihydro-1H-pyrazole-3-carboxylic acid methyl ester (1.2 g, 3.1 mmol) prepared in Step 1, TBAA (94.0 mg, 0.3 mmol), and CF$_3$TMS (1.4 mL, 9.4 mmol) were added at 0° C. to dichloromethane (10.0 mL). The reaction mixture was stirred at 0° C. for 20 minutes. Since the reaction was not completed, CF$_3$TMS (1.4 mL, 9.4 mmol) was added at room temperature to the reaction mixture, which was then stirred at room temperature for 10 minutes. The reaction mixture was quenched with a 6N hydrochloric acid solution. TBAA (471.0 mg, 1.6 mmol) was added to the separated organic layer, which was then stirred at room temperature for 10 minutes. The reaction mixture was quenched with a 1N hydrochloric acid solution, washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/10) to give 1.3 g of the titled compound as a pale yellow liquid.

$^1$H NMR (400 MHz, CDCl$_3$) 7.46 (d, 1H), 7.30-7.20 (m, 3H), 7.09-7.00 (m, 3H), 6.62 (d, 1H), 5.82 (dd, 1H), 4.78 (s, 1H), 3.78 (dd, 1H), 2.92 (dd, 1H)

Example 1

1-(2-chloro-phenyl)-5-(4'-(methylsulfanyl)-biphenyl-4-yl)-3-pentafluoroethyl-4,5-dihydro-1H-pyrazole A solution of 5-(4-bromo-phenyl)-1-(2-chloro-phenyl)-3-pentafluoroethyl-4,5-dihydro-1H-pyrazole (100.0 mg, 0.19 mmol) prepared in Step 3 of Preparation 1, 4-(methylthio) phenylboronic acid (80.0 mg, 0.28 mmol), Pd(PPh$_3$)$_4$ (26 mg, cat.), and a 2N sodium carbonate solution 0.6 mL in N,N-dimethylformamide (5 mL) were stirred at 80° C. for 6 hours. The reaction mixture was concentrated under reduced pressure and then extracted with ethyl acetate. The extract was washed with distilled water, dried on anhydrous magnesium sulfate, and then concentrated under reduced pressure to give a yellow liquid residue. The resulting residue was purified by silica gel column chromatography (eluent: ethyl acetate/n-hexane=1/20) to give 55.5 mg of the titled compound as a pale yellow liquid.

$^1$H NMR (400 MHz, CDCl$_3$) 7.43-7.40 (m, 3H), 7.28-7.18 (m, 5H), 7.10 (t, 1H), 6.94 (t, 1H), 5.93 (dd, 1H), 3.70 (dd, 1H), 3.27 (dd, 1H), 2.49 (s, 3H)

Examples 2 and 3

The compounds of Examples 2 and 3 were prepared in accordance with the same procedures as in Example 1, except for using 5-(4-bromo-phenyl)-1-(2-chloro-phenyl)-3-pentafluoroethyl-4,5-dihydro-1H-pyrazole prepared in Step 3 of Preparation 1; and using each boronic acid corresponding to the compounds of Examples 2 and 3 instead of 4-(methylthio) phenylboronic acid.

Example 2

1-(2-chloro-phenyl)-3-pentafluoroethyl-5-[4'-(trifluoromethyl)-biphenyl-4-yl]-4,5-dihydro-1H-pyrazole $^1$H NMR (400 MHz, CDCl$_3$) 7.72 (d, 2H), 7.58 (d, 2H), 7.45 (d, 2H), 7.26-6.23 (m, 4H), 7.07 (t, 1H), 6.95 (t, 1H), 5.95 (dd, 1H), 3.71 (dd, 1H), 3.27 (dd, 1H)

Example 3

1-(2-chloro-phenyl)-5-[4'-(N,N-dimethylamino)-biphenyl-4-yl]-3-pentafluoroethyl-4,5-dihydro-1H-pyrazole $^1$H NMR (400 MHz, CDCl$_3$) 7.41 (m, 3H), 7.37 (m, 1H), 7.21 (d, 2H), 7.15 (t, 1H), 6.91 (t, 1H), 6.74 (d, 1H), 5.90 (dd, 1H), 3.68 (dd, 1H), 3.28 (dd, 1H), 2.97 (s, 6H)

Example 4

1-(2-chloro-phenyl)-5-[2'-(methylsulfonyl)-biphenyl-4-yl]-3-pentafluoroethyl-4,5-dihydro-1H-pyrazole A solution of 5-(4-bromo-phenyl)-1-(2-chloro-phenyl)-3-pentafluoroethyl-4,5-dihydro-1H-pyrazole (100.0 mg, 0.19 mmol) prepared in Step 3 of Preparation 1, 2-(methylthio) phenylboronic acid (80.0 mg, 0.28 mmol), Pd(PPh$_3$)$_4$ (26 mg, cat.), and a 2N sodium carbonate solution (0.6 mL) in N,N-dimethylformamide (5 mL) was stirred at 80° C. for 6 hours. The reaction mixture was concentrated under reduced pressure and then diluted with ethyl acetate. The organic layer was washed with distilled water, dried on anhydrous magnesium sulfate, and then concentrated under reduced pressure to give a yellow liquid residue. The resulting residue was purified by silica gel column chromatography (eluent: ethyl acetate/n-hexane=1/20) to give 54.0 mg of 1-(2-chloro-phenyl)-5-(2'-methylsulfanyl-biphenyl-4-yl)-3-pentafluoroethyl-4,5-dihydro-1H-pyrazole as a pale yellow liquid.

To a solution of the 1-(2-chloro-phenyl)-5-[2'-(methylsulfanyl)-biphenyl-4-yl]-3-pentafluoroethyl-4,5-dihydro-1H-pyrazole (54.0 mg, 0.11 mmol) in dichloromethane (5 mL), was added 77% meta-chloroperbenzoic acid (35.0 mg, 0.16 mmol). After completing the reaction, the reaction mixture was washed with a saturated solution of sodium hydrogen carbonate and then concentrated under reduced pressure. Distilled water was added to the reaction mixture, which was then extracted with ethyl acetate. The extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/4) to give 16.3 mg of the titled compound as a white solid.

$^1$H NMR (400 MHz, CDCl$_3$) 8.25 (d, 1H), 8.18 (s, 1H), 8.01 (d, 1H), 7.62 (d, 1H), 7.58 (t, 1H), 7.50 (t, 1H), 7.36 (d, 2H), 7.32-7.21 (m, 2H), 7.05 (t, 1H), 6.95 (t, 1H), 5.94 (dd, 1H), 3.75 (dd, 1H), 3.38 (dd, 1H), 2.21 (s, 3H)

Examples 5 to 8

The compounds of Examples 5 to 8 were prepared in accordance with the same procedures as in Example 4, except for using 5-(4-bromo-phenyl)-1-(2-chloro-phenyl)-3-pentafluoroethyl-4,5-dihydro-1H-pyrazole prepared in Step 3 of Preparation 1; and using each boronic acid corresponding to the compounds of Examples 5 to 8 instead of 2-(methylthio) phenylboronic acid.

Example 5

1-(2-chloro-phenyl)-5-[3'-(methylsulfonyl)-biphenyl-4-yl]-3-pentafluoroethyl-4,5-dihydro-1H-pyrazole $^1$H NMR (400 MHz, CDCl$_3$) 8.07 (s, 1H), 7.89 (d, 1H), 7.77 (d, 1H), 7.60 (t, 1H), 7.47 (d, 2H), 7.28-7.21 (m, 4H), 7.08 (t, 1H), 6.95 (t, 1H), 5.97 (dd, 1H), 3.74 (dd, 1H), 3.24 (dd, 1H), 3.06 (s, 3H)

Example 6

1-(2-chloro-phenyl)-5-[4'-(methylsulfonyl)-biphenyl-4-yl]-3-pentafluoroethyl-4,5-dihydro-1H-pyrazole $^1$H NMR (400 MHz, CDCl$_3$) 7.98 (d, 2H), 7.65 (d, 2H), 7.47 (d, 2H), 7.29-7.18 (m, 4H), 7.08 (t, 1H), 6.95 (t, 1H), 5.95 (dd, 1H), 3.74 (dd, 1H), 3.28 (dd, 1H), 3.06 (s, 3H)

Example 7

1-(2-chloro-phenyl)-5-[3'-(methylsulfinyl)-biphenyl-4-yl]-3-pentafluoroethyl-4,5-dihydro-1H-pyrazole $^1$H NMR (400 MHz, CDCl$_3$) 7.80 (s, 1H), 7.71 (m, 1H), 7.62 (d, 2H), 7.48 (d, 2H), 7.27-7.22 (m, 4H), 7.09 (t, 1H), 6.95 (t, 1H), 5.95 (dd, 1H), 3.75 (dd, 1H), 3.29 (dd, 1H), 2.73 (s, 3H)

Example 8

1-(2-chloro-phenyl)-5-[4'-(methylsulfinyl)-biphenyl-4-yl]-3-pentafluoroethyl-4,5-dihydro-1H-pyrazole $^1$H NMR (400 MHz, CDCl$_3$) 7.38 (q, 4H), 7.45 (d, 2H), 7.28-7.22 (m, 4H), 7.09 (t, 1H), 6.95 (t, 1H), 5.95 (dd, 1H), 3.75 (dd, 1H), 3.27 (dd, 1H), 2.74 (s, 3H)

Example 9

1-(2-chloro-phenyl)-5-[4-(1-BOC-1,2,3,6-tetrahydro-pyridin-4-yl)-phenyl]-3-pentafluoroethyl-4,5-dihydro-1H-pyrazole 5-(4-Bromo-phenyl)-1-(2-chloro-phenyl)-3-pentafluoroethyl-4,5-dihydro-1H-pyrazole prepared in Step 3 of Preparation 1 (760.0 mg, 1.68 mmol), 4-(4,4,5,5-tetramethyl-[1,3,2]dioxaborolan-2-yl)-3,6-dihydro-2H-pyridin-1-carboxylic acid tert-butyl ester (622.0 mg, 2.01 mmol), potassium carbonate (695.0 mg, 5.03 mmol), and Pd(dppf)Cl$_2$ (137.0 mg, 0.17 mmol) were added to a mixed solvent of 1,4-dioxane (24.0 mL) and distilled water (6.0 mL). The reaction mixture was stirred for 15 minutes, additionally at 90° C. for 16 hours, and cooled to room temperature. Distilled water was added to the reaction mixture, which was then extracted with ethyl acetate. The extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/9) to give 630.0 mg of the titled compound as a white solid.

$^1$H NMR (400 MHz, CDCl$_3$) 7.24-7.20 (m, 4H), 7.10-7.05 (m, 3H), 6.95-6.91 (t, 1H), 5.97 (br, 1H), 5.88 (dd, 1H), 4.02 (s, 2H), 3.68 (dd, 1H), 3.57 (t, 2H), 3.21 (dd, 1H), 2.41 (s, 2H), 1.47 (s, 9H)

Example 10

1-(2-chloro-phenyl)-5-[4-(1,2,3,6-tetrahydropyridin-4-yl)-phenyl]-3-pentafluoroethyl-4,5-dihydro-1H-pyrazole trifluoroacetate To a solution of 1-(2-chloro-phenyl)-5-[4-(1-BOC-1,2,3,6-tetrahydropyridin-4-yl)-phenyl]-3-pentafluoroethyl-4,5-dihydro-1H-pyrazole (630 mg, 1.13 mmol) prepared in Example 9 in dichloromethane (6 mL), was slowly added trifluoroacetic acid (867.0 uL, 11.33 mmol) at 0° C. The reaction mixture was stirred at room temperature for 1 hour and then concentrated under reduced pressure to give 680.0 mg of the titled compound as a yellow liquid.

$^1$H NMR (400 MHz, CD$_3$OD) 7.34 (d, 2H), 7.27-7.20 (m, 4H), 7.11 (t, 1H), 6.98 (t, 1H), 6.09 (s, 1H), 5.97 (dd, 1H), 3.79 (br, 2H), 3.76 (dd, 1H), 3.40 (t, 2H), 3.20 (dd, 1H), 2.70 (br, 2H)

Example 11

1-(2-chloro-phenyl)-5-[4-(1-methanesulfonyl-1,2,3,6-tetrahydropyridin-4-yl)-phenyl]-3-pentafluoroethyl-4,5-dihydro-1H-pyrazole To a solution of 1-(2-chloro-phenyl)-5-[4-(1,2,3,6-tetrahydropyridin-4-yl)-phenyl]-3-pentafluoroethyl-4,5-dihydro-1H-pyrazole trifluoroacetate (80.0 mg, 0.14 mmol) prepared in Example 10 in dichloromethane (1.0 mL), was added triethylamine (59.0 uL, 0.43 mmol). Methanesulfonyl chloride (16.5 uL, 0.22 mmol) was dropwisely added at 0° C. to the reaction mixture, which was then stirred at room temperature for 2 hours. Distilled water was added to the reaction mixture, which was then extracted with ethyl acetate. The extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/2) to give 50.8 mg of the titled compound as a pale yellow liquid.

$^1$H NMR (400 MHz, CDCl$_3$) 7.25-7.20 (m, 4H), 7.12-7.06 (m, 3H), 7.06-6.92 (t, 1H), 6.00 (s, 1H), 5.91 (dd, 1H), 3.92 (s, 2H), 3.66 (dd, 1H), 3.46 (t, 2H), 3.20 (dd, 1H), 2.83 (s, 3H), 2.56 (s, 2H)

Example 12

1-(2-chloro-phenyl)-5-(3'-methylsulfanyl-biphenyl-4-yl)-3-pentafluoroethyl-4,5-dihydro-1H-pyrazole 4,4,5,5,5-Pentafluoro-1-(3'-methylsulfanyl-biphenyl-4-yl)-pent-1-en-3-one (200.0 mg, 0.54 mmol) prepared in Step 2 of Preparation 2, 2-chlorophenylhydrazine hydrochloride (115.0 mg, 0.64 mmol) and conc. hydrochloric acid (200.0 uL) were added to ethanol (5.0 mL). The reaction mixture was stirred at 100° C. for 18 hours, quenched with a saturated solution of sodium hydrogen carbonate, and then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/60) to give 154.0 mg of the titled compound as a yellow liquid.

$^1$H NMR (400 MHz, CDCl$_3$) 7.41 (d, 2H), 7.36 (s, 1H), 7.33-7.22 (m, 7H), 7.09 (t, 1H), 6.95 (t, 1H), 3.68 (dd, 1H), 3.26 (dd, 1H), 2.50 (s, 3H)

Examples 13 to 15

The compounds of Examples 13 to 15 were prepared in accordance with the same procedures as in Example 12, except for using 4,4,5,5,5-pentafluoro-1-(3'-methylsulfanyl-biphenyl-4-yl)-pent-1-en-3-one prepared in Step 2 of Preparation 2; and using each hydrazine hydrochloride corresponding to the compounds of Examples 13 to 15 instead of 2-chlorophenylhydrazine hydrochloride.

Example 13

1-(2,4-dichloro-phenyl)-5-(3'-methylsulfanyl-biphenyl-4-yl)-3-pentafluoroethyl-4,5-dihydro-1H-pyrazole $^1$H NMR (400 MHz, CDCl$_3$) 7.43 (d, 2H), 7.38 (s, 1H), 7.31 (d, 1H), 7.26-7.20 (m, 4H), 7.17 (d, 2H), 7.06 (dd, 1H), 5.90 (dd, 1H), 3.69 (dd, 1H), 3.27 (dd, 1H), 2.51 (s, 3H)

Example 14

1-(2,4-difluoro-phenyl)-5-(3'-methylsulfanyl-biphenyl-4-yl)-3-pentafluoroethyl-4,5-dihydro-1H-pyrazole $^1$H NMR (400 MHz, CDCl$_3$) 7.45 (d, 2H), 7.39 (s, 1H), 7.39-7.35 (m, 1H), 7.31 (d, 1H), 7.28-7.20 (m, 3H), 7.19 (d, 2H), 6.77-6.66 (m, 2H), 5.63 (dd, 1H), 3.67 (dd, 1H), 3.18 (dd, 1H), 2.51 (s, 3H)

Example 15

1-(2-chloro-benzyl)-5-(3'-methylsulfanyl-biphenyl-4-yl)-3-pentafluoroethyl-4,5-dihydro-1H-pyrazole $^1$H NMR (400 MHz, CDCl$_3$) 7.54 (d, 2H), 7.45-7.29 (m, 7H), 7.26-7.17 (m, 3H), 4.55 (dd, 1H), 4.50-4.39 (m, 2H), 3.28 (dd, 1H), 2.89 (dd, 1H), 2.54 (s, 3H)

Example 16

1-(2,4-dichloro-phenyl)-5-(3'-methanesulfonyl-biphenyl-4-yl)-3-pentafluoroethyl-4,5-dihydro-1H-pyrazole To a mixture of 1-(2,4-dichloro-phenyl)-5-(3'-methylsulfanyl-biphenyl-4-yl)-3-pentafluoroethyl-4,5-dihydro-1H-pyrazole (261.0 mg, 0.49 mmol) prepared in Example 13 in dichloromethane (5.0 mL), was slowly added meta-chloroperbenzoic acid (77%, 121.0 mg, 0.54 mmol) at 0° C. The reaction mixture was stirred at room temperature for 30 minutes, quenched with a saturated solution of sodium hydrogen carbonate, and then extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/5, 1/1) to give 113.0 mg of the titled compound as a yellow liquid.

$^1$H NMR (400 MHz, CDCl$_3$) 8.07 (s, 1H), 7.90 (d, 1H), 7.78 (d, 1H), 7.62 (t, 1H), 7.49 (d, 2H), 7.26-7.22 (m, 1H), 7.23 (d, 2H), 7.08 (dd, 1H), 5.93 (dd, 1H), 3.73 (dd, 1H), 3.26 (dd, 1H), 3.07 (s, 3H)

Examples 17 and 18

The compounds of Examples 17 and 18 were prepared in accordance with the same procedures as in Example 16, except for using the respective compounds prepared in Examples 13 and 14 and meta-chloroperbenzoic acid.

Example 17

1-(2,4-dichloro-phenyl)-5-(3'-methanesulfinyl-biphenyl-4-yl)-3-pentafluoroethyl-4,5-dihydro-1H-pyrazole $^1$H NMR (400 MHz, CDCl$_3$) 8.07 (s, 1H), 7.89 (d, 1H), 7.78 (d, 1H), 7.61 (t, 1H), 7.50 (d, 2H), 7.51-7.46 (m, 1H), 7.24 (d, 2H), 7.05-7.01 (m, 1H), 6.89 (s, 1H), 6.89 (d, 1H), 5.78-5.75 (m, 1H), 3.71 (dd, 1H), 3.16 (dd, 1H), 3.07 (s, 3H)

Example 18

1-(2,4-difluoro-phenyl)-5-(3'-methanesulfonyl-biphenyl-4-yl)-3-pentafluoroethyl-4,5-dihydro-1H-pyrazole $^1$H NMR (400 MHz, CDCl$_3$) 8.08 (s, 1H), 7.90 (d, 1H), 7.89 (d, 1H), 7.62 (t, 1H), 7.51 (d, 2H), 7.41-7.35 (m, 1H), 7.24 (m, 2H), 6.78-6.66 (m, 2H), 5.67-5.64 (m, 1H), 3.18 (dd, 1H), 3.07 (s, 3H)

Example 19

1-(2-chloro-phenyl)-5-[5-(3-acetyl-phenyl)-pyridin-2-yl]-3-pentafluoroethyl-4,5-dihydro-1H-pyrazole 5-(3-Bromo-pyridin-6-yl)-1-(2-chloro-phenyl)-3-pentafluoroethyl-4,5-dihydro-1H-pyrazole (20.0 mg, 0.04 mmol) prepared in Step 4 of Preparation 3, 3-acetylphenylboronic acid (11.0 mg, 0.07 mmol), Pd(PPh$_3$)$_4$ (2.0 mg, cat.) and a 2N sodium carbonate solution (210.0 uL) were added to a mixed solvent of ethanol (210.0 uL) and toluene (310.0 uL). The reaction mixture was stirred at 80° C. for 1 hour and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/6) to give 4.0 mg of the titled compound as a white liquid.

$^1$H NMR (400 MHz, CDCl$_3$) 8.74 (s, 1H), 8.08 (s, 1H), 7.95 (d, 1H), 7.73 (t, 2H), 7.54 (t, 1H), 7.24 (m, 2H), 7.18 (d, 1H), 7.08 (d, 1H), 6.96 (t, 1H), 6.02 (dd, 1H), 3.70-3.63 (td, 1H), 3.49 (dd, 1H), 2.64 (s, 3H)

Examples 20 to 22

The compounds of Examples 20 to 22 were prepared in accordance with the same procedures as in Example 19, except for using 5-(3-bromo-pyridin-6-yl)-1-(2-chloro-phenyl)-3-pentafluoroethyl-4,5-dihydro-1H-pyrazole prepared in Step 4 of Preparation 3; and using each boronic acid corresponding to the compounds of Examples 20 to 22 instead of 3-acetylphenylboronic acid.

Example 20

1-(2-chloro-phenyl)-5-[5-(4-methoxy-phenyl)-pyridin-2-yl]-3-pentafluoroethyl-4,5-dihydro-1H-pyrazole $^1$H NMR (400 MHz, CDCl$_3$) 8.68 (s, 1H), 7.64 (d, 1H), 7.45 (d, 2H), 7.25 (d, 2H), 7.12 (d, 1H), 7.07 (t, 1H), 6.97-6.93 (m, 3H), 5.98 (dd, 1H), 3.88 (s, 3H), 3.68-3.61 (td, 1H), 3.47 (dd, 1H)

Example 21

1-(2-chloro-phenyl)-5-[5-(3-methylsulfanyl-phenyl)-pyridin-2-yl]-3-pentafluoroethyl-4,5-dihydro-1H-pyrazole $^1$H NMR (400 MHz, CDCl$_3$) 8.70 (s, 1H), 7.66 (d, 1H), 7.35 (m, 2H), 7.28-7.24 (m, 4H), 7.15 (d, 1H), 7.08 (t, 1H), 6.95 (t, 1H), 6.00 (dd, 1H), 3.69-3.62 (td, 1H), 3.47 (dd, 1H), 2.51 (s, 3H)

Example 22

1-(2-chloro-phenyl)-5-[5-(4-methanesulfonyl-phenyl)-pyridin-2-yl]-3-pentafluoroethyl-4,5-dihydro-1H-pyrazole $^1$H NMR (400 MHz, CDCl$_3$) 8.75 (s, 1H), 8.01 (d, 2H), 7.73-7.67 (m, 3H), 7.27-7.24 (m, 2H), 7.21 (d, 1H), 7.08 (t, 1H), 6.96 (t, 1H), 6.03 (dd, 1H), 3.71-3.64 (td, 1H), 3.48 (dd, 1H), 3.08 (s, 3H)

Example 23

1-(4-chloro-phenyl)-5-(4'-methylsulfanyl-biphenyl-3-yl)-3-pentafluoroethyl-4,5-dihydro-1H-pyrazole 4,4,5,5,5-Pentafluoro-1-(4'-methylsulfanyl-biphenyl-3-yl)-pent-1-en-3-one (200.0 mg, 0.54 mmol) prepared in Step 3 of Preparation 4 and 4-chlorophenylhydrazine hydrochloride (106.0 mg, 0.59 mmol) were added to acetic acid (3.0 mL). The reaction mixture was stirred at 120° C. for 8 hours, concentrated under reduced pressure, and then ethyl acetate was added thereto. The reaction mixture was washed with a saturated solution of sodium hydrogen carbonate, dried on anhydrous magnesium sulfate, and then concentrated under reduced pressure to give a yellow liquid residue. The resulting residue was purified by silica gel column chromatography (eluent: ethyl acetate/n-hexane=1/60) to give 163.0 mg of the titled compound as a yellow liquid.

$^1$H NMR (400 MHz, CDCl$_3$) 7.52 (d, 1H), 7.49 (d, 1H), 7.46 (d, 2H), 7.44-7.40 (m, 2H), 7.33 (s, 1H), 7.32 (d, 2H), 7.18 (d, 1H), 7.13 (d, 2H), 6.95 (d, 2H), 5.39 (dd, 1H), 3.73 (dd, 1H), 3.06 (dd, 1H), 2.52 (s, 3H)

Example 24

1-(3-chloro-phenyl)-5-(4'-methylsulfanyl-biphenyl-3-yl)-3-pentafluoroethyl-4,5-dihydro-1H-pyrazole The titled compound was prepared in accordance with the same procedures as in Example 23, except for using 4,4,5,5,5-pentafluoro-1-(4'-methylsulfanyl-biphenyl-3-yl)-pent-1-en-3-one prepared in Step 3 of Preparation 4; and using 3-chlorophenylhydrazine hydrochloride instead of 4-chlorophenylhydrazine hydrochloride.

$^1$H NMR (400 MHz, CDCl$_3$) 7.51 (d, 1H), 7.46 (d, 2H), 7.42 (d, 2H), 7.32 (d, 2H), 7.18 (d, 1H), 7.13 (s, 1H), 7.07 (t, 1H), 6.84 (d, 1H), 6.80 (d, 1H), 5.39 (dd, 1H), 3.77-3.69 (m, 1H), 3.06 (dd, 1H), 2.52 (s, 3H)

Example 25

1-(2,4-dichloro-phenyl)-5-(4'-methylsulfanyl-biphenyl-3-yl)-3-pentafluoroethyl-4,5-dihydro-1H-pyrazole 4,4,5,5-Pentafluoro-1-(4'-methylsulfanyl-biphenyl-3-yl)-pent-1-en-3-one (200.0 mg, 0.54 mmol) prepared in Step 3 of Preparation 4, 2,4-dichlorophenylhydrazine hydrochloride (127.0 mg, 0.59 mmol) and conc. hydrochloric acid (200.0 uL) were added to ethanol (5.0 mL). The reaction mixture was stirred at 100° C. for 18 hours, quenched with a saturated solution of sodium hydrogen carbonate, and then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/60) to give 92.0 mg of the titled compound as a yellow liquid.

$^1$H NMR (400 MHz, CDCl$_3$) 4.40 (d, 1H), 7.37 (d, 2H), 7.30 (d, 2H), 7.29 (d, 2H), 7.24 (d, 21H), 7.20 (d, 1H), 7.07-7.04 (m, 2H), 5.91 (dd, 1H), 3.71 (dd, 1H), 3.30 (dd, 1H), 2.52 (s, 3H)

Examples 26 to 32

The compounds of Examples 26 to 32 were prepared in accordance with the same procedures as in Example 25, except for using 4,4,5,5,5-pentafluoro-1-(4'-methylsulfanyl-biphenyl-3-yl)-pent-1-en-3-one prepared in Step 3 of Preparation 4; and using each hydrazine hydrochloride corresponding to the compounds of Examples 26 to 32 instead of 2,4-dichlorophenylhydrazine hydrochloride.

Example 26

5-(4'-methylsulfanyl-biphenyl-3-yl)-3-pentafluoroethyl-1-(2-trifluoromethyl-phenyl)-4,5-dihydro-1H-pyrazole $^1$H NMR (400 MHz, CDCl$_3$) 7.63 (d, 1H), 7.46-7.43 (m, 2H), 7.41 (d, 2H), 7.35 (t, 1H), 7.30-7.26 (m, 1H), 7.30 (d, 2H), 7.20 (d, 1H), 7.11 (t, 1H), 7.00 (d, 1H), 5.56 (dd, 1H), 3.64 (dd, 1H), 3.19 (dd, 1H), 2.52 (s, 3H)

Example 27

5-(4'-methylsulfanyl-biphenyl-3-yl)-3-pentafluoroethyl-1-ortho-tolyl-4,5-dihydro-1H-pyrazole $^1$H NMR (400 MHz, CDCl$_3$) 7.44-7.38 (m, 4H), 7.36-7.30 (m, 3H), 7.23 (t, 1H), 7.13 (d, 1H), 7.04 (t, 1H), 6.98 (t, 1H), 6.91 (d, 1H), 5.46 (dd, 1H), 3.57 (dd, 1H), 3.13 (dd, 1H), 2.52 (s, 3H), 2.35 (s, 3H)

Example 28

1-(2-methoxy-phenyl)-5-(4'-methylsulfanyl-biphenyl-3-yl)-3-pentafluoroethyl-4,5-dihydro-1H-pyrazole $^1$H NMR (400 MHz, CDCl$_3$) 7.37-7.35 (m, 4H), 7.29 (d, 2H), 7.24 (d, 2H), 7.05 (d, 1H), 6.95 (t, 1H), 6.83 (t, 1H), 6.73 (d, 1H), 5.83 (dd, 1H), 3.77 (s, 3H), 3.65 (dd, 1H), 3.19 (dd, 1H), 2.51 (s, 3H)

Example 29

5-(4'-methylsulfanyl-biphenyl-3-yl)-3-pentafluoroethyl-1-phenyl-4,5-dihydro-1H-pyrazole $^1$H NMR (400 MHz, CDCl$_3$) 7.51-7.31 (m, 5H), 7.32 (d, 2H), 7.22-7.17 (m, 3H), 7.03 (d, 2H), 6.88 (t, 1H), 5.41 (dd, 1H), 3.71 (dd, 1H), 3.05 (dd, 1H), 2.52 (s, 3H)

Example 30

1-(2,4-difluoro-phenyl)-5-(4'-methylsulfanyl-biphenyl-3-yl)-3-pentafluoroethyl-4,5-dihydro-1H-pyrazole $^1$H NMR (400 MHz, CDCl$_3$) 7.44-7.29 (m, 8H), 7.08 (d, 1H), 6.76-6.65 (m, 2H), 5.63 (dd, 1H), 3.68 (dd, 1H), 3.20 (dd, 1H), 2.51 (s, 3H)

Example 31

1-(4-chloro-2-fluoro-phenyl)-5-(4'-methylsulfanyl-biphenyl-3-yl)-3-pentafluoroethyl-4,5-dihydro-1H-pyrazole $^1$H NMR (400 MHz, CDCl$_3$) 7.44-7.38 (m, 4H), 7.36-7.29 (m, 4H), 7.05 (d, 1H), 6.99 (d, 1H), 6.91 (d, 1H), 5.70 (dd, 1H), 3.69 (dd, 1H), 3.20 (dd, 1H), 2.52 (s, 3H)

Example 32

1-(2-chloro-benzyl)-5-(4'-methylsulfanyl-biphenyl-3-yl)-3-pentafluoroethyl-4,5-dihydro-1H-pyrazole $^1$H NMR (400 MHz, CDCl$_3$) 7.55 (s, 1H), 7.49 (d, 2H), 7.48 (s, 1H), 7.41-7.33 (m, 5H), 7.29-7.26 (m, 1H), 7.21-7.15 (m, 2H), 4.54 (dd, 1H), 4.46 (s, 2H), 3.29 (dd, 1H), 2.90 (dd, 1H), 2.53 (s, 3H)

Example 33

1-cyclohexyl-5-(4'-methylsulfanyl-biphenyl-3-yl)-3-pentafluoroethyl-4,5-dihydro-1H-pyrazole 4,4,5,5,5-Pentafluoro-1-(4'-methylsulfanyl-biphenyl-3-yl)-pent-1-en-3-one (200.0 mg, 0.54 mmol) prepared in Step 3 of Preparation 4, cyclohexylhydrazine hydrochloride (98.0 mg, 0.59 mmol), and piperidine (107.0 uL, 1.08 mmol) were added to ethanol (5.0 mL). The reaction mixture was stirred at 100° C. for 18 hours, concentrated under reduced pressure, and then ethyl acetate was added thereto. The reaction mixture was washed with distilled water, dried on anhydrous magnesium sulfate, and then concentrated under reduced pressure to give a yellow liquid residue. The resulting residue was purified by silica gel column chromatography (eluent: ethyl acetate/n-hexane=1/60) to give 10.0 mg of the titled compound as a yellow liquid.

$^1$H NMR (400 MHz, CDCl$_3$) 7.63 (brs, 1H), 7.55-7.51 (m, 3H), 7.44-7.37 (m, 2H), 7.33 (d, 2H), 3.49 (m, 1H), 3.38 (dd, 1H), 2.93 (dd, 1H), 2.79-2.73 (m, 1H), 2.53 (s, 3H), 2.05-1.05 (m, 7H)

Examples 34 to 36

The compounds of Examples 34 to 36 were prepared in accordance with the same procedures as in Example 33, except for using 4,4,5,5,5-pentafluoro-1-(4'-methylsulfanyl-biphenyl-3-yl)-pent-1-en-3-one prepared in Step 3 of Preparation 4; and using each hydrazine hydrochloride corresponding to the compounds of Examples 34 to 36 instead of cyclohexylhydrazine hydrochloride.

Example 34

1-(pyridin-2-yl)-5-(4'-methylsulfanyl-biphenyl-3-yl)-3-pentafluoroethyl-4,5-dihydro-1H-pyrazole $^1$H NMR (400 MHz, CDCl$_3$) 8.04 (d, 1H), 7.55 (t, 1H), 7.47-7.42 (m, 5H), 7.36 (t, 1H), 7.30 (d, 2H), 7.17 (d, 1H), 6.74 (dd, 1H), 5.90 (dd, 1H), 3.68 (dd, 1H), 3.08 (dd, 1H), 2.51 (s, 3H)

Example 35

1-(6-chloro-pyridazin-3-yl)-5-(4'-methylsulfanyl-biphenyl-3-yl)-3-pentafluoroethyl-4,5-dihydro-1H-pyrazole $^1$H NMR (400 MHz, CDCl$_3$) 7.65 (d, 1H), 7.46-7.44 (m, 4H), 7.37 (t, 1H), 7.35-7.29 (m, 3H), 7.20 (d, 1H), 5.98 (dd, 1H), 3.78 (dd, 1H), 3.21 (dd, 1H), 2.51 (s, 3H)

Example 36

1-benzyl-5-(4'-methylsulfanyl-biphenyl-3-yl)-3-pentafluoroethyl-4,5-dihydro-1H-pyrazole $^1$H NMR (400 MHz, CDCl$_3$) 7.55-7.49 (m, 4H), 7.44 (t, 1H), 7.35-7.28 (m, 6H), 7.18 (d, 2H), 7.48 (d, 1H), 4.42 (dd, 1H), 4.00 (d, 1H), 3.19 (dd, 1H), 2.87 (dd, 1H), 2.54 (s, 3H)

Example 37

1-(3-chloro-phenyl)-5-(4'-methanesulfinyl-biphenyl-3-yl)-3-pentafluoroethyl-4,5-dihydro-1H-pyrazole To a mixture of 1-(3-Chloro-phenyl)-5-(4'-methylsulfanyl-biphenyl-3-yl)-3-pentafluoroethyl-4,5-dihydro-1H-pyrazole (127.0 mg, 0.26 mmol) prepared in Example 24 in dichloromethane (5.0 mL), was slowly added meta-chloroperbenzoic acid (77%, 69.0 mg, 0.31 mmol) at 0° C. The reaction mixture was stirred at room temperature 30 minutes, quenched with a saturated solution of sodium hydrogen carbonate, and then extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/5, 1/1) to give 61.0 mg of the titled compound as a yellow liquid.

$^1$H NMR (400 MHz, CDCl$_3$) 7.75 (d, 2H), 7.68 (d, 2H), 7.58 (d, 1H), 7.48 (t, 1H), 7.44 (s, 1H), 7.25 (d, 1H), 7.12 (s, 1H), 7.09 (t, 1H), 6.85 (d, 1H), 6.80 (d, 1H), 5.43 (dd, 1H), 3.76 (dd, 1H), 3.07 (dd, 1H), 2.77 (s, 3H)

Example 38

1-(3-chloro-phenyl)-5-(4'-methanesulfonyl-biphenyl-3-yl)-3-pentafluoroethyl-4,5-dihydro-1H-pyrazole The compound of Example 38 was prepared in accordance with the same procedures as in Example 37, using the compound prepared in Example 24 and 2 equivalents of meta-chloroperbenzoic acid.

$^1$H NMR (400 MHz, CDCl$_3$) 8.01 (d, 2H), 7.71 (d, 2H), 7.57 (d, 1H), 7.51 (t, 1H), 7.43 (s, 1H), 7.29 (d, 1H), 7.11 (s, 1H), 7.09 (t, 1H), 6.86 (d, 1H), 6.80 (d, 1H), 5.44 (dd, 1H), 3.76 (dd, 1H), 3.09 (s, 3H), 3.07 (dd, 1H)

Example 39

1-(4-chloro-phenyl)-5-(4'-methanesulfonyl-biphenyl-3-yl)-3-pentafluoroethyl-4,5-dihydro-1H-pyrazole The compound of Example 39 was prepared in accordance with the same procedures as in Example 37, using the compound prepared in Example 23 and 2 equivalents of meta-chloroperbenzoic acid.

$^1$H NMR (400 MHz, CDCl$_3$) 8.01 (d, 2H), 7.70 (d, 2H), 7.56 (d, 1H), 7.50 (t, 1H), 7.44 (s, 1H), 7.29 (d, 1H), 7.14 (d, 2H), 6.95 (d, 2H), 5.43 (dd, 1H), 3.76 (dd, 1H), 3.09 (s, 3H), 3.06 (dd, 1H)

Example 40

1-(4-chloro-phenyl)-5-(4'-methanesulfinyl-biphenyl-3-yl)-3-pentafluoroethyl-4,5-dihydro-1H-pyrazole The compound of Example 40 was prepared in accordance with the same procedures as in Example 37, using the compound prepared in Example 23 and meta-chloroperbenzoic acid.

¹H NMR (400 MHz, CDCl₃) 7.77 (s, 1H), 7.72 (d, 2H), 7.67 (d, 2H), 7.57-7.55 (m, 1H), 7.47 (t, 1H), 7.44 (s, 1H), 7.16 (d, 2H), 6.95 (d, 2H), 5.41 (dd, 1H), 3.74 (dd, 1H), 3.07 (dd, 1H), 2.77 (s, 3H)

Example 41

1-(2,4-dichloro-phenyl)-5-(4'-methanesulfonyl-biphenyl-3-yl)-3-pentafluoroethyl-4,5-dihydro-1H-pyrazole The compound of Example 41 was prepared in accordance with the same procedures as in Example 37, using the compound prepared in Example 25 and 2 equivalents of meta-chloroperbenzoic acid.

¹H NMR (400 MHz, CDCl₃) 8.00 (d, 2H), 7.62 (d, 2H), 7.45 (d, 1H), 7.36 (t, 1H), 7.34 (s, 1H), 7.25 (d, 1H), 7.22 (d, 1H), 7.18 (d, 1H), 7.07 (dd, 1H), 5.95 (dd, 1H), 3.74 (dd, 1H), 3.29 (dd, 1H), 3.10 (s, 3H)

Example 42

1-(2,4-dichloro-phenyl)-5-(4'-methanesulfinyl-biphenyl-3-yl)-3-pentafluoroethyl-4,5-dihydro-1H-pyrazole The compound of Example 42 was prepared in accordance with the same procedures as in Example 37, using the compound prepared in Example 25 and meta-chloroperbenzoic acid.

¹H NMR (400 MHz, CDCl₃) 7.71 (d, 2H), 7.59 (d, 2H), 7.44 (d, 1H), 7.34 (t, 1H), 7.34 (s, 1H), 7.25 (d, 1H), 7.21 (d, 1H), 7.13 (d, 1H), 7.07 (d, 1H), 5.94 (dd, 1H), 3.73 (dd, 1H), 3.30 (dd, 1H), 2.77 (s, 3H)

Example 43

5-(4'-methanesulfonyl-biphenyl-3-yl)-3-pentafluoroethyl-1-(2-trifluoromethyl-phenyl)-4,5-dihydro-1H-pyrazole The compound of Example 43 was prepared in accordance with the same procedures as in Example 37, using the compound prepared in Example 26 and 2 equivalents of meta-chloroperbenzoic acid.

¹H NMR (400 MHz, CDCl₃) 8.00 (d, 2H), 7.64 (d, 2H), 7.50 (d, 1H), 7.46 (s, 1H), 7.42 (t, 1H), 7.35-7.31 (m, 2H), 7.13 (t, 1H), 7.03 (d, 1H) 5.60 (dd, 1H), 3.67 (dd, 1H), 3.19 (dd, 1H), 3.09 (s, 3H)

Example 44

5-(4'-methanesulfinyl-biphenyl-3-yl)-3-pentafluoroethyl-1-(2-trifluoromethyl-phenyl)-4,5-dihydro-1H-pyrazole The compound of Example 44 was prepared in accordance with the same procedures as in Example 37, using the compound prepared in Example 26 and meta-chloroperbenzoic acid.

¹H NMR (400 MHz, CDCl₃) 7.71 (d, 2H), 7.64 (d, 1H), 7.62 (d, 2H), 7.49 (d, 1H), 7.46 (s, 1H), 7.40 (t, 1H), 7.32 (t, 1H), 7.29 (s, 1H), 7.13 (t, 1H), 7.02 (d, 1H) 5.59 (dd, 1H), 3.66 (dd, 1H), 3.20 (dd, 1H), 2.77 (s, 3H)

Example 45

5-(4'-methanesulfonyl-biphenyl-3-yl)-3-pentafluoroethyl-1-ortho-tolyl-4,5-dihydro-1H-pyrazole The compound of Example 45 was prepared in accordance with the same procedures as in Example 37, using the compound prepared in Example 27 and 2 equivalents of meta-chloroperbenzoic acid.

¹H NMR (400 MHz, CDCl₃) 8.01 (d, 2H), 7.63 (d, 2H), 7.50-7.40 (m, 3H), 7.34 (d, 1H), 7.15 (d, 1H), 7.05-7.00 (m, 2H), 6.92 (d, 1H), 5.50 (dd, 1H), 3.61 (dd, 1H), 3.14 (dd, 1H), 3.09 (s, 3H), 2.36 (s, 3H)

Example 46

5-(4'-methanesulfonyl-biphenyl-3-yl)-1-(2-methoxyphenyl)-3-pentafluoroethyl-4,5-dihydro-1H-pyrazole The compound of Example 46 was prepared in accordance with the same procedures as in Example 37, using the compound prepared in Example 28 and 2 equivalents of meta-chloroperbenzoic acid.

¹H NMR (400 MHz, CDCl₃) 7.97 (d, 2H), 7.59 (d, 2H), 7.41-7.30 (m, 4H), 7.17 (d, 1H), 6.97 (t, 1H), 6.85 (t, 1H), 6.75 (d, 1H), 5.86 (dd, 1H), 3.77 (s, 3H), 3.68 (dd, 1H), 3.18 (dd, 1H), 3.09 (s, 3H)

Example 47

1-(pyridin-2-yl)-5-(4'-methanesulfonyl-biphenyl-3-yl)-3-pentafluoroethyl-4,5-dihydro-1H-pyrazole The compound of Example 47 was prepared in accordance with the same procedures as in Example 37, using the compound prepared in Example 34 and 2 equivalents of meta-chloroperbenzoic acid.

¹H NMR (400 MHz, CDCl₃) 8.03 (d, 1H), 7.99 (d, 2H), 7.70 (d, 2H), 7.57 (t, 1H), 7.50-7.42 (m, 4H), 7.27 (d, 1H), 6.76 (dd, 1H), 5.93 (dd, 1H), 3.71 (dd, 1H), 3.09 (s, 3H), 3.07 (dd, 1H)

Example 48

1-(6-chloro-pyridazin-3-yl)-5-(4'-methanesulfonyl-biphenyl-3-yl)-3-pentafluoroethyl-4,5-dihydro-1H-pyrazole The compound of Example 48 was prepared in accordance with the same procedures as in Example 37, using the compound prepared in Example 35 and 2 equivalents of meta-chloroperbenzoic acid.

¹H NMR (400 MHz, CDCl₃) 8.00 (d, 2H), 7.71 (d, 2H), 7.67 (d, 1H), 7.51 (m, 2H), 7.45 (t, 1H), 7.35 (d, 1H), 7.30 (d, 1H), 6.00 (dd, 1H), 3.81 (dd, 1H), 3.23 (dd, 1H), 3.09 (s, 3H)

Example 49

1-benzyl-5-(4'-methanesulfonyl-biphenyl-3-yl)-3-pentafluoroethyl-4,5-dihydro-1H-pyrazole The compound of Example 49 was prepared in accordance with the same procedures as in Example 37, using the compound prepared in Example 36 and 2 equivalents of meta-chloroperbenzoic acid.

¹H NMR (400 MHz, CDCl₃) 8.03 (d, 2H), 7.75 (d, 2H), 7.58 (m, 2H), 7.50 (t, 1H), 7.40 (d, 1H), 7.31-7.28 (m, 3H), 7.17 (d, 2H), 4.67 (d, 1H), 4.45 (dd, 1H), 4.04 (d, 1H), 3.23 (dd, 1H), 3.11 (s, 3H), 2.87 (dd, 1H)

Example 50

5-(4'-methanesulfonyl-biphenyl-3-yl)-3-pentafluoroethyl-1-phenyl-4,5-dihydro-1H-pyrazole The compound of Example 50 was prepared in accordance with the same procedures as in Example 37, using the compound prepared in Example 29 and 2 equivalents of meta-chloroperbenzoic acid.

¹H NMR (400 MHz, CDCl₃) 8.00 (d, 2H), 7.70 (d, 2H), 7.56-7.47 (m, 3H), 7.32 (d, 1H), 7.20 (t, 2H), 7.03 (d, 2H), 6.90 (t, 1H), 5.45 (dd, 1H), 3.74 (dd, 1H), 3.10 (s, 3H), 3.03 (dd, 1H)

Example 51

1-(2,4-difluoro-phenyl)-5-(4'-methanesulfonyl-biphenyl-3-yl)-3-pentafluoroethyl-4,5-dihydro-1H-pyrazole The compound of Example 51 was prepared in accordance with the same procedures as in Example 37, using the compound prepared in Example 30 and 2 equivalents of meta-chloroperbenzoic acid.

¹H NMR (400 MHz, CDCl₃) 8.00 (d, 2H), 7.65 (d, 2H), 7.48 (d, 1H), 7.41-7.36 (m, 3H), 7.20 (d, 1H), 6.79-6.66 (m, 2H), 5.66 (dd, 1H), 3.74 (dd, 1H), 3.20 (dd, 1H), 3.09 (s, 3H)

Example 52

1-(2,4-difluoro-phenyl)-5-(4'-methanesulfinyl-biphenyl-3-yl)-3-pentafluoroethyl-4,5-dihydro-1H-pyrazole The compound of Example 52 was prepared in accordance with the same procedures as in Example 37, using the compound prepared in Example 30 and meta-chloroperbenzoic acid.

¹H NMR (400 MHz, CDCl₃) 7.71 (d, 2H), 7.62 (d, 2H), 7.47 (d, 1H), 7.40-7.35 (m, 3H), 7.16 (d, 1H), 6.78-6.66 (m, 2H), 5.66 (dd, 1H), 3.71 (dd, 1H), 3.20 (dd, 1H), 2.76 (s, 3H)

Example 53

1-(4-chloro-2-fluoro-phenyl)-5-(4'-methanesulfonyl-biphenyl-3-yl)-3-pentafluoroethyl-4,5-dihydro-1H-pyrazole The compound of Example 53 was prepared in accordance with the same procedures as in Example 37, using the compound prepared in Example 31 and 2 equivalents of meta-chloroperbenzoic acid.

¹H NMR (400 MHz, CDCl₃) 8.00 (d, 2H), 7.64 (d, 2H), 7.50-7.38 (m, 3H), 7.33 (s, 1H), 7.16 (d, 1H), 7.02 (d, 1H), 6.93 (d, 1H), 5.75 (dd, 1H), 3.73 (dd, 1H), 3.19 (dd, 1H), 3.10 (s, 3H)

Example 54

1-(2-chloro-benzyl)-5-(4'-methanesulfonyl-biphenyl-3-yl)-3-pentafluoroethyl-4,5-dihydro-1H-pyrazole The compound of Example 54 was prepared in accordance with the same procedures as in Example 37, using the compound prepared in Example 32 and 2 equivalents of meta-chloroperbenzoic acid.

¹H NMR (400 MHz, CDCl₃) 8.03 (d, 2H), 7.23 (d, 2H), 7.60 (s, 1H), 7.54 (d, 1H), 7.48-7.40 (m, 3H), 7.28 (d, 1H), 7.22-7.16 (m, 2H), 4.57 (dd, 1H), 4.47 (s, 2H), 3.31 (dd, 1H), 3.11 (s, 3H), 2.89 (dd, 1H)

Example 55

1-(2,4-difluoro-phenyl)-5-[3-(6-fluoro-pyridin-3-yl)-phenyl]-3-pentafluoroethyl-4,5-dihydro-1H-pyrazole 5-(3-Bromo-phenyl)-1-(2,4-difluoro-phenyl)-3-pentafluoroethyl-4,5-dihydro-1H-pyrazole (35.0 mg, 0.08 mmol) prepared in Step 2 of Preparation 5, 2-fluoro-5-pyridineboronic acid (16.3 mg, 0.11 mmol), Pd(PPh₃)₄ (8.9 mg, cat.) and a 2N sodium carbonate solution (385.0 uL) were added to a mixed solvent of ethanol (400.0 uL) and 1,2-dimethylethane (1.5 mL). The reaction mixture was stirred at 88° C. for 2 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/6) to give 15.0 mg of the titled compound as a white liquid.

¹H NMR (400 MHz, CDCl₃) 8.30 (s, 1H), 7.84 (t, 1H), 7.40-7.37 (m, 3H), 7.25 (d, 2H), 7.17 (d, 1H), 6.99 (d, 1H), 6.76 (t, 1H), 6.68 (t, 1H), 5.66 (dd, 1H), 3.70 (dd, 1H), 3.21 (dd, 1H)

Examples 56 to 60

The compounds of Examples 56 to 60 were prepared in accordance with the same procedures as in Example 55, except for using 5-(3-bromo-phenyl)-1-(2,4-difluoro-phenyl)-3-pentafluoroethyl-4,5-dihydro-1H-pyrazole prepared in Step 2 of Preparation 5; and using each boronic acid corresponding to the compounds of Examples 56 to 60 instead of 2-fluoro-5-pyridineboronic acid.

Example 56

1-(2,4-difluoro-phenyl)-5-[3-(6-methoxy-pyridin-3-yl)-phenyl]-3-pentafluoroethyl-4,5-dihydro-1H-pyrazole ¹H NMR (400 MHz, CDCl₃) 8.26 (s, 1H), 7.66 (d, 1H), 7.39-7.31 (m, 3H), 7.26 (m, 1H), 7.10 (d, 1H), 6.81-6.65 (m, 3H), 5.63 (dd, 1H), 3.98 (s, 3H), 3.68 (dd, 1H), 3.19 (dd, 1H)

Example 57

1-(2,4-difluoro-phenyl)-3-pentafluoroethyl-5-[3-(5-pyrimidyl)-phenyl]-4,5-dihydro-1H-pyrazole ¹H NMR (400 MHz, CDCl₃) 9.21 (s, 1H), 8.84 (s, 2H), 7.47-7.36 (m, 3H), 7.32 (s, 1H), 7.24 (d, 1H), 6.77 (t, 1H), 6.69 (t, 1H), 5.67 (dd, 1H), 3.71 (dd, 1H), 3.18 (dd, 1H)

Example 58

1-(2,4-difluoro-phenyl)-3-pentafluoroethyl-5-[4'-(1-tetrazolyl)-biphenyl-3-yl]-4,5-dihydro-1H-pyrazole $^1$H NMR (400 MHz, CDCl$_3$) 9.04 (s, 1H), 7.79 (d, 2H), 7.67 (d, 2H), 7.49 (d, 1H), 7.41-7.37 (m, 3H), 7.18 (d, 1H), 6.76 (t, 1H), 6.69 (t, 1H), 5.68 (dd, 1H), 3.72 (dd, 1H), 3.22 (dd, 1H)

Example 59

1-(2,4-difluoro-phenyl)-3-pentafluoroethyl-5-[3-(1H-pyrazol-4-yl)-phenyl]-4,5-dihydro-1H-pyrazole $^1$H NMR (400 MHz, CDCl$_3$) 7.78 (s, 2H), 7.38-7.31 (m, 2H), 7.28-7.26 (m, 3H), 7.00 (d, 1H), 6.75-6.65 (m, 2H), 5.60 (dd, 1H), 3.67 (dd, 1H), 3.20 (dd, 1H)

Example 60

5-[3-(1-BOC-1,2,3,6-tetrahydropyridin-4-yl)-phenyl]-1-(2,4-difluoro-phenyl)-3-pentafluoroethyl-4,5-dihydro-1H-pyrazole $^1$H NMR (400 MHz, CDCl$_3$) 7.34 (q, 1H), 7.31-7.20 (m, 2H), 7.12 (s, 1H), 7.00 (d, 1H), 6.73 (t, 1H), 6.66 (dt, 1H), 5.95 (s, 1H), 5.57 (dd, 1H), 4.05 (s, 2H), 3.63 (dd, 1H), 3.60 (s, 2H), 3.15 (dd, 1H), 2.42 (s, 2H), 1.49 (s, 9H)

Example 61

1-(2,4-difluoro-phenyl)-5-[3-(1,2,3,6-tetrahydropyridin-4-yl)-phenyl]-3-pentafluoroethyl-4,5-dihydro-1H-pyrazole trifluoroacetate 5-[3-(1-BOC-1,2,3,6-tetrahydropyridin-4-yl)-phenyl]-1-(2,4-difluoro-phenyl)-3-pentafluoroethyl-4,5-dihydro-1H-pyrazole (800.0 mg, 1.32 mmol) prepared in Example 60 and trifluoroacetic acid (1011.0 uL, 13.21 mmol) were added at 0° C. to dichloromethane (6.6 mL). The reaction mixture was stirred at room temperature for 3 hours and then concentrated under reduced pressure to give 820.0 mg of the titled compound as a yellow liquid.

$^1$H NMR (400 MHz, CD$_3$OD) 7.39-7.28 (m, 5H), 7.17 (d, 1H), 6.86 (t, 2H), 6.09 (s, 1H), 5.72 (dd, 1H), 3.85 (s, 2H), 3.76 (dd, 1H), 3.47 (t, 2H), 3.15 (dd, 1H), 2.72 (s, 2H)

Example 62

1-(2,4-difluoro-phenyl)-5-[3-(1-methanesulfonyl-1,2,3,6-tetrahydropyridin-4-yl)-phenyl]-3-pentafluoroethyl-4,5-dihydro-1H-pyrazole 1-(2,4-difluoro-phenyl)-5-[3-(1,2,3,6-tetrahydropyridin-4-yl)-phenyl]-3-pentafluoroethyl-4,5-dihydro-1H-pyrazole trifluoroacetate (30.0 mg, 0.05 mmol) prepared in Example 61, triethylamine (20.3 uL, 0.15 mmol) and methanesulfonyl chloride (1.9 uL, 0.06 mmol) were added at 0° C. to dichloromethane (1.0 mL). The reaction mixture was stirred at room temperature for 2 hours. Distilled water was added to the reaction mixture, which was then extracted with dichloromethane two times. The combined extract was washed with a 1N hydrochloric acid solution, a saturated sodium carbonate solution, and brine, dried on anhydrous magnesium sulfate, and then concentrated under reduced pressure to give a yellow liquid residue. The resulting residue was purified by silica gel column chromatography (eluent: ethyl acetate/n-hexane=1/3) to give 1.9 mg of the titled compound as a yellow liquid.

$^1$H NMR (400 MHz, CDCl$_3$) 7.34 (q, 1H), 7.30-7.24 (m, 4H), 7.11 (s, 1H), 7.04 (s, 1H), 6.74 (t, 1H), 6.67 (t, 1H), 5.98 (s, 1H), 5.58 (dd, 1H), 3.95 (s, 2H), 3.65 (d, 1H), 3.50 (t, 2H), 3.15 (dd, 1H), 2.85 (s, 3H), 2.56 (s, 2H)

Examples 63 and 64

The compounds of Examples 63 and 64 were prepared in accordance with the same procedures as in Example 62, except for using 1-(2,4-difluoro-phenyl)-5-[3-(1,2,3,6-tetrahydropyridin-4-yl)-phenyl]-3-pentafluoroethyl-4,5-dihydro-1H-pyrazole trifluoroacetate prepared in Example 61; and using acyl chloride or carbamoyl chloride corresponding to the compounds of Examples 63 and 64 instead of methanesulfonyl chloride.

Example 63

1-(2,4-difluoro-phenyl)-5-[3-(1-isobutyryl-1,2,3,6-tetrahydropyridin-4-yl)-phenyl]-3-pentafluoroethyl-4,5-dihydro-1H-pyrazole $^1$H NMR (400 MHz, CDCl$_3$) 7.34 (q, 1H), 7.30-7.22 (m, 2H), 7.11 (s, 1H), 7.03 (s, 1H), 6.74 (t, 1H), 6.67 (t, 1H), 6.02-5.95 (d, 1H) 5.58 (dd, 1H), 4.22-4.17 (d, 2H), 3.80 (s, 1H), 3.69-3.64 (s, 2H), 3.14 (dd, 1H), 2.87-2.81 (m, 1H), 2.49-2.44 (d, 2H), 1.16 (t, 6H)

Example 64

1-(2,4-difluoro-phenyl)-5-[3-(1-dimethylcarbamoyl-1,2,3,6-tetrahydropyridin-4-yl)-phenyl]-3-pentafluoroethyl-4,5-dihydro-1H-pyrazole $^1$H NMR (400 MHz, CDCl$_3$) 7.34 (q, 1H), 7.30-7.22 (m, 2H), 7.11 (s, 1H), 7.03 (s, 1H), 6.74 (t, 1H), 6.67 (t, 1H), 5.98 (s, 1H), 5.58 (dd, 1H), 3.91 (s, 2H), 3.64 (d, 1H), 3.43 (t, 2H), 3.14 (dd, 1H), 2.86 (s, 6H), 2.49 (s, 2H)

Example 65

1-(2,4-difluoro-phenyl)-5-[3-(morpholin-4-yl)-phenyl]-3-pentafluoroethyl-4,5-dihydro-1H-pyrazole 5-(3-Bromo-phenyl)-1-(2,4-difluoro-phenyl)-3-pentafluoroethyl-4,5-dihydro-1H-pyrazole (30.0 mg, 0.07 mmol) prepared in Step 2 of Preparation 5, morpholine (17.2 mg, 0.20 mmol), Pd$_2$(dba)$_3$ (3.0 mg, cat.), BINAP (4.1 mg, cat.) and sodium t-butoxide (9.5 mg, 0.10 mmol) were added to toluene (1.0 mL). The reaction mixture was stirred at 100° C. for 12 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/2) to give 7.0 mg of the titled compound as a yellow liquid.

$^1$H NMR (400 MHz, CDCl$_3$) 7.34-7.26 (m, 2H), 7.14 (t, 1H), 6.76-6.63 (m, 4H), 5.50 (dd, 1H), 3.82 (d, 4H), 3.62 (dd, 1H), 3.16 (dd, 1H), 3.05 (d, 4H)

Examples 66 and 67

The compounds of Examples 66 and 67 were prepared in accordance with the same procedures as in Example 65, except for using 5-(3-bromo-phenyl)-1-(2,4-difluoro-phenyl)-3-pentafluoroethyl-4,5-dihydro-1H-pyrazole prepared in Step 2 of Preparation 5; and using each substituted amine corresponding to the compounds of Examples 66 and 67 instead of morpholine.

Example 66

1-(2,4-difluoro-phenyl)-3-pentafluoroethyl-5-(3-pyrrolidin-1-yl-phenyl)-4,5-dihydro-1H-pyrazole $^1$H NMR (400 MHz, CDCl$_3$) 7.38-7.30 (m, 1H), 7.09 (t, 1H), 6.74-6.65 (m, 2H), 6.39 (d, 2H), 6.25 (s, 1H), 5.50 (dd, 1H), 3.62 (dd, 1H), 3.20-3.16 (m, 5H), 1.97 (s, 4H)

Example 67

1-(2,4-difluoro-phenyl)-3-pentafluoroethyl-5-[3-(piperidin-1-yl)-phenyl]-4,5-dihydro-1H-pyrazole $^1$H NMR (400 MHz, CDCl$_3$) 7.37-7.28 (m, 1H), 7.05 (t, 1H), 6.77-6.65 (m, 4H), 6.54 (d, 1H), 5.49 (dd, 1H), 3.60 (dd, 1H), 3.16 (dd, 1H), 3.06 (s, 4H), 1.64 (s, 4H), 1.40 (s, 2H)

Example 68

5-(2',5'-difluoro-4'-methanesulfonyl-biphenyl-3-yl)-1-(2,4-difluoro-phenyl)-3-pentafluoroethyl-4,5-dihydro-1H-pyrazole

Step 1: 1-(2,4-difluoro-phenyl)-3-pentafluoroethyl-5-(3-(4,4,5,5-tetramethyl-1,3,2-dioxaborolan-2-yl)phenyl)-4,5-dihydro-1H-pyrazole 5-(3-Bromo-phenyl)-1-(2,4-difluoro-phenyl)-3-pentafluoroethyl-4,5-dihydro-1H-pyrazole (19.0 g, 41.74 mmol) prepared in Step 2 of Preparation 5, bis(pinacolato)diboron (15.9 g, 62.61 mmol), Pd(dppf)Cl$_2$ (3.06 g, 4.17 mmol), dppf (2.31 g, 4.17 mmol) and potassium acetate (16.39 g, 166.97 mmol) were added to 1,4-dioxane (200 mL). The reaction mixture was stirred at 80° C. for 3 hours and then filtered through celite pad. Distilled water was added to the filtrate, which was then extracted with diethyl ether three times. The combined extract was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/100) to give 18.0 g of the titled compound as a white liquid.

$^1$H NMR (400 MHz, CDCl$_3$) 7.67 (d, 1H), 7.60 (s, 1H), 7.33-7.23 (m, 2H), 7.18 (d, 1H), 6.74-6.64 (m, 2H), 5.55 (dd, 1H), 3.60 (dd, 1H), 3.11 (dd, 1H), 1.33 (s, 12H)

Step 2: 5-(2',5'-difluoro-4'-methanesulfonyl-biphenyl-3-yl)-1-(2,4-difluoro-phenyl)-3-pentafluoroethyl-4,5-dihydro-1H-pyrazole To 1-bromo-2,5-difluoro-4-(methylsulfonyl)benzene (19.0 mg, 0.07 mmol), were added 1,2-dimethylethane (1.5 mL) and Pd(PPh$_3$)$_4$ (8.1 mg, cat.). To the reaction mixture, were added 1-(2,4-difluoro-phenyl)-3-pentafluoroethyl-5-(3-(4,4,5,5-tetramethyl-1,3,2-dioxaborolan-2-yl)phenyl)-4,5-dihydro-1H-pyrazole (35 mg, 0.07 mmol) prepared in Step 1, ethanol (350.0 uL), and a 2N sodium carbonate solution (350.0 uL). The reaction mixture was stirred at 88° C. for 2 hours. Distilled water was added to the reaction mixture, which was then extracted with diethyl ether two times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/5) to give 10.0 mg of the titled compound as a pale yellow liquid.

$^1$H NMR (400 MHz, CDCl$_3$) 7.82 (t, 1H), 7.45-7.30 (m, 4H), 7.22-7.12 (m, 2H), 6.78 (t, 1H), 6.69 (t, 1H), 5.64 (dd, 1H), 3.71 (dd, 1H), 3.28 (s, 3H), 3.15 (dd, 1H)

Examples 69 to 88

The compounds of Examples 69 to 88 were prepared in accordance with the same procedures as in Step 2 of Example 68, except for using 1-(2,4-difluoro-phenyl)-3-pentafluoroethyl-5-(3-(4,4,5,5-tetramethyl-1,3,2-dioxaborolan-2-yl)phenyl)-4,5-dihydro-1H-pyrazole prepared in Step 1 of Example 68; and using each substituted aryl bromide or heteroaryl bromide corresponding to the compounds of Examples 69 to 88 instead of 1-bromo-2,5-difluoro-4-(methylsulfonyl)benzene.

Example 69

1-(2,4-difluoro-phenyl)-5-(4'-methanesulfonyl-3'-trifluoromethyl-biphenyl-3-yl)-3-pentafluoroethyl-4,5-dihydro-1H-pyrazole $^1$H NMR (400 MHz, CDCl$_3$) 8.36 (d, 1H), 7.94 (s, 1H), 7.82 (d, 1H), 7.82 (t, 1H), 7.50 (d, 1H), 7.43-7.36 (m, 3H), 7.25 (d, 1H), 6.78 (t, 1H), 6.69 (t, 1H), 5.69 (dd, 1H), 3.72 (dd, 1H), 3.22-3.17 (m, 4H)

Example 70

5-[3'-cyano-4'-(methanesulfonyl)-biphenyl-3-yl]-1-(2,4-difluoro-phenyl)-3-pentafluoroethyl-4,5-dihydro-1H-pyrazole $^1$H NMR (400 MHz, CDCl$_3$) 8.24 (d, 1H), 7.96 (s, 1H), 7.85 (d, 1H), 7.50 (d, 1H), 7.47-7.35 (m, 3H), 7.26 (m, 1H), 6.78 (t, 1H), 6.69 (t, 1H), 5.69 (dd, 1H), 3.72 (dd, 1H), 3.31 (s, 3H), 3.17 (dd, 1H)

Example 71

1-(2,4-difluoro-phenyl)-5-(3-(2-methyl-pyridin-3-yl)-phenyl)-3-pentafluoroethyl-4,5-dihydro-1H-pyrazole $^1$H NMR (400 MHz, CDCl$_3$) 8.50 (d, 1H), 7.39-7.32 (m, 3H), 7.18-7.16 (m, 3H), 7.06 (s, 1H), 6.75 (t, 1H), 6.68 (t, 1H), 5.63 (dd, 1H), 3.68 (dd, 1H), 3.22 (dd, 1H), 2.32 (s, 3H)

Example 72

1-(2,4-difluoro-phenyl)-3-pentafluoroethyl-5-(3-(2-trifluoromethyl-pyridin-5-yl)-phenyl)-4,5-dihydro-1H-pyrazole $^1$H NMR (400 MHz, CDCl$_3$) 8.81 (s, 1H), 7.91 (d, 1H), 7.75 (d, 1H), 7.48-7.36 (m, 3H), 7.34 (s, 1H), 7.23 (d, 1H), 6.77 (t, 1H), 6.68 (t, 1H), 5.67 (dd, 1H), 3.71 (dd, 1H), 3.20 (dd, 1H)

Example 73

1-(2,4-difluoro-phenyl)-5-(3-(3-formyl-2-methoxy-pyridin-5-yl)-phenyl)-3-pentafluoroethyl-4,5-dihydro-1H-pyrazole $^1$H NMR (400 MHz, CDCl$_3$) 10.42 (s, 1H), 8.49 (s, 1H), 8.21 (s, 1H), 7.43-7.35 (m, 3H), 7.30 (s, 1H), 7.14 (d, 1H), 6.75 (t, 1H), 6.68 (t, 1H), 5.65 (dd, 1H), 4.36 (s, 3H), 3.68 (dd, 1H), 3.20 (dd, 1H)

Example 74

1-(2,4-difluoro-phenyl)-5-(3-(5-fluoro-pyridin-3-yl)-phenyl)-3-pentafluoroethyl-4,5-dihydro-1H-pyrazole $^1$H NMR (400 MHz, CDCl$_3$) 8.54 (s, 1H), 8.46 (s, 1H), 7.48-7.35 (m, 4H), 7.32 (s, 1H), 7.20 (d, 1H), 6.77 (t, 1H), 6.68 (t, 1H), 5.66 (dd, 1H), 3.70 (dd, 1H), 3.18 (dd, 1H)

Example 75

1-(2,4-difluoro-phenyl)-5-(3-(2-methoxy-pyridin-3-yl)-phenyl)-3-pentafluoroethyl-4,5-dihydro-1H-pyrazole $^1$H NMR (400 MHz, CDCl$_3$) 8.15 (d, 1H), 7.47 (d, 1H), 7.41 (d, 1H), 7.40-7.29 (m, 3H), 7.11 (d, 1H), 6.96 (t, 1H), 6.75 (t, 1H), 6.68 (t, 1H), 5.63 (dd, 1H), 3.93 (s, 3H), 3.67 (dd, 1H), 3.21 (dd, 1H)

Example 76

1-(2,4-difluoro-phenyl)-5-[3'-fluoro-4'-(hydroxymethyl)-5'-(methylsulfonyl)-biphenyl-3-yl]-3-pentafluoroethyl-4,5-dihydro-1H-pyrazole $^1$H NMR (400 MHz, CDCl$_3$) 7.99 (s, 1H), 7.50-7.46 (m, 2H), 7.41-7.37 (m, 2H), 7.34 (s, 1H), 7.20 (d, 1H), 6.77 (t, 1H), 6.68 (t, 1H), 5.66 (dd, 1H), 5.06 (d, 2H), 3.70 (dd, 1H), 3.26 (s, 3H), 3.18 (dd, 1H), 2.92 (t, 1H)

Example 77

1-(2,4-difluoro-phenyl)-5-[3-(2-methylsulfanyl-pyridin-5-yl)-phenyl]-3-pentafluoroethyl-4,5-dihydro-1H-pyrazole $^1$H NMR (400 MHz, CDCl$_3$) 8.55 (s, 1H), 7.58 (d, 1H), 7.41-7.28 (m, 4H), 7.23 (d, 1H), 7.13 (d, 1H), 6.77 (t, 1H), 6.68 (t, 1H), 5.64 (dd, 1H), 3.68 (dd, 1H), 3.20 (dd, 1H), 2.60 (s, 3H)

Example 78

5-[3-(2-cyano-pyridin-5-yl)-phenyl]-1-(2,4-difluoro-phenyl)-3-pentafluoroethyl-4,5-dihydro-1H-pyrazole $^1$H NMR (400 MHz, CDCl$_3$) 8.82 (s, 1H), 7.88 (d, 1H), 7.76 (d, 1H). 7.48-7.34 (m, 4H), 7.25 (d, 1H), 6.77 (t, 1H), 6.68 (t, 1H), 5.67 (dd, 1H), 3.70 (dd, 1H), 3.18 (dd, 1H)

Example 79

1-(2,4-difluoro-phenyl)-5-[3-(5-formyl-pyridin-2-yl)-phenyl]-3-pentafluoroethyl-4,5-dihydro-1H-pyrazole $^1$H NMR (400 MHz, CDCl$_3$) 10.14 (s, 1H), 9.12 (s, 1H), 8.23 (d, 1H), 7.96 (d, 1H), 7.92 (s, 1H), 7.81 (d, 1H), 7.43-7.34 (m, 2H), 7.26 (d, 1H), 6.75 (t, 1H), 6.66 (t, 1H), 5.70 (dd, 1H), 3.70 (dd, 1H), 3.21 (dd, 1H)

Example 80

1-(2,4-difluoro-phenyl)-5-[3-(6-hydroxy-pyridin-3-yl)-phenyl]-3-pentafluoroethyl-4,5-dihydro-1H-pyrazole $^1$H NMR (400 MHz, CDCl$_3$) 7.34-7.26 (m, 4H), 7.12 (t, 1H), 6.76-6.70 (m, 4H), 6.60 (s, 1H), 5.52 (dd, 1H), 4.82 (s, 1H), 3.62 (dd, 1H), 3.15 (dd, 1H)

Example 81

1-(2,4-difluoro-phenyl)-5-[3-(5-methanesulfonyl-pyridin-2-yl)-phenyl]-3-pentafluoroethyl-4,5-dihydro-1H-pyrazole $^1$H NMR (400 MHz, CDCl$_3$) 9.19 (s, 1H), 8.26 (d, 1H), 7.93 (d, 2H), 7.81 (d, 1H), 7.44-7.34 (m, 2H), 7.27 (d, 1H), 6.75 (t, 1H), 6.67 (t, 1H), 5.68 (dd, 1H), 3.71 (dd, 1H), 3.21 (dd, 1H), 3.14 (s, 3H)

Example 82

1-(2,4-difluoro-phenyl)-5-[3-(2,5-difluoro-4-[1,2,4]triazol-1-yl-phenyl)-phenyl]-3-pentafluoroethyl-4,5-dihydro-1H-pyrazole $^1$H NMR (400 MHz, CDCl$_3$) 8.77 (s, 1H), 8.18 (s, 1H), 7.78 (t, 1H), 7.47-7.36 (m, 3H), 7.28-7.24 (m, 2H), 7.19 (d, 1H), 6.76 (t, 1H), 6.69 (t, 1H), 5.66 (dd, 1H), 3.71 (dd, 1H), 3.20 (dd, 1H)

Example 83

1-(2,4-difluoro-phenyl)-5-{3'-[(2-hydroxy-ethyl)-methyl-sulfamoyl]-biphenyl-3-yl}-3-pentafluoroethyl-4,5-dihydro-1H-pyrazole $^1$H NMR (400 MHz, CDCl$_3$) 7.88 (s, 1H), 7.78 (d, 1H), 7.69 (d, 1H), 7.60 (dd, 1H), 7.46 (d, 1H), 7.42-7.33 (m, 3H), 7.17 (d, 1H), 6.79 (dd, 1H), 6.70 (dd, 1H), 5.67 (dd, 1H), 3.80 (t, 2H), 3.70 (dd, 1H), 3.23-3.17 (m, 3H), 2.88 (s, 3H)

Example 84

1-(2,4-difluoro-phenyl)-5-{4'-[(2-hydroxy-ethyl)-(methanesulfonyl)-amino]-biphenyl-3-yl}-3-pentafluoroethyl-4,5-dihydroxy-1H-pyrazole $^1$H NMR (400 MHz, CDCl$_3$) 7.52-7.32 (m, 8H), 7.13 (d, 1H), 6.75 (dd, 1H), 6.68 (dd, 1H), 5.65 (dd, 1H), 3.89-3.83 (m, 2H), 3.75-3.65 (m, 3H), 3.20 (dd, 1H), 3.01 (s, 3H)

Example 85

5-{3'-[3-(N-BOC-N-methyl-amino)-propane-1-sulfonyl]-biphenyl-3-yl}-1-(2,4-difluoro-phenyl)-3-pentafluoroethyl-4,5-dihydro-1H-pyrazole $^1$H NMR (400 MHz, CDCl$_3$) 8.00 (s, 1H), 7.88 (d, 1H), 7.75 (d, 1H), 7.64 (t, 1H), 7.48 (t, 1H), 7.41-7.37 (m, 3H), 7.17 (d, 1H), 6.78 (t, 1H), 6.70 (t, 1H), 5.68 (dd, 1H), 3.70 (dd, 1H), 3.31 (t, 2H), 3.21 (dd, 1H), 3.12 (t, 2H), 2.81 (s, 3H), 1.99 (m, 2H), 1.39 (s, 9H)

Example 86

5-{4'-[3-(N-BOC-N-methyl-amino)-propane-1-sulfonyl]-biphenyl-3-yl}-1-(2,4-difluoro-phenyl)-3-pentafluoroethyl-4,5-dihydro-1H-pyrazole $^1$H NMR (400 MHz, CDCl$_3$) 7.95 (d, 2H), 7.64 (d, 2H), 7.47 (d, 1H), 7.41-7.36 (m, 3H), 7.19 (d, 1H), 6.77 (t, 1H), 6.68 (t, 1H), 5.67 (dd, 1H), 3.71 (dd, 1H), 3.31 (t, 2H), 3.21 (dd, 1H), 3.11 (t, 2H), 2.82 (s, 3H), 1.97 (m, 2H), 1.41 (s, 9H)

Example 87

1-(2,4-difluoro-phenyl)-5-(3'-dimethylsulfamoyl-biphenyl-3-yl)-3-pentafluoroethyl-4,5-dihydro-1H-pyrazole $^1$H NMR (400 MHz, CDCl$_3$) 7.85 (s, 1H), 7.75 (d, 1H), 7.69 (d, 1H), 7.60 (t, 1H), 7.47 (d, 1H), 7.41-7.34 (m, 3H), 7.17 (d, 1H), 6.78 (t, 1H), 6.69 (t, 1H), 5.67 (dd, 1H), 3.71 (dd, 1H), 3.21 (dd, 1H), 2.74 (s, 6H)

Example 88

1-(2,4-difluoro-phenyl)-5-{4'-[(2-hydroxy-ethyl)-methyl-sulfamoyl]-biphenyl-3-yl}-3-pentafluoroethyl-4,5-dihydro-1H-pyrazole $^1$H NMR (400 MHz, CDCl$_3$) 7.86 (d, 2H), 7.61 (d, 2H), 7.47 (d, 1H), 7.40-7.36 (m, 3H), 7.17 (d, 1H), 6.76 (t, 1H), 6.69 (t, 1H), 5.65 (dd, 1H), 3.80 (m, 2H), 3.73 (dd, 1H), 3.23-3.17 (m, 3H), 2.88 (s, 3H), 2.12 (t, 1H)

Example 89

1-(2,4-difluoro-phenyl)-5-{3'-[3-(N-methyl-amino)-propane-1-sulfonyl]-biphenyl-3-yl}-3-pentafluoroethyl-4,5-dihydro-1H-pyrazole 5-{3'[3-(N-BOC-N-methyl-amino)-propane-1-sulfonyl]-biphenyl-3-yl}-1-(2,4-difluoro-phenyl)-3-pentafluoroethyl-4,5-dihydro-1H-pyrazole (20.0 mg, 0.03 mmol) prepared in Example 85 and trifluoroacetic acid (22.3 uL, 0.29 mmol) were added at 0° C. to dichloromethane (1.0 mL). The reaction mixture was stirred at room temperature for 1 hour, quenched with a saturated solution of sodium hydrogen carbonate, and then extracted with dichloromethane three times. The combined extract was washed with brine, dried on anhydrous magnesium sulfate, and then concentrated under reduced pressure to give a residue as a white liquid. The resulting residue was purified by silica gel column chromatography (eluent: ethyl acetate/n-hexane=1/2) to give 5.0 mg of the titled compound as a white solid.

$^1$H NMR (400 MHz, CDCl$_3$) 8.00 (s, 1H), 7.88 (d, 1H), 7.75 (d, 1H), 7.64 (t, 1H), 7.48 (t, 1H), 7.41-7.37 (m, 3H), 7.17 (d, 1H), 6.78 (t, 1H), 6.70 (t, 1H), 5.68 (dd, 1H), 3.70 (dd, 1H), 3.22 (t, 2H), 3.20 (dd, 1H), 2.67 (t, 2H), 2.37 (s, 3H), 1.96 (m, 2H)

Example 90

1-(2,4-difluoro-phenyl)-5-[3-(5-hydroxymethyl-6-methoxy-pyridin-3-yl)-phenyl]-3-pentafluoroethyl-4,5-dihydro-1H-pyrazole To a solution of 1-(2,4-difluoro-phenyl)-5-(3-(3-formyl-2-methoxy-pyridin-5-yl)-phenyl)-3-pentafluoroethyl-4,5-dihydro-1H-pyrazole (20 mg, 0.04 mmol) prepared in Example 73 in ethanol (1 mL), was slowly added sodium borohydride (6.0 mg, 0.16 mmol) at 0° C. The reaction mixture was stirred at room temperature for 1 hour, quenched with a 1N hydrochloric acid solution, and then extracted with ethyl acetate three times. The combined extract was washed with brine, dried on anhydrous magnesium sulfate, and then concentrated under reduced pressure to give a residue as a pale yellow liquid. The resulting residue was purified by silica gel column chromatography (eluent: ethyl acetate/n-hexane=2/1) to give 3.0 mg of the titled compound as a white solid.

$^1$H NMR (400 MHz, CDCl$_3$) 8.18 (s, 1H), 7.70 (s, 1H), 7.40-7.31 (m, 3H), 7.26 (d, 1H), 7.10 (d, 1H), 6.72 (t, 1H), 6.67 (t, 1H), 5.63 (dd, 1H), 4.70 (s, 2H), 4.04 (s, 3H), 3.69 (dd, 1H), 3.21 (dd, 1H)

Example 91

1-(2,4-difluoro-phenyl)-5-[3-(5-hydroxymethyl-pyridin-2-yl)-phenyl]-3-pentafluoroethyl-4,5-dihydro-1H-pyrazole To a solution of 1-(2,4-difluoro-phenyl)-5-[3-(5-formyl-pyridin-2-yl)-phenyl]-3-pentafluoroethyl-4,5-dihydro-1H-pyrazole (20 mg, 0.04 mmol) prepared in Example 79 in ethanol (1 mL), was slowly added sodium borohydride (6.0 mg, 0.16 mmol) at 0° C. The reaction mixture was stirred at room temperature for 1 hour, quenched with a 1N hydrochloric acid solution, and then extracted with ethyl acetate three times. The combined extract was washed with brine, dried on anhydrous magnesium sulfate, and then concentrated under reduced pressure to give a residue as a pale yellow liquid. The resulting residue was purified by silica gel column chromatography (eluent: ethyl acetate/n-hexane=2/1) to give 3.0 mg of the titled compound as a white solid.

$^1$H NMR (400 MHz, CDCl$_3$) 8.63 (s, 1H), 7.83-7.61 (m, 3H), 7.62 (d, 1H), 7.38-7.32 (m, 2H), 7.16 (d, 1H), 6.74-6.63 (m, 2H), 5.66 (dd, 1H), 4.76 (s, 2H), 3.67 (dd, 1H), 3.21 (dd, 1H)

Example 92

1-(2,4-difluoro-phenyl)-5-[3-(6-methanesulfonyl-pyridin-3-yl)-phenyl]-3-pentafluoroethyl-4,5-dihydro-1H-pyrazole To a mixture of 1-(2,4-difluoro-phenyl)-5-[3-(2-methylsulfanyl-pyridin-5-yl)-phenyl]-3-pentafluoroethyl-4,5-dihydro-1H-pyrazole (150 mg, 0.28 mmol) prepared in Example 77 in dichloromethane (5.0 mL), was slowly added meta-chloroperbenzoic acid (77%, 134.5 mg, 0.56 mmol) at 0° C. The reaction mixture was stirred at room temperature for 1 hour, quenched with a saturated solution of sodium hydrogen carbonate, and then extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/5, 1/1) to give 135.0 mg of the titled compound as a yellow liquid.

$^1$H NMR (400 MHz, CDCl$_3$) 8.80 (s, 1H), 8.15 (d, 1H), 8.01 (d, 1H), 7.50-7.36 (m, 4H), 7.26 (d, 1H), 6.77 (t, 1H), 6.66 (t, 1H), 5.69 (dd, 1H), 3.73 (dd, 1H), 3.27 (s, 3H), 3.20 (dd, 1H)

Example 93

1-(2,4-difluoro-phenyl)-5-[3-(2-methanesulfonyl-pyrimidin-5-yl)-phenyl]-3-pentafluoroethyl-4,5-dihydro-1H-pyrazole To 5-bromo-2-(methylthio)pyrimidine (30.6 mg, 0.15 mmol), were added 1,2-dimethylethane (2 mL) and Pd(PPh$_3$)$_4$ (12.0 mg, cat.). To the reaction mixture, were added 1-(2,4-difluoro-phenyl)-3-pentafluoroethyl-5-(3-(4,4,5,5-tetramethyl-1,3,2-dioxaborolan-2-yl)phenyl)-4,5-dihydro-1H-pyrazole (50 mg, 0.10 mmol) prepared in Step 1 of Example 68, ethanol (500.0 uL), and a 2N sodium carbonate solution (500.0 uL). The reaction mixture was stirred at 88° C. for 2 hours. Distilled water was added to the reaction mixture, which was then extracted with diethyl ether two times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/8) to give 15.0 mg of the compound as a yellow liquid. To a mixture of the compound in dichloromethane (1.0 mL), was slowly added meta-chloroperbenzoic acid (77%, 15.0 mg, 0.01 mmol) at 0° C. The reaction mixture was stirred at room temperature for 1 hour, quenched with a saturated solution of sodium hydrogen carbonate, and then extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/1) to give 8.8 mg of the titled compound as a yellow liquid.

$^1$H NMR (400 MHz, CDCl$_3$) 8.96 (s, 2H), 7.50 (d, 2H), 7.41 (q, 1H), 7.34-7.31 (m, 2H), 6.80 (t, 1H), 6.69 (t, 1H), 3.74 (dd, 1H), 3.40 (s, 3H)}, 3.21 (dd, 1H)

Example 94

5-biphenyl-3-yl-1-(2,4-difluoro-phenyl)-3-pentafluoroethyl-4,5-dihydro-1H-pyrazole 5-(3-Bromo-phenyl)-1-(2,4-difluoro-phenyl)-3-pentafluoroethyl-4,5-dihydro-1H-pyrazole (500.0 mg, 0.10 mmol) prepared in Step 2 of Preparation 5, phenylboronic acid (201.0 mg, 1.65 mmol), Pd(PPh$_3$)$_4$ (64.0 mg, cat.) and a 2N sodium carbonate solution (3.3 mL) were added to N,N-dimethylformamide (5.0 mL). The reaction mixture was stirred at 80° C. for 18 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/60) to give 437.0 mg of the titled compound as a yellow liquid.

$^1$H NMR (400 MHz, CDCl$_3$) 7.48-7.30 (m, 9H), 7.01 (d, 1H), 6.76 (t, 1H), 6.68 (t, 1H), 5.65 (dd, 1H), 3.68 (dd, 1H), 3.21 (dd, 1H)

Example 95

5-[3-(4-BOC-piperazin-1-yl)-phenyl]-1-(2,4-difluoro-phenyl)-3-pentafluoroethyl-4,5-dihydro-1H-pyrazole 5-(3-Bromo-phenyl)-1-(2,4-difluoro-phenyl)-3-pentafluoroethyl-4,5-dihydro-1H-pyrazole (1.0 g, 2.20 mmol) prepared in Step 2 of Preparation 5, 1-BOC-piperazine (614.0 mg, 3.30 mmol), Pd$_2$(dba)$_3$ (101.0 mg, cat.), BINAP (137.0 mg, cat.) and sodium t-butoxide (380.0 mg, 4.00 mmol) were added to toluene (33.0 mL). The reaction mixture was stirred at 100° C. for 12 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/3) to give 760.0 mg of the titled compound as a yellow liquid.

$^1$H NMR (400 MHz, CDCl$_3$) 7.29 (q, 1H), 7.14 (t, 1H), 6.78-6.61 (m, 5H), 5.52 (dd, 1H), 3.62 (dd, 1H), 3.58 (t, 4H), 3.16 (dd, 1H), 3.05 (t, 4H), 1.48 (s, 9H)

Example 96

1-(2,4-difluoro-phenyl)-5-[3-(4-methanesulfonyl-piperazin-1-yl)-phenyl]-3-pentafluoroethyl-4,5-dihydro-1H-pyrazole

Step 1: 5-[3-(piperazin-1-yl)-phenyl]-1-(2,4-difluoro-phenyl)-3-pentafluoroethyl-4,5-dihydro-1H-pyrazole hydrochloride 5-[3-(4-BOC-piperazin-1-yl)-phenyl]-1-(2,4-difluoro-phenyl)-3-pentafluoroethyl-4,5-dihydro-1H-pyrazole (760.0 mg, 1.6 mmol) prepared in Example 95 was added to a saturated solution of hydrochloric acid in ethyl acetate (10.0 mL). The reaction mixture was stirred at room temperature for 2 hours and then concentrated under reduced pressure to give 700.0 mg of the titled compound as a brown liquid.

Step 2: 1-(2,4-difluoro-phenyl)-5-[3-(4-methanesulfonyl-piperazin-1-yl)-phenyl]-3-pentafluoroethyl-4,5-dihydro-1H-pyrazole 5-[3-(piperazin-1-yl)-phenyl]-1-(2,4-difluoro-phenyl)-3-pentafluoroethyl-4,5-dihydro-1H-pyrazole hydrochloride (100.0 mg, 0.2 mmol) prepared in Step 1, triethylamine (143.0 uL, 1.02 mmol) and methanesulfonyl chloride (35.0 mg, 0.30 mmol) were added to dichloromethane (2.0 mL). The reaction mixture was stirred at room temperature for 18 hours, washed with distilled water, 1N hydrochloride, a saturated solution of sodium hydrogen carbonate, and brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 55.0 mg of the titled compound as a yellow liquid.

$^1$H NMR (400 MHz, CDCl$_3$) 7.30 (q, 1H), 7.16 (t, 1H), 6.79-6.65 (m, 5H), 5.53 (dd, 1H), 3.64 (dd, 1H), 3.36 (t, 4H), 3.20 (t, 4H), 3.16 (dd, 1H), 2.81 (s, 3H)

Example 97

5-[3-(4-cyclopropanesulfonyl-piperazin-1-yl)-phenyl]-1-(2,4-difluoro-phenyl)-3-pentafluoroethyl-4,5-dihydro-1H-pyrazole 5-[3-(Piperazin-1-yl)-phenyl]-1-(2,4-difluoro-phenyl)-3-pentafluoroethyl-4,5-dihydro-1H-pyrazole hydrochloride (100.0 mg, 0.2 mmol) prepared in Step 1 of Example 96, triethylamine (143.0 uL, 1.02 mmol) and cyclopropanesulfonyl chloride (43.0 mg, 0.30 mmol) were added to dichloromethane (2.0 mL). The reaction mixture was stirred at room temperature for 18 hours, washed with distilled water, 1N hydrochloride, a saturated solution of sodium hydrogen carbonate, and brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 80.0 mg of the titled compound as a yellow liquid.

$^1$H NMR (400 MHz, CDCl$_3$) 7.30 (q, 1H), 7.16 (t, 1H), 6.79-6.65 (m, 5H), 5.53 (dd, 1H), 3.60 (dd, 1H), 3.42 (t, 4H), 3.17 (t, 4H), 3.14 (dd, 1H), 2.28 (m, 1H), 1.21 (m, 2H), 1.01 (m, 2H)

Example 98

5-{3-[4-(N-BOC-amino)-piperidin-1-yl]-phenyl}-1-(2,4-difluoro-phenyl)-3-pentafluoroethyl-4,5-dihydro-1H-pyrazole 5-(3-Bromo-phenyl)-1-(2,4-difluoro-phenyl)-3-pentafluoroethyl-4,5-dihydro-1H-pyrazole (200.0 mg, 0.44 mmol) prepared in Step 2 of Preparation 5, 4-(N-BOC-amino)-piperidine (132.0 mg, 0.66 mmol), Pd$_2$(dba)$_3$ (20.0 mg, cat.), BINAP (27.0 mg, cat.) and sodium t-butoxide (76.0 mg, 0.79 mmol) were added to toluene (4.0 mL). The reaction mixture was stirred at 100° C. for 12 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/3) to give 110.0 mg of the titled compound as a yellow liquid.

$^1$H NMR (400 MHz, CDCl$_3$) 7.30 (q, 1H), 7.10 (t, 1H), 6.78-6.64 (m, 4H), 6.57 (d, 1H), 5.49 (dd, 1H), 4.45 (br, NH), 3.65-3.57 (m, 2H), 3.49 (dd, 2H), 3.13 (dd, 1H), 2.76 (t, 2H), 2.03 (d, 2H), 1.50 (m, 2H), 1.48 (s, 9H)

Example 99

5-[3-(4-amino-piperidin-1-yl)-phenyl]-1-(2,4-difluoro-phenyl)-3-pentafluoroethyl-4,5-dihydro-1H-pyrazole hydrochloride 5-{3-[4-(N-BOC-amino)-piperidin-1-yl]-phenyl}-1-(2,4-difluoro-phenyl)-3-pentafluoroethyl-4,5-dihydro-1H-pyrazole (110.0 mg, 6.6 mmol) prepared in Example 98 was added to a saturated solution of hydrochloric acid in ethyl acetate (3.0 mL). The reaction mixture was stirred at room temperature for 2 hours and then concentrated under reduced pressure to give 100.0 mg of the titled compound as a brown liquid.

$^1$H NMR (400 MHz, CD$_3$OD) 7.45-7.37 (m, 4H), 7.18 (d, 1H), 6.90-6.84 (m, 2H), 5.69 (dd, 1H), 3.82-3.71 (m, 3H), 3.54-3.46 (m, 3H), 3.12 (dd, 1H), 2.29 (d, 2H), 2.12 (m, 2H)

Example 100

1-(2,4-difluoro-phenyl)-5-[3-(4-methanesulfonylamino-piperidin-1-yl)-phenyl]-3-pentafluoroethyl-4,5-dihydro-1H-pyrazole 5-[3-(4-Amino-piperidin-1-yl)-phenyl]-1-(2,4-difluoro-phenyl)-3-pentafluoroethyl-4,5-dihydro-1H-pyrazole hydrochloride (50.0 mg, 0.11 mmol) prepared in Example 99, triethylamine (55.0 mg, 0.54 mmol) and methanesulfonyl chloride (18.5 mg, 0.16 mmol) were added to dichloromethane (1.0 mL). The reaction mixture was stirred at room temperature for 18 hours, washed with distilled water, 1N hydrochloride, a saturated solution of sodium hydrogen carbonate, and brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 15.0 mg of the titled compound as a yellow liquid.

$^1$H NMR (400 MHz, CDCl$_3$) 7.31 (q, 1H), 7.12 (t, 1H), 6.78-6.59 (m, 5H), 5.58 (dd, 1H), 4.20 (d, 1H), 3.61 (dd, 1H), 3.53-3.48 (m, 3H), 3.15 (dd, 1H), 3.01 (s, 3H), 2.81 (t, 2H), 2.07 (d, 2H), 1.60 (m, 2H)

Example 101

1-(2-chloro-phenyl)-3-pentafluoroethyl-5-(3'-trifluoromethyl-biphenyl-3-yl)-4,5-dihydro-1H-pyrazole 5-(3-Bromo-phenyl)-1-(2-chloro-phenyl)-3-pentafluoroethyl-4,5-dihydro-1H-pyrazole (20.0 mg, 0.04 mmol) prepared in Step 1 of Preparation 6, 3-(trifluoromethyl)phenylboronic acid (17.0 mg, 0.09 mmol), Pd(PPh$_3$)$_4$ (2.5 mg, cat.) and a 2N sodium carbonate solution (1.0 mL) were added to N,N-dimethylformamide (2.0 mL). The reaction mixture was stirred at 80° C. for 2 hours and then filtered through celite pad. A saturated solution of ammonium chloride was added to filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/8) to give 18.0 mg of the titled compound as a yellow liquid.

$^1$H NMR (400 MHz, CDCl$_3$) 7.66-7.57 (m, 3H), 7.56-7.50 (m, 1H), 7.40 (d, 1H), 7.36-7.29 (m, 2H), 7.29-7.21 (m, 2H), 7.17 (d, 1H), 7.13-7.06 (m, 1H), 6.99-6.92 (m, 1H), 5.98 (dd, 1H), 3.77-3.67 (m, 1H), 3.30 (dd, 1H)

Examples 102 to 107

The compounds of Examples 102 to 107 were prepared in accordance with the same procedures as in Example 101, except for using 5-(3-bromo-phenyl)-1-(2-chloro-phenyl)-3-pentafluoroethyl-4,5-dihydro-1H-pyrazole prepared in Step 1 of Preparation 6; and using each boronic acid corresponding to the compounds of Examples 102 to 107 instead of 3-(trifluoromethyl)phenylboronic acid.

Example 102

1-(2-chloro-phenyl)-5-(4'-methoxy-biphenyl-3-yl)-3-pentafluoroethyl-4,5-dihydro-1H-pyrazole $^1$H NMR (400 MHz, CDCl$_3$) 7.41-7.33 (m, 3H), 7.31 (s, 1H), 7.28-7.21 (m, 3H), 7.12-7.03 (m, 2H), 6.99-6.90 (m, 3H), 5.93 (dd, 1H), 3.85 (s, 3H), 3.76-3.65 (m, 1H), 3.30 (dd, 1H)

Example 103

1-(2-chloro-phenyl)-5-(4'-fluoro-biphenyl-3-yl)-3-pentafluoroethyl-4,5-dihydro-1H-pyrazole $^1$H NMR (400 MHz, CDCl$_3$) 7.42-7.33 (m, 3H), 7.32-7.21 (m, 4H), 7.15-7.06 (m, 4H), 6.95 (t, 1H), 5.99-5.90 (dd, 1H), 3.77-3.65 (m, 1H), 3.29 (dd, 1H)

Example 104

1-(2-chloro-phenyl)-5-(4'-dimethylamino-biphenyl-3-yl)-3-pentafluoroethyl-4,5-dihydro-1H-pyrazole $^1$H NMR (400 MHz, CDCl$_3$) 7.39-7.33 (m, 3H), 7.32 (s, 1H), 7.28-7.18 (m, 3H), 7.07 (t, 1H), 7.01 (d, 1H), 6.93 (t, 1H), 6.77 (d, 2H), 5.92 (dd, 1H), 3.73-3.65 (m, 1H), 3.31 (dd, 1H), 2.99 (s, 6H)

Example 105

1-(2-chloro-phenyl)-5-(4'-methylsulfanyl-biphenyl-3-yl)-3-pentafluoroethyl-4,5-dihydro-1H-pyrazole $^1$H NMR (400 MHz, CDCl$_3$) 7.50 (d, 1H), 7.40-7.28 (m, 6H), 7.28-7.21 (m, 2H), 7.13-7.04 (m, 2H), 6.94 (t, 1H), 5.94 (dd, 1H), 3.77-3.65 (m, 1H), 3.30 (dd, 1H), 2.52 (s, 3H)

Example 106

1-(2-chloro-phenyl)-5-(4'-methylsulfonyl-biphenyl-3-yl)-3-pentafluoroethyl-4,5-dihydro-1H-pyrazole $^1$H NMR (400 MHz, CDCl$_3$) 7.99 (d, 2H), 7.61 (d, 2H), 7.43 (d, 1H), 7.38-7.32 (m, 2H), 7.31-7.18 (m, 3H), 7.10 (t, 1H), 6.96 (t, 1H), 5.99 (dd, 1H), 3.77-3.70 (m, 1H), 3.30 (dd, 1H), 3.09 (s, 3H)

Example 107

5-(4'-acetyl-biphenyl-3-yl)-1-(2-chloro-phenyl)-3-pentafluoroethyl-4,5-dihydro-1H-pyrazole $^1$H NMR (400 MHz, CDCl$_3$) 8.01 (d, 2H), 7.53 (d, 2H), 7.44 (d, 1H), 7.38 (s, 1H), 7.32 (t, 1H), 7.29-7.22 (m, 2H), 7.17 (d, 1H), 7.09 (t, 1H), 6.95 (t, 1H), 5.98 (dd, 1H), 3.77-3.69 (m, 1H), 3.30 (dd, 1H), 2.64 (s, 3H)

Example 108

1-(2-chloro-phenyl)-5-[4'-(1-hydroxy-ethyl)-biphenyl-3-yl]-3-pentafluoroethyl-4,5-dihydro-1H-pyrazole 5-(4'-Acetyl-biphenyl-3-yl)-1-(2-chloro-phenyl)-3-pentafluoroethyl-4,5-dihydro-1H-pyrazole (18.0 mg, 0.04 mmol) prepared in Example 107 and sodium borohydride (2.0 mg, 0.06 mmol) were added at 0° C. to methanol (2.0 mL). The reaction mixture was stirred at room temperature for 3 hours, quenched with distilled water, and then extracted with ethyl acetate three times. The combined extract was washed with brine, dried on anhydrous magnesium sulfate, and then concentrated under reduced pressure to give 17.0 mg of the titled compound as a yellow liquid.

$^1$H NMR (400 MHz, CDCl$_3$) 7.49-7.37 (m, 5H), 7.35 (s, 1H), 7.31-7.19 (m, 3H), 7.15-7.04 (m, 2H), 6.94 (t, 1H), 5.95 (dd, 1H), 4.95 (q, 1H), 3.75-3.67 (m, 1H), 3.30 (dd, 1H), 1.53 (d, 3H)

Example 109

1-(2-chloro-phenyl)-5-[4'-(1-hydroxyimino-ethyl)-biphenyl-3-yl]-3-pentafluoroethyl-4,5-dihydro-1H-pyrazole 5-(4'-acetyl-biphenyl-3-yl)-1-(2-chloro-phenyl)-3-pentafluoroethyl-4,5-dihydro-1H-pyrazole (18.0 mg, 0.04 mmol) prepared in Example 107 and hydroxylamine hydrochloride (5.0 mg, 0.07 mmol) were added to a mixed solvent of distilled water (30.0 uL) and ethanol (1.5 mL). The reaction mixture was stirred at 50° C. for 3 hours, concentrated under reduced pressure and then ethyl acetate was added thereto. The reaction mixture was washed with distilled water and brine, dried on anhydrous magnesium sulfate, and then concentrated under reduced pressure to give 17.0 mg of the titled compound as a yellow liquid.

$^1$H NMR (400 MHz, CDCl$_3$) 7.69 (d, 2H), 7.61 (brs, 1H), 7.45 (d, 2H), 7.42 (d, 1H), 7.36 (s, 1H), 7.33-7.20 (m, 3H), 7.17-7.05 (m, 2H), 6.95 (t, 1H), 5.96 (dd, 1H), 3.76-3.67 (m, 1H), 3.30 (dd, 1H), 2.31 (s, 3H)

Example 110

5-(2'-acetyl-biphenyl-3-yl)-1-(2-chloro-phenyl)-3-pentafluoroethyl-4,5-dihydro-1H-pyrazole 5-(3-Bromo-phenyl)-1-(2-chloro-phenyl)-3-pentafluoroethyl-4,5-dihydro-1H-pyrazole (20.0 mg, 0.04 mmol) prepared in Step 1 of Preparation 6, 2-acetylphenylboronic acid (9.0 mg, 0.06 mmol), Pd(dppf)Cl$_2$ (2.0 mg, cat.) and a 2N sodium carbonate solution (0.5 mL) were added to N,N-dimethylformamide (0.5 mL). The reaction mixture was stirred at 80° C. for 2 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/5) to give 10.0 mg of the titled compound as a yellow liquid.

$^1$H NMR (400 MHz, CDCl$_3$) 7.54-7.47 (m, 2H), 7.43-7.39 (m, 1H), 7.27-7.18 (m, 5H), 7.13-7.06 (m, 3H), 6.94 (t, 1H), 5.95 (dd, 1H), 3.73 (dd, 1H), 3.31 (dd, 1H), 1.67 (s, 3H)

Examples 111 to 115

The compounds of Examples 111 to 115 were prepared in accordance with the same procedures as in Example 110, except for using 5-(3-bromo-phenyl)-1-(2-chloro-phenyl)-3-pentafluoroethyl-4,5-dihydro-1H-pyrazole prepared in Step 1 of Preparation 6; and using each boronic acid corresponding to the compounds of Examples 111 to 115 instead of 2-acetylphenylboronic acid.

Example 111

1-(2-chloro-phenyl)-5-(3'-hydroxy-biphenyl-3-yl)-3-pentafluoroethyl-4,5-dihydro-1H-pyrazole $^1$H NMR (400 MHz, CDCl$_3$) 7.39-7.22 (m, 6H), 7.11 (t, 2H), 7.01 (d, 1H), 6.95 (t, 1H), 6.90 (s, 1H), 6.81 (d, 1H), 5.94 (dd, 1H), 4.83 (s, 1H), 3.75-3.66 (m, 1H), 3.29 (dd, 1H)

Example 112

1-(2-chloro-phenyl)-5-(3',4'-dimethoxy-biphenyl-3-yl)-3-pentafluoroethyl-4,5-dihydro-1H-pyrazole $^1$H NMR (400 MHz, CDCl$_3$) 7.37 (d, 1H), 7.32 (s, 1H), 7.28-7.22 (m, 3H), 7.09-7.06 (m, 2H), 7.02-6.91 (m, 4H), 5.95 (dd, 1H), 3.94 (s, 3H), 3.92 (s, 3H), 3.71 (dd, 1H), 3.31 (dd, 1H)

Example 113

1-(2-chloro-phenyl)-5-(3-pyrimidin-5-yl-phenyl)-3-pentafluoroethyl-4,5-dihydro-1H-pyrazole $^1$H NMR (400 MHz, CDCl$_3$) 9.20 (s, 1H), 8.79 (s, 2H), 7.40 (d, 2H), 7.32-7.23 (m, 4H), 7.11 (t, 1H), 6.97 (t, 1H), 6.00 (dd, 1H), 3.79-3.70 (m, 1H), 3.29 (dd, 1H)

Example 114

1-(2-chloro-phenyl)-3-pentafluoroethyl-5-(3-quinolin-3-yl-phenyl)-4,5-dihydro-1H-pyrazole $^1$H NMR (400 MHz, CDCl$_3$) 9.03 (s, 1H), 8.15 (d, 2H), 7.87 (d, 1H), 7.74 (t, 1H), 7.60 (t, 1H), 7.53 (d, 1H), 7.46 (s, 1H), 7.39 (t, 1H), 7.32-7.219 m, 3H), 7.12 (t, 1H), 6.97 (t, 1H), 6.02 (dd, 1H), 3.80-3.72 (m, 1H), 3.33 (dd, 1H)

Example 115

1-(2-chloro-phenyl)-5-[3-(6-methoxy-pyridin-3-yl)-phenyl]-3-pentafluoroethyl-4,5-dihydro-1H-pyrazole $^1$H NMR (400 MHz, CDCl$_3$) 8.23 (d, 1H), 7.63 (dd, 1H), 7.33-7.22 (m, 5H), 7.13-7.07 (m, 2H), 6.95 (t, 1H), 6.80 (d, 1H), 5.95 (dd, 1H), 3.98 (s, 3H), 3.72 (dd, 1H), 3.30 (dd, 1H)

Example 116

5-[3-(1-BOC-1,2,3,6-tetrahydropyridin-4-yl)-phenyl]-1-(2-chloro-phenyl)-3-pentafluoroethyl-4,5-dihydro-1H-pyrazole 5-(3-Bromo-phenyl)-1-(2-chloro-phenyl)-3-pentafluoroethyl-4,5-dihydro-1H-pyrazole (1.0 g, 2.2 mmol) prepared in Step 1 of Preparation 6, 4-(4,4,5,5-tetramethyl-[1,3,2]dioxaborolan-2-yl)-3,6-dihydro-2H-pyridin-1-carboxylic acid tert-butyl ester (820.0 mg, 2.6 mmol), Pd(dppf)Cl$_2$ (181.0 mg, cat.) and potassium carbonate (915.0 mg, 6.6 mmol) were added to a mixed solvent of 1,4-dioxane (32.0 mL) and distilled water (8.0 mL). The reaction mixture was stirred at 90° C. for 12 hours and then filtered through celite pad. A saturated solution of ammonium chloride was added to the filtrate, which was then extracted with ethyl acetate three times. The combined extract washed with brine, dried on anhydrous magnesium sulfate, and then concentrated under reduced pressure to give a yellow liquid residue. The resulting residue was purified by silica gel column chromatography (eluent: ethyl acetate/n-hexane=1/8) to give 1.1 g of the titled compound as a yellow liquid.

$^1$H NMR (400 MHz, CDCl$_3$) 7.23-7.16 (m, 4H), 7.11-7.04 (m, 3H). 6.94 (t, 1H), 5.91 (br, 1H), 5.89 (dd, 1H), 5.30 (s, 1H), 4.04 (s, 2H), 3.67-3.58 (m, 3H), 3.23 (dd, 1H), 2.39 (br, 2H), 1.48 (s, 9H)

Example 117

1-(2-chloro-phenyl)-5-[3-(1,2,3,6-tetrahydropyridin-4-yl)-phenyl]-3-pentafluoroethyl-4,5-dihydro-1H-pyrazole trifluoroacetate 5-[3-(1-BOC-1,2,3,6-tetrahydropyridin-4-yl)-phenyl]-1-(2-chloro-phenyl)-3-pentafluoroethyl-4,5-dihydro-1H-pyrazole (1.0 g, 1.8 mmol) prepared in Example 116 and trifluoroacetic acid (1.4 mL, 18.0 mmol) were added at 0° C. to dichloromethane (9.0 mL). The reaction mixture was stirred at room temperature for 1 hour and then concentrated under reduced pressure to give 1.1 g of the titled compound as a yellow liquid.

$^1$H NMR (400 MHz, CD$_3$OD) 7.32-7.23 (m, 5H), 7.18-7.10 (m, 2H), 6.99 (m, 1H), 6.04 (s, 1H), 5.97 (dd, 1H), 3.81 (s, 1H), 3.81-3.73 (dt, 1H), 3.43 (t, 2H), 3.27 (dd, 1H), 2.69 (br, 2H)

Example 118

1-(2-chloro-phenyl)-5-[3-(1-methanesulfonyl-1,2,3,6-tetrahydropyridin-4-yl)-phenyl]-3-pentafluoroethyl-4,5-dihydro-1H-pyrazole 1-(2-Chloro-phenyl)-5-[3-(1,2,3,6-tetrahydropyridin-4-yl)-phenyl]-3-pentafluoroethyl-4,5-dihydro-1H-pyrazole trifluoroacetate (100.0 mg, 0.18 mmol) prepared in Example 117, triethylamine (74.0 uL, 0.53 mmol) and methanesulfonyl chloride (20.0 uL, 0.26 mmol) were added to dichloromethane (1.0 mL). The reaction mixture was stirred at room temperature for 1 hour, washed with distilled water, 1N hydrochloride, a saturated solution of sodium hydrogen carbonate, and brine, dried on anhydrous magnesium sulfate, and then concentrated under reduced pressure to give a yellow liquid residue. The resulting residue was purified by silica gel column chromatography (eluent: ethyl acetate/n-hexane=1/3) to give 51.0 mg of the titled compound as a yellow liquid.

$^1$H NMR (400 MHz, CD$_3$OD) 7.23-7.16 (m, 4H), 7.11-7.04 (m, 3H). 6.94 (t, 1H), 5.94 (s, 1H), 5.88 (dd, 1H), 3.98 (s, 2H), 3.68 (td, 1H), 3.48 (t, 2H), 3.23 (dd, 1H), 2.84 (s, 3H) 2.53 (br, 2H)

Example 119

5-[3-(4-BOC-piperazin-1-yl)-phenyl]-1-(2-chloro-phenyl)-3-pentafluoroethyl-4,5-dihydro-1H-pyrazole 5-(3-Bromo-phenyl)-1-(2-chloro-phenyl)-3-pentafluoroethyl-4,5-dihydro-1H-pyrazole (650.0 mg, 1.4 mmol) prepared in Step 1 of Preparation 6, 1-BOC-piperazine (402.0 mg, 2.2 mmol), Pd$_2$(dba)$_3$ (66.0 mg, cat.), BINAP (90.0 mg, cat.) and sodium t-butoxide (250.0 mg, 2.6 mmol) were added to toluene (10.0 mL). The reaction mixture was stirred at 100° C. for 12 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/6) to give 600.0 mg of the titled compound as a yellow liquid.

$^1$H NMR (400 MHz, CDCl$_3$) 7.21 (t, 2H), 7.09 (q, 2H), 6.94 (t, 1H), 6.72 (d, 1H), 6.65-6.63 (m, 2H), 5.82 (dd, 1H), 3.64 (dd, 1H), 3.53 (s, 4H), 3.25 (dd, 1H), 3.01 (s, 4H), 1.48 (s, 9H)

Example 120

1-(2-chloro-phenyl)-5-[3-(4-methanesulfonyl-piperazin-1-yl)-phenyl]-3-pentafluoroethyl-4,5-dihydro-1H-pyrazole Step 1: 1-(2-chloro-phenyl)-5-[3-(piperazin-1-yl)-phenyl]-3-pentafluoroethyl-4,5-dihydro-1H-pyrazole hydrochloride 5-[3-(4-BOC-piperazin-1-yl)-phenyl]-1-(2-chloro-phenyl)-3-pentafluoroethyl-4,5-dihydro-1H-pyrazole (600.0 mg, 1.1 mmol) prepared in Example 119 was added to a saturated solution of hydrochloric acid in ethyl acetate (5.0 mL). The reaction mixture was stirred at room temperature for 3 hours and then concentrated under reduced pressure to give 610.0 mg of the titled compound as a brown liquid.

$^1$H NMR (400 MHz, CD$_3$OD) 7.30 (d, 1H), 7.25 (d, 1H), 7.17 (q, 2H), 7.04 (t, 1H), 6.90-6.86 (m, 2H), 6.79 (d, 1H), 5.91 (dd, 1H), 3.75 (dd, 1H), 3.72 (m, 2H), 3.21 (dd, 1H)

Step 2: 1-(2-chloro-phenyl)-5-[3-(4-methanesulfonyl-piperazin-1-yl)-phenyl]-3-pentafluoroethyl-4,5-dihydro-1H-pyrazole 1-(2-Chloro-phenyl)-5-[3-(piperazin-1-yl)-phenyl]-3-pentafluoroethyl-4,5-dihydro-1H-pyrazole hydrochloride (30.0 mg, 0.06 mmol) prepared in Step 1, triethylamine (41.0 uL, 0.30 mmol) and methanesulfonyl chloride (8.3 mg, 0.07 mmol) were added to dichloromethane (1.0 mL). The reaction mixture was stirred at room temperature for 3 hours, washed with distilled water, 1N hydrochloride, a saturated solution of sodium hydrogen carbonate, and brine, dried on anhydrous magnesium sulfate, and then concentrated under reduced pressure to give a yellow liquid residue. The resulting residue was purified by silica gel column chromatography (eluent: ethyl acetate/n-hexane=1/2) to give 15.0 mg of the titled compound as a yellow liquid.

$^1$H NMR (400 MHz, CDCl$_3$) 7.21 (t, 2H), 7.14-7.06 (m, 2H), 6.95 (t, 1H), 6.74-6.66 (m, 3H), 5.83 (dd, 1H), 3.65 (dd, 1H), 3.33 (s, 4H), 3.25 (dd, 1H), 3.14 (s, 4H), 2.81 (s, 3H)

Examples 121 to 123

The compounds of Examples 121 to 123 were prepared in accordance with the same procedures as in Step 2 of Example 120, except for using 1-(2-chloro-phenyl)-5-[3-(piperazin-1-yl)-phenyl]-3-pentafluoroethyl-4,5-dihydro-1H-pyrazole hydrochloride prepared in Step 1 of Example 120; and using sulfamoyl chloride, carbamoyl chloride or acyl chloride corresponding to the compounds of Examples 121 to 123 instead of methanesulfonyl chloride.

Example 121

1-(2-chloro-phenyl)-5-[3-(4-dimethylsulfamoyl-piperazin-1-yl)-phenyl]-3-pentafluoroethyl-4,5-dihydro-1H-pyrazole $^1$H NMR (400 MHz, CDCl$_3$) 7.24-7.19 (m, 2H), 7.13-7.05 (m, 2H), 6.95 (dd, 1H), 6.73-6.66 (m, 3H), 5.82 (dd, 1H), 3.65 (dd, 1H), 3.35-3.32 (m, 4H), 3.23 (dd, 1H), 3.12-3.08 (m, 4H), 2.86 (s, 6H)

Example 122

1-(2-chloro-phenyl)-5-[3-(4-isobutyryl-piperazin-1-yl)-phenyl]-3-pentafluoroethyl-4,5-dihydro-1H-pyrazole $^1$H NMR (400 MHz, CDCl$_3$) 7.23-7.20 (m, 2H), 7.13-7.05 (m, 2H), 6.94 (dd, 1H), 6.74-6.66 (m, 3H), 5.83 (dd, 1H), 3.81-3.60 (m, 5H), 3.24 (dd, 1H), 3.10-3.00 (m, 4H), 2.86-2.78 (m, 1H), 1.15 (d, 6H)

Example 123

1-(2-chloro-phenyl)-5-[3-(4-dimethylcarbamoyl-piperazin-1-yl)-phenyl]-3-pentafluoroethyl-4,5-dihydro-1H-pyrazole $^1$H NMR (400 MHz, CDCl$_3$) 7.23-7.19 (m, 2H), 7.12-7.05 (m, 2H), 6.94 (dd, 1H), 6.72 (d, 1H), 6.67-6.62 (m, 2H), 5.81 (dd, 1H), 3.64 (dd, 1H), 3.36-3.30 (m, 4H), 3.24 (dd, 1H), 3.09-3.02 (m, 4H), 2.86 (s, 6H)

Example 124

5-[3-(4-BOC-homopiperazin-1-yl)-phenyl]-1-(2-chloro-phenyl)-3-pentafluoroethyl-4,5-dihydro-1H-pyrazole 5-(3-Bromo-phenyl)-1-(2-chloro-phenyl)-3-pentafluoroethyl-4,5-dihydro-1H-pyrazole (650.0 mg, 1.4 mmol) prepared in Step 1 of Preparation 6, 1-BOC-homopiperazine (432.0 mg, 2.2 mmol), Pd$_2$(dba)$_3$ (66.0 mg, cat.), BINAP (90.0 mg, cat.) and sodium t-butoxide (250.0 mg, 2.6 mmol) were added to toluene (10.0 mL). The reaction mixture was stirred at 100° C. for 12 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/6) to give 550.0 mg of the titled compound as a yellow liquid.

$^1$H NMR (400 MHz, CDCl$_3$) 7.21 (t, 2H), 7.05 (q, 2H), 6.93 (t, 1H), 6.49-6.43 (m, 2H), 6.40 (s, 1H) 5.79 (dd, 1H), 3.64 (dd, 1H), 3.43 (br, 6H), 3.25 (dd, 1H), 3.10-2.98 (br, 2H), 1.86 (d, 2H), 1.43-1.39 (br, 9H)

Example 125

1-(2-chloro-phenyl)-5-[3-(4-methanesulfonyl-homopiperazin-1-yl)-phenyl]-3-pentafluoroethyl-4,5-dihydro-1H-pyrazole Step 1: 1-(2-chloro-phenyl)-5-[3-(homopiperazin-1-yl)-phenyl]-3-pentafluoroethyl-4,5-dihydro-1H-pyrazole hydrochloride 5-[3-(4-BOC-homopiperazin-1-yl)-phenyl]-1-(2-chloro-phenyl)-3-pentafluoroethyl-4,5-dihydro-1H-pyrazole (550.0 mg, 1.0 mmol) prepared in Example 124 was added to a saturated solution of hydrochloric acid in ethyl acetate (5.0 mL). The reaction mixture was stirred at room temperature for 3 hours and then concentrated under reduced pressure to give 550.0 mg of the titled compound as a brown liquid.

$^1$H NMR (400 MHz, CD$_3$OD) 7.30 (t, 2H), 7.15 (q, 2H), 7.03 (t, 1H), 6.68 (d, 1H), 6.60 (m, 2H), 3.76 (dd, 1H), 3.72 (m, 2H), 3.53 (t, 2H), 3.33 (t, 2H), 3.19 (dd, 1H), 3.15 (t, 2H), 2.15 (t, 2H)

Step 2: 1-(2-chloro-phenyl)-5-[3-(4-methanesulfonyl-homopiperazin-1-yl)-phenyl]-3-pentafluoroethyl-4,5-dihydro-1H-pyrazole 1-(2-Chloro-phenyl)-5-[3-(homopiperazin-1-yl)-phenyl]-3-pentafluoroethyl-4,5-dihydro-1H-pyrazole hydrochloride (30.0 mg, 0.06 mmol) prepared in Step 1, triethylamine (41.0 uL, 0.30 mmol) and methanesulfonyl chloride (8.1 mg, 0.07 mmol) were added to dichloromethane (1.0 mL). The reaction mixture was stirred at room temperature for 3 hours, washed with distilled water, 1N hydrochloride, a saturated solution of sodium hydrogen carbonate, and brine, dried on anhydrous magnesium sulfate, and then concentrated under reduced pressure to give a yellow liquid residue. The resulting residue was purified by silica gel column chromatography (eluent: ethyl acetate/n-hexane=1/2) to give 3.4 mg of the titled compound as a yellow liquid.

$^1$H NMR (400 MHz, CDCl$_3$) 7.23 (t, 2H), 7.07 (q, 2H), 6.94 (t, 1H), 6.48 (d, 2H), 6.41 (s, 1H), 5.84 (dd, 1H), 3.65 (dd, 1H), 3.57 (t, 4H), 3.39 (d, 2H), 3.25 (dd, 1H), 3.09 (br, 2H), 2.60 (s, 3H), 1.94 (t, 2H)

Examples 126 to 128

The compounds of Examples 126 to 128 were prepared in accordance with the same procedures as in Step 2 of Example 125, except for using 1-(2-chloro-phenyl)-5-[3-(homopiperazin-1-yl)-phenyl]-3-pentafluoroethyl-4,5-dihydro-1H-pyrazole hydrochloride prepared in Step 1 of Example 125; and using sulfamoyl chloride, carbamoyl chloride or acyl chloride corresponding to the compounds of Examples 126 to 128 instead of methanesulfonyl chloride.

Example 126

1-(2-chloro-phenyl)-5-[3-(4-dimethylsulfamoyl-homopiperazin-1-yl)-phenyl]-3-pentafluoroethyl-4,5-dihydro-1H-pyrazole $^1$H NMR (400 MHz, CDCl$_3$) 7.22 (d, 2H), 7.07 (q, 2H), 6.93 (t, 1H), 6.46 (d, 2H), 6.39 (s, 1H), 5.82 (dd, 1H), 3.69-3.54 (m, 5H), 3.37 (d, 2H), 3.27 (dd, 1H), 3.06 (m, 2H), 2.68 (s, 6H), 1.95 (t, 2H)

Example 127

1-(2-chloro-phenyl)-5-[3-(4-isobutyryl-homopiperazin-1-yl)-phenyl]-3-pentafluoroethyl-4,5-dihydro-1H-pyrazole $^1$H NMR (400 MHz, CDCl$_3$) 7.21 (d, 2H), 7.06-7.02 (m, 2H), 6.94 (t, 1H), 6.50-6.41 (m, 3H), 5.82 (dd, 1H), 3.68-3.62 (m, 2H), 3.53-3.41 (m, 5H), 3.30-3.17 (m, 3H) 2.74-2.58 (m, 1H), 1.89 (m, 2H), 1.38-1.25 (dt, 6H)

Example 128

1-(2-chloro-phenyl)-5-[3-(4-dimethylcarbamoyl-homopiperazin-1-yl)-phenyl]-3-pentafluoroethyl-4,5-dihydro-1H-pyrazole $^1$H NMR (400 MHz, CDCl$_3$) 7.22 (d, 2H), 7.05 (q, 2H), 6.93 (t, 1H), 6.49 (d, 1H) 6.45-6.42 (m, 2H), 5.81 (dd, 1H), 3.64 (dd, 1H), 3.52 (d, 2H), 3.46 (t, 2H), 3.38 (t, 2H), 3.27 (dd, 1H), 3.07 (br, 2H), 2.76 (s, 6H), 1.93 (t, 2H)

Example 129

1-(2,4-difluoro-phenyl)-5-(6-fluoro-4'-methanesulfonyl-biphenyl-3-yl)-3-pentafluoroethyl-4,5-dihydro-1H-pyrazole 5-(3-Bromo-4-fluoro-phenyl)-1-(2,4-difluoro-phenyl)-3-pentafluoroethyl-4,5-dihydro-1H-pyrazole (250.0 mg, 0.53 mmol) prepared in Step 5 of Preparation 7, 4-methylsulfonylphenylboronic acid (116.0 mg, 0.58 mmol), Pd(PPh$_3$)$_4$ (61.0 mg, cat.) and a 2N sodium carbonate solution (3.5 mL) were added to a mixed solvent of ethanol (3.5 mL) and N,N-dimethylformamide (15.0 mL). The reaction mixture was stirred at 90° C. for 3 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/3) to give 150.0 mg of the titled compound as a yellow liquid.

$^1$H NMR (400 MHz, CDCl$_3$) 8.01 (d, 2H), 7.61 (d, 2H), 7.38 (q, 1H), 7.21 (d, 1H), 7.16 (s, 1H), 7.10 (t, 1H), 6.79 (t, 1H), 6.68 (t, 1H), 6.71 (t, 1H), 5.64 (dd, 1H), 3.71 (dd, 1H), 3.18 (dd, 1H), 3.11 (s, 3H)

Examples 130 to 134

The compounds of Examples 130 to 134 were prepared in accordance with the same procedures as in Example 129, except for using 5-(3-bromo-4-fluoro-phenyl)-1-(2,4-difluoro-phenyl)-3-pentafluoroethyl-4,5-dihydro-1H-pyrazole prepared in Step 5 of Preparation 7; and using each boronic acid corresponding to the compounds of Examples 130 to 134 instead of 4-methylsulfonylphenylboronic acid.

Example 130

1-(2,4-difluoro-phenyl)-5-[4-fluoro-3-(6-chloro-pyridin-3-yl)-phenyl]-3-pentafluoroethyl-4,5-dihydro-1H-pyrazole $^1$H NMR (400 MHz, CDCl$_3$) 8.41 (s, 1H), 7.73 (d, 1H), 7.37 (m, 2H), 7.17 (t, 2H), 7.09 (m, 1H), 6.78 (t, 1H), 6.70 (t, 1H), 5.64 (dd, 1H), 3.71 (dd, 1H), 3.16 (dd, 1H)

Example 131

1-(2,4-difluoro-phenyl)-5-[4-fluoro-3-(6-methoxy-pyridin-3-yl)-phenyl]-3-pentafluoroethyl-4,5-dihydro-1H-pyrazole $^1$H NMR (400 MHz, CDCl$_3$) 8.21 (s, 1H), 7.66 (d, 1H), 7.37 (m, 1H), 7.16 (d, 1H), 7.07-7.03 (m, 2H), 6.82-6.77 (m, 2H), 6.70 (t, 1H), 5.61 (dd, 1H), 3.98 (s, 3H), 3.69 (dd, 1H), 3.18 (dd, 1H)

Example 132

1-(2,4-difluoro-phenyl)-5-[4-fluoro-3-(pyrimidin-5-yl)-phenyl]-3-pentafluoroethyl-4,5-dihydro-1H-pyrazole $^1$H NMR (400 MHz, CDCl$_3$) 8.80 (s, 1H), 7.43-7.33 (m, 3H), 7.20 (d, 1H), 7.18-7.09 (m, 2H), 6.78 (t, 1H), 6.71 (t, 1H), 5.65 (dd, 1H), 3.71 (dd, 1H), 3.18 (dd, 1H)

Example 133

1-(2,4-difluoro-phenyl)-5-(4-fluoro-3-pyrrolidin-1-yl-phenyl)-3-pentafluoroethyl-4,5-dihydro-1H-pyrazole $^1$H NMR (400 MHz, CDCl$_3$) 7.35 (m 1H), 6.95-6.75 (m, 3H), 6.42 (m, 2H), 5.48 (dd, 1H), 3.61 (dd, 1H), 3.56 (d, 4H), 3.16 (dd, 1H), 1.91 (s, 4H)

Example 134

1-(2,4-difluoro-phenyl)-5-[6-fluoro-(4'-tetrazol-1-yl)-biphenyl-3-yl]-3-pentafluoroethyl-4,5-dihydro-1H-pyrazole $^1$H NMR (400 MHz, CDCl$_3$) 9.03 (s, 1H), 7.79 (d, 2H), 7.64 (d, 2H), 7.39-7.35 (m, 1H), 7.25 (d, 1H), 7.17-7.08 (m, 2H), 6.78 (t, 1H), 6.72 (t, 1H), 5.64 (dd, 1H), 3.70 (dd, 1H), 3.19 (dd, 1H)

Example 135

1-(2,4-difluoro-phenyl)-5-(4-fluoro-3-morpholin-4-yl-phenyl)-3-pentafluoroethyl-4,5-dihydro-1H-pyrazole 5-(3-Bromo-4-fluoro-phenyl)-1-(2,4-difluoro-phenyl)-3-pentafluoroethyl-4,5-dihydro-1H-pyrazole (30.0 mg, 0.06 mmol) prepared in Step 5 of Preparation 7, morpholine (7.0 uL, 0.08 mmol), Pd$_2$(dba)$_3$ (3.0 mg, cat.), BINAP (4.0 mg, cat.) and sodium t-butoxide (9.0 mg, 0.10 mmol) were added to toluene (1.0 mL). The reaction mixture was stirred at 100° C. for 7 hours and then filtered through celite pad. Ethyl acetate was added to the filtrate, which was washed with a saturated solution of sodium hydrogen carbonate and brine, dried on anhydrous magnesium sulfate, and then concentrated under reduced pressure to give a yellow liquid residue. The resulting residue was purified by silica gel column chromatography (eluent: ethyl acetate/n-hexane=1/8) to give 15.0 mg of the titled compound as a yellow liquid.

$^1$H NMR (400 MHz, CDCl$_3$) 7.34-7.26 (m, 1H), 6.92-6.86 (m, 1H), 6.77-6.63 (m, 4H), 5.52 (dd, 1H), 3.85-3.80 (m, 4H), 3.63 (dd, 1H), 3.14 (dd, 1H), 3.03-2.91 (m, 4H)

Examples 136 and 137

The compounds of Examples 136 and 137 were prepared in accordance with the same procedures as in Example 135, except for using 5-(3-bromo-4-fluoro-phenyl)-1-(2,4-difluoro-phenyl)-3-pentafluoroethyl-4,5-dihydro-1H-pyrazole prepared in Step 5 of Preparation 7; and using each amine corresponding to the compounds of Examples 136 and 137 instead of morpholine.

Example 136

1-(2,4-difluoro-phenyl)-5-(4-fluoro-3-piperidin-1-yl-phenyl)-3-pentafluoroethyl-4,5-dihydro-1H-pyrazole $^1$H NMR (400 MHz, CDCl$_3$) 7.32-7.26 (m, 1H), 6.88-6.82 (m, 1H), 6.76-6.62 (m, 4H), 5.49 (dd, 1H), 3.62 (dd, 1H), 3.15 (dd, 1H), 2.95-2.88 (m, 4H), 1.72-1.66 (m, 4H), 1.59-1.54 (m, 2H)

Example 137

1-(2,4-difluoro-phenyl)-5-[4-fluoro-3-(2-oxo-pyrrolidin-1-yl)-phenyl]-3-pentafluoroethyl-4,5-dihydro-1H-pyrazole $^1$H NMR (400 MHz, CDCl$_3$) 7.35-7.26 (m, 1H), 7.05-6.95 (m, 2H), 6.78-6.67 (m, 3H), 5.53 (dd, 1H), 3.84-3.67 (m, 2H), 3.58 (dd, 1H), 3.15 (dd, 1H), 2.55 (t, 2H), 2.23-2.15 (m, 2H)

Example 138

1-(2,4-difluoro-phenyl)-5-(4-fluoro-3'-(methylsulfanyl)biphenyl-3-yl)-3-pentafluoroethyl-4,5-dihydro-1H-pyrazole 5-(5-Bromo-2-fluoro-phenyl)-1-(2,4-difluoro-phenyl)-3-pentafluoroethyl-4,5-dihydro-1H-pyrazole (50.0 mg, 0.11 mmol) prepared in Step 5 of Preparation 8, 3-(methylthio)phenylboronic acid (26.7 mg, 0.16 mmol), Pd(PPh$_3$)$_4$ (12.3 mg, cat.) and a 2N sodium carbonate solution (500.0 uL) were added to a mixed solvent of ethanol (500.0 uL) and 1,2-dimethylethane (2.0 mL). The reaction mixture was stirred at 88° C. for 2 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/15) to give 35.0 mg of the titled compound as a white liquid.

$^1$H NMR (400 MHz, CDCl$_3$) 7.42-7.30 (m, 4H), 7.25-7.21 (m, 2H), 7.14 (d, 1H), 7.05 (t, 1H), 6.78 (t, 1H), 6.66 (t, 1H), 5.89 (dd, 1H), 3.68 (dd, 1H), 3.20 (dd, 1H), 2.51 (s, 3H)

Examples 139 and 140

The compounds of Examples 139 and 140 were prepared in accordance with the same procedures as in Example 138, except for using 5-(5-bromo-2-fluoro-phenyl)-1-(2,4-difluoro-phenyl)-3-pentafluoroethyl-4,5-dihydro-1H-pyrazole prepared in Step 5 of Preparation 8; and using each boronic acid corresponding to the compounds of Examples 139 and 140 instead of 3-methylthiophenylboronic acid.

Example 139

1-(2,4-difluoro-phenyl)-5-(4-fluoro-4'-methylsulfonyl-biphenyl-3-yl)-3-pentafluoroethyl-4,5-dihydro-1H-pyrazole $^1$H NMR (400 MHz, CDCl$_3$) 8.26 (s, 1H), 7.66 (d, 1H), 7.39-7.31 (m, 3H), 7.26 (m, 1H), 7.10 (d, 1H), 6.81-6.65 (m, 3H), 5.63 (dd, 1H), 3.98 (s, 3H), 3.68 (dd, 1H), 3.19 (dd, 1H)

Example 140

1-(2,4-difluoro-phenyl)-5-[6-fluoro-3-(6-methylsulfanyl-pyridin-3-yl)-phenyl]-3-pentafluoroethyl-4,5-dihydro-1H-pyrazole $^1$H NMR (400 MHz, CDCl$_3$) 8.48 (s, 1H), 7.50 (d, 1H), 7.38 (t, 2H), 7.28 (d, 1H), 7.22 (d, 1H), 7.08 (t, 1H), 6.77 (t, 1H), 6.66 (t, 1H), 5.87 (dd, 1H), 3.69 (dd, 1H), 3.18 (dd, 1H), 2.59 (s, 3H)

Example 141

1-(2,4-difluoro-phenyl)-5-(4-fluoro-3'-methanesulfonyl-biphenyl-3-yl)-3-pentafluoroethyl-4,5-dihydroxy-1H-pyrazole To a solution of 1-(2,4-difluoro-phenyl)-5-(4-fluoro-3'-(methylsulfanyl)biphenyl-3-yl)-3-pentafluoroethyl-4,5-dihydro-1H-pyrazole (20.0 mg, 0.01 mmol) prepared in Example 138 in dichloromethane (1 mL), was added 77% meta-chloroperbenzoic acid (20.0 mg, 0.02 mmol). After completing the reaction, the reaction mixture was washed with a saturated solution of sodium hydrogen carbonate and then distilled under reduced pressure. Distilled water was added to the reaction mixture, which was then extracted with ethyl acetate. The extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/4) to give 3.5 mg of the titled compound as a white solid.

$^1$H NMR (400 MHz, CDCl$_3$) 7.96 (s, 1H), 7.92 (d, 1H), 7.68-7.61 (m, 2H), 7.48-7.36 (m, 3H), 7.11 (t, 1H), 6.80 (t, 1H), 6.66 (t, 1H), 5.90 (dd, 1H), 3.67 (dd, 1H), 3.19 (dd, 1H), 3.09 (s, 3H)

Example 142

1-(2,4-difluoro-phenyl)-5-[6-fluoro-3-(6-methane-sulfonyl-pyridin-3-yl)-phenyl]-3-pentafluoroethyl-4,5-dihydro-1H-pyrazole To a solution of 1-(2,4-difluoro-phenyl)-5-[6-fluoro-3-(6-methylsulfanyl-pyridin-3-yl)-phenyl]-3-pentafluoroethyl-4,5-dihydro-1H-pyrazole (20.0 mg, 0.01 mmol) prepared in Example 140 in dichloromethane (1 mL), was added 77% meta-chloroperbenzoic acid (20.0 mg, 0.02 mmol). After completing the reaction, the reaction mixture was washed with a saturated solution of sodium hydrogen carbonate and then distilled under reduced pressure. Distilled water was added to the reaction mixture, which was then extracted with ethyl acetate. The extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/3) to give 3.5 mg of the titled compound as a white solid.

$^1$H NMR (400 MHz, CDCl$_3$) 8.74 (s, 1H), 8.14 (d, 1H), 7.96 (d, 1H), 7.49-7.34 (m, 3H), 7.20-7.16 (m, 2H), 6.80 (t, 1H), 6.66 (t, 1H), 5.90 (dd, 1H), 3.70 (dd, 1H), 3.26 (s, 3H), 3.19 (dd, 1H)

Example 143

1-(2,4-difluoro)-5-[2-fluoro-5-(4-BOC-piperazin-1-yl)-phenyl]-3-pentafluoroethyl-4,5-dihydro-1H-pyrazole 5-(5-Bromo-2-fluoro-phenyl)-1-(2,4-difluoro-phenyl)-3-pentafluoroethyl-4,5-dihydro-1H-pyrazole (500.0 mg, 1.06 mmol) prepared in Step 5 of Preparation 8, 1-BOC-piperazine (295.2 mg, 1.59 mmol), Pd$_2$(dba)$_3$ (48.5 mg, cat.), BINAP (65.8 mg, cat.) and sodium t-butoxide (182.8 mg, 1.90 mmol) were added to toluene (10.0 mL). The reaction mixture was stirred at 100° C. for 12 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/15) to give 400.0 mg of the titled compound as a yellow liquid.

$^1$H NMR (400 MHz, CDCl$_3$) 7.34 (q, 1H), 6.89 (t, 1H), 6.78-6.75 (m, 2H), 6.73-6.62 (m, 2H), 5.75 (dd, 1H), 3.64 (dd, 1H), 3.59 (d, 4H), 3.11 (dd, 1H), 2.93 (d, 4H), 1.48 (s, 9H)

Example 144

1-(2,4-difluoro)-5-[2-fluoro-5-(piperazin-1-yl)-phenyl]-3-pentafluoroethyl-4,5-dihydro-1H-pyrazole hydrochloride 1-(2,4-Difluoro)-5-[2-fluoro-5-(4-BOC-piperazin-1-yl)-phenyl]-3-pentafluoroethyl-4,5-dihydro-1H-pyrazole (400.0 mg, 0.78 mmol) prepared in Example 143 was added to a saturated solution of hydrochloric acid in ethyl acetate (5.0 mL). The reaction mixture was stirred at room temperature for 3 hours and then concentrated under reduced pressure to give 400.0 mg of the titled compound as a brown liquid.

$^1$H NMR (400 MHz, CD$_3$OD) 7.34 (q, 1H), 6.98-6.95 (m, 2H), 6.87-6.80 (m, 3H), 5.83 (dd, 1H), 3.74 (dd, 1H), 3.35 (d, 4H), 3.26 (d, 4H), 3.17 (dd, 1H)

Example 145

1-(2,4-difluoro)-5-[2-fluoro-5-(4-methanesulfonyl-piperazin-1-yl)-phenyl]-3-pentafluoroethyl-4,5-dihydro-1H-pyrazole 1-(2,4-Difluoro)-5-[2-fluoro-5-(piperazin-1-yl)-phenyl]-3-pentafluoroethyl-4,5-dihydro-1H-pyrazole hydrochloride (30.0 mg, 0.06 mmol) prepared in Example 144, triethylamine (41.0 uL, 0.30 mmol) and methanesulfonyl chloride (8.1 mg, 0.07 mmol) were added to dichloromethane (1.0 mL). The reaction mixture was stirred at room temperature for 3 hours, washed with distilled water, 1N hydrochloride, a saturated solution of sodium hydrogen carbonate, and brine, dried on anhydrous magnesium sulfate, and then concentrated under reduced pressure to give a yellow liquid residue. The resulting residue was purified by silica gel column chromatography (eluent: ethyl acetate/n-hexane=1/2) to give 15 mg of the titled compound as a yellow liquid.

$^1$H NMR (400 MHz, CDCl$_3$) 7.37-7.32 (m, 1H), 6.91 (t, 1H), 6.77 (s, 2H), 6.72-6.64 (m, 2H), 5.77 (dd, 1H), 3.64 (dd, 1H), 3.36-3.33 (brs, 4H), 3.15-3.07 (m, 5H), 2.82 (s, 3H)

Example 146

1-(2,4-difluoro)-5-[2-fluoro-5-(4-cyclopropanesulfonyl-piperazin-1-yl)-phenyl]-3-pentafluoroethyl-4,5-dihydro-1H-pyrazole The compound of Example 146 was prepared in accordance with the same procedures as in Example 145, except for using 1-(2,4-difluoro)-5-[2-fluoro-5-(piperazin-1-yl)-phenyl]-3-pentafluoroethyl-4,5-dihydro-1H-pyrazole hydrochloride prepared in Example 144; and using cyclopropanesulfonyl chloride instead of methanesulfonyl chloride.

$^1$H NMR (400 MHz, CDCl$_3$) 7.37-7.31 (m, 1H), 6.91 (t, 1H), 6.77 (s, 2H), 6.72-6.64 (m, 2H), 5.77 (dd, 1H), 3.64 (dd, 1H), 3.44-3.40 (brs, 4H), 3.16-3.05 (m, 5H), 2.30-2.26 (m, 1H), 1.28-1.20 (m, 2H), 1.04-0.99 (m, 2H)

Example 147

1-(2,4-difluoro-phenyl)-5-[2-fluoro-5-(1-BOC-1,2,3,6-tetrahydropyridin-4-yl)-phenyl]-3-pentafluoroethyl-4,5-dihydro-1H-pyrazole 5-(5-Bromo-2-fluoro-phenyl)-1-(2,4-difluoro-phenyl)-3-pentafluoroethyl-4,5-dihydro-1H-pyrazole (500.0 mg, 1.06 mmol) prepared in Step 5 of Preparation 8, 4-(4,4,5,5-tetramethyl-[1,3,2]dioxaborolan-2-yl)-3,6-dihydro-2H-pyridin-1- carboxylic acid tert-butyl ester (26.7 mg, 1.59 mmol), Pd(PPh$_3$)$_4$ (123.0 mg, cat.) and a 2N sodium carbonate solution (5.0 mL) were added to a mixed solvent of ethanol (5.0 mL) and 1,2-dimethylethane (20.0 mL). The reaction mixture was stirred at 88° C. for 2 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/15) to give 360.0 mg of the titled compound as a white liquid.

$^1$H NMR (400 MHz, CDCl$_3$) 7.34 (q, 1H), 7.22 (q, 1H), 7.11 (d, 1H), 6.94 (t, 1H), 6.76 (t, 1H), 6.66 (t, 1H), 5.86 (br, 1H), 5.80 (dd, 1H), 4.04 (s, 2H), 3.64 (dd, 1H), 3.60 (t, 2H), 3.13 (dd, 1H), 2.35 (m, 2H), 1.48 (s, 9H)

Example 148

1-(2,4-difluoro-phenyl)-5-[2-fluoro-5-(1,2,3,6-tetrahydropyridin-4-yl)-phenyl]-3-pentafluoroethyl-4,5-dihydro-1H-pyrazole hydrochloride 1-(2,4-Difluoro-phenyl)-5-[2-fluoro-5-(1-BOC-1,2,3,6-tetrahydropyridin-4-yl)-phenyl]-3-pentafluoroethyl-4,5-dihydro-1H-pyrazole (360.0 mg, 0.70 mmol) prepared in Example 147 was added to a saturated solution of hydrochloric acid in ethyl acetate (5.0 mL). The reaction mixture was stirred at room temperature for 3 hours and then concentrated under reduced pressure to give 360.0 mg of the titled compound as a brown liquid.

$^1$H NMR (400 MHz, CD$_3$OD) 7.41-7.29 (m, 3H), 7.06 (t, 1H), 6.85-6.79 (m, 2H), 6.03 (s, 1H), 5.90 (dd, 1H), 3.83 (s, 2H), 3.75 (dd, 1H), 3.45 (t, 2H), 3.19 (dd, 1H), 2.68 (m, 2H)

Example 149

1-(2,4-difluoro-phenyl)-5-[2-fluoro-5-(1-methanesulfonyl-1,2,3,6-tetrahydropyridin-4-yl)-phenyl]-3-pentafluoroethyl-4,5-dihydro-1H-pyrazole 1-(2,4-Difluoro-phenyl)-5-[2-fluoro-5-(1,2,3,6-tetrahydropyridin-4-yl)-phenyl]-3-pentafluoroethyl-4,5-dihydro-1H-pyrazole hydrochloride (30.0 mg, 0.06 mmol) prepared in Example 148, triethylamine (41.0 uL, 0.30 mmol) and methanesulfonyl chloride (8.1 mg, 0.07 mmol) were added to dichloromethane (1.0 mL). The reaction mixture was stirred at room temperature for 3 hours, washed with distilled water, 1N hydrochloride, a saturated solution of sodium hydrogen carbonate, and brine, dried on anhydrous magnesium sulfate, and then concentrated under reduced pressure to give a yellow liquid residue. The resulting residue was purified by silica gel column chromatography (eluent: ethyl acetate/n-hexane=1/2) to give 15 mg of the titled compound as a yellow liquid.

$^1$H NMR (400 MHz, CDCl$_3$) 7.38-7.33 (m, 1H), 7.22 (d, 1H), 7.11 (d, 1H), 6.97 (t, 1H), 6.77 (t, 1H), 6.67 (t, 1H), 5.90 (s, 1H), 5.82 (dd, 1H), 3.93 (brs, 2H), 3.65 (dd, 1H), 3.49 (brs, 2H), 3.13 (dd, 1H), 2.85 (s, 3H), 2.52 (brs, 2H)

Example 150

5-[2-(2-acetyl-phenyl)-pyridin-6-yl]-1-(2-chloro-phenyl)-3-pentafluoroethyl-4,5-dihydro-1H-pyrazole 5-(2-Bromo-pyridin-6-yl)-1-(2-chloro-phenyl)-3-pentafluoroethyl-4,5-dihydro-1H-pyrazole (20.0 mg, 0.04 mmol) prepared in Step 4 of Preparation 9, 2-acetylphenylboronic acid (11.0 mg, 0.07 mmol), Pd(PPh$_3$)$_4$ (2.0 mg, cat.) and a 2N sodium carbonate solution (210.0 uL) were added to a mixed solvent of ethanol (210.0 uL) and toluene (310.0 uL). The reaction mixture was stirred at 80° C. for 1 hour and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/6) to give 8.0 mg of the titled compound as a white liquid.

$^1$H NMR (400 MHz, CDCl$_3$) 7.61-7.45 (m, 5H), 7.33 (d, 1H), 7.27 (d, 1H), 7.18 (d, 1H). 7.09-7.05 (m, 2H), 6.98 (t, 1H), 5.91 (dd, 1H), 3.62 (td, 1H), 3.45 (dd, 1H), 2.18 (s, 3H)

Examples 151 to 155

The compounds of Examples 151 to 155 were prepared in accordance with the same procedures as in Example 150, except for using 5-(2-bromo-pyridin-6-yl)-1-(2-chloro-phenyl)-3-pentafluoroethyl-4,5-dihydro-1H-pyrazole prepared in Step 4 of Preparation 9; and using each boronic acid corresponding to the compounds of Examples 151 to 155 instead of 2-acetylphenylboronic acid.

Example 151

1-(2-chloro-phenyl)-5-[2-(4-methoxy-phenyl)-pyridin-6-yl]-3-pentafluoroethyl-4,5-dihydro-1H-pyrazole $^1$H NMR (400 MHz, CDCl$_3$) 7.92 (d, 2H), 7.45 (d, 2H), 7.21 (d, 1H), 7.16 (d, 1H), 6.98-6.86 (m, 5H), 5.97 (dd, 1H), 3.87 (s, 3H), 3.65-3.62 (m, 2H)

Example 152

1-(2-chloro-phenyl)-5-[2-(3-methylsulfanyl-phenyl)-pyridin-6-yl]-3-pentafluoroethyl-4,5-dihydro-1H-pyrazole $^1$H NMR (400 MHz, CDCl$_3$) 7.85 (s, 1H), 7.62 (d, 1H), 7.51-6.89 (m, 9H), 6.02 (dd, 1H), 3.70-3.57 (m, 2H), 2.55 (s, 3H)

Example 153

1-(2-chloro-phenyl)-5-[2-(4-methylsulfanyl-phenyl)-pyridin-6-yl]-3-pentafluoroethyl-4,5-dihydro-1H-pyrazole $^1$H NMR (400 MHz, CDCl$_3$) 7.87 (d, 2H), 7.50 (d, 2H), 7.47-6.86 (m, 7H), 6.00 (dd, 1H), 3.67-3.59 (m, 2H), 2.54 (s, 3H)

Example 154

1-(2-chloro-phenyl)-5-[2-(4-methanesulfonyl-phenyl)-pyridin-6-yl]-3-pentafluoroethyl-4,5-dihydro-1H-pyrazole $^1$H NMR (400 MHz, CDCl$_3$) 8.14 (d, 2H), 8.02 (d, 2H), 7.61 (s, 2H), 7.22 (d, 1H), 7.16 (d, 1H), 7.08 (d, 1H), 6.97 (t, 1H), 6.90 (t, 1H), 6.06 (dd, 1H), 3.72-3.57 (m, 2H), 3.10 (s, 3H)

Example 155

5-[2-(1-BOC-1,2,3,6-tetrahydropyridin-4-yl)-pyridin-6-yl]-1-(2-chloro-phenyl)-3-pentafluoroethyl-4,5-dihydro-1H-pyrazole $^1$H NMR (400 MHz, CDCl$_3$) 7.40 (t, 1H), 7.20 (d, 1H), 7.14 (t, 2H), 7.00 (t, 1H), 6.92-6.88 (m, 2H), 6.52 (br, 1H), 5.94 (dd, 1H), 4.11 (br, 2H), 3.63-3.49 (m, 2H), 2.54 (br, d, 2H), 1.50 (s, 9H)

Example 156

1-(2-chloro-phenyl)-5-[2-(4-methanesulfinyl-phenyl)-pyridin-6-yl]-3-pentafluoroethyl-4,5-dihydro-1H-pyrazole To a mixture of 1-(2-chloro-phenyl)-5-[2-(4-methylsulfanyl-phenyl)-pyridin-6-yl]-3-pentafluoroethyl-4,5-dihydro-1H-pyrazole (9.0 mg, 0.02 mmol) prepared in Example 153 in dichloromethane (1.0 mL), was slowly added meta-chloroperbenzoic acid (77%, 2.0 mg, 0.01 mmol) at 0° C. The reaction mixture was stirred at room temperature for 30 minutes, quenched with a saturated solution of sodium hydrogen carbonate, and then extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=3/1) to give 2.0 mg of the titled compound as a white solid.

$^1$H NMR (400 MHz, CDCl$_3$) 8.11 (d, 2H), 7.73 (d, 2H), 7.57 (t, 2H), 7.22 (d, 1H), 7.16 (d, 1H), 7.05 (d, 1H), 6.97 (t, 1H), 6.90 (t, 1H), 6.04 (dd, 1H), 3.72-3.59 (m, 2H), 2.78 (s, 3H)

Example 157

1-(2-chloro-phenyl)-5-[2-(3-methanesulfonyl-phenyl)-pyridin-6-yl]-3-pentafluoroethyl-4,5-dihydro-1H-pyrazole The compound of Example 157 was prepared in accordance with the same procedures as in Example 156, except for using the compound prepared in Example 152 and 2 equivalents of meta-chloroperbenzoic acid.

$^1$H NMR (400 MHz, CDCl$_3$) 8.45 (s, 1H), 8.27 (d, 1H), 7.99 (d, 1H), 7.67 (t, 1H), 7.60 (d, 2H), 7.21 (t, 2H), 7.08 (t, 1H), 7.00 (t, 1H), 6.90 (t, 1H), 6.06 (dd, 1H), 3.72-3.65 (td, 1H), 3.56 (dd, 1H), 3.11 (s, 3H)

Example 158

1-(2-chloro-phenyl)-5-[2-(1-methanesulfonyl-1,2,3,6-tetrahydropyridin-4-yl)-pyridin-6-yl]-3-pentafluoroethyl-4,5-dihydro-1H-pyrazole Step 1: 1-(2-chloro-phenyl)-5-[2-(1,2,3,6-tetrahydropyridin-4-yl)-pyridin-6-yl]-3-pentafluoroethyl-4,5-dihydro-1H-pyrazole trifluoroacetate 5-[2-(1-BOC-1,2,3,6-tetrahydropyridin-4-yl)-pyridin-6-yl]-1-(2-chloro-phenyl)-3-pentafluoroethyl-4,5-dihydro-1H-pyrazole (280.0 mg, 0.50 mmol) prepared in Example 155 and trifluoroacetic acid (400.0 uL, 5.0 mmol) were added at 0° C. to dichloromethane (3.0 mL). The reaction mixture was stirred at room temperature for 1 hour and then concentrated under reduced pressure to give 300.0 mg of the titled compound as a yellow liquid.

$^1$H NMR (400 MHz, CD$_3$OD) 7.58 (t, 1H), 7.40 (d, 1H), 7.23 (d, 1H), 7.14 (d, 1H), 7.09 (d, 1H), 7.02 (t, 1H), 6.96 (t, 1H), 6.61 (s, 1H), 6.05 (dd, 1H), 5.48 (s, 1H), 3.87 (s, 2H), 3.68 (dd, 1H), 3.49-3.40 (m, 3H), 3.3 (m, 4H)

Step 2: 1-(2-chloro-phenyl)-5-[2-(1-methanesulfonyl-1,2,3,6-tetrahydropyridin-4-yl)-pyridin-6-yl]-3-pentafluoroethyl-4,5-dihydro-1H-pyrazole 1-(2-Chloro-phenyl)-5-[2-(1,2,3,6-tetrahydropyridin-4-yl)-pyridin-6-yl]-3-pentafluoroethyl-4,5-dihydro-1H-pyrazole trifluoroacetate (20.0 mg, 0.04 mmol) prepared in Step 1, triethylamine (15.0 uL, 0.11 mmol) and methanesulfonyl chloride (4.1 uL, 0.05 mmol) were added at 0° C. to dichloromethane (0.5 mL). The reaction mixture was stirred at room temperature for 2 hours. Distilled water was added to the reaction mixture, which was then extracted with dichloromethane two times. The combined extract was washed with 1N hydrochloride, a saturated solution of sodium carbonate, and brine, dried on anhydrous magnesium sulfate, and then concentrated under reduced pressure to give a yellow liquid residue. The resulting residue was purified by silica gel column chromatography (eluent: ethyl acetate/n-hexane=1/2) to give 3.0 mg of the titled compound as a yellow liquid.

$^1$H NMR (400 MHz, CDCl$_3$) 7.43 (t, 1H), 7.21-7.11 (m, 3H), 7.00 (t, 1H), 6.94-6.89 (m, 2H), 6.54 (br, 1H), 5.96 (dd, 1H), 4.00 (br, 2H), 3.64-3.46 (m, 4H), 2.86 (s, 3H), 2.69 (dd, br, 2H)

Example 159

1-(2-chloro-phenyl)-5-[2-(1-dimethylsulfamoyl-1,2,3,6-tetrahydropyridin-4-yl)-pyridin-6-yl]-3-pentafluoroethyl-4,5-dihydro-1H-pyrazole The titled compound was prepared in accordance with the same procedures as in Step 2 of Example 158, except for using 1-(2-chloro-phenyl)-5-[2-(1,2,3,6-tetrahydropyridin-4-yl)-pyridin-6-yl]-3-pentafluoroethyl-4,5-dihydro-1H-pyrazole trifluoroacetate prepared in Step 1 of Example 158; and using dimethylsulfamoyl chloride instead of methanesulfonyl chloride.

$^1$H NMR (400 MHz, CDCl$_3$) 7.42 (t, 1H), 7.21-7.12 (m, 3H), 7.00 (t, 1H), 6.92-6.88 (m, 2H), 6.53 (br, 1H), 5.95 (dd, 1H), 3.97 (br, 2H), 3.67-3.44 (m, 4H), 2.88 (s, 6H), 2.64 (dd, 2H)

Example 160

1-(2,4-difluoro-phenyl)-5-[3-(3-methylsulfanyl-phenyl)-pyridin-5-yl]-3-pentafluoroethyl-4,5-dihydro-1H-pyrazole 5-(3-Bromo-pyridin-5-yl)-1-(2,4-difluoro-phenyl)-3-pentafluoroethyl-4,5-dihydro-1H-pyrazole (50.0 mg, 0.11 mmol) prepared in Step 4 of Preparation 10, 3-(methylthio)phenylboronic acid (28.0 mg, 0.17 mmol), Pd(PPh$_3$)$_4$ (12.7 mg, cat.) and a 2N sodium carbonate solution (550.0 uL) were added to a mixed solvent of ethanol (600.0 uL) and 1,2-dimethoxyethane (2.0 mL). The reaction mixture was stirred at 88° C. for 2 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/6) to give 20.0 mg of the titled compound as a white liquid.

$^1$H NMR (400 MHz, CDCl$_3$) 8.70 (s, 1H), 8.42 (s, 1H), 7.61 (s, 1H), 7.42-7.37 (m, 2H), 7.30-7.26 (m, 2H), 7.20 (d, 1H), 6.78 (t, 1H), 6.69 (t, 1H), 5.68 (dd, 1H), 3.73 (dd, 1H), 3.21 (dd, 1H), 2.52 (s, 3H)

Examples 161 to 164

The compounds of Examples 161 to 164 were prepared in accordance with the same procedures as in Example 160, except for using 5-(3-bromo-pyridin-5-yl)-1-(2,4-difluoro-phenyl)-3-pentafluoroethyl-4,5-dihydro-1H-pyrazole prepared in Step 4 of Preparation 10; and using each boronic acid corresponding to the compounds of Examples 161 to 164 instead of 3-(methylthio)phenylboronic acid.

Example 161

1-(2,4-difluoro-phenyl)-5-[3-(4-methylsulfanyl-phenyl)-pyridin-5-yl]-3-pentafluoroethyl-4,5-dihydro-1H-pyrazole $^1$H NMR (400 MHz, CDCl$_3$) 8.70 (s, 1H), 8.38 (s, 1H), 7.60 (s, 1H), 7.41-7.32 (m, 5H), 6.77 (t, 1H), 6.69 (t, 1H), 5.68 (dd, 1H), 3.73 (dd, 1H), 3.21 (dd, 1H), 2.52 (s, 3H)

Example 162

1-(2,4-difluoro-phenyl)-5-[3-(4-methanesulfonyl-phenyl)-pyridin-5-yl]-3-pentafluoroethyl-4,5-dihydro-1H-pyrazole $^1$H NMR (400 MHz, CDCl$_3$) 8.75 (s, 1H), 8.50 (s, 1H), 8.05 (d, 2H), 7.66 (s, 1H), 7.65 (d, 2H), 7.43-7.37 (m, 1H), 6.79 (t, 1H), 6.70 (t, 1H), 5.68 (dd, 1H), 3.77 (dd, 1H), 3.21 (dd, 1H), 3.11 (s, 3H)

Example 163

1-(2,4-difluoro-phenyl)-5-[3-(6-methylsulfanyl-pyridin-3-yl)-pyridin-5-yl]-3-pentafluoroethyl-4,5-dihydro-1H-pyrazole $^1$H NMR (400 MHz, CDCl$_3$) 8.70 (s, 1H), 8.54 (s, 1H), 8.44 (s, 1H), 7.57 (d, 2H), 7.42-7.37 (m, 1H), 7.27 (d, 1H), 6.79 (t, 1H), 6.69 (t, 1H), 5.68 (dd, 1H), 3.74 (dd, 1H), 3.21 (dd, 1H), 2.61 (s, 3H)

Example 164

5-[3-(1-BOC-1,2,3,6-tetrahydropyridin-4-yl)-pyridin-5-yl]-1-(2,4-difluoro-phenyl)-3-pentafluoroethyl-4,5-dihydro-1H-pyrazole $^1$H NMR (400 MHz, CDCl$_3$) 8.53 (s, 1H), 8.31 (s, 1H), 7.38-7.33 (m, 2H), 6.77 (t, 1H), 6.69 (t, 1H), 6.03 (s, 1H), 5.60 (dd, 1H), 4.08 (s, 2H), 3.70 (dd, 1H), 3.62 (s, 2H), 3.14 (dd, 1H), 2.41 (s, 2H), 1.49 (s, 9H)

Example 165

1-(2,4-difluoro-phenyl)-5-[3-(3-methanesulfonyl-phenyl)-pyridin-5-yl]-3-pentafluoroethyl-4,5-dihydro-1H-pyrazole To a mixture of 1-(2,4-difluoro-phenyl)-5-[3-(3-methylsulfanyl-phenyl)-pyridin-5-yl]-3-pentafluoroethyl-4,5-dihydro-1H-pyrazole (20.0 mg, 0.04 mmol) prepared in Example 160 in dichloromethane (2.0 mL), was slowly added meta-chloroperbenzoic acid (77%, 12.0 mg, 0.08 mmol) at 0° C. The reaction mixture was stirred at room temperature for 30 minutes, quenched with a saturated solution of sodium hydrogen carbonate, and then extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 10.0 mg of the titled compound as a yellow liquid.

$^1$H NMR (400 MHz, CDCl$_3$) 8.76 (s, 1H), 8.49 (s, 1H), 8.03 (s, 1H), 8.00 (d, 1H), 7.76-7.67 (m, 3H), 7.44-7.40 (m, 1H), 6.82 (t, 1H), 6.71 (t, 1H), 5.68 (dd, 1H), 3.73 (dd, 1H), 3.21 (dd, 1H), 3.11 (s, 3H)

Example 166

1-(2,4-difluoro-phenyl)-5-[3-(6-methanesulfonyl-pyridin-3-yl)-pyridin-5-yl]-3-pentafluoroethyl-4,5-dihydro-1H-pyrazole To a mixture of 1-(2,4-difluoro-phenyl)-5-[3-(6-methylsulfanyl-pyridin-3-yl)-pyridin-5-yl]-3-pentafluoroethyl-4,5-dihydro-1H-pyrazole (20.0 mg, 0.04 mmol) prepared in Example 163 in dichloromethane (2.0 mL), was slowly added meta-chloroperbenzoic acid (77%, 12.0 mg, 0.08 mmol) at 0° C. The reaction mixture was stirred at room temperature for 30 minutes, quenched with a saturated solution of sodium hydrogen carbonate, and then extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 10.0 mg of the titled compound as a yellow liquid.

$^1$H NMR (400 MHz, CDCl$_3$) 8.79 (d, 2H), 8.57 (s, 1H), 8.20 (d, 1H), 8.03 (d, 1H), 7.66 (s, 1H), 7.44-7.41 (m, 1H), 7.27 (d, 1H), 6.81 (t, 1H), 6.71 (t, 1H), 5.68 (dd, 1H), 3.76 (dd, 1H), 3.28 (s, 3H), 3.21 (dd, 1H)

Example 167

1-(2,4-difluoro-phenyl)-5-[3-(1,2,3,6-tetrahydropyridin-4-yl)-pyridin-5-yl]-3-pentafluoroethyl-4,5-dihydro-1H-pyrazole hydrochloride 5-[3-(1-BOC-1,2,3,6-tetrahydropyridin-4-yl)-pyridin-5-yl]-1-(2,4-difluoro-phenyl)-3-pentafluoroethyl-4,5-dihydro-1H-pyrazole (330.0 mg, 0.6 mmol) prepared in Example 164 was added to a saturated solution of hydrochloric acid in ethyl acetate (2.0 mL). The reaction mixture was stirred at room temperature for 2 hours and then concentrated under reduced pressure to give 310.0 mg of the titled compound as a brown liquid.

¹H NMR (400 MHz, CD₃OD) 8.95 (s, 1H), 8.80 (s, 1H), 8.60 (s, 1H), 7.47-7.41 (m, 1H), 6.98-6.92 (m, 2H), 6.53 (s, 1H), 5.83 (dd, 1H), 3.95 (s, 2H), 3.88 (dd, 1H), 3.51 (t, 2H), 3.30 (dd, 1H), 2.84 (s, 2H)

Example 168

1-(2,4-difluoro-phenyl)-5-[3-(1-cyclopropanesulfo-nyl-1,2,3,6-tetrahydropyridin-4-yl)-pyridin-5-yl]-3-pentafluoroethyl-4,5-dihydro-1H-pyrazole 1-(2,4-Difluoro-phenyl)-5-[3-(1,2,3,6-tetrahydropyridin-4-yl)-pyridin-5-yl]-3-pentafluoroethyl-4,5-dihydro-1H-pyrazole hydrochloride (30.0 mg, 0.06 mmol) prepared in Example 167, triethylamine (42.3 uL, 0.30 mmol) and cyclopropanesulfonyl chloride (12.8 mg, 0.09 mmol) were added to dichloromethane (1.0 mL). The reaction mixture was stirred at room temperature for 1 hour, washed with distilled water, 1N hydrochloride, a saturated solution of sodium hydrogen carbonate, and brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 15.0 mg of the titled compound as a yellow liquid.
¹H NMR (400 MHz, CDCl₃) 8.53 (s, 1H), 8.34 (S, 1H), 7.39 (s, 1H), 7.38-7.33 (m, 1H), 6.78 (t, 1H), 6.68 (t, 1H), 6.06 (s, 1H), 5.63 (dd, 1H), 3.97 (s, 2H), 3.71 (dd, 1H), 3.51 (t, 2H), 3.16 (dd, 1H), 2.57 (s, 2H), 2.32 (m, 1H), 1.21 (m, 2H), 1.01 (d, 2H)

Example 169

5-[3-(4-BOC-piperazin-1-yl)-pyridin-5-yl]-1-(2,4-difluoro-phenyl)-3-pentafluoroethyl-4,5-dihydro-1H-pyrazole 5-(3-Bromo-pyridin-5-yl)-1-(2,4-difluoro-phenyl)-3-pentafluoroethyl-4,5-dihydro-1H-pyrazole (340.0 mg, 0.75 mmol) prepared in Step 4 of Preparation 10, 1-BOC-piperazine (208.0 mg, 1.12 mmol), Pd₂(dba)₃ (34.1 mg, cat.), BINAP (46.4 mg, cat.) and sodium t-butoxide (128.9 mg, 1.34 mmol) were added to toluene (10.0 mL). The reaction mixture was stirred at 100° C. for 12 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/3) to give 220.0 mg of the titled compound as a yellow liquid.
¹H NMR (400 MHz, CDCl₃) 8.18 (s, 1H), 7.92 (s, 1H), 7.37-7.31 (m, 1H), 6.88 (s, 1H), 6.77 (t, 1H), 6.68 (t, 1H), 5.54 (dd, 1H), 3.67 (dd, 1H), 3.57 (t, 4H), 3.15 (dd, 1H), 3.08 (s, 4H), 1.48 (s, 9H)

Example 170

1-(2,4-difluoro-phenyl)-5-[3-(piperazin-1-yl)-pyridin-5-yl]-3-pentafluoroethyl-4,5-dihydro-1H-pyrazole hydrochloride 5-[3-(4-BOC-piperazin-1-yl)-pyridin-5-yl]-1-(2,4-difluoro-phenyl)-3-pentafluoroethyl-4,5-dihydro-1H-pyrazole (220.0 mg, 0.4 mmol) prepared in Example 169 was added to a saturated solution of hydrochloric acid in ethyl acetate (2.0 mL). The reaction mixture was stirred at room temperature 2 hours and then concentrated under reduced pressure to give 210.0 mg of the titled compound as a brown liquid.
¹H NMR (400 MHz, CD₃OD) 8.47 (s, 1H), 8.19 (s, 1H), 8.09 (s, 1H), 7.46-7.40 (m, 1H), 7.00-6.93 (m, 2H), 5.74 (dd, 1H), 3.85 (dd, 1H), 3.71 (s, 4H), 3.35 (s, 4H), 3.22 (dd, 1H)

Example 171

1-(2,4-difluoro-phenyl)-5-[3-(4-methanesulfonyl-piperazin-1-yl)-pyridin-5-yl]-3-pentafluoroethyl-4,5-dihydro-1H-pyrazole 1-(2,4-Difluoro-phenyl)-5-[3-(piperazin-1-yl)-pyridin-5-yl]-3-pentafluoroethyl-4,5-dihydro-1H-pyrazole hydrochloride (30.0 mg, 0.06 mmol) prepared in Example 170, triethylamine (42.3 uL, 0.30 mmol) and methanesulfonyl chloride (10.4 mg, 0.09 mmol) were added to dichloromethane (1.0 mL). The reaction mixture was stirred at room temperature for 1 hour, washed with distilled water, 1N hydrochloride, a saturated solution of sodium hydrogen carbonate, and brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 15.0 mg of the titled compound as a yellow liquid.
¹H NMR (400 MHz, CDCl₃) 8.20 (s, 1H), 7.97 (s, 1H), 7.38-7.32 (m, 1H), 6.91 (s, 1H), 6.77 (t, 1H), 6.69 (t, 1H), 5.58 (dd, 1H), 3.68 (dd, 1H), 3.37 (t, 4H), 3.23 (t, 4H), 3.12 (dd, 1H), 2.83 (s, 3H)

Example 172

1-(2,4-difluoro-phenyl)-5-[4-(3-methylsulfanyl-phenyl)-pyridin-2-yl]-3-pentafluoroethyl-4,5-dihydro-1H-pyrazole 5-(4-Bromo-pyridin-2-yl)-1-(2,4-difluoro-phenyl)-3-pentafluoroethyl-4,5-dihydro-1H-pyrazole (50.0 mg, 0.11 mmol) prepared in Step 4 of Preparation 11, 3-(methylthio)phenylboronic acid (28.0 mg, 0.17 mmol), Pd(PPh₃)₄ (12.8 mg, cat.) and a 2N sodium carbonate solution (550.0 uL) were added to a mixed solvent of ethanol (550.0 uL) and 1,2-dimethoxyethane (1.2 mL). The reaction mixture was stirred at 85° C. for 3 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/6) to give 35.0 mg of the titled compound as a white liquid.
¹H NMR (400 MHz, CDCl₃) 8.55 (d, 1H), 7.39-7.29 (m, 6H), 7.23 (D, 1H), 6.78-6.67 (m, 2H), 5.73 (dd, 1H), 3.66 (Dd, 1H), 3.35 (dd, 1H), 2.51 (s, 3H)

Examples 173 to 176

The compounds of Examples 173 to 176 were prepared in accordance with the same procedures as in Example 172, except for using 5-(4-bromo-pyridin-2-yl)-1-(2,4-difluoro-phenyl)-3-pentafluoroethyl-4,5-dihydro-1H-pyrazole prepared in Step 4 of Preparation 11; and using each boronic acid corresponding to the compounds of Examples 173 to 176 instead of 3-(methylthio)phenylboronic acid.

Example 173

1-(2,4-difluoro-phenyl)-5-[4-(4-methylsulfanyl-phenyl)-pyridin-2-yl]-3-pentafluoroethyl-4,5-dihydro-1H-pyrazole $^1$H NMR (400 MHz, CDCl$_3$) 8.53 (d, 1H), 7.41 (d, 2H), 7.35-7.29 (m, 5H), 6.78-6.67 (m, 2H), 5.72 (dd, 1H), 3.68 (dd, 1H), 3.37 (dd, 1H), 2.52 (s, 3H)

Example 174

1-(2,4-difluoro-phenyl)-5-[4-(4-methanesulfonyl-phenyl)-pyridin-2-yl]-3-pentafluoroethyl-4,5-dihydro-1H-pyrazole $^1$H NMR (400 MHz, CDCl$_3$) 8.63 (d, 1H), 8.05 (d, 2H), 7.67 (d, 2H), 7.41-7.32 (m, 3H), 6.78-6.67 (m, 2H), 5.74 (dd, 1H), 3.68 (dd, 1H), 3.37 (dd, 1H), 3.09 (s, 3H)

Example 175

1-(2,4-difluoro-phenyl)-5-[4-(6-methylsulfanyl-pyridin-3-yl)-pyridin-2-yl]-3-pentafluoroethyl-4,5-dihydro-1H-pyrazole $^1$H NMR (400 MHz, CDCl$_3$) 8.58 (d, 2H), 7.60 (d, 1H), 7.40-7.33 (m, 2H), 7.27 (d, 2H), 6.79-6.67 (m, 2H), 5.72 (dd, 1H), 3.68 (dd, 1H), 3.38 (dd, 1H), 2.60 (s, 3H)

Example 176

5-[4-(1-BOC-1,2,3,6-tetrahydropyridin-4-yl)-pyridin-2-yl]-1-(2,4-difluoro-phenyl)-3-pentafluoroethyl-4,5-dihydro-1H-pyrazole $^1$H NMR (400 MHz, CDCl$_3$) 8.44 (d, 1H), 7.34 (q, 1H), 7.11 (d, 1H), 7.06 (s, 1H), 6.75 (t, 1H), 6.67 (t, 1H), 6.206 (br, 1H), 5.66 (dd, 1H), 4.00 (s, 2H), 3.64 (dd, 1H), 3.60 (t, 2H), 3.30 (dd, 1H), 2.39 (m, 2H), 1.48 (s, 9H)

Example 177

1-(2,4-difluoro-phenyl)-5-[4-(3-methanesulfonyl-phenyl)-pyridin-2-yl]-3-pentafluoroethyl-4,5-dihydro-1H-pyrazole To a mixture of 1-(2,4-difluoro-phenyl)-5-[4-(3-methylsulfanyl-phenyl)-pyridin-2-yl]-3-pentafluoroethyl-4,5-dihydro-1H-pyrazole (30.0 mg, 0.06 mmol) prepared in Example 172 in dichloromethane (2.0 mL), was slowly added meta-chloroperbenzoic acid (77%, 18.0 mg, 0.12 mmol) at 0° C. The reaction mixture was stirred at room temperature for 30 minutes, quenched with a saturated solution of sodium hydrogen carbonate, and then extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 10.0 mg of the titled compound as a yellow liquid.

$^1$H NMR (400 MHz, CDCl$_3$) 8.62 (d, 1H), 8.06 (s, 1H), 8.01 (d, 1H), 7.77 (d, 1H), 7.69 (t, 1H), 7.40-7.34 (m, 3H), 6.80-6.69 (m, 2H), 5.75 (dd, 1H), 3.69 (dd, 1H), 3.40 (dd, 1H), 3.12 (s, 3H)

Example 178

1-(2,4-difluoro-phenyl)-5-[4-(6-methanesulfonyl-pyridin-3-yl)-pyridin-2-yl]-3-pentafluoroethyl-4,5-dihydro-1H-pyrazole To a mixture of 1-(2,4-difluoro-phenyl)-5-[4-(6-methylsulfanyl-pyridin-3-yl)-pyridin-2-yl]-3-pentafluoroethyl-4,5-dihydro-1H-pyrazole (30.0 mg, 0.06 mmol) prepared in Example 175 in dichloromethane (2.0 mL), was slowly added meta-chloroperbenzoic acid (77%, 18.0 mg, 0.12 mmol) at 0° C. The reaction mixture was stirred at room temperature for 30 minutes, quenched with a saturated solution of sodium hydrogen carbonate, and then extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 10.0 mg of the titled compound as a yellow liquid.

$^1$H NMR (400 MHz, CDCl$_3$) 8.81 (s, 1H), 8.70 (d, 1H), 8.19 (d, 1H), 8.05 (d, 1H), 7.40 (q, 2H), 7.33 (s, 1H), 6.78 (t, 1H), 6.70 (t, 1H), 5.77 (dd, 1H), 3.70 (dd, 1H), 3.39 (dd, 1H), 3.28 (s, 3H)

Example 179

1-(2,4-difluoro-phenyl)-5-[4-(1,2,3,6-tetrahydropyridin-4-yl)-pyridin-2-yl]-3-pentafluoroethyl-4,5-dihydro-1H-pyrazole hydrochloride 5-[4-(1-BOC-1,2,3,6-tetrahydropyridin-4-yl)-pyridin-2-yl]-1-(2,4-difluoro-phenyl)-3-pentafluoroethyl-4,5-dihydro-1H-pyrazole (500.0 mg, 6.0 mmol) prepared in Example 176 was added to a saturated solution of hydrochloric acid in ethyl acetate (20.0 mL). The reaction mixture was stirred at room temperature for 2 hours and then concentrated under reduced pressure to give 380.0 mg of the titled compound as a brown liquid.

$^1$H NMR (400 MHz, CD$_3$OD) 8.79 (d, 1H), 8.06 (s, 2H), 7.42 (q, 1H), 7.01-6.93 (m, 2H), 6.86 (s, 1H), 5.77 (dd, 1H), 4.00 (s, 2H), 3.96 (dd, 1H), 3.53 (t, 2H), 3.30 (dd, 1H), 2.60 (m, 2H)

Example 180

1-(2,4-difluoro-phenyl)-5-[4-(1-methanesulfonyl-1,2,3,6-tetrahydropyridin-4-yl)-pyridin-2-yl]-3-pentafluoroethyl-4,5-dihydro-1H-pyrazole 1-(2,4-Difluoro-phenyl)-5-[4-(1,2,3,6-tetrahydropyridin-4-yl)-pyridin-2-yl]-3-pentafluoroethyl-4,5-dihydro-1H-pyrazole hydrochloride (30.0 mg, 0.06 mmol) prepared in Example 179, triethylamine (42.0 uL, 0.30 mmol) and methanesulfonyl chloride (7.0 uL, 0.09 mmol) were added to dichloromethane (1.0 mL). The reaction mixture was stirred at room temperature for 18 hours, washed with distilled water, 1N hydrochloride, a saturated solution of sodium hydrogen carbonate, and brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 15.0 mg of the titled compound as a yellow liquid.

$^1$H NMR (400 MHz, CDCl$_3$) 8.48 (s, 1H), 7.37-7.31 (m, 1H), 7.12-7.06 (m, 2H), 6.78-6.67 (m, 2H), 6.19 (s, 1H), 5.66

(dd, 1H), 3.93-3.90 (m, 2H), 3.64 (dd, 1H), 3.51-3.49 (m, 2H), 3.28 (dd, 1H), 2.86 (s, 3H), 2.56-2.52 (m, 2H)

Example 181

5-[4-(4-BOC-piperazin-1-yl)-pyridin-2-yl]-1-(2,4-difluoro-phenyl)-3-pentafluoroethyl-4,5-dihydro-1H-pyrazole 5-(4-Bromo-pyridin-2-yl)-1-(2,4-difluoro-phenyl)-3-pentafluoroethyl-4,5-dihydro-1H-pyrazole (300.0 mg, 0.66 mmol) prepared in Step 4 of Preparation 11, 1-BOC-piperazine (184.0 mg, 0.99 mmol), $Pd_2(dba)_3$ (30.2 mg, cat.), BINAP (41.1 mg, cat.) and sodium t-butoxide (114.0 mg, 1.19 mmol) were added to toluene (10.0 mL). The reaction mixture was stirred at 100° C. for 12 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/3) to give 350.0 mg of the titled compound as a yellow liquid.

$^1$H NMR (400 MHz, $CDCl_3$) 8.18 (s, 1H), 7.34 (q, 1H), 6.78-6.69 (m, 2H), 6.50 (d, 1H), 6.45 (s, 1H), 5.53 (dd, 1H), 3.61 (dd, 1H), 3.52 (d, 4H), 3.26 (dd, 1H), 3.23 (d, 4H), 1.48 (s, 9H)

Example 182

1-(2,4-difluoro-phenyl)-5-[4-(piperazin-1-yl)-pyridin-2-yl]-3-pentafluoroethyl-4,5-dihydro-1H-pyrazole hydrochloride 5-[4-(4-BOC-piperazin-1-yl)-pyridin-2-yl]-1-(2,4-difluoro-phenyl)-3-pentafluoroethyl-4,5-dihydro-1H-pyrazole (350.0 mg, 0.6 mmol) prepared in Example 181 was added to a saturated solution of hydrochloric acid in ethyl acetate (3.0 mL). The reaction mixture was stirred at room temperature for 2 hours and then concentrated under reduced pressure to give 325.0 mg of the titled compound as a brown liquid.

$^1$H NMR (400 MHz, $CD_3OD$) 8.25 (d, 1H), 7.40 (q, 1H), 7.29-7.24 (m, 2H), 7.04-6.97 (m, 2H), 5.48 (dd, 1H), 3.99 (s, 4H), 3.87 (dd, 1H), 3.33 (dd, 1H), 3.29 (s, 4H)

Example 183

1-(2,4-difluoro-phenyl)-5-[4-(4-methanesulfonyl-piperazin-1-yl)-pyridin-2-yl]-3-pentafluoroethyl-4,5-dihydro-1H-pyrazole 1-(2,4-Difluoro-phenyl)-5-[4-(piperazin-1-yl)-pyridin-2-yl]-3-pentafluoroethyl-4,5-dihydro-1H-pyrazole hydrochloride (30.0 mg, 0.06 mmol) prepared in Example 182, triethylamine (42.0 uL, 0.30 mmol) and methanesulfonyl chloride (7.0 uL, 0.09 mmol) were added to dichloromethane (1.0 mL). The reaction mixture was stirred at room temperature for 18 hours, washed with distilled water, 1N hydrochloride, a saturated solution of sodium hydrogen carbonate, and brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 15.0 mg of the titled compound as a yellow liquid.

$^1$H NMR (400 MHz, $CDCl_3$) 8.23 (d, 1H), 7.36-7.30 (m, 1H), 6.80-6.68 (m, 2H), 6.54-6.47 (m, 2H), 5.55 (dd, 1H), 3.61 (dd, 1H), 3.38-3.24 (m, 9H), 2.81 (s, 3H)

Example 184

1-(2,4-difluoro-phenyl)-5-[4-(4-cyclopropanesulfonyl-piperazin-1-yl)-pyridin-2-yl]-3-pentafluoroethyl-4,5-dihydro-1H-pyrazole 1-(2,4-Difluoro-phenyl)-5-[4-(piperazin-1-yl)-pyridin-2-yl]-3-pentafluoroethyl-4,5-dihydro-1H-pyrazole hydrochloride (30.0 mg, 0.06 mmol) prepared in Example 182, triethylamine (42.0 uL, 0.30 mmol) and cyclopropanesulfonyl chloride (9.0 uL, 0.09 mmol) were added to dichloromethane (1.0 mL). The reaction mixture was stirred at room temperature for 1 hour, washed with distilled water, 1N hydrochloride, a saturated solution of sodium hydrogen carbonate, and brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 15.0 mg of the titled compound as a yellow liquid.

$^1$H NMR (400 MHz, $CDCl_3$) 8.22 (d, 1H), 7.36-7.30 (m, 1H), 6.80-6.68 (m, 2H), 6.54-6.47 (m, 2H), 5.55 (dd, 1H), 3.61 (dd, 1H), 3.37-3.24 (m, 9H), 2.28-2.24 (m, 1H), 1.23-1.17 (m, 2H), 1.04-0.98 (m, 2H)

Example 185

1-(2,4-difluoro-phenyl)-5-[2-(3-methylsulfanyl-phenyl)-pyridin-4-yl]-3-pentafluoroethyl-4,5-dihydro-1H-pyrazole 5-(2-Bromo-pyridin-4-yl)-1-(2,4-difluoro-phenyl)-3-pentafluoroethyl-4,5-dihydro-1H-pyrazole (50.0 mg, 0.11 mmol) prepared in Step 4 of Preparation 12, 3-(methylthio)phenylboronic acid (28.0 mg, 0.17 mmol), $Pd(PPh_3)_4$ (12.8 mg, cat.) and a 2N sodium carbonate solution (550.0 uL) were added to a mixed solvent of ethanol (550.0 uL) and 1,2-dimethoxyethane (1.2 mL). The reaction mixture was stirred at 85° C. for 3 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/6) to give 15.0 mg of the titled compound as a white liquid.

$^1$H NMR (400 MHz, $CDCl_3$) 8.58 (d, 1H), 7.80 (s, 1H), 7.62 (d, 1H), 7.47 (s, 1H), 7.44-7.35 (m, 2H), 7.30 (d, 1H), 6.99 (d, 1H), 6.79 (t, 1H), 6.68 (m, 1H), 5.63 (dd, 1H), 3.71 (dd, 1H), 3.16 (dd, 1H), 2.52 (s, 3H)

Examples 186 and 187

The compounds of Examples 186 and 187 were prepared in accordance with the same procedures as in Example 185, except for using 5-(2-bromo-pyridin-4-yl)-1-(2,4-difluoro-phenyl)-3-pentafluoroethyl-4,5-dihydro-1H-pyrazole prepared in Step 4 of Preparation 12; and using each boronic acid corresponding to the compounds of Examples 186 and 187 instead of 3-(methylthio)phenylboronic acid.

Example 186

1-(2,4-difluoro-phenyl)-5-[2-(6-methylsulfanyl-pyridin-3-yl)-pyridin-4-yl]-3-pentafluoroethyl-4,5-dihydro-1H-pyrazole $^1$H NMR (400 MHz, CDCl$_3$) 8.89 (s, 1H), 8.60 (d, 1H), 8.07 (d, 1H), 7.42 (q, 2H), 7.26 (d, 1H), 7.01 (d, 1H), 6.81 (t, 1H), 6.70 (t, 1H), 5.64 (dd, 1H), 3.73 (dd, 1H), 3.16 (dd, 1H), 2.61 (s, 3H)

Example 187

5-[2-(1-BOC-1,2,3,6-tetrahydropyridin-4-yl)-pyridin-4-yl]-1-(2,4-difluoro-phenyl)-3-pentafluoroethyl-4,5-dihydro-1H-pyrazole $^1$H NMR (400 MHz, CDCl$_3$) 8.46 (d, 1H), 7.37 (q, 1H), 7.11 (s, 1H), 6.89 (d, 1H), 6.79 (t, 1H), 6.67 (t, 1H), 6.56 (s, 1H), 5.57 (dd, 1H), 4.11 (s, 2H), 3.71 (dd, 1H), 3.62 (t, 2H), 3.11 (dd, 1H), 2.55 (m, 2H), 1.48 (s, 9H)

Example 188

1-(2,4-difluoro-phenyl)-5-[2-(3-methanesulfonyl-phenyl)-pyridin-4-yl]-3-pentafluoroethyl-4,5-dihydro-1H-pyrazole To a mixture of 1-(2,4-difluoro-phenyl)-5-[2-(3-methylsulfanyl-phenyl)-pyridin-4-yl]-3-pentafluoroethyl-4,5-dihydro-1H-pyrazole (30.0 mg, 0.06 mmol) prepared in Example 185 in dichloromethane (2.0 mL), was slowly added meta-chloroperbenzoic acid (77%, 18.0 mg, 0.12 mmol) at 0° C. The reaction mixture was stirred at room temperature for 30 minutes, quenched with a saturated solution of sodium hydrogen carbonate, and then extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 15.0 mg of the titled compound as a yellow liquid.

$^1$H NMR (400 MHz, CDCl$_3$) 8.63 (d, 1H), 8.49 (s, 1H), 8.22 (d, 1H), 8.00 (d, 1H), 7.68 (t, 1H), 7.56 (s, 1H), 7.44 (q, 1H), 7.06 (s, 1H), 6.82 (t, 1H), 6.72 (t, 1H), 5.67 (dd, 1H), 3.74 (dd, 1H), 3.14 (dd, 1H), 3.10 (s, 3H)

Example 189

1-(2,4-difluoro-phenyl)-5-[2-(6-methanesulfonyl-pyridin-3-yl)-pyridin-4-yl]-3-pentafluoroethyl-4,5-dihydro-1H-pyrazole To a mixture of 1-(2,4-difluoro-phenyl)-5-[2-(6-methylsulfanyl-pyridin-3-yl)-pyridin-4-yl]-3-pentafluoroethyl-4,5-dihydro-1H-pyrazole (20.0 mg, 0.04 mmol) prepared in Example 186 in dichloromethane (2.0 mL), was slowly added meta-chloroperbenzoic acid (77%, 12.0 mg, 0.08 mmol) at 0° C. The reaction mixture was stirred at room temperature for 30 minutes, quenched with a saturated solution of sodium hydrogen carbonate, and then extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 5.0 mg of the titled compound as a yellow liquid.

$^1$H NMR (400 MHz, CDCl$_3$) 9.18 (s, 1H), 8.69 (d, 1H), 8.49 (d, 1H), 8.17 (d, 1H), 7.55 (s, 1H), 7.45 (q, 1H), 7.14 (d, 1H), 6.82 (t, 1H), 6.71 (t, 1H), 5.69 (dd, 1H), 3.77 (dd, 1H), 3.27 (s, 3H), 3.14 (dd, 1H)

Example 190

1-(2,4-difluoro-phenyl)-5-[2-(1,2,3,6-tetrahydropyridin-4-yl)-pyridin-4-yl]-3-pentafluoroethyl-4,5-dihydro-1H-pyrazole hydrochloride 5-[2-(1-BOC-1,2,3,6-tetrahydropyridin-4-yl)-pyridin-4-yl]-1-(2,4-difluoro-phenyl)-3-pentafluoroethyl-4,5-dihydro-1H-pyrazole (350.0 mg, 4.2 mmol) prepared in Example 187 was added to a saturated solution of hydrochloric acid in ethyl acetate (10.0 mL). The reaction mixture was stirred at room temperature for 2 hours and then concentrated under reduced pressure to give 300.0 mg of the titled compound as a brown liquid.

$^1$H NMR (400 MHz, CD$_3$OD) 8.67 (d, 1H), 8.00 (s, 1H), 7.73 (d, 1H), 7.46 (q, 1H), 6.98-6.91 (m, 2H), 6.79 (s, 1H), 5.89 (dd, 1H), 4.01 (s, 2H), 3.93 (dd, 1H), 3.52 (t, 2H), 3.23 (dd, 1H), 2.90 (m, 2H)

Example 191

1-(2,4-difluoro-phenyl)-5-[2-(1-methanesulfonyl-1,2,3,6-tetrahydropyridin-4-yl)-pyridin-4-yl]-3-pentafluoroethyl-4,5-dihydro-1H-pyrazole 1-(2,4-Difluoro-phenyl)-5-[2-(1,2,3,6-tetrahydropyridin-4-yl)-pyridin-4-yl]-3-pentafluoroethyl-4,5-dihydro-1H-pyrazole hydrochloride (30.0 mg, 0.06 mmol) prepared in Example 190, triethylamine (42.0 uL, 0.30 mmol) and methanesulfonyl chloride (7.0 uL, 0.09 mmol) were added to dichloromethane (1.0 mL). The reaction mixture was stirred at room temperature for 18 hours, washed with distilled water, 1N hydrochloride, a saturated solution of sodium hydrogen carbonate, and brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 5.0 mg of the titled compound as a yellow liquid.

$^1$H NMR (400 MHz, CDCl$_3$) 8.49 (s, 1H), 7.42-7.38 (m, 1H), 7.13 (s, 1H), 6.94 (s, 1H), 6.80 (t, 1H), 6.70 (t, 1H), 6.59 (s, 1H), 5.58 (dd, 1H), 4.01 (s, 2H), 3.70 (dd, 1H), 3.51 (s, 2H), 3.10 (dd, 1H), 2.85 (s, 3H), 2.71 (s, 2H)

Example 192

5-[2-(4-BOC-piperazin-1-yl)-pyridin-4-yl]-1-(2,4-difluoro-phenyl)-3-pentafluoroethyl-4,5-dihydro-1H-pyrazole 5-(2-Bromo-pyridin-4-yl)-1-(2,4-difluoro-phenyl)-3-pentafluoroethyl-4,5-dihydro-1H-pyrazole (300.0 mg, 0.66 mmol) prepared in Step 4 of Preparation 12, 1-BOC-piperazine (184.0 mg, 0.99 mmol), Pd$_2$(dba)$_3$ (30.2 mg, cat.), BINAP (41.1 mg, cat.) and sodium t-butoxide (114.0 mg, 1.19 mmol) were added to toluene (10.0 mL). The reaction mixture was stirred at 100° C. for 12 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/3) to give 320.0 mg of the titled compound as a yellow liquid.

¹H NMR (400 MHz, CDCl₃) 8.05 (d, 1H), 7.34 (q, 1H), 6.80-6.68 (m, 2H), 6.37 (d, 1H), 6.34 (s, 1H), 5.47 (dd, 1H), 3.65 (dd, 1H), 3.47 (d, 4H), 3.43 (d, 4H), 3.11 (dd, 1H), 1.48 (s, 9H)

Example 193

1-(2,4-difluoro-phenyl)-5-[2-(piperazin-1-yl)-pyridin-4-yl]-3-pentafluoroethyl-4,5-dihydro-1H-pyrazole hydrochloride 5-[2-(4-BOC-piperazin-1-yl)-pyridin-4-yl]-1-(2,4-difluoro-phenyl)-3-pentafluoroethyl-4,5-dihydro-1H-pyrazole (320.0 mg, 0.6 mmol) prepared in Example 192 was added to a saturated solution of hydrochloric acid in ethyl acetate (3.0 mL). The reaction mixture was stirred at room temperature for 2 hours and then concentrated under reduced pressure to give 300.0 mg of the titled compound as a brown liquid.

¹H NMR (400 MHz, CD₃OD) 8.02 (d, 1H), 7.44 (q, 1H), 7.36 (s, 1H), 6.99-6.91 (m, 3H), 5.73 (dd, 1H), 3.96 (s, 4H), 3.86 (dd, 1H), 3.45 (s, 4H), 3.16 (dd, 1H)

Example 194

1-(2,4-difluoro-phenyl)-5-[2-(4-methanesulfonyl-piperazin-1-yl)-pyridin-4-yl]-3-pentafluoroethyl-4,5-dihydro-1H-pyrazole 1-(2,4-difluoro-phenyl)-5-[2-(piperazin-1-yl)-pyridin-4-yl]-3-pentafluoroethyl-4,5-dihydro-1H-pyrazole (30.0 mg, 0.06 mmol) prepared in Example 193, triethylamine (42.0 uL, 0.30 mmol) and methanesulfonyl chloride (7.0 uL, 0.09 mmol) were added to dichloromethane (1.0 mL). The reaction mixture was stirred at room temperature for 18 hours, washed with distilled water, 1N hydrochloride, a saturated solution of sodium hydrogen carbonate, and brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 5.0 mg of the titled compound as a yellow liquid.

¹H NMR (400 MHz, CDCl₃) 8.10 (d, 1H), 7.40-7.35 (m, 1H), 6.81-6.68 (m, 2H), 6.43-6.37 (m, 2H), 5.48 (dd, 1H), 3.69-3.54 (m, 5H), 3.31-3.25 (m, 4H), 3.11 (dd, 1H), 2.79 (s, 3H)

Example 195

1-(2,4-difluoro-phenyl)-5-{5-[3-(methylsulfanyl)-phenyl]-thiophen-2-yl}-3-pentafluoroethyl-4,5-dihydro-1H-pyrazole 5-(5-Bromo-thiophen-2-yl)-1-(2,4-difluoro-phenyl)-3-pentafluoroethyl-4,5-dihydro-1H-pyrazole (50.0 mg, 0.11 mmol) prepared in Step 8 of Preparation 13, 3-(methylthio)phenylboronic acid (28.0 mg, 0.17 mmol), Pd(PPh₃)₄ (12.5 mg, cat.) and a 2N sodium carbonate solution (500.0 uL) were added to a mixed solvent of ethanol (500.0 uL) and 1,2-dimethoxyethane (2.0 mL). The reaction mixture was stirred at 90° C. for 3 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/6) to give 15.0 mg of the titled compound as a white liquid.

¹H NMR (400 MHz, CDCl₃) 7.44-7.27 (m, 4H), 7.15 (d, 1H), 6.98 (s, 1H), 6.82 (s, 1H), 6.78-6.74 (m, 2H), 5.83 (d, 1H), 3.62 (dd, 1H), 3.34 (dd, 1H), 2.50 (s, 3H)

Examples 196 and 197

The compounds of Examples 196 and 197 were prepared in accordance with the same procedures as in Example 195, except for using 5-(5-bromo-thiophen-2-yl)-1-(2,4-difluoro-phenyl)-3-pentafluoroethyl-4,5-dihydro-1H-pyrazole prepared in Step 8 of Preparation 13; and using each boronic acid corresponding to the compounds of Examples 196 and 197 instead of 3-(methylthio)phenylboronic acid.

Example 196

1-(2,4-difluoro-phenyl)-5-[5-(6-methylsulfanyl-pyridin-3-yl)-thiophen-2-yl]-3-pentafluoroethyl-4,5-dihydro-1H-pyrazole ¹H NMR (400 MHz, CDCl₃) 8.57 (s, 1H), 7.54 (d, 1H), 7.35-7.29 (m, 1H), 7.14 (d, 1H), 6.97 (s, 1H), 6.83 (s, 1H), 6.79-6.74 (m, 2H), 5.84 (d, 1H), 3.62 (dd, 1H), 3.33 (dd, 1H), 2.56 (s, 3H)

Example 197

5-[5-(1-BOC-1,2,3,6-tetrahydropyridin-4-yl)-thiophen-2-yl]-1-(2,4-difluoro-phenyl)-3-pentafluoroethyl-4,5-dihydro-1H-pyrazole ¹H NMR (400 MHz, CDCl₃) 7.33-7.27 (m, 1H), 6.76-6.72 (m, 3H), 6.62 (s, 1H), 5.94 (s, 1H), 5.78 (d, 1H), 4.01 (s, 2H), 3.58 (dd, 1H), 3.56 (s, 2H), 3.25 (dd, 1H), 2.39 (s, 2H), 1.46 (s, 9H)

Example 198

1-(2,4-difluoro-phenyl)-5-{5-[3-(methylsulfonyl)-phenyl]-thiophen-2-yl}-3-pentafluoroethyl-4,5-dihydro-1H-pyrazole To a mixture of 1-(2,4-difluoro-phenyl)-5-{5-[3-(methylsulfanyl)-phenyl]-thiophen-2-yl}-3-pentafluoroethyl-4,5-dihydro-1H-pyrazole (15.0 mg, 0.03 mmol) prepared in Example 195 in dichloromethane (2.0 mL), was slowly added meta-chloroperbenzoic acid (77%, 9.0 mg, 0.06 mmol) at 0° C. The reaction mixture was stirred at room temperature for 30 minutes, quenched with a saturated solution of sodium hydrogen carbonate, extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 5.0 mg of the titled compound as a yellow liquid.

¹H NMR (400 MHz, CDCl₃) 8.03 (s, 1H), 7.82 (d, 1H), 7.73 (d, 1H), 7.54 (t, 1H), 7.37-7.33 (m, 1H), 7.11 (s, 1H), 6.88 (s, 1H), 6.79-6.75 (m, 2H), 5.86 (d, 1H), 3.64 (dd, 1H), 3.34 (dd, 1H), 3.07 (s, 3H)

Example 199

1-(2,4-difluoro-phenyl)-5-[5-(6-methanesulfonyl-pyridin-3-yl)-thiophen-2-yl]-3-pentafluoroethyl-4,5-dihydro-1H-pyrazole To a mixture of 1-(2,4-difluoro-phenyl)-5-[5-(6-methylsulfanyl-pyridin-3-yl)-thiophen-2-yl]-3-pentafluoroethyl-4,5-dihydro-1H-pyrazole (15.0 mg, 0.03 mmol) prepared in Example 196 in dichloromethane (2.0 mL), was slowly added meta-chloroperbenzoic acid (77%, 9.0 mg, 0.06 mmol) at 0° C. The reaction mixture was stirred at room temperature for 30 minutes, quenched with a saturated solution of sodium hydrogen carbonate, extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 5.0 mg of the titled compound as a yellow liquid.

$^1$H NMR (400 MHz, CDCl$_3$) 8.83 (s, 1H), 8.05 (d, 1H), 7.96 (d, 1H), 7.35-7.29 (m, 1H), 7.20 (s, 1H), 6.93 (s, 1H), 6.78-6.74 (m, 2H), 5.89 (d, 1H), 3.66 (dd, 1H), 3.33 (dd, 1H), 3.22 (s, 3H)

Example 200

1-(2,4-difluoro-phenyl)-5-[5-(1-methanesulfonyl-1,2,3,6-tetrahydropyridin-4-yl)-thiophen-2-yl]-3-pentafluoroethyl-4,5-dihydro-1H-pyrazole

Step 1: 1-(2,4-difluoro-phenyl)-5-[5-(1,2,3,6-tetrahydropyridin-4-yl)-thiophen-2-yl]-3-pentafluoroethyl-4,5-dihydro-1H-pyrazole trifluoroacetate 5-[5-(1-BOC-1,2,3,6-tetrahydropyridin-4-yl)-thiophen-2-yl]-1-(2,4-difluoro-phenyl)-3-pentafluoroethyl-4,5-dihydro-1H-pyrazole (480.0 mg, 0.85 mmol) prepared in Example 197 and trifluoroacetic acid (600.0 uL, 7.84 mmol) were added at 0° C. to dichloromethane (5.0 mL). The reaction mixture was stirred at room temperature for 3 hours and then concentrated under reduced pressure to give 450.0 mg of the titled compound as a yellow liquid.

Step 2: 1-(2,4-difluoro-phenyl)-5-[5-(1-methanesulfonyl-1,2,3,6-tetrahydropyridin-4-yl)-thiophen-2-yl]-3-pentafluoroethyl-4,5-dihydro-1H-pyrazole 1-(2,4-Difluoro-phenyl)-5-[5-(1,2,3,6-tetrahydropyridin-4-yl)-thiophen-2-yl]-3-pentafluoroethyl-4,5-dihydro-1H-pyrazole trifluoroacetate (27.0 mg, 0.05 mmol) prepared in Step 1, triethylamine (32.5 uL, 0.23 mmol) and methanesulfonyl chloride (8.0 mg, 0.07 mmol) were added to dichloromethane (1.0 mL). The reaction mixture was stirred at room temperature for 18 hours, washed with distilled water, 1N hydrochloride, a saturated solution of sodium hydrogen carbonate, and brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 5.0 mg of the titled compound as a yellow liquid.

$^1$H NMR (400 MHz, CDCl$_3$) 7.33-7.27 (m, 1H), 6.77-6.73 (m, 3H), 6.66 (s, 1H), 5.99 (s, 1H), 5.80 (d, 1H), 3.91 (s, 2H), 3.60 (dd, 1H), 3.45 (s, 2H), 3.28 (dd, 1H), 2.82 (s, 3H), 2.54 (s, 2H)

Example 201

1-(2,4-difluoro-phenyl)-5-[5-(1-dimethylsulfamoyl-1,2,3,6-tetrahydropyridin-4-yl)-thiophen-2-yl]-3-pentafluoroethyl-4,5-dihydro-1H-pyrazole The titled compound was prepared in accordance with the same procedures as in Step 2 of Example 200, except for using 1-(2,4-difluoro-phenyl)-5-[5-(1,2,3,6-tetrahydropyridin-4-yl)-thiophen-2-yl]-3-pentafluoroethyl-4,5-dihydro-1H-pyrazole trifluoroacetate Prepared in Step 1 of Example 200; and using dimethylsulfamoyl chloride instead of methanesulfonyl chloride.

$^1$H NMR (400 MHz, CDCl$_3$) 7.33-7.27 (m, 1H), 6.77-6.73 (m, 3H), 6.65 (s, 1H), 5.97 (s, 1H), 5.80 (d, 1H), 3.87 (s, 2H), 3.58 (dd, 1H), 3.42 (s, 2H), 3.28 (dd, 1H), 2.81 (s, 6H), 2.50 (s, 2H)

Example 202

5-[5-(4-BOC-piperazin-1-yl)-thiophen-2-yl]-1-(2,4-difluoro-phenyl)-3-pentafluoroethyl-4,5-dihydro-1H-pyrazole 5-(5-Bromo-thiophen-2-yl)-1-(2,4-difluoro-phenyl)-3-pentafluoroethyl-4,5-dihydro-1H-pyrazole (500.0 mg, 1.08 mmol) prepared in Step 8 of Preparation 13, 1-BOC-piperazine (303.0 mg, 1.63 mmol), Pd$_2$(dba)$_3$ (50.2 mg, cat.), BINAP (67.3 mg, cat.) and sodium t-butoxide (187.6 mg, 1.95 mmol) were added to toluene (10.0 mL). The reaction mixture was stirred at 100° C. for 12 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/3) to give 483.0 mg of the titled compound as a yellow liquid.

$^1$H NMR (400 MHz, CDCl$_3$) 7.33-7.27 (m, 1H), 6.74-6.72 (m, 2H), 6.54 (s, 1H), 5.75 (s, 1H), 5.70 (d, 1H), 3.58 (dd, 1H), 3.50 (s, 4H), 3.24 (dd, 1H), 2.98 (s, 4H), 1.46 (s, 9H)

Example 203

1-(2,4-difluoro-phenyl)-5-[5-(4-methanesulfonyl-piperazin-1-yl)-thiophen-2-yl]-3-pentafluoroethyl-4,5-dihydro-1H-pyrazole

Step 1: 1-(2,4-difluoro-phenyl)-5-[5-(piperazin-1-yl)-thiophen-2-yl]-3-pentafluoroethyl-4,5-dihydro-1H-pyrazole hydrochloride 5-[5-(4-BOC-piperazin-1-yl)-thiophen-2-yl]-1-(2,4-difluoro-phenyl)-3-pentafluoroethyl-4,5-dihydro-1H-pyrazole (340.0 mg, 0.7 mmol) prepared in Example 202 was added to a saturated solution of hydrochloric acid in ethyl acetate (5.0 mL). The reaction mixture was stirred at room temperature for 2 hours and then concentrated under reduced pressure to give 300.0 mg of the titled compound as a brown liquid.

Step 2: 1-(2,4-difluoro-phenyl)-5-[5-(4-methanesulfonyl-piperazin-1-yl)-thiophen-2-yl]-3-pentafluoroethyl-4,5-dihydro-1H-pyrazole 1-(2,4-Difluoro-phenyl)-5-[5-(piperazin-1-yl)-thiophen-2-yl]-3-pentafluoroethyl-4,5-dihydro-1H-pyrazole hydrochloride (30.0 mg, 0.07 mmol) prepared in Step 1, triethylamine (47.0 uL, 0.34 mmol) and methanesulfonyl chloride (11.6 mg, 0.10 mmol) were added to dichloromethane (1.0 mL). The reaction mixture was stirred at room temperature for 18 hours, washed with distilled water, 1N hydrochloride, a saturated solution of sodium hydrogen carbonate, and brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 15.0 mg of the titled compound as a yellow liquid.

$^1$H NMR (400 MHz, CDCl$_3$) 7.33-7.27 (m, 1H), 6.74-6.72 (m, 2H), 6.56 (s, 1H), 5.79 (s, 1H), 5.71 (d, 1H), 3.52 (dd, 1H), 3.31 (s, 4H), 3.26 (dd, 1H), 3.14 (s, 4H), 2.79 (s, 3H)

Example 204

5-(2,4-difluoro-phenyl)-1-[3'-(methylsulfanyl)-biphenyl-3-yl]-3-pentafluoroethyl-4,5-dihydro-1H-pyrazole 1-(3-Bromo-phenyl)-5-(2,4-difluoro-phenyl)-3-pentafluoroethyl-4,5-dihydro-1H-pyrazole (50.0 mg, 0.11 mmol) prepared in Step 4 of Preparation 14, 3-(methylthio)phenylboronic acid (28.0 mg, 0.17 mmol), Pd(PPh$_3$)$_4$ (13.0 mg, cat.) and a 2N sodium carbonate solution (550.0 uL) were added to a mixed solvent of ethanol (550.0 uL) and 1,2-dimethoxyethane (2.0 mL). The reaction mixture was stirred at 90° C. for 3 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/6) to give 15.0 mg of the titled compound as a white liquid.

$^1$H NMR (400 MHz, CDCl$_3$) 7.30 (d, 2H), 7.29-7.10 (m, 6H), 6.94 (d, 1H), 6.91-6.85 (m, 2H), 5.69 (dd, 1H), 3.73 (dd, 1H), 3.01 (dd, 1H), 2.50 (s, 3H)

Example 205

1-[3-(1-BOC-1,2,3,6-tetrahydropyridin-4-yl)-phenyl]-5-(2,4-difluoro-phenyl)-3-pentafluoroethyl-4,5-dihydro-1H-pyrazole The titled compound was prepared in accordance with the same procedures as in Example 204, except for using 1-(3-bromo-phenyl)-5-(2,4-difluoro-phenyl)-3-pentafluoroethyl-4,5-dihydro-1H-pyrazole prepared in Step 4 of Preparation 14; and using 1-BOC-4-(4,4,5,5-tetramethyl-[1,3,2]dioxaborolan-2-yl)-1,2,3,6-tetrahydropyridine instead of 3-(methylthio)phenylboronic acid.

$^1$H NMR (400 MHz, CDCl$_3$) 7.18-7.05 (m, 3H), 6.93-6.80 (m, 4H), 5.94 (s, 1H), 5.65 (dd, 1H), 4.04 (brs, 2H), 3.72 (dd, 1H), 3.60 (t, 2H), 2.98 (dd, 1H), 2.50-2.35 (m, 2H), 1.49 (s, 9H)

Example 206

5-(2,4-difluoro-phenyl)-1-[3'-(methylsulfonyl)-biphenyl-3-yl]-3-pentafluoroethyl-4,5-dihydro-1H-pyrazole To a mixture of 5-(2,4-difluoro-phenyl)-1-[3'-(methylsulfanyl)-biphenyl-3-yl]-3-pentafluoroethyl-4,5-dihydro-1H-pyrazole (20.0 mg, 0.04 mmol) prepared in Example 204 in dichloromethane (2.0 mL), was slowly added meta-chloroperbenzoic acid (77%, 12.0 mg, 0.08 mmol) at 0° C. The reaction mixture was stirred at room temperature for 30 minutes, quenched with a saturated solution of sodium hydrogen carbonate, and then extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 5.0 mg of the titled compound as a yellow liquid.

$^1$H NMR (400 MHz, CDCl$_3$) 8.02 (s, 1H), 7.92 (d, 1H), 7.77 (d, 1H), 7.62 (t, 1H), 7.32-7.26 (m, 2H0, 7.17-7.13 (m, 2H), 6.98-6.88 (m, 3H), 5.72 (dd, 1H), 3.72 (dd, 1H), 3.10 (s, 3H), 3.05 (dd, 1H)

Example 207

5-(2,4-difluoro-phenyl)-1-[3-(5-methanesulfonyl-pyridin-3-yl)-phenyl]-3-pentafluoroethyl-4,5-dihydro-1H-pyrazole Step 1: 5-(2,4-difluoro-phenyl)-3-pentafluoroethyl-1-[3-(4,4,5,5-tetramethyl-1,3,2-dioxaborolan-2-yl)phenyl]-4,5-dihydro-1H-pyrazole 1-(3-Bromo-phenyl)-5-(2,4-difluoro-phenyl)-3-pentafluoroethyl-4,5-dihydro-1H-pyrazole (950.0 mg, 2.1 mmol) prepared in Step 4 of Preparation 14, bis(pinacolato)diboron (795.0 mg, 3.1 mmol), Pd(dppf)Cl$_2$ (153.0 mg, 0.2 mmol), dppf (116.0 mg, 0.2 mmol) and potassium acetate (1.23 g, 12.5 mmol) were added to 1,4-dioxane (10 mL). The reaction mixture was stirred at 80° C. for 3 hours and then filtered through celite pad. Distilled water was added to the filtrate, which was then extracted with diethyl ether three times. The combined extract was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/100) to give 1.0 g of the titled compound as a yellow liquid.

$^1$H NMR (400 MHz, CDCl$_3$) 7.48 (s, 1H), 7.34 (d, 1H), 7.20 (t, 1H), 7.09-6.99 (m, 2H), 6.89-6.76 (m, 2H), 5.69 (dd, 1H), 3.69 (dd, 1H), 2.98 (dd, 1H), 1.31 (s, 12H)

Step 2: 5-(2,4-difluoro-phenyl)-1-[3-(5-methanesulfonyl-pyridin-3-yl)-phenyl]-3-pentafluoroethyl-4,5-dihydro-1H-pyrazole 5-(2,4-Difluoro-phenyl)-3-pentafluoroethyl-1-[3-(4,4,5,5-tetramethyl-1,3,2-dioxaborolan-2-yl)phenyl]-4,5-dihydro-1H-pyrazole (30.0 mg, 0.06 mmol) prepared in Step 1,3-bromo-5-methanesulfonyl-pyridine (13.5 mg, 0.06 mmol), Pd(PPh$_3$)$_4$ (7.0 mg, cat.) and a 2N sodium carbonate solution (300.0 uL) were added to a mixed solvent of ethanol (300.0 uL) and 1,2-dimethoxyethane (1.0 mL). The reaction mixture was stirred at 90° C. for 3 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/6) to give 15.0 mg of the titled compound as a white liquid.

¹H NMR (400 MHz, CDCl₃) 9.11 (s, 1H), 8.99 (s, 1H), 8.28 (s, 1H), 7.35 (t, 1H), 7.27 (d, 1H), 7.18-7.12 (m, 2H), 7.01 (d, 1H), 6.95-6.86 (m, 2H), 5.71 (dd, 1H), 3.78 (dd, 1H), 3.16 (s, 3H), 3.04 (dd, 1H)

Examples 208 to 211

The compounds of Examples 208 to 211 were prepared in accordance with the same procedures as in Step 2 of Example 207, except for using 5-(2,4-difluoro-phenyl)-3-pentafluoroethyl-1-[3-(4,4,5,5-tetramethyl-1,3,2-dioxaborolan-2-yl) phenyl]-4,5-dihydro-1H-pyrazole prepared in Step 1 of Example 207; and using each aryl bromide corresponding to the compounds of Examples 208 to 211 instead of 3-bromo-5-methanesulfonyl-pyridine.

Example 208

5-(2,4-difluoro-phenyl)-1-[3-(6-methanesulfonyl-pyridin-2-yl)-phenyl]-3-pentafluoroethyl-4,5-dihydro-1H-pyrazole ¹H NMR (400 MHz, CDCl₃) 8.01 (t, 2H), 7.91 (d, 1H), 7.73 (s, 1H), 7.55 (d, 1H), 7.34 (t, 1H), 7.21-7.12 (m, 2H), 6.95-6.84 (m, 2H), 5.73 (dd, 1H), 3.78 (dd, 1H), 3.24 (s, 3H), 3.05 (dd, 1H)

Example 209

5-(2,4-difluoro-phenyl)-1-[3-(6-dimethylsulfamoyl-pyridin-2-yl)-phenyl]-3-pentafluoroethyl-4,5-dihydro-1H-pyrazole ¹H NMR (400 MHz, CDCl₃) 7.84 (s, 1H), 7.75-7.70 (m, 2H), 7.59 (t, 1H), 7.42 (t, 1H), 7.30 (t, 1H), 7.18-7.12 (m, 2H), 6.99-6.87 (m, 2H), 5.71 (dd, 1H), 3.75 (dd, 1H), 3.08 (dd, 1H), 2.75 (s, 6H)

Example 210

5-(2,4-difluoro-phenyl)-1-{3'-[(2-hydroxy-ethyl)-methyl-sulfamoyl]-biphenyl-3-yl}-3-pentafluoroethyl-4,5-dihydro-1H-pyrazole ¹H NMR (400 MHz, CDCl₃) 7.87 (s, 1H), 7.76 (d, 1H), 7.73 (d, 1H), 7.56 (t, 1H), 7.30 (t, 1H), 7.17-7.12 (m, 2H), 6.98-6.87 (m, 3H), 5.72 (dd, 1H), 3.80 (t, 2H), 3.77 (dd, 1H), 3.19 (t, 2H), 3.10 (dd, 1H), 2.87 (s, 3H)

Example 211

5-(2,4-difluoro-phenyl)-1-{3'-[3-(N-BOC-N-methyl-amino)-propane-1-sulfonyl]-biphenyl-3-yl}-3-pentafluoroethyl-4,5-dihydro-1H-pyrazole ¹H NMR (400 MHz, CDCl₃) 7.98 (s, 1H), 7.85 (t, 1H), 7.78 (t, 1H), 6.72 (t, 1H), 7.46 (t, 1H), 7.30 (t, 1H), 7.17-7.12 (m, 2H), 6.97-6.88 (m, 3H), 5.72 (dd, 1H), 3.75 (dd, 1H), 3.31 (br, 2H), 3.11 (br, 2H) m 3.07 (dd, 1H), 2.81 (s, 3H), 1.95 (br, 2H), 1.42 (s, 9H)

Example 212

5-(2,4-difluoro-phenyl)-1-[3'-(3-methylamino-propane-1-sulfonyl)-biphenyl-3-yl]-3-pentafluoroethyl-4,5-dihydro-1H-pyrazole hydrochloride 5-(2,4-Difluoro-phenyl)-1-{3'-[3-(N-BOC-N-methyl-amino)-propane-1-sulfonyl]-biphenyl-3-yl}-3-pentafluoroethyl-4,5-dihydro-1H-pyrazole (10.0 mg, 0.01 mmol) prepared in Example 211 was added to a saturated solution of hydrochloric acid in ethyl acetate (1.0 mL). The reaction mixture was stirred at room temperature for 2 hours and then concentrated under reduced pressure to give 5.0 mg of the titled compound as a brown liquid.

¹H NMR (400 MHz, CDCl₃) 9.57 (br, 2H), 8.00 (s, 1H), 7.91 (d, 1H), 7.77 (d, 1H), 7.60 (t, 1H), 7.44 (t, 1H), 7.30 (d, 1H), 7.23 (D, 1H), 7.15 (t, 1H), 6.98-6.84 (m, 3H), 5.74 (dd, 1H), 3.74 (dd, 1H), 3.47 (br, 2H), 3.23 (br, 2H), 3.02 (dd, 1H), 2.71 (s, 3H), 2.40 (br, 2H)

Example 213

5-(2,4-difluoro-phenyl)-1-[3-(1,2,3,6-tetrahydropyridin-4-yl)-phenyl]-3-pentafluoroethyl-4,5-dihydro-1H-pyrazole hydrochloride 1-[3-(1-BOC-1,2,3,6-tetrahydropyridin-4-yl)-phenyl]-5-(2,4-difluoro-phenyl)-3-pentafluoroethyl-4,5-dihydro-1H-pyrazole (300.0 mg, 0.54 mmol) prepared in Example 205 was added to a saturated solution of hydrochloric acid in ethyl acetate (3.0 mL). The reaction mixture was stirred at room temperature for 2 hours and then concentrated under reduced pressure to give 260.0 mg of the titled compound as a white solid.

¹H NMR (400 MHz, CD₃OD) 7.26-7.17 (m, 2H), 7.12 (s, 1H), 7.07-6.92 (m, 4H), 6.04 (s, 1H), 5.86 (dd, 1H), 3.87-3.78 (m, 3H), 3.45-3.41 (m, 2H), 3.06 (dd, 1H), 2.77-2.65 (m, 2H)

Example 214

5-(2,4-difluoro-phenyl)-1-[3-(1-methanesulfonyl-1,2,3,6-tetrahydropyridin-4-yl)-phenyl]-3-pentafluoroethyl-4,5-dihydro-1H-pyrazole 5-(2,4-Difluoro-phenyl)-1-[3-(1,2,3,6-tetrahydropyridin-4-yl)-phenyl]-3-pentafluoroethyl-4,5-dihydro-1H-pyrazole hydrochloride (20.0 mg, 0.04 mmol) prepared in Example 213, triethylamine (28.0 uL, 0.20 mmol) and methanesulfonyl chloride (5.0 uL, 0.06 mmol) were added to dichloromethane (1.0 mL). The reaction mixture was stirred at room temperature for 18 hours, washed with distilled water, 1N hydrochloride, a saturated solution of sodium hydrogen carbonate, and brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 10.0 mg of the titled compound as a yellow liquid.

¹H NMR (400 MHz, CDCl₃) 7.19-7.05 (m, 3H), 6.92-6.80 (m, 4H), 5.98 (s, 1H), 5.65 (dd, 1H), 3.94 (m, 2H), 3.73 (dd, 1H), 3.49 (t, 2H), 2.99 (dd, 1H), 2.84 (s, 3H), 2.63-2.51 (m, 2H)

Example 215

1-[3-(4-BOC-piperazin-1-yl)-phenyl]-5-(2,4-difluoro-phenyl)-3-pentafluoroethyl-4,5-dihydro-1H-pyrazole 1-(3-Bromo-phenyl)-5-(2,4-difluoro-phenyl)-3-pentafluoroethyl-4,5-dihydro-1H-pyrazole (500.0 mg, 1.10 mmol) prepared in Step 4 of Preparation 14, 1-BOC-piperazine (266.0 mg, 1.43 mmol), Pd₂(dba)₃ (50.0 mg, cat.), BINAP (68.0 mg, cat.) and sodium t-butoxide (158.0 mg, 1.65 mmol) were added to toluene (10.0 mL). The reaction mixture was stirred at 100° C. for 12 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/3) to give 300.0 mg of the titled compound as a yellow liquid.

$^1$H NMR (400 MHz, CDCl$_3$) 7.13-7.04 (m, 2H), 6.91-6.80 (m, 2H), 6.71 (s, 1H), 6.48 (dd, 1H), 6.34 (dd, 1H), 5.62 (dd, 1H), 3.70 (dd, 1H), 3.54 (t, 4H), 3.12-3.04 (m, 4H), 2.95 (dd, 1H), 1.48 (s, 9H)

Example 216

5-(2,4-difluoro-phenyl)-1-[3-(piperazin-1-yl)-phenyl]-3-pentafluoroethyl-4,5-dihydro-1H-pyrazole hydrochloride 1-[3-(4-BOC-piperazin-1-yl)-phenyl]-5-(2,4-difluoro-phenyl)-3-pentafluoroethyl-4,5-dihydro-1H-pyrazole (275.0 mg, 0.49 mmol) prepared in Example 215 was added to a saturated solution of hydrochloric acid in ethyl acetate (3.0 mL). The reaction mixture was stirred at room temperature for 2 hours and then concentrated under reduced pressure to give 240.0 mg of the titled compound as a yellow liquid.

$^1$H NMR (400 MHz, CD$_3$OD) 7.26-7.20 (m, 1H), 7.17-7.13 (m, 1H), 7.06-7.00 (m, 1H), 6.96-6.91 (m, 1H), 6.86 (s, 1H), 6.68 (dd, 1H), 6.61 (dd, 1H), 5.84 (dd, 1H), 3.82 (dd, 1H), 3.46-3.39 (m, 8H), 3.05 (dd, 1H)

Example 217

5-(2,4-difluoro-phenyl)-1-[3-(4-methanesulfonyl-piperazin-1-yl)-phenyl]-3-pentafluoroethyl-4,5-dihydro-1H-pyrazole 5-(2,4-Difluoro-phenyl)-1-[3-(piperazin-1-yl)-phenyl]-3-pentafluoroethyl-4,5-dihydro-1H-pyrazole hydrochloride (20.0 mg, 0.04 mmol) prepared in Example 216, triethylamine (28.0 uL, 0.20 mmol) and methanesulfonyl chloride (5.0 uL, 0.06 mmol) were added to dichloromethane (1.0 mL). The reaction mixture was stirred at room temperature for 18 hours, washed with distilled water, 1N hydrochloride, a saturated solution of sodium hydrogen carbonate, and brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 10.0 mg of the titled compound as a yellow liquid.

$^1$H NMR (400 MHz, CDCl$_3$) 7.14-6.90 (m, 2H), 6.86-6.80 (m, 2H), 6.73 (s, 1H), 6.49 (dd, 1H), 6.37 (dd, 1H), 5.63 (dd, 1H), 3.71 (dd, 1H), 3.35 (t, 4H), 3.25-3.20 (dd, 4H), 2.97 (dd, 1H), 2.82 (s, 3H)

Example 218

5-(2,4-difluoro-phenyl)-1-[3'-(methylsulfanyl)-biphenyl-4-yl]-3-pentafluoroethyl-4,5-dihydro-1H-pyrazole 1-(4-Bromo-phenyl)-5-(2,4-difluoro-phenyl)-3-pentafluoroethyl-4,5-dihydro-1H-pyrazole (50.0 mg, 0.11 mmol) prepared in Preparation 15, 3-(methylthio)phenylboronic acid (28.0 mg, 0.17 mmol), Pd(PPh$_3$)$_4$ (13.0 mg, cat.) and a 2N sodium carbonate solution (550.0 uL) were added to a mixed solvent of ethanol (550.0 uL) and 1,2-dimethoxyethane (2.0 mL). The reaction mixture was stirred at 90° C. for 3 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/6) to give 20.0 mg of the titled compound as a white liquid.

$^1$H NMR (400 MHz, CDCl$_3$) 7.43 (d, 2H), 7.38 (s, 1H), 7.30 (d, 1H), 7.27 (d, 1H), 7.18 (t, 1H), 7.14 (q, 1H), 7.06 (d, 2H), 6.93-6.83 (m, 2H), 5.68 (dd, 1H), 3.74 (dd, 1H), 3.00 (dd, 1H), 2.51 (s, 3H)

Examples 219 and 220

The compounds of Examples 219 and 220 were prepared in accordance with the same procedures as in Example 218, except for using 1-(4-bromo-phenyl)-5-(2,4-difluoro-phenyl)-3-pentafluoroethyl-4,5-dihydro-1H-pyrazole prepared in Preparation 15; and using each boronic acid corresponding to the compounds of Examples 219 and 210 instead of 3-(methylthio)phenylboronic acid.

Example 219

5-(2,4-difluoro-phenyl)-1-[4-(6-methylsulfanyl-pyridin-3-yl)-phenyl]-3-pentafluoroethyl-4,5-dihydro-1H-pyrazole $^1$H NMR (400 MHz, CDCl$_3$) 8.62 (s, 1H), 7.61 (d, 1H), 7.41 (d, 2H), 7.20 (d, 1H), 7.15-7.06 (m, 2H), 6.94-6.83 (m, 2H), 5.68 (dd, 1H), 3.78 (dd, 1H), 3.01 (dd, 1H), 2.59 (s, 3H)

Example 220

1-[4-(1-BOC-1,2,3,6-tetrahydropyridin-4-yl)-phenyl]-5-(2,4-difluoro-phenyl)-3-pentafluoroethyl-4,5-dihydro-1H-pyrazole $^1$H NMR (400 MHz, CDCl$_3$) 7.23 (d, 2H), 7.09 (q, 1H), 6.95-6.80 (m, 4H), 5.92 (br, 1H), 5.63 (dd, 1H), 4.04 (s, 2H), 3.72 (dd, 1H), 3.58 (t, 2H), 2.97 (dd, 1H), 2.45 (br, 22H), 1.48 (s, 9H)

Example 221

5-(2,4-difluoro-phenyl)-1-[3'-(methylsulfonyl)-biphenyl-4-yl]-3-pentafluoroethyl-4,5-dihydro-1H-pyrazole To a mixture of 5-(2,4-difluoro-phenyl)-1-[3'-(methylsulfanyl)-biphenyl-4-yl]-3-pentafluoroethyl-4,5-dihydro-1H-pyrazole (20.0 mg, 0.04 mmol) prepared in Example 218 in dichloromethane (2.0 mL), was slowly added meta-chloroperbenzoic acid (77%, 12.0 mg, 0.08 mmol) at 0° C. The reaction mixture was stirred at room temperature for 30 minutes, quenched with a saturated solution of sodium hydrogen carbonate, and then extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 10.0 mg of the titled compound as a yellow liquid.

¹H NMR (400 MHz, CDCl₃) 8.07 (s, 1H), 7.84 (d, 1H), 7.78 (d, 1H), 7.59 (t, 1H), 7.48 (d, 2H), 7.14-7.07 (m, 3H), 6.94-6.83 (m, 2H), 5.71 (dd, 1H), 3.77 (dd, 1H), 3.08 (s, 3H), 3.73 (dd, 1H)

Example 222

5-(2,4-difluoro-phenyl)-1-[4-(6-methanesulfonyl-pyridin-3-yl)-phenyl]-3-pentafluoroethyl-4,5-dihydro-1H-pyrazole To a mixture of 5-(2,4-difluoro-phenyl)-1-[4-(6-methylsulfanyl-pyridin-3-yl)-phenyl]-3-pentafluoroethyl-4,5-dihydro-1H-pyrazole (27.0 mg, 0.05 mmol) prepared in Example 219 in dichloromethane (2.0 mL), was slowly added meta-chloroperbenzoic acid (77%, 16.0 mg, 0.12 mmol) at 0° C. The reaction mixture was stirred at room temperature for 30 minutes, quenched with a saturated solution of sodium hydrogen carbonate, and then extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 15.0 mg of the titled compound as a yellow liquid.

¹H NMR (400 MHz, CDCl₃) 8.86 (s, 1H), 8.09 (d, 1H), 8.02 (d, 1H), 7.49 (d, 2H), 7.12 (d, 2H), 6.94-6.84 (m, 2H), 5.71 (dd, 1H), 3.78 (dd, 1H), 3.24 (s, 3H), 3.04 (dd, 1H)

Example 223

5-(2'-acetyl-biphenyl-3-yl)-1-(2-chloro-phenyl)-3-[di-(trifluoromethyl)-hydroxy-methyl]-4,5-dihydro-1H-pyrazole 5-(3-Bromo-phenyl)-1-(2-chloro-phenyl)-3-[di-(trifluoromethyl)-hydroxy-methyl]-4,5-dihydro-1H-pyrazole (20.0 mg, 0.04 mmol) prepared in Step 4 of Preparation 16, 2-acetylphenylboronic acid (8.0 mg, 0.05 mmol), Pd(dppf)Cl₂ (2.0 mg, cat.), and a 2N sodium carbonate solution (0.5 mL) were added to N,N-dimethylformamide (0.5 mL). The reaction mixture was stirred at 80° C. for 16 hours and then ethyl acetate was added thereto. The reaction mixture was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/2) to give 5.0 mg of the titled compound as a yellow liquid.

¹H NMR (400 MHz, CDCl₃) 7.53-7.39 (m, 6H), 7.20-7.06 (m, 5H), 6.95 (t, 1H), 5.96 (dd, 1H), 4.92 (s, 1H), 3.70 (dd, 1H), 3.29 (dd, 1H), 1.66 (s, 3H)

Examples 224 to 226

The compounds of Examples 224 to 226 were prepared in accordance with the same procedures as in Example 223, except for using 5-(3-bromo-phenyl)-1-(2-chloro-phenyl)-3-[di-(trifluoromethyl)-hydroxy-methyl]-4,5-dihydro-1H-pyrazole prepared in Step 4 of Preparation 16; and using each boronic acid corresponding to the compounds of Examples 224 to 226 instead of 2-acetylphenylboronic acid.

Example 224

5-(3'-acetyl-biphenyl-3-yl)-1-(2-chloro-phenyl)-3-[di-(trifluoromethyl)-hydroxy-methyl]-4,5-dihydro-1H-pyrazole ¹H NMR (400 MHz, CDCl₃) 8.03 (s, 1H), 7.93 (d, 1H), 7.64 (d, 1H), 7.53 (t, 1H), 7.44 (d, 1H), 7.38 (s, 1H), 7.35-7.26 (m, 2H), 7.18 (t, 2H), 7.10 (t, 1H), 6.97 (t, 1H), 5.97 (dd, 1H), 4.92 (s, 1H), 3.69 (dd, 1H), 3.29 (dd, 1H), 2.65 (s, 3H)

Example 225

5-(4'-acetyl-biphenyl-3-yl)-1-(2-chloro-phenyl)-3-[di-(trifluoromethyl)-hydroxy-methyl]-4,5-dihydro-1H-pyrazole ¹H NMR (400 MHz, CDCl₃) 8.01 (d, 2H), 7.53 (d, 2H), 7.44 (d, 1H), 7.39 (s, 1H), 7.32 (t, 1H), 7.28-7.26 (m, 1H), 7.18 (d, 2H), 7.09 (t, 1H), 6.97 (t, 1H), 5.97 (dd, 1H), 4.92 (s, 1H), 3.69 (dd, 1H), 3.28 (dd, 1H), 2.64 (s, 3H)

Example 226

1-(2-chloro-phenyl)-5-[4'-(methylsulfonyl)-biphenyl-3-yl]-3-[di-(trifluoromethyl)-hydroxy-methyl]-4,5-dihydro-1H-pyrazole ¹H NMR (400 MHz, CDCl₃) 7.99 (d, 2H), 7.61 (d, 2H), 7.43 (d, 1H), 7.37-7.32 (m, 2H), 7.27 (d, 1H), 7.23-7.17 (m, 2H), 7.10 (t, 1H), 6.97 (t, 1H), 5.98 (dd, 1H), 4.91 (s, 1H), 3.70 (dd, 1H), 3.28 (dd, 1H), 3.09 (s, 3H)

Example 227

1-(2-chloro-phenyl)-5-[3'-(1-hydroxy-1-methyl-ethyl)-biphenyl-3-yl]-3-[di-(trifluoromethyl)-hydroxy-methyl]-4,5-dihydro-1H-pyrazole To a mixture of 5-(3'-acetyl-biphenyl-3-yl)-1-(2-chloro-phenyl)-3-[di-(trifluoromethyl)-hydroxy-methyl]-4,5-dihydro-1H-pyrazole (39.0 mg, 0.07 mmol) prepared in Example 224 in tetrahydrofuran (1.0 mL), was slowly added methylmagnesium chloride (in 3.0 M tetrahydrofuran, 120.0 uL, 0.36 mmol) under nitrogen atmosphere at −78° C. The reaction mixture was stirred at −78° C. for 5 hours, quenched with a saturated solution of ammonium chloride at 0° C., and then extracted with ethyl acetate. The extract was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/3) to give 20.0 mg of the titled compound as a yellow liquid.

¹H NMR (400 MHz, CDCl₃) 7.58 (s, 1H), 7.48-7.25 (m, 7H), 7.18-7.12 (m, 2H), 7.07 (t, 1H), 6.95 (t, 1H), 5.94 (dd, 1H), 4.97 (s, 1H), 3.67 (dd, 1H), 3.29 (dd, 1H), 1.78 (s, 1H), 1.62 (s, 6H)

Example 228

1-(2-chloro-phenyl)-5-[4'-(1-hydroxy-1-methyl-ethyl)-biphenyl-3-yl]-3-[di-(trifluoromethyl)-hydroxy-methyl]-4,5-dihydro-1H-pyrazole To a mixture of 5-(4'-acetyl-biphenyl-3-yl)-1-(2-chloro-phenyl)-3-[di-(trifluoromethyl)-hydroxy-methyl]-4,5-dihydro-1H-pyrazole (25.0 mg, 0.05 mmol) prepared in Example 225 in tetrahydrofuran (1.0 mL), was slowly added methylmagnesium chloride (in 3.0 M tetrahydrofuran, 77.0 uL, 0.23 mmol) under nitrogen atmosphere at −78° C. The reaction mixture was stirred at −78° C. for 5 hours, quenched with a saturated solution of ammonium chloride at 0° C., and then extracted with ethyl acetate. The extract was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/3) to give 20.0 mg of the titled compound as a yellow liquid.

$^1$H NMR (400 MHz, CDCl$_3$) 7.54 (d, 2H), 7.44-7.37 (m, 4H), 7.26 (d, 2H), 7.18-7.05 (m, 3H), 6.95 (t, 1H), 5.93 (dd, 1H), 4.95 (s, 1H), 3.67 (dd, 1H), 3.28 (dd, 1H), 1.76 (s, 1H), 1.62 (s, 6H)

Example 229

1-(2-chloro-phenyl)-5-[3-(1-BOC-1,2,3,6-tetrahydropyridin-4-yl)-phenyl]-3-[di-(trifluoromethyl)-hydroxy-methyl]-4,5-dihydro-1H-pyrazole 5-(3-Bromo-phenyl)-1-(2-chloro-phenyl)-3-[di-(trifluoromethyl)-hydroxy-methyl]-4,5-dihydro-1H-pyrazole (1.1 g, 2.2 mmol) prepared in Step 4 of Preparation 16, tert-butyl 4-(4,4,5,5-tetramethyl-1,3,2-dioxaborolan-2-yl)-5,6-dihydropyridin-1 (2H)-carboxylic acid (805.5 mg, 2.6 mmol), potassium carbonate (900.0 mg, 6.5 mmol), and Pd(dppf)Cl$_2$ (159.0 mg, 0.20 mmol) were added to a mixed solvent of 1,4-dioxane (35.0 mL) and distilled water (9.0 mL). The reaction mixture was stirred for 15 minutes, additionally at 90° C. for 16 hours, and then ethyl acetate was added thereto. The reaction mixture was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/4) to give 820.0 mg of the titled compound as a white solid.

$^1$H NMR (400 MHz, CDCl$_3$) 7.26-7.06 (m, 6H), 7.03 (d, 1H), 6.96 (t, 1H), 5.92 (br, 1H), 5.89 (dd, 1H), 4.96 (s, 1H), 4.04 (br, 2H), 3.71 (dd, 1H), 3.64 (br, 2H), 3.22 (dd, 1H), 2.40 (br, 2H), 1.49 (s, 9H)

Example 230

1-(2-chloro-phenyl)-5-[3-(1,2,3,6-tetrahydropyridin-4-yl)-phenyl]-3-[di-(trifluoromethyl)-hydroxy-methyl]-4,5-dihydro-1H-pyrazole trifluoroacetate 1-(2-Chloro-phenyl)-5-[3-(1-BOC-1,2,3,6-tetrahydropyridin-4-yl)-phenyl]-3-[di-(trifluoromethyl)-hydroxy-methyl]-4,5-dihydro-1H-pyrazole (350.0 mg, 0.58 mmol) prepared in Example 229 and trifluoroacetic acid (444.0 uL, 5.79 mmol) were slowly added to dichloromethane (5.8 mL) at 0° C. The reaction mixture was stirred at room temperature for 2 hours and then concentrated under reduced pressure to give 400.0 mg of the titled compound as a yellow liquid.

$^1$H NMR (400 MHz, CD$_3$OD) 7.36 (d, 1H), 7.29 (d, 1H), 7.24-7.20 (m, 3H), 7.15-7.09 (m, 2H), 6.93 (t, 1H), 6.06 (s, 1H), 5.95 (dd, 1H), 5.51 (s, 1H), 4.11 (br, 2H), 3.71 (dd, 1H), 3.43 (br, 2H), 3.33 (dd, 1H), 2.69 (br, 2H)

Example 231

5-[3-(1-acetyl-1,2,3,6-tetrahydropyridin-4-yl)-phenyl]-1-(2-chloro-phenyl)-3-[di-(trifluoromethyl)-hydroxy-methyl]-4,5-dihydro-1H-pyrazole 1-(2-Chloro-phenyl)-5-[3-(1,2,3,6-tetrahydropyridin-4-yl)-phenyl]-3-[di-(trifluoromethyl)-hydroxy-methyl]-4,5-dihydro-1H-pyrazole trifluoroacetate (11.0 mg, 0.02 mmol) prepared in Example 230, acetyl chloride (1.5 uL, 0.02 mmol), and triethylamine (7.5 uL, 0.05 mmol) were added to dichloromethane (0.5 mL). The reaction mixture was stirred at room temperature for 1 hour, washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/1) to give 3.0 mg of the titled compound as a yellow liquid.

$^1$H NMR (400 MHz, CDCl$_3$) 7.24-7.06 (m, 7H), 5.94 (d, 1H), 5.98 (dd, 1H), 4.96 (s, 1H), 4.15 (d, 2H), 3.72 (dt, 2H), 3.68-3.62 (dd, 1H), 3.22 (dd, 1H), 2.43 (d, 2H), 2.14 (d, 3H)

Examples 232 to 240

The compounds of Examples 232 to 240 were prepared in accordance with the same procedures as in Example 231, except for using 1-(2-chloro-phenyl)-5-[3-(1,2,3,6-tetrahydropyridin-4-yl)-phenyl]-3-[di-(trifluoromethyl)-hydroxy-methyl]-4,5-dihydro-1H-pyrazole trifluoroacetate prepared in Example 230; and using each sulfonyl chloride or acyl chloride corresponding to the compounds of Examples 232 to 240 instead of acetyl chloride.

Example 232

1-(2-chloro-phenyl)-5-{3-[1-(2-cyclopentyl-acetyl)-1,2,3,6-tetrahydropyridin-4-yl]-phenyl}-3-[di-(trifluoromethyl)-hydroxy-methyl]-4,5-dihydro-1H-pyrazole $^1$H NMR (400 MHz, CDCl$_3$) 7.25 (d, 1H), 7.18-7.04 (m, 6H), 6.96 (t, 1H), 5.94 (d, 1H), 5.88 (dd, 1H), 4.94 (br, 1H), 4.13 (d, 2H), 3.73 (dt, 2H), 3.64 (dd, 1H), 3.22 (dd, 1H), 2.42 (d, 2H), 2.39 (t, 2H), 2.33-2.24 (m, 1H), 1.85 (m, 2H), 1.56 (m, 6H), 1.18 (m, 2H)

Example 233

1-(2-chloro-phenyl)-5-{3-[1-(3-cyclopentyl-propionyl)-1,2,3,6-tetrahydropyridin-4-yl]-phenyl}-3-[di-(trifluoromethyl)-hydroxy-methyl]-4,5-dihydro-1H-pyrazole $^1$H NMR (400 MHz, CDCl$_3$) 7.25 (d, 1H), 7.18-7.04 (m, 6H), 6.96 (t, 1H), 5.94 (d, 1H), 5.88 (dd, 1H), 4.13 (d, 2H), 3.73 (dt, 2H), 3.63 (dd, 1H), 3.22 (dd, 1H), 2.42 (d, 2H), 2.33-2.24 (m, 3H), 1.79 (m, 4H), 1.66-1.50 (m, 10H), 1.11 (m, 2H)

Example 234

1-(2-chloro-phenyl)-5-{3-[1-(thiophene-2-carbonyl)-1,2,3,6-tetrahydropyridin-4-yl]-phenyl}-3-[di-(trifluoromethyl)-hydroxy-methyl]-4,5-dihydro-1H-pyrazole $^1$H NMR (400 MHz, CDCl$_3$) 7.48 (d, 1H), 7.37 (d, 1H), 7.24-7.06 (m, 7H), 6.96 (t, 1H), 5.95 (s, 1H), 5.88 (dd, 1H), 4.93 (br, 1H), 4.37 (s, 2H), 3.92 (t, 2H), 3.64 (dd, 1H), 3.22 (dd, 1H), 2.52 (s, 2H)

Example 235

5-[3-(1-benzoyl-1,2,3,6-tetrahydropyridin-4-yl)-phenyl]-1-(2-chloro-phenyl)-3-[di-(trifluoromethyl)-hydroxy-methyl]-4,5-dihydro-1H-pyrazole $^1$H NMR (400 MHz, CDCl$_3$) 7.48 (s, 5H), 7.24-7.06 (m, 7H), 6.96 (t, 1H), 6.05 (s, 1H), 5.88 (dd, 1H), 4.99 (br, 1H), 4.37 (s, 1H), 4.00 (d, 2H), 3.64 (dd, 1H), 3.60 (s, 1H), 3.22 (dd, 1H), 2.48 (d, 2H)

Example 236

1-(2-chloro-phenyl)-5-[3-(1-phenylacetyl-1,2,3,6-tetrahydropyridin-4-yl)-phenyl]-3-[di-(trifluoromethyl)-hydroxy-methyl]-4,5-dihydro-1H-pyrazole $^1$H NMR (400 MHz, CDCl$_3$) 7.48 (s, 5H), 7.24-7.06 (m, 7H), 6.96 (t, 1H), 6.05 (s, 1H), 5.88 (dd, 1H), 4.99 (br, 1H), 4.37 (s, 1H), 4.00 (d, 2H), 3.64 (dd, 1H), 3.60 (s, 1H), 3.22 (dd, 1H), 2.48 (d, 2H)

Example 237

5-{3-[1-(4-chloro-benzoyl)-1,2,3,6-tetrahydropyridin-4-yl]-phenyl}-1-(2-chloro-phenyl)-3-[di-(trifluoromethyl)-hydroxy-methyl]-4,5-dihydro-1H-pyrazole $^1$H NMR (400 MHz, CDCl$_3$) 7.43 (s, 3H), 7.26-7.23 (m, 2H), 7.19-7.06 (m, 5H), 6.96 (t, 1H), 6.03 (br, 1H), 5.87 (dd, 1H), 4.92 (s, 1H), 4.35 (br, 1H), 3.99 (d, 1H), 3.64 (dd, 1H), 3.62 (br, 1H), 3.21 (dd, 1H), 2.47 (d, 2H)

Example 238

1-(2-chloro-phenyl)-5-[3-(1-methanesulfonyl-1,2,3,6-tetrahydropyridin-4-yl)-phenyl]-3-[di-(trifluoromethyl)-hydroxy-methyl]-4,5-dihydro-1H-pyrazole $^1$H NMR (400 MHz, CDCl$_3$) 7.24-7.06 (m, 7H), 6.96 (t, 1H), 5.95 (s, 1H), 5.89 (dd, 1H), 4.90 (s, 1H), 3.94 (s, 2H), 3.66 (dd, 1H), 3.49 (t, 2H), 3.22 (dd, 1H), 2.84 (s, 3H), 2.53 (s, 2H)

Example 239

1-(2-chloro-phenyl)-5-[3-(1-trifluoromethanesulfonyl-1,2,3,6-tetrahydropyridin-4-yl)-phenyl]-3-[di-(trifluoromethyl)-hydroxy-methyl]-4,5-dihydro-1H-pyrazole $^1$H NMR (400 MHz, CDCl$_3$) 7.24 (d, 1H), 7.20-7.06 (m, 6H), 6.96 (t, 1H), 5.92 (s, 1H), 5.90 (dd, 1H), 4.90 (s, 1H), 4.14 (s, 2H), 3.71 (br, 2H), 3.65 (dd, 1H), 3.22 (dd, 1H), 2.54 (s, 2H)

Example 240

1-(2-chloro-phenyl)-5-[3-(1-dimethylsulfamoyl-1,2,3,6-tetrahydropyridin-4-yl)-phenyl]-3-[di-(trifluoromethyl)-hydroxy-methyl]-4,5-dihydro-1H-pyrazole $^1$H NMR (400 MHz, CDCl$_3$) 7.24 (d, 1H), 7.19-7.06 (m, 6H), 6.96 (t, 1H), 4.91 (s, 1H), 3.91 (s, 2H), 3.64 (dd, 1H), 3.46 (t, 2H), 3.21 (dd, 1H), 2.84 (s, 6H), 2.49 (br, 2H)

Example 241

5-(2'-acetyl-biphenyl-4-yl)-1-(2-chloro-phenyl)-3-[di-(trifluoromethyl)-hydroxy-methyl]-4,5-dihydro-1H-pyrazole 5-(4-Bromo-phenyl)-1-(2-chloro-phenyl)-3-[di-(trifluoromethyl)-hydroxy-methyl]-4,5-dihydro-1H-pyrazole (50.0 mg, 0.10 mmol) prepared in Step 4 of Preparation 17, 2-acetylphenylboronic acid (21.0 mg, 0.13 mmol), Pd(PPh$_3$)$_4$ (4.0 mg, cat.) and a 2N sodium carbonate solution (0.5 mL) were added to N,N-dimethylformamide (0.5 mL). The reaction mixture was stirred at 80° C. for 2 hours and then filtered through celite pad. A saturated solution of ammonium chloride was added to the filtrate, which was then extracted with ethyl acetate three times. The extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/3) to give 10.0 mg of the titled compound as a yellow liquid.

$^1$H NMR (400 MHz, CDCl$_3$) 7.50-7.12 (m, 10H), 7.03 (t, 1H), 6.94 (t, 1H), 5.95 (dd, 1H), 4.93 (s, 1H), 3.70 (dd, 1H), 3.33 (dd, 1H), 1.62 (s, 3H)

Examples 242 to 265

The compounds of Examples 242 to 265 were prepared in accordance with the same procedures as in Example 241, except for using 5-(4-bromo-phenyl)-1-(2-chloro-phenyl)-3-[di-(trifluoromethyl)-hydroxy-methyl]-4,5-dihydro-1H-pyrazole prepared in Step 4 of Preparation 17; and using each boronic acid corresponding to the compounds of Examples 242 to 265 instead of 2-acetylphenylboronic acid.

Example 242

1-(2-chloro-phenyl)-5-(4'-methoxy-biphenyl-4-yl)-3-[di-(trifluoromethyl)-hydroxy-methyl]-4,5-dihydro-1H-pyrazole $^1$H NMR (400 MHz, CDCl$_3$) 7.43 (d, 2H), 7.40 (d, 2H), 7.26 (m, 1H), 7.19 (d, 3H), 7.09 (t, 1H), 6.98-6.91 (m, 3H), 5.90 (dd, 1H), 4.95 (s, 1H), 3.83 (s, 3H), 3.65 (dd, 1H), 3.24 (dd, 1H)

Example 243

1-(2-chloro-phenyl)-5-[4'-(methylsulfanyl)-biphenyl-4-yl]-3-[di-(trifluoromethyl)-hydroxy-methyl]-4,5-dihydro-1H-pyrazole $^1$H NMR (400 MHz, CDCl$_3$) 7.42 (d, 2H), 7.35 (d, 2H), 7.28-7.09 (m, 5H), 7.03-6.96 (m, 3H), 5.91 (dd, 1H), 4.94 (s, 1H), 3.65 (dd, 1H), 3.23 (dd, 1H), 2.50 (s, 3H)

Example 244

1-(2-chloro-phenyl)-5-[4'-(methanesulfonyl)-biphenyl-4-yl]-3-[di-(trifluoromethyl)-hydroxy-methyl]-4,5-dihydro-1H-pyrazole $^1$H NMR (400 MHz, CDCl$_3$) 7.97 (d, 2H), 7.68 (d, 2H), 7.59 (d, 1H), 7.47 (d, 2H), 7.27 (d, 2H), 7.20 (d, 1H), 7.11 (t, 1H), 6.98 (t, 1H), 5.95 (dd, 1H), 4.93 (s, 1H), 3.68 (dd, 1H), 3.23 (dd, 1H), 3.06 (s, 3H)

Example 245

1-(2-chloro-phenyl)-5-(2',6'-dimethoxy-biphenyl-4-yl)-3-[di-(trifluoromethyl)-hydroxy-methyl]-4,5-dihydro-1H-pyrazole $^1$H NMR (400 MHz, CDCl$_3$) 7.42 (d, 1H), 7.34 (d, 1H), 7.30-7.22 (m, 2H), 7.20-7.06 (m, 3H), 7.03-6.96 (m, 2H), 6.61 (d, 2H), 5.82 (dd, 1H), 4.95 (s, 1H), 3.65 (s, 6H), 3.61 (dd, 1H), 3.30 (dd, 1H)

Example 246

1-(2-chloro-phenyl)-5-(4'-fluoro-biphenyl-4-yl)-3-[di-(trifluoromethyl)-hydroxy-methyl]-4,5-dihydro-1H-pyrazole $^1$H NMR (400 MHz, CDCl$_3$) 7.47-7.43 (m, 2H), 7.39 (d, 2H), 7.28-7.17 (m, 4H), 7.11-7.06 (m, 3H), 6.97 (t, 1H), 5.92 (dd, 1H), 4.93 (s, 1H), 3.66 (dd, 1H), 3.23 (dd, 1H)

Example 247

1-(2-chloro-phenyl)-5-[4'-(trifluoromethyl)-biphenyl-4-yl]-3-[di-(trifluoromethyl)-hydroxy-methyl]-4,5-dihydro-1H-pyrazole $^1$H NMR (400 MHz, CDCl$_3$) 7.65 (d, 2H), 7.59 (d, 2H), 7.46 (d, 2H), 7.28-7.24 (m, 3H), 7.20 (d, 1H), 7.10 (t, 1H), 6.98 (t, 1H), 5.94 (dd, 1H), 4.92 (s, 1H), 3.67 (dd, 1H), 3.24 (dd, 1H)

Example 248

1-(2-chloro-phenyl)-5-[3'-(trifluoromethoxy)-biphenyl-4-yl]-3-[di-(trifluoromethyl)-hydroxy-methyl]-4,5-dihydro-1H-pyrazole $^1$H NMR (400 MHz, CDCl$_3$) 7.44-7.42 (m, 4H), 7.33 (s, 1H), 7.28-7.18 (m, 5H), 7.10 (t, 1H), 6.97 (t, 1H), 5.94 (dd, 1H), 4.93 (s, 1H), 3.67 (dd, 1H), 3.24 (dd, 1H)

Example 249

1-(2-chloro-phenyl)-5-(2'-methyl-biphenyl-4-yl)-3-[di-(trifluoromethyl)-hydroxy-methyl]-4,5-dihydro-1H-pyrazole $^1$H NMR (400 MHz, CDCl$_3$) 7.35 (d, 1H), 7.28-7.08 (m, 9H), 7.03-6.97 (m, 2H), 5.88 (dd, 1H), 4.93 (s, 1H), 3.66 (dd, 1H), 3.30 (dd, 1H), 2.12 (s, 3H)

Example 250

1-(2-chloro-phenyl)-5-(4'-methyl-biphenyl-4-yl)-3-[di-(trifluoromethyl)-hydroxy-methyl]-4,5-dihydro-1H-pyrazole $^1$H NMR (400 MHz, CDCl$_3$) 7.44-7.33 (m, 4H), 7.21-6.96 (m, 8H), 5.90 (dd, 1H), 4.93 (s, 1H), 3.66 (dd, 1H), 3.24 (dd, 1H), 2.37 (s, 3H)

Example 251

1-(2-chloro-phenyl)-5-(3'-ethoxy-biphenyl-4-yl)-3-[di-(trifluoromethyl)-hydroxy-methyl]-4,5-dihydro-1H-pyrazole $^1$H NMR (400 MHz, CDCl$_3$) 7.43 (d, 2H), 7.31-7.16 (m, 5H), 7.11-7.06 (m, 2H), 7.02 (s, 1H), 6.96 (t, 1H), 6.85 (d, 1H), 5.91 (dd, 1H), 4.93 (s, 1H), 4.06 (q, 2H), 3.65 (dd, 1H), 3.24 (dd, 1H), 1.42 (t, 3H)

Example 252

1-(2-chloro-phenyl)-5-(3'-hydroxy-biphenyl-4-yl)-3-[di-(trifluoromethyl)-hydroxy-methyl]-4,5-dihydro-1H-pyrazole $^1$H NMR (400 MHz, CDCl$_3$) 7.42 (d, 2H), 7.28-7.16 (m, 5H), 7.11-7.06 (m, 2H), 6.98-6.95 (m, 2H), 6.79 (d, 1H), 5.91 (dd, 1H), 4.93 (s, 1H), 4.77 (s, 1H), 3.65 (dd, 1H), 3.24 (dd, 1H)

Example 253

5-(3'-amino-biphenyl-4-yl)-1-(2-chloro-phenyl)-3-[di-(trifluoromethyl)-hydroxy-methyl]-4,5-dihydro-1H-pyrazole $^1$H NMR (400 MHz, CDCl$_3$) 7.41 (d, 2H), 7.25 (d, 1H), 7.20-7.15 (m, 4H), 7.08 (t, 1H), 6.96 (t, 1H), 6.89 (d, 1H), 6.81 (s, 1H), 6.65 (d, 1H), 5.90 (dd, 1H), 4.94 (s, 1H), 3.70 (brs, 2H), 3.65 (dd, 1H), 3.24 (dd, 1H)

Example 254

1-(2-chloro-phenyl)-5-(4'-dimethylamino-biphenyl-4-yl)-3-[di-(trifluoromethyl)-hydroxy-methyl]-4,5-dihydro-1H-pyrazole $^1$H NMR (400 MHz, CDCl$_3$) 7.48-7.38 (m, 5H), 7.25 (d, 1H), 7.16 (d, 2H), 7.08 (t, 1H), 6.95 (t, 1H), 6.75 (d, 2H), 5.88 (dd, 1H), 4.95 (s, 1H), 3.63 (dd, 1H), 3.24 (dd, 1H), 2.97 (s, 6H)

Example 255

5-(2'-chloro-4'-methoxy-biphenyl-4-yl)-1-(2-chloro-phenyl)-3-[di-(trifluoromethyl)-hydroxy-methyl]-4,5-dihydro-1H-pyrazole $^1$H NMR (400 MHz, CDCl$_3$) 7.29-7.26 (m, 4H), 7.20-7.07 (m, 4H), 7.00-6.97 (m, 2H), 6.82 (dd, 1H), 5.88 (dd, 1H), 4.93 (s, 1H), 3.82 (s, 3H), 3.65 (dd, 1H), 3.28 (dd, 1H)

Example 256

5-(3'-chloro-4'-fluoro-biphenyl-4-yl)-1-(2-chloro-phenyl)-3-[di-(trifluoromethyl)-hydroxy-methyl]-4,5-dihydro-1H-pyrazole $^1$H NMR (400 MHz, CDCl$_3$) 7.52 (d, 1H), 7.51-7.32 (m, 3H), 7.26-7.08 (m, 6H), 6.98 (t, 1H), 5.93 (dd, 1H), 4.92 (s, 1H), 3.66 (dd, 1H), 3.22 (dd, 1H)

Example 257

1-(2-chloro-phenyl)-5-(4-furan-3-yl-phenyl)-3-[di-(trifluoromethyl)-hydroxy-methyl]-4,5-dihydro-1H-pyrazole $^1$H NMR (400 MHz, CDCl$_3$) 7.66 (s, 1H), 7.44 (s, 1H), 7.33 (d, 2H), 7.25 (d, 2H), 7.18-7.13 (m, 2H), 7.09 (t, 1H), 6.96 (t, 1H), 6.61 (s, 1H), 5.89 (dd, 1H), 4.92 (s, 1H), 3.64 (dd, 1H), 3.22 (dd, 1H)

Example 258

1-(2-chloro-phenyl)-5-(4-pyrimidin-5-yl-phenyl)-3-[di-(trifluoromethyl)-hydroxy-methyl]-4,5-dihydro-1H-pyrazole $^1$H NMR (400 MHz, CDCl$_3$) 9.18 (s, 1H), 8.87 (s, 2H), 7.45 (d, 2H), 7.31 (d, 2H), 7.27 (d, 1H), 7.20 (d, 1H), 7.12 (t, 1H), 6.99 (t, 1H), 5.96 (dd, 1H), 4.94 (s, 1H), 3.69 (dd, 1H), 3.23 (dd, 1H)

Example 259

1-(2-chloro-phenyl)-5-(4-quinolin-3-yl-phenyl)-3-[di-(trifluoromethyl)-hydroxy-methyl]-4,5-dihydro-1H-pyrazole $^1$H NMR (400 MHz, CDCl$_3$) 9.08 (s, 1H), 8.23 (s, 1H), 8.12 (d, 1H), 7.85 (d, 1H), 7.72 (t, 1H), 7.59-7.56 (m, 3H), 7.33-7.21 (m, 4H), 7.12 (t, 1H), 6.99 (t, 1H), 5.97 (dd, 1H), 4.98 (s, 1H), 3.70 (dd, 1H), 3.26 (dd, 1H)

Example 260

1-(2-chloro-phenyl)-5-[4-(6-methoxy-pyridin-3-yl)-phenyl]-3-[di-(trifluoromethyl)-hydroxy-methyl]-4,5-dihydro-1H-pyrazole $^1$H NMR (400 MHz, CDCl$_3$) 8.29 (s, 1H), 7.70 (dd, 1H), 7.38 (d, 2H), 7.28-7.18 (m, 4H), 7.11 (t, 1H), 7.03-6.96 (m, 1H), 6.78 (d, 1H), 5.93 (dd, 1H), 4.95 (s, 1H), 3.96 (s, 3H), 3.67 (dd, 1H), 3.23 (dd, 1H)

Example 261

1-(2-chloro-phenyl)-5-[4-(2-fluoro-pyridin-3-yl)-phenyl]-3-[di-(trifluoromethyl)-hydroxy-methyl]-4,5-dihydro-1H-pyrazole $^1$H NMR (400 MHz, CDCl$_3$) 8.17 (d, 1H), 7.79 (t, 1H), 7.44 (d, 2H), 7.29-7.22 (m, 4H), 7.19 (d, 1H), 7.11 (t, 1H), 6.99 (t, 1H), 5.93 (dd, 1H), 4.92 (s, 1H), 3.67 (dd, 1H), 3.24 (dd, 1H)

Example 262

5-(4-benzofuran-2-yl-phenyl)-1-(2-chloro-phenyl)-3-[di-(trifluoromethyl)-hydroxy-methyl]-4,5-dihydro-1H-pyrazole $^1$H NMR (400 MHz, CDCl$_3$) 7.71 (d, 2H), 7.55 (d, 1H), 7.47 (d, 1H), 7.26-7.17 (m, 6H), 7.09 (t, 1H), 6.96 (s, 2H), 5.92 (dd, 1H), 4.93 (s, 1H), 3.67 (dd, 1H), 3.24 (dd, 1H)

Example 263

5-(4-benzo[b]thiophen-2-yl-phenyl)-1-(2-chloro-phenyl)-3-[di-(trifluoromethyl)-hydroxy-methyl]-4,5-dihydro-1H-pyrazole $^1$H NMR (400 MHz, CDCl$_3$) 7.80 (d, 1H), 7.74 (d, 1H), 7.57 (d, 2H), 7.48 (s, 1H), 7.36-7.18 (m, 5H), 7.11 (t, 1H), 7.03-6.97 (m, 2H), 5.92 (dd, 1H), 4.92 (s, 1H), 3.66 (dd, 1H), 3.23 (dd, 1H)

Example 264

5-(4'-carboxy-biphenyl-4-yl)-1-(2-chloro-phenyl)-3-[di-(trifluoromethyl)-hydroxy-methyl]-4,5-dihydro-1H-pyrazole $^1$H NMR (400 MHz, CDCl$_3$) 8.13 (d, 2H), 7.60 (d, 2H), 7.50 (d, 2H), 7.27-7.25 (m, 3H), 7.20 (d, 1H), 7.10 (t, 1H), 6.97 (t, 1H), 5.94 (dd, 1H), 3.68 (dd, 1H), 3.24 (dd, 1H)

Example 265

1-(2-chloro-phenyl)-5-(2'-fluoro-4'-methyl-biphenyl-4-yl)-3-[di-(trifluoromethyl)-hydroxy-methyl]-4,5-dihydro-1H-pyrazole $^1$H NMR (400 MHz, CDCl$_3$) 7.39 (d, 2H), 7.28-7.07 (m, 6H), 7.00-6.91 (m, 3H), 5.89 (dd, 1H), 4.93 (s, 1H), 3.64 (dd, 1H), 3.23 (dd, 1H), 2.36 (s, 3H)

Example 266

1-(2-chloro-phenyl)-5-[4-(6-methylsulfanyl-pyridin-3-yl)-phenyl]-3-[di-(trifluoromethyl)-hydroxy-methyl]-4,5-dihydro-1H-pyrazole Step 1: 1-(2-chloro-phenyl)-5-[4-(4,4,5,5-tetramethyl-1,3,2-dioxaborolan-2-yl)-phenyl]-3-[di-(trifluoromethyl)-hydroxy-methyl]-4,5-dihydro-1H-pyrazole 5-(4-Bromo-phenyl)-1-(2-chloro-phenyl)-3-[di-(trifluoromethyl)-hydroxy-methyl]-4,5-dihydro-1H-pyrazole (3.0 g, 5.98 mmol) prepared in Step 4 of Preparation 17, bis(pinacolato)diboron (3.65 g, 14.35 mmol), Pd(dppf)Cl$_2$ (0.29 g, 0.36 mmol), dppf (0.20 g, 0.36 mmol) and potassium acetate (3.52 g, 35.88 mmol) were added to 1,4-dioxane (30 mL). The reaction mixture was stirred at 80° C. for 3 hours and then filtered through celite pad. Distilled water was added to the filtrate, which was then extracted with diethyl ether three times. The combined extract was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/100) to give 3.5 g of the titled compound as a white liquid.

¹H NMR (400 MHz, CDCl₃) 7.65 (d, 2H), 7.23 (d, 1H), 7.22-7.13 (m, 3H), 7.07 (dd, 1H), 6.95 (dd, 1H), 5.89 (dd, 1H), 4.92 (s, 1H), 3.63 (dd, 1H), 3.17 (dd, 1H), 1.30 (s, 12H)

Step 2: 1-(2-chloro-phenyl)-5-[4-(6-methylsulfanyl-pyridin-3-yl)-phenyl]-3-[di-(trifluoromethyl)-hydroxy-methyl]-4,5-dihydro-1H-pyrazole To 5-bromo-2-(methylthio)pyridine (14.0 mg, 0.07 mmol), were added 1,2-dimethoxyethane (1.5 mL) and Pd(PPh₃)₄ (8.4 mg, cat.). To the reaction mixture, were added 1-(2-chloro-phenyl)-5-[4-(4,4,5,5-tetramethyl-1,3,2-dioxaborolan-2-yl)-phenyl]-3-[di-(trifluoromethyl)-hydroxy-methyl]-4,5-dihydro-1H-pyrazole (25.0 mg, 0.05 mmol) prepared in Step 1, ethanol 183.0 uL, and a 2N sodium carbonate solution (183.0 uL). The reaction mixture was stirred at 88° C. for 2 hours and then distilled water was added thereto. The reaction mixture was extracted with diethyl ether two times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/5) to give 8.0 mg of the titled compound as a white liquid.

¹H NMR (400 MHz, CDCl₃) 8.58 (s, 1H), 7.60 (d, 1H), 7.40 (d, 2H), 7.28-7.18 (m, 5H), 7.10 (t, 1H), 6.97 (t, 1H), 5.92 (dd, 1H), 4.94 (s, 1H), 3.66 (dd, 1H), 3.22 (dd, 1H), 2.58 (s, 3H)

Examples 267 to 290

The compounds of Examples 267 to 290 were prepared in accordance with the same procedures as in Step 2 of Example 266, except for using 1-(2-chloro-phenyl)-5-[4-(4,4,5,5-tetramethyl-1,3,2-dioxaborolan-2-yl)-phenyl]-3-[di-(trifluoromethyl)-hydroxy-methyl]-4,5-dihydro-1H-pyrazole prepared in Step 1 of Example 266; and using each substituted aryl bromide corresponding to the compounds of Examples 267 to 290 instead of 5-bromo-2-(methylthio)pyridine.

Example 267

1-(2-chloro-phenyl)-5-[4-(6-cyano-pyridin-3-yl)-phenyl]-3-[di-(trifluoromethyl)-hydroxy-methyl]-4,5-dihydro-1H-pyrazole ¹H NMR (400 MHz, CDCl₃) 8.87 (s, 1H), 7.90 (d, 1H), 7.72 (d, 1H), 7.47 (d, 2H), 7.31 (d, 2H), 7.28 (d, 1H), 7.20 (d, 1H), 7.11 (t, 1H), 6.98 (t, 1H), 5.96 (dd, 1H), 4.93 (s, 1H), 3.71 (dd, 1H), 3.22 (dd, 1H)

Example 268

1-(2-chloro-phenyl)-5-[4-(6-fluoro-pyridin-3-yl)-phenyl]-3-[di-(trifluoromethyl)-hydroxy-methyl]-4,5-dihydro-1H-pyrazole ¹H NMR (400 MHz, CDCl₃) 8.32 (s, 1H), 7.87 (t, 1H), 7.39 (d, 2H), 7.28-7.25 (m, 3H), 7.20 (d, 1H), 7.10 (t, 1H), 7.00-6.95 (m, 2H), 5.94 (dd, 1H), 4.95 (s, 1H), 3.67 (dd, 1H), 3.22 (dd, 1H)

Example 269

1-(2-chloro-phenyl)-5-[4-(6-ethoxy-pyridin-3-yl)-phenyl]-3-[di-(trifluoromethyl)-hydroxy-methyl]-4,5-dihydro-1H-pyrazole ¹H NMR (400 MHz, CDCl₃) 8.27 (s, 1H), 7.69 (d, 1H), 7.37 (d, 2H), 7.25-7.17 (m, 4H), 7.10 (t, 1H), 6.97 (t, 1H), 6.74 (d, 1H), 5.90 (dd, 1H), 4.92 (s, 1H), 4.37 (m, 2H), 3.63 (dd, 1H), 3.22 (dd, 1H), 1.40 (t, 3H)

Example 270

1-(2-chloro-phenyl)-5-[4-(6-methoxy-4-methyl-pyridin-3-yl)-phenyl]-3-[di-(trifluoromethyl)-hydroxy-methyl]-4,5-dihydro-1H-pyrazole ¹H NMR (400 MHz, CDCl₃) 7.86 (s, 1H), 7.28-7.11 (m, 7H), 7.08 (t, 1H), 6.97 (t, 1H), 6.60 (s, 1H), 5.89 (dd, 1H), 4.92 (s, 1H), 3.93 (s, 3H), 3.65 (dd, 1H), 3.28 (dd, 1H), 2.08 (s, 3H)

Example 271

1-(2-chloro-phenyl)-5-[4-(4-methyl-pyridin-3-yl)-phenyl]-3-[di-(trifluoromethyl)-hydroxy-methyl]-4,5-dihydro-1H-pyrazole ¹H NMR (400 MHz, CDCl₃) 8.40 (d, 1H), 8.30 (s, 1H), 7.28-7.22 (m, 3H), 7.15 (d, 4H), 7.08 (t, 1H), 6.97 (t, 1H), 5.89 (dd, 1H), 5.36 (s, 1H), 3.67 (dd, 1H), 3.28 (dd, 1H), 2.15 (s, 3H)

Example 272

1-(2-chloro-phenyl)-5-[4-(6-trifluoromethyl-pyridin-3-yl)-phenyl]-3-[di-(trifluoromethyl)-hydroxy-methyl]-4,5-dihydro-1H-pyrazole ¹H NMR (400 MHz, CDCl₃) 8.84 (s, 1H), 7.94 (d, 1H), 7.71 (d, 1H), 7.30 (d, 2H), 7.29 (d, 2H), 7.25 (m, 1H), 7.20 (d, 2H), 7.11 (t, 1H), 6.98 (t, 1H), 5.95 (dd, 1H), 4.90 (s, 1H), 3.69 (dd, 1H), 3.23 (dd, 1H)

Example 273

1-(2-chloro-phenyl)-5-[4-(5-methoxycarbonyl-pyridin-3-yl)-phenyl]-3-[di-(trifluoromethyl)-hydroxy-methyl]-4,5-dihydro-1H-pyrazole ¹H NMR (400 MHz, CDCl₃) 9.18 (s, 1H), 8.90 (s, 1H), 8.38 (s, 1H), 7.47 (d, 2H), 7.28 (d, 2H), 7.25 (m, 1H), 7.20 (d, 1H), 7.10 (t, 1H), 6.97 (t, 1H), 5.95 (dd, 1H), 5.10 (s, 1H), 3.97 (s, 1H), 3.68 (dd, 1H), 3.23 (dd, 1H)

Example 274

1-(2-chloro-phenyl)-5-[4-(5-formyl-6-methoxy-pyridin-3-yl)-phenyl]-3-[di-(trifluoromethyl)-hydroxy-methyl]-4,5-dihydro-1H-pyrazole ¹H NMR (400 MHz, CDCl₃) 10.44 (s, 1H), 8.51 (s, 1H), 8.22 (s, 1H), 7.41 (d, 2H), 7.26 (d, 2H), 7.19 (d, 1H), 7.08 (t, 1H), 6.97 (t, 1H), 5.93 (dd, 1H), 4.92 (s, 1H), 4.10 (s, 3H), 3.67 (dd, 1H), 3.23 (dd, 1H)

Example 275

1-(2-chloro-phenyl)-5-[4-(5-methyl-pyridin-3-yl)-phenyl]-3-[di-(trifluoromethyl)-hydroxy-methyl]-4,5-dihydro-1H-pyrazole ¹H NMR (400 MHz, CDCl₃) 8.55 (s, 1H), 8.39 (s, 1H), 7.58 (s, 1H), 7.42 (d, 2H), 7.27 (m, 1H), 7.25 (d, 2H), 7.19 (d, 1H), 7.09 (t, 1H), 6.97 (t, 1H), 5.92 (dd, 1H), 5.14 (s, 1H), 3.66 (dd, 1H), 3.23 (dd, 1H), 2.36 (s, 3H)

Example 276

1-(2-chloro-phenyl)-5-[4-(6-methyl-pyridin-2-yl)-phenyl]-3-[di-(trifluoromethyl)-hydroxy-methyl]-4,5-dihydro-1H-pyrazole $^1$H NMR (400 MHz, CDCl$_3$) 7.84 (d, 2H), 7.59 (t, 1H), 7.42 (d, 1H), 7.26-7.18 (m, 4H), 7.08-7.05 (m, 2H), 6.94 (t, 1H), 5.94 (dd, 1H), 4.93 (s, 1H), 3.66 (dd, 1H), 3.22 (dd, 1H), 2.58 (s, 3H)

Example 277

1-(2-chloro-phenyl)-5-[4-(pyridin-3-yl)-phenyl]-3-[di-(trifluoromethyl)-hydroxy-methyl]-4,5-dihydro-1H-pyrazole $^1$H NMR (400 MHz, CDCl$_3$) 8.75 (s, 1H), 8.57 (s, 1H), 7.79 (d, 1H), 7.44 (d, 2H), 7.33 (t, 1H), 7.28-7.25 (m, 3H), 7.20 (d, 1H), 7.10 (t, 1H), 6.97 (t, 1H), 5.93 (dd, 1H), 3.68 (dd, 1H), 3.23 (dd, 1H)

Example 278

1-(2-chloro-phenyl)-5-[4-(5-cyano-pyridin-3-yl)-phenyl]-3-[di-(trifluoromethyl)-hydroxy-methyl]-4,5-dihydro-1H-pyrazole $^1$H NMR (400 MHz, CDCl$_3$) 8.94 (s, 1H), 8.83 (s, 1H), 8.04 (s, 1H), 7.44 (d, 2H), 7.33-7.26 (m, 3H), 7.20 (d, 1H), 7.12 (t, 1H), 6.99 (t, 1H), 5.96 (dd, 1H), 4.91 (s, 1H), 3.69 (dd, 1H), 3.22 (dd, 1H)

Example 279

1-(2-chloro-phenyl)-5-[4-(2-methoxy-pyrimidin-5-yl)-phenyl]-3-[di-(trifluoromethyl)-hydroxy-methyl]-4,5-dihydro-1H-pyrazole $^1$H NMR (400 MHz, CDCl$_3$) 8.63 (s, 2H), 7.37 (d, 2H), 7.28-7.25 (m, 3H), 7.19 (d, 1H), 7.11 (t, 1H), 6.98 (t, 1H), 5.93 (dd, 1H), 4.92 (s, 1H), 4.04 (s, 3H), 3.67 (dd, 1H), 3.22 (dd, 1H)

Example 280

1-(2-chloro-phenyl)-5-[4-(2,4-dimethoxy-pyrimidin-5-yl)-phenyl]-3-[di-(trifluoromethyl)-hydroxy-methyl]-4,5-dihydro-1H-pyrazole $^1$H NMR (400 MHz, CDCl$_3$) 8.18 (s, 1H), 7.37 (d, 2H), 7.29-7.17 (m, 4H), 7.09 (t, 1H), 6.99 (t, 1H), 5.89 (dd, 1H), 4.92 (s, 1H), 4.02 (s, 3H), 3.99 (s, 3H), 3.64 (dd, 1H), 3.22 (dd, 1H)

Example 281

1-(2-chloro-phenyl)-5-[4-(2-chloro-pyrimidin-5-yl)-phenyl]-3-[di-(trifluoromethyl)-hydroxy-methyl]-4,5-dihydro-1H-pyrazole $^1$H NMR (400 MHz, CDCl$_3$) 8.46 (s, 2H), 7.32 (d, 2H), 7.29-7.17 (m, 4H), 7.10 (t, 1H), 6.96 (t, 1H), 5.90 (dd, 1H), 4.93 (s, 1H), 3.65 (dd, 1H), 3.21 (dd, 1H)

Example 282

1-(2-chloro-phenyl)-5-{4'-[(2-hydroxy-ethyl)-methanesulfonyl-amino]-biphenyl-4-yl}-3-[di-(trifluoromethyl)-hydroxy-methyl]-4,5-dihydro-1H-pyrazole $^1$H NMR (400 MHz, CDCl$_3$) 7.53 (d, 2H), 7.45-7.38 (m, 5H), 7.27-7.22 (m, 2H), 7.18 (d, 1H), 7.09 (dd, 1H), 6.97 (dd, 1H), 5.92 (dd, 1H), 4.96 (brs, 1H), 3.86 (t, 2H), 3.71-3.62 (m, 3H), 3.24 (dd, 1H), 2.98 (s, 3H), 1.94 (brs, 1H)

Example 283

1-(2-chloro-phenyl)-5-{3'-[(2-hydroxy-ethyl)-methyl-sulfamoyl]-biphenyl-4-yl}-3-[di-(trifluoromethyl)-hydroxy-methyl]-4,5-dihydro-1H-pyrazole $^1$H NMR (400 MHz, CDCl$_3$) 7.97 (s, 1H), 7.81 (d, 1H), 7.73 (dd, 1H), 7.62-7.52 (m, 1H), 7.46 (d, 2H), 7.28-7.24 (m, 3H), 7.21 (d, 1H), 7.11 (dd, 1H), 6.98 (dd, 1H), 5.95 (dd, 1H), 4.95 (brs, 1H), 3.79-3.75 (m, 2H), 3.68 (dd, 1H), 3.26-3.17 (m, 3H), 2.85 (s, 3H), 2.02 (brs, 1H)

Example 284

1-(2-chloro-phenyl)-5-(3'-dimethylsulfamoyl-biphenyl-4-yl)-3-[di-(trifluoromethyl)-hydroxy-methyl]-4,5-dihydro-1H-pyrazole $^1$H NMR (400 MHz, CDCl$_3$) 7.89 (s, 1H), 7.72 (d, 2H), 7.57 (dd, 1H), 7.46 (d, 2H), 7.28-7.25 (m, 3H), 7.20 (d, 1H), 7.11 (dd, 1H), 6.98 (dd, 1H), 5.95 (dd, 1H), 4.92 (brs, 1H), 3.68 (dd, 1H), 3.23 (dd, 1H), 2.73 (s, 6H)

Example 285

5-{3'-[3-(N-BOC-N-methyl-amino)-propane-1-sulfonyl]-biphenyl-4-yl}-1-(2-chloro-phenyl)-3-[di-(trifluoromethyl)-hydroxy-methyl]-4,5-dihydro-1H-pyrazole $^1$H NMR (400 MHz, CDCl$_3$) 8.01 (s, 1H), 7.92 (d, 2H), 7.67 (dd, 1H), 7.47 (d, 2H), 7.28-7.25 (m, 3H), 7.20 (d, 1H), 7.11 (dd, 1H), 6.98 (dd, 1H), 5.95 (dd, 1H), 4.96 (brs, 1H), 3.68 (dd, 1H), 3.31-3.20 (m, 3H), 3.18-3.05 (m, 2H), 2.80 (s, 3H), 1.96-1.92 (m, 2H), 1.41 (s, 9H)

Example 286

1-(2-chloro-phenyl)-5-{4-[6-(methylsulfonyl)-pyridin-2-yl]-phenyl}-3-[di-(trifluoromethyl)-hydroxy-methyl]-4,5-dihydro-1H-pyrazole $^1$H NMR (400 MHz, CDCl$_3$) 7.98 (d, 2H), 7.94-7.89 (m, 3H), 7.30-7.24 (m, 3H), 7.20 (d, 1H), 7.10 (t, 1H), 6.97 (t, 1H), 5.95 (dd, 1H), 4.94 (s, 1H), 3.68 (dd, 1H), 3.28 (s, 3H), 3.24 (dd, 1H)

Example 287

1-(2-chloro-phenyl)-5-[2',5'-difluoro-4'-(1H-1,2,4-triazol-1-yl)-biphenyl-4-yl]-3-[di-(trifluoromethyl)-hydroxy-methyl]-4,5-dihydro-1H-pyrazole $^1$H NMR (400 MHz, CDCl$_3$) 8.74 (s, 1H), 8.13 (s, 1H), 7.77 (dd, 1H), 7.43 (d, 2H), 7.32-7.26 (m, 4H), 7.20 (d, 1H), 7.11 (t, 1H), 6.99 (t, 1H), 5.94 (dd, 1H), 4.96 (s, 1H), 3.68 (dd, 1H), 3.23 (dd, 1H)

Example 288

1-(2-chloro-phenyl)-5-[2',6'-difluoro-4'-(methylsulfonyl)-biphenyl-4-yl]-3-[di-(trifluoromethyl)-hydroxy-methyl]-4,5-dihydro-1H-pyrazole $^1$H NMR (400 MHz, CDCl$_3$) 7.56 (d, 2H), 7.34 (d, 2H), 7.30-7.26 (m, 3H), 7.17 (d, 1H), 7.11 (t, 1H), 7.00 (t, 1H), 5.91 (dd, 1H), 4.90 (s, 1H), 3.68 (dd, 1H), 3.24 (dd, 1H), 3.10 (s, 3H)

Example 289

1-(2-chloro-phenyl)-5-[4'-(methylsulfonyl)-2'-(trifluoromethyl)-biphenyl-4-yl]-3-[di-(trifluoromethyl)-hydroxy-methyl]-4,5-dihydro-1H-pyrazole $^1$H NMR (400 MHz, CDCl$_3$) 8.28 (s, 1H), 8.09 (d, 1H), 7.45 (d, 1H), 7.27 (d, 1H), 7.26-7.21 (m, 2H), 7.16-7.09 (m, 4H), 7.00 (t, 1H), 5.90 (dd, 1H), 4.93 (s, 1H), 3.68 (dd, 1H), 3.29 (dd, 1H), 3.12 (s, 3H)

Example 290

1-(2-chloro-phenyl)-5-[3'-cyano-4'-(methylsulfonyl)-biphenyl-4-yl]-3-[di-(trifluoromethyl)-hydroxy-methyl]-4,5-dihydro-1H-pyrazole $^1$H NMR (400 MHz, CDCl$_3$) 8.21 (d, 1H), 8.00 (s, 1H), 7.89 (d, 1H), 7.47 (d, 2H), 7.32 (d, 2H), 7.27 (d, 1H), 7.20 (d, 1H), 7.11 (t, 1H), 7.00 (t, 1H), 5.97 (dd, 1H), 4.90 (s, 1H), 3.70 (dd, 1H), 3.33 (s, 3H), 3.24 (dd, 1H)

Example 291

1-(2-chloro-phenyl)-5-[4-(1-BOC-1,2,3,6-tetrahydropyridin-4-yl)-phenyl]-3-[di-(trifluoromethyl)-hydroxy-methyl]-4,5-dihydro-1H-pyrazole 5-(4-Bromo-phenyl)-1-(2-chloro-phenyl)-3-[di-(trifluoromethyl)-hydroxy-methyl]-4,5-dihydro-1H-pyrazole (1801.0 mg, 3.59 mmol) prepared in Step 4 of Preparation 17, tert-butyl 4-(4,4,5,5-tetramethyl-1,3,2-dioxaborolan-2-yl)-5,6-dihydropyridin-1(2H)-carboxylic acid (1332.1 mg, 0.13 mmol), Pd(dppf)Cl$_2$ (262.7 mg, cat.) and potassium carbonate (1448.6 mg, 10.77 mmol) were added to a mixed solvent of 1,4-dioxane (57.6 mL) and water (14.4 mL). The reaction mixture was stirred at 90° C. for 12 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/6) to give 1.46 g of the titled compound as a white solid.

$^1$H NMR (400 MHz, CDCl$_3$) 7.26-7.06 (m, 7H), 6.95 (t, 1H), 5.97 (br, 1H), 5.86 (dd, 1H), 4.97 (s, 1H), 4.02 (br, 2H), 3.70-3.49 (m, 3H), 3.18 (dd, 1H), 2.42 (br, 2H), 1.47 (s, 9H)

Example 292

1-(2-chloro-phenyl)-5-[4-(1,2,3,6-tetrahydropyridin-4-yl)-phenyl]-3-[di-(trifluoromethyl)-hydroxy-methyl]-4,5-dihydro-1H-pyrazole trifluoroacetate 1-(2-Chloro-phenyl)-5-[4-(1-BOC-1,2,3,6-tetrahydropyridin-4-yl)-phenyl]-3-[di-(trifluoromethyl)-hydroxy-methyl]-4,5-dihydro-1H-pyrazole (350.0 mg, 0.58 mmol) prepared in Example 291 and trifluoroacetic acid (444.0 uL, 5.79 mmol) were added at 0° C. to dichloromethane (5.0 mL). The reaction mixture was stirred at room temperature for 3 hours and then concentrated under reduced pressure to give 400.0 mg of the titled compound as a yellow liquid.

$^1$H NMR (400 MHz, CDCl$_3$) 9.68 (br, 2H), 7.26-7.11 (m, 6H), 7.07 (t, 1H), 6.95 (t, 1H), 5.90 (s, 1H), 5.86 (dd, 1H), 3.75 (br, 2H), 3.64 (dd, 1H), 3.34 (br, 2H), 3.18 (dd, 1H), 2.67 (br, 2H)

Example 293

1-(2-chloro-phenyl)-5-[4-(1-acetyl-1,2,3,6-tetrahydropyridin-4-yl)-phenyl]-3-[di-(trifluoromethyl)-hydroxy-methyl]-4,5-dihydro-1H-pyrazole 1-(2-Chloro-phenyl)-5-[4-(1,2,3,6-tetrahydropyridin-4-yl)-phenyl]-3-[di-(trifluoromethyl)-hydroxy-methyl]-4,5-dihydro-1H-pyrazole trifluoroacetate (15.0 mg, 0.02 mmol) prepared in Example 292, triethylamine (9.3 uL, 0.07 mmol) and acetyl chloride (3.6 uL, 0.03 mmol) were added at 0° C. to dichloromethane (1.0 mL). The reaction mixture was stirred at room temperature for 2 hours and then distilled water was added thereto. The reaction mixture was extracted with dichloromethane two times. The combined extract was washed with 1N hydrochloric acid, a saturated solution of sodium carbonate, and brine, dried on anhydrous magnesium sulfate, and then concentrated under reduced pressure to give a yellow liquid residue. The resulting residue was purified by silica gel column chromatography (eluent: ethyl acetate/n-hexane=1/3) to give 4.9 mg of the titled compound as a yellow liquid.

$^1$H NMR (400 MHz, CDCl$_3$) 7.24-7.06 (m, 7H), 6.96 (t, 1H), 5.99 (d, 1H), 5.86 (dd, 1H), 4.94 (s, 1H), 4.14 (d, 2H), 3.68 (dt, 2H), 3.62 (dd, 1H), 3.16 (dd, 1H), 2.47 (d, 2H), 2.13 (d, 3H)

Examples 294 to 308

The compounds of Examples 294 to 308 were prepared in accordance with the same procedures as in Example 293, except for using 1-(2-chloro-phenyl)-5-[4-(1,2,3,6-tetrahydropyridin-4-yl)-phenyl]-3-[di-(trifluoromethyl)-hydroxymethyl]-4,5-dihydro-1H-pyrazole trifluoroacetate prepared in Example 292; and using each acyl chloride or sulfonyl chloride corresponding to the compounds of Examples 294 to 308 instead of acetyl chloride.

Example 294

1-(2-chloro-phenyl)-5-{4-[1-(2-thiophenecarbonyl)-1,2,3,6-tetrahydropyridin-4-yl]-phenyl}-3-[di-(trifluoromethyl)-hydroxy-methyl]-4,5-dihydro-1H-pyrazole $^1$H NMR (400 MHz, CDCl$_3$) 7.45 (d, 1H), 7.34 (d, 1H), 7.24-7.06 (m, 7H), 6.96 (t, 1H), 5.89 (s, 1H), 5.87 (dd, 1H), 4.94 (s, 1H), 4.35 (s, 2H), 3.88 (t, 2H), 3.62 (dd, 1H), 3.19 (dd, 1H), 2.55 (d, 2H)

Example 295

1-(2-chloro-phenyl)-5-[4-(1-benzoyl-1,2,3,6-tetrahydropyridin-4-yl)-phenyl]-3-[di-(trifluoromethyl)-hydroxy-methyl]-4,5-dihydro-1H-pyrazole $^1$H NMR (400 MHz, CDCl$_3$) 7.42 (s, 5H), 7.24-7.06 (m, 7H), 6.96 (t, 1H), 6.11 (br, 1H), 5.87 (dd, 1H), 4.93 (s, 1H), 4.35 (br, 1H), 4.05 (br, 1H), 3.92 (br, 1H), 3.62 (dd, 1H), 3.58 (br, 1H) 3.18 (dd, 1H), 2.51 (d, 2H)

Example 296

1-(2-chloro-phenyl)-5-[4-(1-phenylacetyl-1,2,3,6-tetrahydropyridin-4-yl)-phenyl]-3-[di-(trifluoromethyl)-hydroxy-methyl]-4,5-dihydro-1H-pyrazole $^1$H NMR (400 MHz, CDCl$_3$) 7.34-7.06 (m, 12H), 6.96 (t, 1H), 6.01-5.88 (d, 1H), 5.85 (dd, 1H), 4.92 (s, 1H), 4.23 (br, 1H), 4.07 (br, 1H), 3.81-3.74 (m, 3H), 3.65-3.57 (m, 2H), 3.17 (dd, 1H), 2.34 (d, 2H)

Example 297

1-(2-chloro-phenyl)-5-{4-[1-(4-chlorobenzoyl)-1,2,3,6-tetrahydropyridin-4-yl]-phenyl}-3-[di-(trifluoromethyl)-hydroxy-methyl]-4,5-dihydro-1H-pyrazole $^1$H NMR (400 MHz, CDCl$_3$) 7.41 (s, 4H), 7.24-7.06 (m, 7H), 6.96 (t, 1H), 6.09 (br, 1H), 5.87 (dd, 1H), 4.94 (s, 1H), 4.32-4.04 (br, d, 2H), 3.94-3.61 (br, d, 2H), 3.62 (dd, 1H), 3.19 (dd, 1H), 2.50 (br, d, 2H)

Example 298

1-(2-chloro-phenyl)-5-[4-(1-methanesulfonyl-1,2,3,6-tetrahydropyridin-4-yl)-phenyl]-3-[di-(trifluoromethyl)-hydroxy-methyl]-4,5-dihydro-1H-pyrazole $^1$H NMR (400 MHz, CDCl$_3$) 7.24-7.06 (m, 7H), 6.96 (t, 1H), 6.01 (br, 1H), 5.87 (dd, 1H), 4.92 (s, 1H), 3.92 (br, 2H), 3.63 (dd, 1H), 3.46 (t, 2H), 3.18 (dd, 1H), 2.82 (s, 3H), 2.57 (s, 2H)

Example 299

1-(2-chloro-phenyl)-5-[4-(1-ethanesulfonyl-1,2,3,6-tetrahydropyridin-4-yl)-phenyl]-3-[di-(trifluoromethyl)-hydroxy-methyl]-4,5-dihydro-1H-pyrazole $^1$H NMR (400 MHz, CDCl$_3$) 7.24-7.06 (m, 7H), 6.96 (t, 1H), 6.00 (s, 1H), 5.87 (dd, 1H), 4.92 (s, 1H), 3.96 (s, 2H), 3.62 (dd, 1H), 3.51 (t, 2H), 3.18 (dd, 1H), 3.02 (ddd, 2H), 2.53 (s, 2H), 1.25 (t, 3H)

Example 300

1-(2-chloro-phenyl)-5-{4-[1-(propane-1-sulfonyl)-1,2,3,6-tetrahydropyridin-4-yl]-phenyl}-3-[di-(trifluoromethyl)-hydroxy-methyl]-4,5-dihydro-1H-pyrazole $^1$H NMR (400 MHz, CDCl$_3$) 7.24-7.06 (m, 7H), 6.96 (t, 1H), 6.00 (s, 1H), 5.87 (dd, 1H), 4.91 (s, 1H), 3.96 (s, 2H), 3.63 (dd, 1H), 3.49 (t, 2H), 3.17 (dd, 1H), 2.92 (dd, 2H), 2.54 (s, 2H), 1.86 (m, 2H), 1.05 (t, 3H)

Example 301

1-(2-chloro-phenyl)-5-{4-[1-(propane-2-sulfonyl)-1,2,3,6-tetrahydropyridin-4-yl]-phenyl}-3-[di-(trifluoromethyl)-hydroxy-methyl]-4,5-dihydro-1H-pyrazole $^1$H NMR (400 MHz, CDCl$_3$) 7.24-7.06 (m, 7H), 6.96 (t, 1H), 6.00 (s, 1H), 5.87 (dd, 1H), 4.91 (s, 1H), 4.00 (s, 2H), 3.62 (dd, 1H), 3.55 (t, 2H), 3.22 (m, 1H), 3.17 (dd, 1H), 2.52 (s, 2H), 1.35 (d, 6H)

Example 302

1-(2-chloro-phenyl)-5-{4-[1-(2-methyl-propane-1-sulfonyl)-1,2,3,6-tetrahydropyridin-4-yl]-phenyl}-3-[di-(trifluoromethyl)-hydroxy-methyl]-4,5-dihydro-1H-pyrazole $^1$H NMR (400 MHz, CDCl$_3$) 7.24-7.06 (m, 7H), 6.96 (t, 1H), 6.00 (s, 1H), 5.87 (dd, 1H), 4.91 (s, 1H), 3.94 (s, 2H), 3.60 (dd, 1H), 3.46 (t, 2H), 3.18 (dd, 1H), 2.80 (d, 2H), 2.53 (s, 2H), 1.10 (d, 6H)

Example 303

1-(2-chloro-phenyl)-5-[4-(1-trifluoromethanesulfonyl-1,2,3,6-tetrahydropyridin-4-yl)-phenyl]-3-[di-(trifluoromethyl)-hydroxy-methyl]-4,5-dihydro-1H-pyrazole $^1$H NMR (400 MHz, CDCl$_3$) 7.24-7.06 (m, 7H), 6.96 (t, 1H), 5.97 (s, 1H), 5.88 (dd, 1H), 4.91 (s, 1H), 4.14 (br, 2H), 3.67 (br, 2H), 3.63 (dd, 1H), 3.18 (dd, 1H), 2.57 (s, 2H)

Example 304

1-(2-chloro-phenyl)-5-[4-(1-cyclopropanesulfonyl-1,2,3,6-tetrahydropyridin-4-yl)-phenyl]-3-[di-(trifluoromethyl)-hydroxy-methyl]-4,5-dihydro-1H-pyrazole $^1$H NMR (400 MHz, CDCl$_3$) 7.24-7.06 (m, 7H), 6.96 (t, 1H), 6.01 (br, 1H), 5.88 (dd, 1H), 4.93 (s, 1H), 3.98 (s, 2H), 3.65 (dd, 1H), 3.51 (t, 2H), 3.18 (dd, 1H), 2.56 (s, 2H), 2.30 (m, 1H), 1.25 (m, 2H), 0.98 (m, 2H)

Example 305

1-(2-chloro-phenyl)-5-{4-[1-dimethylsulfamoyl-1,2,3,6-tetrahydropyridin-4-yl]-phenyl}-3-[di-(trifluoromethyl)-hydroxy-methyl]-4,5-dihydro-1H-pyrazole $^1$H NMR (400 MHz, CDCl$_3$) 7.24-7.06 (m, 7H), 6.96 (t, 1H), 6.01 (br, 1H), 5.87 (dd, 1H), 4.91 (s, 1H), 3.89 (s, 2H), 3.65 (dd, 1H), 3.44 (t, 2H), 3.18 (dd, 1H), 2.82 (s, 6H), 2.52 (s, 2H)

Example 306

1-(2-chloro-phenyl)-5-[4-(1-cyclopentanesulfonyl-1,2,3,6-tetrahydropyridin-4-yl)-phenyl]-3-[di-(trifluoromethyl)-hydroxy-methyl]-4,5-dihydro-1H-pyrazole $^1$H NMR (400 MHz, CDCl$_3$) 7.24-7.06 (m, 7H), 6.96 (t, 1H), 6.00 (br, 1H), 5.88 (dd, 1H), 4.91 (s, 1H), 3.99 (s, 2H), 3.60 (dd, 1H), 3.52 (t, 2H), 3.49 (m, 1H), 3.18 (dd, 1H), 2.51 (s, 2H), 2.00 (m, 4H), 1.79 (m, 2H), 1.60 (m, 2H)

Example 307

1-(2-chloro-phenyl)-5-[4-(1-cyclohexanesulfonyl-1,2,3,6-tetrahydropyridin-4-yl)-phenyl]-3-[di-(trifluoromethyl)-hydroxy-methyl]-4,5-dihydro-1H-pyrazole $^1$H NMR (400 MHz, CDCl$_3$) 7.24-7.06 (m, 7H), 6.96 (t, 1H), 6.00 (s, 1H), 5.87 (dd, 1H), 4.91 (s, 1H), 3.99 (s, 2H), 3.62 (dd, 1H), 3.53 (t, 2H), 3.18 (dd, 1H), 2.89 (m, 1H), 2.51 (s, 2H), 2.10 (m, 2H), 1.88 (m, 2H), 1.68 (m, 2H), 1.30 (m, 4H)

Example 308

1-(2-chloro-phenyl)-5-{4-[1-(pyrrolidine-1-sulfonyl)-1,2,3,6-tetrahydropyridin-4-yl]-phenyl}-3-[di-(trifluoromethyl)-hydroxy-methyl]-4,5-dihydro-1H-pyrazole $^1$H NMR (400 MHz, CDCl$_3$) 7.26-7.20 (m, 3H), 7.19-7.06 (m, 4H), 6.95 (dd, 1H), 6.00 (brs, 1H), 6.87 (dd, 1H), 4.93 (brs, 1H), 3.90-3.86 (m, 2H), 3.62 (dd, 1H), 3.44 (t, 2H), 3.35-3.25 (m, 4H), 3.18 (dd, 1H), 2.54-2.48 (m, 2H), 1.94-1.87 (m, 4H)

Example 309

5-(3'-acetaminobiphenyl-4-yl)-1-(2-chloro-phenyl)-3-[di-(trifluoromethyl)-hydroxy-methyl]-4,5-dihydro-1H-pyrazole 5-(3'-Amino-biphenyl-4-yl)-1-(2-chloro-phenyl)-3-[di-(trifluoromethyl)-hydroxy-methyl]-4,5-dihydro-1H-pyrazole (8.0 mg, 0.02 mmol) prepared in Example 253, pyridine (2.2 uL, 0.02 mmol) and acetyl chloride (1.4 uL, 0.02 mmol) were added at 0° C. to dichloromethane (0.3 mL). The reaction mixture was stirred at room temperature for 2 hours and then distilled water was added thereto. The reaction mixture was extracted with dichloromethane two times. The combined extract was washed with a 1N hydrochloric acid solution, a saturated solution of sodium carbonate, and brine, dried on anhydrous magnesium sulfate, and then concentrated under reduced pressure to give a yellow liquid residue. The resulting residue was purified by silica gel column chromatography (eluent: ethyl acetate/n-hexane=1/1) to give 1.9 mg of the titled compound as a yellow liquid.

$^1$H NMR (400 MHz, CDCl$_3$) 7.71 (s, 1H), 7.43 (d, 2H), 7.40-7.31 (m, 2H), 7.25-7.17 (m, 5H), 7.08 (t, 1H), 6.96 (t, 1H), 5.91 (dd, 1H), 4.96 (s, 1H), 3.65 (dd, 1H), 3.24 (dd, 1H), 2.18 (s, 3H)

Example 310

5-(3'-methanesulfonyl-aminobiphenyl-4-yl)-1-(2-chloro-phenyl)-3-[di-(trifluoromethyl)-hydroxy-methyl]-4,5-dihydro-1H-pyrazole The compound of Example 310 was prepared in accordance with the same procedures as in Example 309, except for using 5-(3'-amino-biphenyl-4-yl)-1-(2-chloro-phenyl)-3-[di-(trifluoromethyl)-hydroxy-methyl]-4,5-dihydro-1H-pyrazole prepared in Example 253; and using methanesulfonyl chloride instead of acetyl chloride.

$^1$H NMR (400 MHz, CDCl$_3$) 7.42 (d, 2H), 7.38-7.14 (m, 8H), 7.10 (t, 1H), 6.97 (t, 1H), 6.38 (s, 1H), 5.93 (dd, 1H), 4.92 (s, 1H), 3.66 (dd, 1H), 3.01 (s, 3H)

Example 311

1-(2-chloro-phenyl)-5-[4-(4-BOC-piperazin-1-yl)-phenyl]-3-[di-(trifluoromethyl)-hydroxy-methyl]-4,5-dihydro-1H-pyrazole 5-(4-Bromo-phenyl)-1-(2-chloro-phenyl)-3-[di-(trifluoromethyl)-hydroxy-methyl]-4,5-dihydro-1H-pyrazole (1.0 g, 1.99 mmol) prepared in Step 4 of Preparation 17, 1-BOC-piperazine (557.0 mg, 2.99 mmol), Pd$_2$(dba)$_3$ (91.0 mg, cat.), BINAP (124.0 mg, cat.) and sodium t-butoxide (287.0 mg, 2.99 mmol) were added to toluene (20.0 mL). The reaction mixture was stirred at 100° C. for 12 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/4) to give 480.0 mg of the titled compound as a yellow liquid.

$^1$H NMR (400 MHz, CDCl$_3$) 7.23 (dd, 1H), 7.10 (d, 1H), 7.06-7.01 (m, 3H), 6.94 (dd, 1H), 6.71 (d, 2H), 5.80 (dd, 1H), 5.01 (s, 1H), 3.62-3.48 (m, 5H), 3.17 (dd, 1H), 3.07-3.02 (m, 4H), 1.46 (s, 9H)

Example 312

1-(2-chloro-phenyl)-5-[4-(4-methanesulfonyl-piperazin-1-yl)-phenyl]-3-[di-(trifluoromethyl)-hydroxy-methyl]-4,5-dihydro-1H-pyrazole Step 1: 1-(2-chloro-phenyl)-5-[4-(piperazin-1-yl)-phenyl]-3-[di-(trifluoromethyl)-hydroxy-methyl]-4,5-dihydro-1H-pyrazole hydrochloride 1-(2-Chloro-phenyl)-5-[4-(4-BOC-piperazin-1-yl)-phenyl]-3-[di-(trifluoromethyl)-hydroxy-methyl]-4,5-dihydro-1H-pyrazole (480.0 mg, 0.8 mmol) prepared in Example 311 was added to a saturated solution of hydrochloric acid in ethyl acetate (5.0 mL). The reaction mixture was stirred at room temperature for 2 hours and then concentrated under reduced pressure to give 450.0 mg of the titled compound as a pale yellow solid.

$^1$H NMR (400 MHz, CD$_3$OD) 7.31 (d, 1H), 7.21 (d, 1H), 7.11-7.09 (m, 3H), 6.94 (t, 1H), 6.84 (d, 2H), 5.83 (dd, 1H), 3.62 (dd, 1H), 3.30 (m, 8H), 3.14 (dd, 1H)

Step 2: 1-(2-chloro-phenyl)-5-[4-(4-methanesulfonyl-piperazin-1-yl)-phenyl]-3-[di-(trifluoromethyl)-hydroxy-methyl]-4,5-dihydro-1H-pyrazole 1-(2-Chloro-phenyl)-5-[4-(piperazin-1-yl)-phenyl]-3-[di-(trifluoromethyl)-hydroxy-methyl]-4,5-dihydro-1H-pyrazole hydrochloride (30.0 mg, 0.06 mmol) prepared in Step 1, triethylamine (42.3 uL, 0.30 mmol) and methanesulfonyl chloride (10.4 mg, 0.09 mmol) were added to dichloromethane (1.0 mL). The reaction mixture was stirred at room temperature for 1 hour, washed with distilled water, 1N hydrochloride, a saturated solution of sodium hydrogen carbonate, and brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 15.0 mg of the titled compound as a yellow liquid.

$^1$H NMR (400 MHz, CDCl$_3$) 8.20 (s, 1H), 7.97 (s, 1H), 7.38-7.32 (m, 1H), 6.91 (s, 1H), 6.77 (t, 1H), 6.69 (t, 1H), 5.58 (dd, 1H), 3.68 (dd, 1H), 3.37 (t, 4H), 3.23 (t, 4H), 3.12 (dd, 1H), 2.83 (s, 3H)

Examples 313 to 319

The compounds of Examples 313 to 319 were prepared in accordance with the same procedures as in Step 2 of Example 312, except for using 1-(2-chloro-phenyl)-5-[4-(piperazin-1-yl)-phenyl]-3-[di-(trifluoromethyl)-hydroxy-methyl]-4,5-dihydro-1H-pyrazole hydrochloride Prepared in Step 1 of Example 312; and using each sulfonyl chloride or acyl chloride corresponding to the compounds of Examples 313 to 319 instead of methanesulfonyl chloride.

Example 313

1-(2-chloro-phenyl)-5-[4-(4-ethanesulfonyl-piperazin-1-yl)-phenyl]-3-[di-(trifluoromethyl)-hydroxy-methyl]-4,5-dihydro-1H-pyrazole $^1$H NMR (400 MHz, CDCl$_3$) 7.23 (d, 1H), 7.13 (d, 1H), 7.09-7.03 (m, 3H), 6.95 (dd, 1H), 6.73 (d, 2H), 5.82 (dd, 1H), 4.95 (s, 1H), 3.59 (dd, 1H), 3.42-3.33 (m, 4H), 3.26-3.11 (m, 5H), 2.97 (q, 2H), 1.38 (t, 3H)

Example 314

1-(2-chloro-phenyl)-5-[4-(4-isopropylsulfonyl-piperazin-1-yl)-phenyl]-3-[di-(trifluoromethyl)-hydroxy-methyl]-4,5-dihydro-1H-pyrazole $^1$H NMR (400 MHz, CDCl$_3$) 7.24 (d, 1H), 7.13 (d, 1H), 7.09-7.03 (m, 3H), 6.95 (dd, 1H), 6.72 (d, 2H), 5.81 (dd, 1H), 4.93 (s, 1H), 3.59 (dd, 1H), 3.47-3.43 (m, 4H), 3.25-3.12 (m, 6H), 1.35 (d, 6H)

Example 315

1-(2-chloro-phenyl)-5-[4-(4-cyclopropanesulfonyl-piperazin-1-yl)-phenyl]-3-[di-(trifluoromethyl)-hydroxy-methyl]-4,5-dihydro-1H-pyrazole $^1$H NMR (400 MHz, CDCl$_3$) 7.24 (d, 1H), 7.14 (d, 1H), 7.09-7.03 (m, 3H), 6.95 (dd, 1H), 6.73 (d, 2H), 5.82 (dd, 1H), 4.95 (s, 1H), 3.59 (dd, 1H), 3.42-3.37 (m, 4H), 3.22-3.13 (m, 5H), 2.30-2.23 (m, 1H), 1.90-1.77 (m, 2H), 1.02-0.96 (m, 2H)

Example 316

1-(2-chloro-phenyl)-5-[4-(4-dimethylsulfamoyl-piperazin-1-yl)-phenyl]-3-[di-(trifluoromethyl)-hydroxy-methyl]-4,5-dihydro-1H-pyrazole $^1$H NMR (400 MHz, CDCl$_3$) 7.24 (d, 1H), 7.13 (d, 1H), 7.09-7.02 (m, 3H), 6.95 (dd, 1H), 6.72 (d, 2H), 5.81 (dd, 1H), 4.93 (s, 1H), 3.59 (dd, 1H), 3.35-3.30 (m, 4H), 3.21-3.13 (m, 5H), 2.84 (s, 6H)

Example 317

1-(2-chloro-phenyl)-5-[4-(4-isobutyryl-piperazin-1-yl)-phenyl]-3-[di-(trifluoromethyl)-hydroxy-methyl]-4,5-dihydro-1H-pyrazole $^1$H NMR (400 MHz, CDCl$_3$) 7.24 (d, 1H), 7.13 (d, 1H), 7.09-7.03 (m, 3H), 6.95 (dd, 1H), 6.72 (d, 2H), 5.81 (dd, 1H), 4.94 (s, 1H), 3.73-3.54 (m, 5H), 3.20-3.09 (m, 5H), 2.83-2.76 (m, 1H), 1.13 (d, 6H)

Example 318

1-(2-chloro-phenyl)-5-[4-(4-dimethylcarbamoyl-piperazin-1-yl)-phenyl]-3-[di-(trifluoromethyl)-hydroxy-methyl]-4,5-dihydro-1H-pyrazole $^1$H NMR (400 MHz, CDCl$_3$) 7.23 (d, 1H), 7.13 (d, 1H), 7.09-7.01 (m, 3H), 6.94 (dd, 1H), 6.72 (d, 2H), 5.80 (dd, 1H), 4.99 (s, 1H), 3.58 (dd, 1H), 3.35-3.29 (m, 4H), 3.21-3.08 (m, 5H), 2.84 (s, 6H)

Example 319

1-(2-chloro-phenyl)-5-{4-[4-(pyrrolidine-1-sulfonyl)-piperazin-1-yl]-phenyl}-3-[di-(trifluoromethyl)-hydroxy-methyl]-4,5-dihydro-1H-pyrazole $^1$H NMR (400 MHz, CDCl$_3$) 7.24 (dd, 1H), 7.13 (d, 1H), 7.10-7.02 (m, 3H), 6.95 (dd, 1H), 6.72 (d, 2H), 5.81 (dd, 1H), 4.95 (s, 1H), 3.58 (dd, 1H), 3.39-3.31 (m, 8H), 3.20-3.10 (m, 5H), 1.96-1.87 (m, 4H)

Example 320

1-(2-chloro-phenyl)-5-{4-[4-(2-hydroxy-2-methylpropionyl)-piperazin-1-yl]-phenyl}-3-(di-(trifluoromethyl)-hydroxy-methyl]-4,5-dihydro-1H-pyrazole To 1-(2-chloro-phenyl)-5-[4-(piperazin-1-yl)-phenyl]-3-[di-(trifluoromethyl)-hydroxy-methyl]-4,5-dihydro-1H-pyrazole hydrochloride (30.0 mg, 0.06 mmol) prepared in Step 1 of Example 312, were added 2-hydroxyisobutyric acid (7.0 mg, 0.07 mmol), dichloromethane (1.0 mL), HOBT (15.0 mg, 0.11 mmol), EDAC (21.0 mg, 0.11 mmol), and triethylamine (23.0 uL, 0.17 mmol). The reaction mixture was stirred at room temperature for 12 hours, washed with distilled water, 1N hydrochloride, a saturated solution of sodium hydrogen carbonate, and brine, dried on anhydrous magnesium sulfate, and then concentrated under reduced pressure to give a yellow liquid residue. The resulting residue was purified by silica gel column chromatography (eluent: ethyl acetate/n-hexane=1/1) to give 10.0 mg of the titled compound as a pale yellow liquid.

$^1$H NMR (400 MHz, CDCl$_3$) 7.24 (d, 1H), 7.14 (d, 1H), 7.10-7.03 (m, 3H), 6.95 (dd, 1H), 6.73 (d, 2H), 5.82 (dd, 1H), 4.94 (brs, 1H), 4.09 (brs, 1H), 3.82-3.77 (m, 4H), 3.59 (dd, 1H), 3.20-3.11 (m, 5H), 1.50 (s, 6H)

Example 321

1-(2-chloro-phenyl)-5-[4-(4-BOC-homopiperazin-1-yl)-phenyl]-3-[di-(trifluoromethyl)-hydroxy-methyl]-4,5-dihydro-1H-pyrazole 5-(4-Bromo-phenyl)-1-(2-chloro-phenyl)-3-[di-(trifluoromethyl)-hydroxy-methyl]-4,5-dihydro-1H-pyrazole (1.0 g, 1.99 mmol) prepared in Step 4 of Preparation 17, 1-BOC-homopiperazine (589.0 uL, 2.99 mmol), $Pd_2(dba)_3$ (91.0 mg, cat.), BINAP (124.0 mg, cat.) and sodium t-butoxide (287.0 mg, 2.99 mmol) were added to toluene (20.0 mL). The reaction mixture was stirred at 100° C. for 12 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/4) to give 350.0 mg of the titled compound as a yellow liquid.

$^1$H NMR (400 MHz, $CDCl_3$) 7.24 (dd, 1H), 7.13-7.03 (m, 2H), 6.97-6.90 (m, 3H), 6.47 (d, 2H), 5.76 (dd, 1H), 5.04 (brs, 1H), 3.60-3.40 (m, 7H), 3.30-3.10 (m, 3H), 1.92-1.80 (m, 2H), 1.36 (d, 9H)

Example 322

1-(2-chloro-phenyl)-5-[4-(4-methanesulfonyl-homopiperazin-1-yl)-phenyl]-3-[di-(trifluoromethyl)-hydroxy-methyl]-4,5-dihydro-1H-pyrazole Step 1: 1-(2-chloro-phenyl)-5-[4-(homopiperazin-1-yl)-phenyl]-3-[di-(trifluoromethyl)-hydroxy-methyl]-4,5-dihydro-1H-pyrazole hydrochloride 1-(2-Chloro-phenyl)-5-[4-(4-BOC-homopiperazin-1-yl)-phenyl]-3-[di-(trifluoromethyl)-hydroxy-methyl]-4,5-dihydro-1H-pyrazole (350.0 mg, 0.8 mmol) prepared in Example 321 was added to a saturated solution of hydrochloric acid in ethyl acetate (5.0 mL). The reaction mixture was stirred at room temperature for 2 hours and then concentrated under reduced pressure to give 330.0 mg of the titled compound as a pale yellow solid.

$^1$H NMR (400 MHz, $CD_3OD$) 7.21 (d, 1H), 7.10 (d, 1H), 7.01-6.93 (m, 3H), 6.84 (t, 1H), 6.53 (d, 2H), 5.71 (dd, 1H), 3.59 (br, 2H), 3.51 (dd, 1H), 3.41 (s, 2H), 3.10 (br, 2H), 3.03 (dd, 1H), 2.02 (br, 2H), 1.91 (br, 2H)

Step 2: 1-(2-chloro-phenyl)-5-[4-(4-methanesulfonyl-homopiperazin-1-yl)-phenyl]-3-[di-(trifluoromethyl)-hydroxy-methyl]-4,5-dihydro-1H-pyrazole 1-(2-Chloro-phenyl)-5-[4-(homopiperazin-1-yl)-phenyl]-3-[di-(trifluoromethyl)-hydroxy-methyl]-4,5-dihydro-1H-pyrazole hydrochloride (30.0 mg, 0.06 mmol) prepared in Step 1, triethylamine (42.3 uL, 0.30 mmol) and methanesulfonyl chloride (10.4 mg, 0.09 mmol) were added to dichloromethane (1.0 mL). The reaction mixture was stirred at room temperature for 1 hour, washed with distilled water, 1N hydrochloride, a saturated solution of sodium hydrogen carbonate, and brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 10.0 mg of the titled compound as a yellow liquid.

$^1$H NMR (400 MHz, $CDCl_3$) 7.24 (d, 1H), 7.12 (d, 1H), 7.09-6.92 (m, 4H), 6.48 (d, 2H), 5.78 (dd, 1H), 4.94 (s, 1H), 3.67-3.40 (m, 7H), 3.30-3.10 (m, 3H), 2.58 (s, 3H), 1.98-1.93 (m, 2H)

Examples 323 to 328

The compounds of Examples 323 to 328 were prepared in accordance with the same procedures as in Step 2 of Example 322, except for using 1-(2-chloro-phenyl)-5-(4-(homopiperazin-1-yl)-phenyl]-3-[di-(trifluoromethyl)-hydroxy-methyl]-4,5-dihydro-1H-pyrazole hydrochloride prepared in Step 1 of Example 322; and using each sulfonyl chloride or acyl chloride corresponding to the compounds of Examples 323 to 328 instead of methanesulfonyl chloride.

Example 323

1-(2-chloro-phenyl)-5-[4-(4-ethanesulfonyl-homopiperazin-1-yl)-phenyl]-3-[di-(trifluoromethyl)-hydroxy-methyl]-4,5-dihydro-1H-pyrazole $^1$H NMR (400 MHz, $CDCl_3$) 7.24 (d, 1H), 7.13-7.04 (m, 2H), 7.00-6.92 (m, 3H), 6.49 (d, 2H), 5.77 (dd, 1H), 4.95 (s, 1H), 3.62-3.52 (m, 5H), 3.46-3.41 (m, 2H), 3.22-3.14 (m, 3H), 2.90 (q, 2H), 2.02-1.96 (m, 2H), 1.24 (t, 3H)

Example 324

1-(2-chloro-phenyl)-5-[4-(4-isopropylsulfonyl-homopiperazin-1-yl)-phenyl]-3-[di-(trifluoromethyl)-hydroxy-methyl]-4,5-dihydro-1H-pyrazole $^1$H NMR (400 MHz, $CDCl_3$) 7.24 (d, 1H), 7.13-7.04 (m, 2H), 6.99-6.92 (m, 3H), 6.47 (d, 2H), 5.77 (dd, 1H), 4.95 (s, 1H), 3.63-3.52 (m, 5H), 3.45-3.42 (m, 2H), 3.22-3.11 (m, 4H), 2.04-1.97 (m, 2H), 1.27 (d, 6H)

Example 325

1-(2-chloro-phenyl)-5-[4-(4-cyclopropanesulfonyl-homopiperazin-1-yl)-phenyl]-3-[di-(trifluoromethyl)-hydroxy-methyl]-4,5-dihydro-1H-pyrazole $^1$H NMR (400 MHz, $CDCl_3$) 7.24 (d, 1H), 7.14-7.04 (m, 2H), 6.99-6.92 (m, 3H), 6.48 (d, 2H), 5.78 (dd, 1H), 4.95 (s, 1H), 3.62-3.46 (m, 7H), 3.25 (t, 2H), 3.17 (dd, 1H), 2.12-2.04 (m, 1H), 1.99-1.94 (m, 2H), 1.09-1.05 (m, 2H), 0.80-0.74 (m, 2H)

Example 326

1-(2-chloro-phenyl)-5-[4-(4-dimethylsulfamoyl-homopiperazin-1-yl)-phenyl]-3-[di-(trifluoromethyl)-hydroxy-methyl]-4,5-dihydro-1H-pyrazole $^1$H NMR (400 MHz, $CDCl_3$) 7.24 (d, 1H), 7.14-7.04 (m, 2H), 6.98-6.92 (m, 3H), 6.47 (d, 2H), 5.78 (dd, 1H), 4.95 (s, 1H), 3.59-3.52 (m, 5H), 3.44-3.40 (m, 2H), 3.22-3.14 (m, 3H), 2.62 (s, 6H), 1.98-1.92 (m, 2H)

Example 327

1-(2-chloro-phenyl)-5-[4-(4-isobutyryl-homopiperazin-1-yl)-phenyl]-3-[di-(trifluoromethyl)-hydroxy-methyl]-4,5-dihydro-1H-pyrazole $^1$H NMR (400 MHz, $CDCl_3$) 7.24 (d, 1H), 7.13 (d, 1H), 7.09-7.03 (m, 3H), 6.95 (dd, 1H), 6.72 (d, 2H), 5.81 (dd, 1H), 4.94 (s, 1H), 3.73-3.54 (m, 5H), 3.20-3.09 (m, 5H), 2.83-2.76 (m, 1H), 1.13 (d, 6H)

Example 328

1-(2-chloro-phenyl)-5-[4-(4-dimethylcarbamoyl-homopiperazin-1-yl)-phenyl]-3-[di-(trifluoromethyl)-hydroxy-methyl]-4,5-dihydro-1H-pyrazole $^1$H NMR (400 MHz, CDCl$_3$) 7.24 (d, 1H), 7.13-7.03 (m, 2H), 6.98-6.91 (m, 3H), 6.49 (d, 2H), 5.76 (dd, 1H), 5.00 (s, 1H), 3.59-3.41 (m, 7H), 3.22-3.16 (m, 3H), 2.73 (s, 6H), 1.96-1.91 (m, 2H)

Example 329

1-(2-chloro-phenyl)-5-[4-(1,1-dioxo-thiomorpholin-4-yl)-phenyl]-3-[di-(trifluoromethyl)-hydroxy-methyl]-4,5-dihydro-1H-pyrazole 5-(4-Bromo-phenyl)-1-(2-chloro-phenyl)-3-[di-(trifluoromethyl)-hydroxy-methyl]-4,5-dihydro-1H-pyrazole (100.0 mg, 0.20 mmol) prepared in Step 4 of Preparation 17, thiomorpholine-1,1-dioxide (32.0 mg, 0.24 mmol), Pd$_2$(dba)$_3$ (9.0 mg, cat.), BINAP (12.0 mg, cat.) and sodium t-butoxide (29.0 mg, 0.30 mmol) were added to toluene (20.0 mL). The reaction mixture was stirred at 100° C. for 12 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/1) to give 40.0 mg of the titled compound as a white liquid.

$^1$H NMR (400 MHz, CDCl$_3$) 7.25 (d, 1H), 7.19-7.00 (m, 4H), 6.98 (d, 1H), 6.71 (d, 2H), 5.83 (dd, 1H), 4.93 (s, 1H), 3.83-3.74 (m, 4H), 3.60 (dd, 1H), 3.17 (dd, 1H), 3.05-2.95 (m, 4H)

Example 330

1-(2-chloro-phenyl)-5-{4-[4-(N-BOC-amino)-piperidin-1-yl]-phenyl}-3-[di-(trifluoromethyl)-hydroxy-methyl]-4,5-dihydro-1H-pyrazole 5-(4-Bromo-phenyl)-1-(2-chloro-phenyl)-3-[di-(trifluoromethyl)-hydroxy-methyl]-4,5-dihydro-1H-pyrazole (300.0 mg, 0.60 mmol) prepared in Step 4 of Preparation 17, 4-(N-BOC-amino)-piperidine (180.0 mg, 0.90 mmol), Pd$_2$(dba)$_3$ (27.0 mg, cat.), BINAP (37.0 mg, cat.) and sodium t-butoxide (115.0 mg, 1.20 mmol) were added to toluene (5.0 mL). The reaction mixture was stirred at 100° C. for 12 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/5) to give 210.0 mg of the titled compound as a white liquid.

$^1$H NMR (400 MHz, CDCl$_3$) 7.26-7.22 (m, 1H), 7.14-6.92 (m, 5H), 6.72 (d, 2H), 5.79 (dd, 1H), 4.94 (s, 1H), 4.44 (brs, 1H), 3.61-3.51 (m, 9H), 3.17 (dd, 1H), 2.76 (t, 2H), 2.05-1.97 (m, 2H), 1.46-1.12 (m, 11H)

Example 331

1-(2-chloro-phenyl)-5-{4-[4-amino-piperidin-1-yl]-phenyl}-3-[di-(trifluoromethyl)-hydroxy-methyl]-4,5-dihydro-1H-pyrazole hydrochloride 1-(2-Chloro-phenyl)-5-{4-[4-(N-BOC-amino)-piperidin-1-yl]-phenyl}-3-[di-(trifluoromethyl)-hydroxy-methyl]-4,5-dihydro-1H-pyrazole (210.0 mg, 0.34 mmol) prepared in Example 330 was added to a saturated solution of hydrochloric acid in ethyl acetate (5.0 mL). The reaction mixture was stirred at room temperature for 2 hours and then concentrated under reduced pressure to give 200.0 mg of the titled compound as a pale yellow solid.

$^1$H NMR (400 MHz, CD$_3$OD) 7.49 (d, 2H), 7.33 (t, 3H), 7.17 (d, 1H), 7.11 (t, 1H), 6.94 (t, 1H), 5.93 (dd, 1H), 3.72-3.63 (m, 3H), 3.61-3.48 (m, 3H), 3.10 (dd, 1H), 2.29 (d, 2H), 2.23-2.09 (m, 2H)

Example 332

1-(2-chloro-phenyl)-5-[4-(4-cyclopropanesulfonylamino-piperidin-1-yl)-phenyl]-3-[di-(trifluoromethyl)-hydroxy-methyl]-4,5-dihydro-1H-pyrazole 1-(2-Chloro-phenyl)-5-{4-[4-amino-piperidin-1-yl]-phenyl}-3-[di-(trifluoromethyl)-hydroxy-methyl]-4,5-dihydro-1H-pyrazole hydrochloride (30.0 mg, 0.06 mmol) prepared in Example 331, triethylamine (37.3 uL, 0.27 mmol) and cyclopropanesulfonyl chloride (10.4 mg, 0.08 mmol) were added to dichloromethane (1.0 mL). The reaction mixture was stirred at room temperature for 1 hour, washed with distilled water, 1N hydrochloride, a saturated solution of sodium hydrogen carbonate, and brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 10.0 mg of the titled compound as a pale yellow liquid.

$^1$H NMR (400 MHz, CDCl$_3$) 7.23 (d, 1H), 7.13 (d, 1H), 7.08 (t, 1H), 7.03 (d, 2H), 6.94 (t, 1H), 6.71 (d, 2H), 5.80 (dd, 1H), 4.94 (s, 1H), 4.16 (d, 1H), 3.69-3.42 (m, 4H), 3.18 (dd, 1H), 2.79 (t, 2H), 2.45-2.68 (m, 1H), 2.10-2.03 (m, 2H), 1.62-1.55 (m, 2H), 1.25-1.17 (m, 2H), 1.02-0.99 (m, 2H)

Example 333

1-(2-chloro-phenyl)-5-[4-(5-carboxypyridin-3-yl)-phenyl]-3-[di-(trifluoromethyl)-hydroxy-methyl]-4,5-dihydro-1H-pyrazole To a mixture of 1-(2-chloro-phenyl)-5-(4-(5-methoxycarbonyl-pyridin-3-yl)-phenyl)-3-[di-(trifluoromethyl)-hydroxy-methyl]-4,5-dihydro-1H-pyrazole (6.0 mg, 0.01 mmol) prepared in Example 273 in methanol (0.5 mL), was added a solution of potassium hydroxide (2.0 mg, 0.03 mmol) in distilled water (0.5 mL). The reaction mixture was stirred at 70° C. for 2 hours and then washed with diethyl ether. A 1N hydrochloric acid solution was added to the reaction mixture, which was then extracted with ethyl acetate. The extract was washed with a saturated solution of sodium hydrogen carbonate and brine, dried on anhydrous magnesium sulfate, and then concentrated under reduced pressure to give 5.0 mg of the titled compound as a pale yellow liquid.

$^1$H NMR (400 MHz, CDCl$_3$) 9.18 (s, 1H), 9.12 (s, 1H), 8.94 (s, 1H), 7.66 (d, 2H), 7.39 (m, 3H), 7.21 (d, 1H), 7.11 (t, 1H), 6.93 (t, 1H), 5.99 (dd, 1H), 3.73 (dd, 1H), 3.21 (dd, 1H)

Example 334

1-(2-chloro-phenyl)-5-{3'-[3-(methyl-amino)-propane-1-sulfonyl]-biphenyl-4-yl}-3-[di-(trifluoromethyl)-hydroxy-methyl]-4,5-dihydro-1H-pyrazole To 5-{3'-[3-(N-BOC-N-methyl-amino)-propane-1-sulfonyl]-biphenyl-4-yl}-1-(2-chloro-phenyl)-3-[di-(trifluoromethyl)-hydroxy-methyl]-4,5-dihydro-1H-pyrazole (9.0 mg, 0.012 mmol) prepared in Example 285, were added dichloromethane (0.5 mL) and trifluoroacetic acid (9.0 uL, 0.12 mmol). The reaction mixture was stirred at room temperature for 48 hours, washed with distilled water, 1N hydrochloride, a saturated solution of sodium hydrogen carbonate, and brine, dried on anhydrous magnesium sulfate, and then concentrated under reduced pressure to give 5.0 mg of the titled compound as a pale yellow liquid.

$^1$H NMR (400 MHz, CDCl$_3$) 8.02 (s, 1H), 7.85 (d, 1H), 7.76 (d, 1H), 7.59 (dd, 1H), 7.47 (d, 2H), 7.27-7.25 (m, 3H), 7.20 (d, 1H), 7.11 (dd, 1H), 6.98 (dd, 1H), 5.94 (dd, 1H), 3.68 (dd, 1H), 3.27-3.17 (m, 3H), 2.65 (t, 2H), 2.36 (s, 3H), 1.95-1.86 (m, 2H)

Example 335

1-(2-chloro-phenyl)-5-[4-(6-methanesulfonyl-pyridin-3-yl)-phenyl]-3-[di-(trifluoromethyl)-hydroxy-methyl]-4,5-dihydro-1H-pyrazole To a mixture of 1-(2-chloro-phenyl)-5-(4-(6-methylsulfanyl-pyridin-3-yl)-phenyl)-3-[di-(trifluoromethyl)-hydroxy-methyl]-4,5-dihydro-1H-pyrazole (9.8 mg, 0.02 mmol) prepared in Example 266 in dichloromethane (2.0 mL), was slowly added meta-chloroperbenzoic acid (77%, 8.1 mg, 0.04 mmol) at 0° C. The reaction mixture was stirred at room temperature for 30 minutes, quenched with a saturated solution of sodium hydrogen carbonate, and then extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 2.5 mg of the titled compound as a pale yellow liquid.

$^1$H NMR (400 MHz, CDCl$_3$) 8.84 (s, 1H), 8.12 (d, 1H), 8.03 (d, 1H), 7.48 (d, 2H), 7.32 (d, 2H), 7.26 (m, 1H), 7.21 (d, 1H), 7.14 (t, 1H), 7.00 (t, 1H), 5.98 (dd, 1H), 3.70 (dd, 1H), 3.25 (s, 3H). 3.22 (dd, 1H)

Example 336

5-(3'-ethoxy-biphenyl-4-yl)-1-(2-fluoro-phenyl)-3-[di-(trifluoromethyl)-hydroxy-methyl]-4,5-dihydro-1H-pyrazole Step 1: 5-(3'-ethoxy-biphenyl-4-yl)-1-(2-fluoro-phenyl)-4,5-dihydro-1H-pyrazole-3-carboxylic acid methyl ester 4-(3'-Ethoxy-biphenyl-4-yl)-2-oxo-3-butenoic acid methyl ester (190.0 mg, 0.61 mmol) prepared in Step 3 of Preparation 18 and 2-fluorophenylhydrazine hydrochloride (110.0 mg, 0.67 mmol) were added to acetic acid (3.0 mL). The reaction mixture was stirred at 125° C. for 1 hour and then concentrated under reduced pressure. Ethyl acetate was added to the reaction mixture, which was washed with a saturated solution of sodium hydrogen carbonate, dried on anhydrous magnesium sulfate, and then concentrated under reduced pressure to give a yellow liquid residue. The resulting residue was purified by silica gel column chromatography (eluent: ethyl acetate/n-hexane=1/5) to give 250.0 mg of the titled compound as a yellow liquid.

$^1$H NMR (400 MHz, CDCl$_3$) 7.57 (t, 1H), 7.44 (d, 2H), 7.31-7.19 (m, 3H), 7.09-7.02 (m, 3H), 6.92-6.84 (m, 3H), 5.77 (d, 1H), 4.06 (q, 2H), 3.90 (s, 3H), 3.71 (t, 1H), 3.23 (d, 1H), 1.42 (t, 3H)

Step 2: 5-(3'-ethoxy-biphenyl-4-yl)-1-(2-fluoro-phenyl)-4,5-dihydro-1H-pyrazole-3-carboxylic acid 5-(3'-Ethoxy-biphenyl-4-yl)-1-(2-fluoro-phenyl)-4,5-dihydro-1H-pyrazole-3-carboxylic acid methyl ester (250.0 mg, 0.60 mmol) prepared in Step 1 and a solution of potassium hydroxide (67.0 mg, 1.19 mmol) in distilled water (4.0 mL) were added to methanol (4.0 mL). The reaction mixture was stirred at 70° C. for 2 hours and then concentrated under reduced pressure to discard methanol. The resulting residue was washed with diethyl ether, acidified by a 1N hydrochloric acid solution, and then extracted with ethyl acetate. The extract was washed with distilled water and brine, dried on anhydrous magnesium sulfate, and then concentrated under reduced pressure to give 200.0 mg of the titled compound as a pale yellow solid.

$^1$H NMR (400 MHz, CDCl$_3$) 7.53 (t, 1H), 7.46 (d, 2H), 7.30 (t, 1H), 7.21 (d, 2H), 7.09-7.01 (m, 3H), 6.95-6.91 (m, 2H), 6.86 (d, 1H), 5.84 (dd, 1H), 4.06 (q, 2H), 3.73 (dd, 1H), 3.25 (dd, 1H), 1.42 (t, 3H)

Step 3: 5-(3'-ethoxy-biphenyl-4-yl)-1-(2-fluoro-phenyl)-3-[di-(trifluoromethyl)-hydroxy-methyl]-4,5-dihydro-1H-pyrazole 5-(3'-Ethoxy-biphenyl-4-yl)-1-(2-fluoro-phenyl)-4,5-dihydro-1H-pyrazole-3-carboxylic acid (200.0 mg, 0.49 mmol) prepared in Step 2 was added to thionyl chloride (2.0 mL). The reaction mixture was stirred at 100° C. for 2 hours and then concentrated under reduced pressure. The resulting residue was concentrated under reduced pressure three times, along with using toluene, to give 5-(3'-ethoxy-biphenyl-4-yl)-1-(2-fluoro-phenyl)-4,5-dihydro-1H-pyrazole-3-carbonyl chloride as a dark brown liquid.

To a mixture of the 5-(3'-ethoxy-biphenyl-4-yl)-1-(2-fluoro-phenyl)-4,5-dihydro-1H-pyrazole-3-carbonyl chloride in the form of a dark brown liquid, TMAF (101.0 mg, 1.09 mmol) in 1,2-dimethoxyethane (2.0 mL), was slowly added CF$_3$TMS (160.0 uL, 1.09 mmol) under nitrogen atmosphere at −78° C. The reaction mixture was stirred at −40° C. for 2 hours, quenched with a 1N hydrochloric acid solution, and then extracted with ethyl acetate. The extract was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/5) to give 175.0 mg of the titled compound as a yellow liquid.

$^1$H NMR (400 MHz, CDCl$_3$) 7.46 (d, 2H), 7.33-7.27 (m, 2H), 7.19 (d, 2H), 7.08 (d, 1H), 7.04-7.00 (m, 2H), 6.98-6.84 (m, 3H), 5.73 (dd, 1H), 4.90 (s, 1H), 4.06 (q, 2H), 3.65 (dd, 1H), 3.15 (dd, 1H), 1.42 (t, 3H)

Example 337

5-(3'-ethoxy-biphenyl-4-yl)-1-(2,4-difluoro-phenyl)-3-[di-(trifluoromethyl)-hydroxy-methyl]-4,5-dihydro-1H-pyrazole The titled compound was prepared in accordance with the same procedures as in Example 336, except for using 4-(3'- ethoxy-biphenyl-4-yl)-2-oxo-3-butenoic acid methyl ester prepared in Step 3 of Preparation 18; and using 2,4-difluorophenylhydrazine hydrochloride instead of 2-fluorophenylhydrazine hydrochloride.

$^1$H NMR (400 MHz, CDCl$_3$) 7.47 (d, 2H), 7.31 (t, 1H), 7.24-7.18 (m, 3H), 7.08 (d, 1H), 7.04 (s, 1H), 6.86 (d, 1H), 6.76-6.68 (m, 2H), 5.61 (dd, 1H), 4.85 (s, 1H), 4.07 (q, 2H), 3.63 (dd, 1H), 3.17 (dd, 1H), 1.42 (t, 3H)

Example 338

1-(2-chloro-phenyl)-5-(3-fluoro-3'-methylsulfanyl-biphenyl-4-yl)-3-[di-(trifluoromethyl)-hydroxy-methyl]-4,5-dihydro-1H-pyrazole 5-(4-Bromo-2-fluoro-phenyl)-1-(2-chloro-phenyl)-3-[di-(trifluoromethyl)-hydroxy-methyl]-4,5-dihydro-1H-pyrazole (50.0 mg, 0.10 mmol) prepared in Step 5 of Preparation 19, 3-methylthiophenylboronic acid (17.8 mg, 0.11 mmol), potassium carbonate (40.0 mg, 0.29 mmol), and Pd(dppf)Cl$_2$ (7.0 mg, cat.) were added to a mixed solvent of 1,4-dioxane (750.0 uL) and distilled water (150.0 uL). The reaction mixture was stirred for 15 minutes, additionally at 90° C. for 2 hours, and then ethyl acetate was added thereto. The reaction mixture was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/4) to give 20.0 mg of the titled compound as a yellow liquid.

$^1$H NMR (400 MHz, CDCl$_3$) 7.32 (d, 2H), 7.29-7.21 (m, 6H), 7.14-7.10 (m, 2H), 6.98 (t, 1H), 6.14 (dd, 1H), 4.94 (s, 1H), 3.65 (dd, 1H), 3.21 (dd, 1H), 2.50 (s, 3H)

Examples 339 to 344

The compounds of Examples 339 to 344 were prepared in accordance with the same procedures as in Example 338, except for using 5-(4-bromo-2-fluoro-phenyl)-1-(2-chloro-phenyl)-3-[di-(trifluoromethyl)-hydroxy-methyl]-4,5-dihydro-1H-pyrazole prepared in Step 5 of Preparation 19; and using each boronic acid corresponding to the compounds of Examples 339 to 344 instead of 3-methylthiophenylboronic acid.

Example 339

1-(2-chloro-phenyl)-5-(3'-ethoxy-3-fluoro-biphenyl-4-yl)-3-[di-(trifluoromethyl)-hydroxy-methyl]-4,5-dihydro-1H-pyrazole $^1$H NMR (400 MHz, CDCl$_3$) 7.32-7.10 (m, 7H), 7.04 (d, 1H), 6.99-6.95 (m, 2H), 6.87 (d, 1H), 6.13 (dd, 1H), 4.93 (s, 1H), 4.05 (q, 2H), 3.65 (dd, 1H), 3.22 (dd, 1H), 1.42 (t, 3H)

Example 340

1-(2-chloro-phenyl)-5-(3-fluoro-2'-methyl-biphenyl-4-yl)-3-[di-(trifluoromethyl)-hydroxy-methyl]-4,5-dihydro-1H-pyrazole $^1$H NMR (400 MHz, CDCl$_3$) 7.28-7.17 (m, 6H), 7.14-7.07 (m, 2H), 7.00-6.87 (m, 3H), 6.11 (dd, 1H), 4.93 (s, 1H), 3.65 (dd, 1H), 3.27 (dd, 1H), 2.12 (s, 3H)

Example 341

1-(2-chloro-phenyl)-5-(4'-acetyl-3-fluoro-biphenyl-4-yl)-3-[di-(trifluoromethyl)-hydroxy-methyl]-4,5-dihydro-1H-pyrazole $^1$H NMR (400 MHz, CDCl$_3$) 7.99 (d, 2H), 7.57 (d, 2H), 7.34-7.20 (m, 5H), 7.13 (t, 1H), 6.99 (t, 1H), 6.16 (dd, 1H), 4.93 (s, 1H), 3.67 (dd, 1H), 3.21 (dd, 1H), 2.62 (s, 3H)

Example 342

1-(2-chloro-phenyl)-5-[2-fluoro-4-(1-BOC-1,2,3,6-tetrahydropyridin-4-yl)-phenyl]-3-[di-(trifluoromethyl)-hydroxy-methyl]-4,5-dihydro-1H-pyrazole $^1$H NMR (400 MHz, CDCl$_3$) 7.22 (d, 2H), 7.17 (t, 1H), 7.11 (t, 1H), 7.01-6.92 (m, 3H), 6.09 (dd, 1H), 6.00 (br, 1H), 4.93 (s, 1H), 4.03 (s, 2H), 3.65-3.57 (m, 3H), 3.16 (dd, 1H), 2.39 (s, 2H), 1.47 (s, 9H)

Example 343

1-(2-chloro-phenyl)-5-[2-fluoro-4-(6-methoxy-pyridin-3-yl)-phenyl]-3-[di-(trifluoromethyl)-hydroxy-methyl]-4,5-dihydro-1H-pyrazole $^1$H NMR (400 MHz, CDCl$_3$) 8.29 (s, 1H), 7.67 (d, 1H), 7.31-7.26 (m, 3H), 7.17-7.09 (m, 3H), 6.98 (t, 1H), 6.77 (d, 1H), 6.14 (dd, 1H), 5.00 (br, 1H), 3.96 (s, 3H), 3.65 (dd, 1H), 3.20 (dd, 1H)

Example 344

1-(2-chloro-phenyl)-5-(3,4'-difluoro-biphenyl-4-yl)-3-[di-(trifluoromethyl)-hydroxy-methyl]-4,5-dihydro-1H-pyrazole $^1$H NMR (400 MHz, CDCl$_3$) 7.43 (t, 2H), 7.29-7.24 (m, 3H), 7.19-7.06 (m, 5H), 6.97 (t, 1H), 6.14 (dd, 1H), 4.93 (s, 1H), 3.65 (dd, 1H), 3.21 (dd, 1H)

Example 345

1-(2-chloro-phenyl)-5-(3-fluoro-3'-methanesulfinyl-biphenyl-4-yl)-3-[di-(trifluoromethyl)-hydroxy-methyl]-4,5-dihydro-1H-pyrazole To a mixture of 1-(2-chloro-phenyl)-5-(3-fluoro-3'-methylsulfanyl-biphenyl-4-yl)-3-[di-(trifluoromethyl)-hydroxy-methyl]-4,5-dihydro-1H-pyrazole (31.0 mg, 0.06 mmol) prepared in Example 338 in dichloromethane (2.0 mL), was slowly added meta-chloroperbenzoic acid (77%, 22.8 mg, 0.12 mmol) at 0° C. The reaction mixture was stirred at room temperature for 2 hours, quenched with a saturated solution of sodium hydrogen carbonate, and then extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=2/1, 1/1) to give 5.0 mg of the titled compound as a yellow liquid.

$^1$H NMR (400 MHz, CDCl$_3$) 7.79 (s, 1H), 7.60-7.56 (m, 3H), 7.33-7.19 (m, 5H), 7.13 (t, 1H), 6.97 (t, 1H), 5.16 (s, 1H), 3.67 (dd, 1H), 3.22 (dd, 1H), 2.74 (s, 3H)

Example 346

1-(2-chloro-phenyl)-5-[3-fluoro-4'-(1-hydroxy-1-methyl-ethyl)-biphenyl-4-yl]-3-[di-(trifluoromethyl)-hydroxy-methyl]-4,5-dihydro-1H-pyrazole To a mixture of 1-(2-chloro-phenyl)-5-(4'-acetyl-3-fluoro-biphenyl-4-yl)-3-[di-(trifluoromethyl)-hydroxy-methyl]-4,5-dihydro-1H-pyrazole (10.0 mg, 0.02 mmol) prepared in Example 341 in tetrahydrofuran (1.0 mL), was slowly added methylmagnesium chloride (in 3.0 M tetrahydrofuran, 30.0 uL, 0.09 mmol) under nitrogen atmosphere at −78° C. The reaction mixture was stirred at −78° C. for 5 hours, quenched with a saturated solution of ammonium chloride at 0° C., and then extracted with ethyl acetate. The extract was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/3) to give 5.0 mg of the titled compound as a yellow liquid.

$^1$H NMR (400 MHz, CDCl$_3$) 7.52 (d, 2H), 7.46 (d, 2H), 7.30-7.21 (m, 4H), 7.19-7.09 (m, 2H), 6.97 (t, 1H), 6.13 (dd, 1H), 4.93 (s, 1H), 3.65 (dd, 1H), 3.22 (dd, 1H), 1.72 (s, 1H), 1.60 (s, 3H), 1.55 (s, 3H)

Example 347

1-(2-chloro-phenyl)-5-(3-fluoro-3'-methanesulfonyl-biphenyl-4-yl)-3-[di-(trifluoromethyl)-hydroxy-methyl]-4,5-dihydro-1H-pyrazole To a mixture of 1-(2-chloro-phenyl)-5-(3-fluoro-3'-methylsulfanyl-biphenyl-4-yl)-3-[di-(trifluoromethyl)-hydroxy-methyl]-4,5-dihydro-1H-pyrazole (31.0 mg, 0.06 mmol) prepared in Example 338 in dichloromethane (2.0 mL), was slowly added meta-chloroperbenzoic acid (77%, 22.8 mg, 0.12 mmol) at 0° C. The reaction mixture was stirred at room temperature for 2 hours, quenched with a saturated solution of sodium hydrogen carbonate, and then extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/3, 1/1) to give 15.0 mg of the titled compound as a yellow liquid.

$^1$H NMR (400 MHz, CDCl$_3$) 8.04 (s, 1H), 7.93 (d, 1H), 7.76 (d, 1H), 7.62 (t, 1H), 7.34 (t, 1H), 7.28-7.24 (m, 3H), 7.21 (d, 1H), 7.14 (t, 1H), 6.99 (t, 1H), 6.17 (dd, 1H), 4.93 (s, 1H), 3.68 (dd, 1H), 3.24 (dd, 1H), 3.07 (s, 3H)

Example 348

5-[6-(2-acetyl-phenyl)-pyridin-3-yl]-1-(2-chloro-phenyl)-3-[di-(trifluoromethyl)-hydroxy-methyl]-4,5-dihydro-1H-pyrazole 5-(6-Bromo-pyridin-3-yl)-1-(2-chloro-phenyl)-3-[di-(trifluoromethyl)-hydroxy-methyl]-4,5-dihydro-1H-pyrazole (20.0 mg, 0.04 mmol) prepared in Step 4 of Preparation 20, 2-acetylphenylboronic acid (8.0 mg, 0.05 mmol), Pd(dppf)Cl$_2$ (3.0 mg, cat.), and a 2N sodium carbonate solution (0.4 mL) were added to N,N-dimethylformamide (0.4 mL). The reaction mixture was stirred at 100° C. for 16 hours and then ethyl acetate was added thereto. The reaction mixture was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 5.0 mg of the titled compound as a yellow liquid.

$^1$H NMR (400 MHz, CDCl$_3$) 8.42 (s, 1H), 7.58-7.44 (m, 6H), 7.25 (m, 1H), 7.16 (d, 1H), 7.09 (t, 1H), 6.97 (t, 1H), 5.96 (dd, 1H), 4.86 (s, 1H), 3.73 (dd, 1H), 3.30 (dd, 1H), 1.94 (s, 3H)

Examples 349 to 353

The compounds of Examples 349 to 353 were prepared in accordance with the same procedures as in Example 348, except for using 5-(6-bromo-pyridin-3-yl)-1-(2-chloro-phenyl)-3-[di-(trifluoromethyl)-hydroxy-methyl]-4,5-dihydro-1H-pyrazole prepared in Step 4 of Preparation 20; and using each boronic acid corresponding to the compounds of Examples 349 to 353 instead of 2-acetylphenylboronic acid.

Example 349

1-(2-chloro-phenyl)-5-[6-(3-methoxy-phenyl)-pyridin-3-yl]-3-[di-(trifluoromethyl)-hydroxy-methyl]-4,5-dihydro-1H-pyrazole $^1$H NMR (400 MHz, CDCl$_3$) 8.47 (s, 1H), 7.60 (d, 1H), 7.54-7.50 (m, 2H), 7.46 (d, 1H), 7.34 (t, 1H), 7.27 (d, 1H), 7.50 (d, 1H), 7.12 (t, 1H), 7.05-6.93 (m, 2H), 5.97 (dd, 1H), 4.89 (s, 1H), 3.86 (s, 3H), 3.70 (dd, 1H), 3.25 (dd, 1H)

Example 350

1-(2-chloro-phenyl)-5-[6-(4-methylsulfanyl-phenyl)-pyridin-3-yl]-3-[di-(trifluoromethyl)-hydroxy-methyl]-4,5-dihydro-1H-pyrazole $^1$H NMR (400 MHz, CDCl$_3$) 8.48 (s, 1H), 7.87 (d, 2H), 7.65-7.57 (m, 2H), 7.31-7.15 (m, 4H), 7.12 (t, 1H), 7.00 (t, 1H), 5.97 (dd, 1H), 4.89 (s, 1H), 3.71 (dd, 1H), 3.23 (dd, 1H), 2.51 (s, 3H)

Example 351

1-(2-chloro-phenyl)-5-[6-(4-methanesulfonyl-phenyl)-pyridin-3-yl]-3-[di-(trifluoromethyl)-hydroxy-methyl]-4,5-dihydro-1H-pyrazole $^1$H NMR (400 MHz, CDCl$_3$) 8.53 (s, 1H), 8.12 (d, 2H), 8.01 (d, 2H), 7.68 (d, 1H), 7.61 (d, 1H), 7.27 (d, 1H), 7.22 (d, 1H), 7.13 (t, 1H), 7.00 (t, 1H), 6.01 (dd, 1H), 4.86 (s, 1H), 3.74 (dd, 1H), 3.25 (dd, 1H), 3.07 (s, 3H)

Example 352

1-(2-chloro-phenyl)-5-[6-(6-methoxy-pyridin-3-yl)-pyridin-3-yl]-3-[di-(trifluoromethyl)-hydroxy-methyl]-4,5-dihydro-1H-pyrazole $^1$H NMR (400 MHz, CDCl$_3$) 8.69 (s, 1H), 8.48 (s, 1H), 8.16 (d, 1H), 7.53 (s, 2H), 7.27 (d, 1H), 7.20 (d, 1H), 7.11 (t, 1H), 6.99 (t, 1H), 6.80 (d, 1H), 5.96 (dd, 1H), 4.88 (s, 1H), 3.97 (s, 3H), 3.70 (dd, 1H), 3.23 (dd, 1H)

Example 353

1-(2-chloro-phenyl)-5-[6-(4-fluoro-phenyl)-pyridin-3-yl]-3-[di-(trifluoromethyl)-hydroxy-methyl]-4,5-dihydro-1H-pyrazole $^1$H NMR (400 MHz, CDCl$_3$) 8.46 (s, 1H), 7.90 (t, 2H), 7.57-7.51 (m, 2H), 7.27 (d, 1H), 7.21 (d, 1H), 7.11 (t, 3H), 6.99 (t, 1H), 5.97 (dd, 1H), 4.92 (s, 1H), 3.71 (dd, 1H), 3.24 (dd, 1H)

Example 354

1-(2-chloro-phenyl)-5-[6-(1-BOC-1,2,3,6-tetrahydro-pyridin-4-yl)-pyridin-3-yl]-3-[di-(trifluoromethyl)-hydroxy-methyl]-4,5-dihydro-1H-pyrazole 5-(6-Bromo-pyridin-3-yl)-1-(2-chloro-phenyl)-3-[di-(trifluoromethyl)-hydroxy-methyl]-4,5-dihydro-1H-pyrazole (400.0 mg, 0.80 mmol) prepared in Step 4 of Preparation 20, tert-butyl 4-(4,4,5,5-tetramethyl-1,3,2-dioxaborolan-2-yl)-5,6-dihydropyridin-1(2H)-carboxylic acid (295.3 mg, 0.96 mmol), Pd(PPh$_3$)$_4$ (92.5 mg, 0.08 mmol), and a 2N sodium carbonate solution (4.0 mL) were added to a mixed solvent of 1,2-dimethoxyethane (10.0 mL) and ethanol (4.0 mL). The reaction mixture was stirred at 90° C. for 3 hours and then ethyl acetate was added thereto. The reaction mixture was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/2) to give 400.0 mg of the titled compound as a yellow liquid.

$^1$H NMR (400 MHz, CDCl$_3$) 8.35 (s, 1H), 7.42 (d, 1H), 7.26-7.21 (m, 2H), 7.17 (d, 1H), 7.08 (t, 1H), 6.97 (t, 1H), 6.55 (s, 1H), 5.92 (dd, 1H), 5.06 (s, 1H), 4.08 (s, 2H), 3.64 (dd, 1H), 3.57 (t, 2H), 3.20 (dd, 1H), 2.53 (d, 2H), 1.48 (s, 9H)

Example 355

1-(2-chloro-phenyl)-5-[6-(4-BOC-piperazin-1-yl)-pyridin-3-yl]-3-[di-(trifluoromethyl)-hydroxy-methyl]-4,5-dihydro-1H-pyrazole 5-(6-Bromo-pyridin-3-yl)-1-(2-chloro-phenyl)-3-[di-(trifluoromethyl)-hydroxy-methyl]-4,5-dihydro-1H-pyrazole (400.0 mg, 0.80 mmol) prepared in Step 4 of Preparation 20, 1-BOC-piperazine (222.4 mg, 1.19 mmol), Pd$_2$(dba)$_3$ (36.7 mg, 0.04 mmol), BINAP (49.8 mg, 0.08 mmol) and sodium t-butoxide (137.8 mg, 1.43 mmol) were added to toluene (20.0 mL). The reaction mixture was stirred at 100° C. for 12 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/2) to give 65.0 mg of the titled compound as a yellow liquid.

$^1$H NMR (400 MHz, CDCl$_3$) 7.95 (s, 1H), 7.27-7.23 (m, 3H), 7.17 (d, 1H), 7.10 (t, 1H), 6.98 (t, 1H), 6.47 (d, 1H), 5.83 (dd, 1H), 4.91 (s, 1H), 3.60 (dd, 1H), 3.45 (d, 8H), 3.14 (dd, 1H), 1.48 (s, 9H)

Example 356

1-(2-chloro-phenyl)-5-[6-(1,2,3,6-tetrahydropyridin-4-yl)-pyridin-3-yl]-3-[di-(trifluoromethyl)-hydroxy-methyl]-4,5-dihydro-1H-pyrazole hydrochloride 1-(2-Chloro-phenyl)-5-[6-(1-BOC-1,2,3,6-tetrahydropyridin-4-yl)-pyridin-3-yl]-3-[di-(trifluoromethyl)-hydroxy-methyl]-4,5-dihydro-1H-pyrazole (400.0 mg, 0.66 mmol) prepared in Example 354 was added to a saturated solution of hydrochloric acid in ethyl acetate (2.0 mL). The reaction mixture was stirred at room temperature for 1 hour and then concentrated under reduced pressure to give 350.0 mg of the titled compound as a yellow liquid.

$^1$H NMR (400 MHz, CD$_3$OD) 8.61 (s, 1H), 8.29 (d, 1H), 8.05 (d, 1H), 7.42 (d, 1H), 7.30 (d, 1H), 7.22 (t, 1H), 7.05 (t, 1H), 6.81 (s, 1H), 6.05 (dd, 1H), 4.00 (s, 2H), 3.81 (dd, 1H), 3.48 (t, 2H), 3.25 (dd, 1H), 2.88 (d, 2H)

Example 357

1-(2-chloro-phenyl)-5-[6-(piperazin-1-yl)-pyridin-3-yl]-3-[di-(trifluoromethyl)-hydroxy-methyl]-4,5-dihydro-1H-pyrazole hydrochloride 1-(2-Chloro-phenyl)-5-[6-(4-BOC-piperazin-1-yl)-pyridin-3-yl]-3-[di-(trifluoromethyl)-hydroxy-methyl]-4,5-dihydro-1H-pyrazole (65.0 mg, 0.11 mmol) prepared in Example 355 was added to a saturated solution of hydrochloric acid in ethyl acetate (2.0 mL). The reaction mixture was stirred at room temperature for 1 hour and then concentrated under reduced pressure to give 60.0 mg of the titled compound as a yellow liquid.

$^1$H NMR (400 MHz, CDCl$_3$) 7.95 (s, 1H), 7.27-7.23 (m, 3H), 7.17 (d, 1H), 7.10 (t, 1H), 6.98 (t, 1H), 6.47 (d, 1H), 5.83 (dd, 1H), 4.91 (s, 1H), 3.56 (dd, 1H), 3.48 (br, 4H), 3.16 (dd, 1H), 3.01 (br, 4H)

Example 358

1-(2-chloro-phenyl)-5-[6-(1-methanesulfonyl-1,2,3,6-tetrahydropyridin-4-yl)-pyridin-3-yl]-3-[di-(trifluoromethyl)-hydroxy-methyl]-4,5-dihydro-1H-pyrazole 1-(2-Chloro-phenyl)-5-[6-(1,2,3,6-tetrahydropyridin-4-yl)-pyridin-3-yl]-3-[di-(trifluoromethyl)-hydroxy-methyl]-4,5-dihydro-1H-pyrazole hydrochloride (30.0 mg, 0.06 mmol) prepared in Example 356, methanesulfonyl chloride (6.0 uL, 0.08 mmol), and triethylamine (38.0 uL, 0.28 mmol) were added to dichloromethane (1.0 mL). The reaction mixture was stirred at room temperature for 16 hours, washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 5.0 mg of the titled compound as a yellow liquid.

$^1$H NMR (400 MHz, CDCl$_3$) 8.37 (s, 1H), 7.51-7.31 (m, 2H), 7.27-7.17 (m, 2H), 7.11 (t, 1H), 6.99 (t, 1H), 6.60 (d,

1H), 5.93 (dd, 1H), 4.85 (s, 1H), 3.98 (brs, 2H), 3.68 (dd, 1H), 3.49 (brs, 2H), 3.19 (dd, 1H), 2.83 (s, 3H), 2.69 (brs, 2H)

Example 359

1-(2-chloro-phenyl)-5-[6-(1-cyclopropanesulfonyl-1,2,3,6-tetrahydropyridin-4-yl)-pyridin-3-yl]-3-[di-(trifluoromethyl)-hydroxy-methyl]-4,5-dihydro-1H-pyrazole 1-(2-chloro-phenyl)-5-[6-(1,2,3,6-tetrahydropyridin-4-yl)-pyridin-3-yl]-3-[di-(trifluoromethyl)-hydroxy-methyl]-4,5-dihydro-1H-pyrazole hydrochloride (30.0 mg, 0.06 mmol) prepared in Example 356, cyclopropanesulfonyl chloride (8.0 uL, 0.08 mmol), and triethylamine (38.0 uL, 0.28 mmol) were added to dichloromethane (1.0 mL). The reaction mixture was stirred at room temperature for 16 hours, washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 10.0 mg of the titled compound as a yellow liquid.

$^1$H NMR (400 MHz, CDCl$_3$) 8.36 (s, 1H), 7.45 (d, 1H), 7.26 (m, 2H), 7.18 (d, 1H), 7.11 (t, 1H), 6.99 (t, 1H), 6.59 (s, 1H), 5.93 (dd, 1H), 4.90 (s, 1H), 4.04 (brs, 2H), 3.68 (dd, 1H), 3.52 (brs, 2H), 3.19 (dd, 1H), 2.68 (brs, 2H), 2.29 (m, 1H), 1.22-1.18 (m, 2H), 1.02-0.96 (m, 2H)

Example 360

1-(2-chloro-phenyl)-5-[6-(4-methanesulfonyl-piperazin-1-yl)-pyridin-3-yl]-3-[di-(trifluoromethyl)-hydroxy-methyl]-4,5-dihydro-1H-pyrazole 1-(2-Chloro-phenyl)-5-[6-(piperazin-1-yl)-pyridin-3-yl]-3-[di-(trifluoromethyl)-hydroxy-methyl]-4,5-dihydro-1H-pyrazole hydrochloride (30.0 mg, 0.06 mmol) prepared in Example 357, methanesulfonyl chloride (7.0 uL, 0.09 mmol), and triethylamine (41.0 uL, 0.30 mmol) were added to dichloromethane (1.0 mL). The reaction mixture was stirred at room temperature for 16 hours, washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/1) to give 5.0 mg of the titled compound as a yellow liquid.

$^1$H NMR (400 MHz, CDCl$_3$) 7.96 (s, 1H), 7.32-7.21 (m, 3H), 7.10 (t, 1H), 6.94 (t, 1H), 6.48 (d, 1H), 5.83 (dd, 1H), 3.65-3.53 (m, 5H), 3.31-3.18 (m, 5H), 2.78 (s, 3H)

Example 361

5-(3'-acetyl-2-fluoro-biphenyl-4-yl)-1-(2-chloro-phenyl)-3-[di-(trifluoromethyl)-hydroxy-methyl]-4,5-dihydro-1H-pyrazole 5-(4-bromo-3-fluoro-phenyl)-1-(2-chloro-phenyl)-3-[di-(trifluoromethyl)-hydroxy-methyl]-4,5-dihydro-1H-pyrazole (30.0 mg, 0.056 mmol) prepared in Step 5 of Preparation 21, 3-acetylphenylboronic acid (10.4 mg, 0.064 mmol), Pd(PPh$_3$)$_4$ (6.7 mg, 0.006 mmol), and a 2N sodium carbonate solution (145.0 uL) were added to a mixed solvent of 1,2-dimethoxyethane (2.0 mL) and ethanol (0.5 mL). The reaction mixture was stirred at 90° C. for 3 hours and then ethyl acetate was added thereto. The reaction mixture was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/5) to give 5.0 mg of the titled compound as a yellow liquid.

$^1$H NMR (400 MHz, CDCl$_3$) 8.04 (s, 1H), 7.94 (d, 1H), 7.67 (d, 1H), 7.52 (t, 1H), 7.37-7.26 (m, 3H), 7.16 (t, 1H), 7.04-6.98 (m, 3H), 5.94 (dd, 1H), 4.97 (s, 1H), 3.67 (dd, 1H), 3.23 (dd, 1H), 2.64 (s, 3H)

Examples 362 to 368

The compounds of Examples 362 to 368 were prepared in accordance with the same procedures as in Example 361, except for using 5-(4-bromo-3-fluoro-phenyl)-1-(2-chloro-phenyl)-3-[di-(trifluoromethyl)-hydroxy-methyl]-4,5-dihydro-1H-pyrazole prepared in Step 5 of Preparation 21; and using each boronic acid corresponding to the compounds of Examples 362 to 368 instead of 3-acetylphenylboronic acid.

Example 362

5-(4'-acetyl-2-fluoro-biphenyl-4-yl)-1-(2-chloro-phenyl)-3-[di-(trifluoromethyl)-hydroxy-methyl]-4,5-dihydro-1H-pyrazole $^1$H NMR (400 MHz, CDCl$_3$) 8.00 (d, 2H), 7.56 (d, 2H), 7.36-7.24 (m, 3H), 7.16 (t, 1H), 7.04-6.98 (m, 3H), 5.94 (dd, 1H), 4.95 (s, 1H), 3.70 (dd, 1H), 3.23 (dd, 1H), 2.64 (s, 3H)

Example 363

1-(2-chloro-phenyl)-5-(2-fluoro-4'-methoxy-biphenyl-4-yl)-3-[di-(trifluoromethyl)-hydroxy-methyl]-4,5-dihydro-1H-pyrazole $^1$H NMR (400 MHz, CDCl$_3$) 7.40 (d, 2H), 7.31-7.25 (m, 3H), 7.21 (d, 1H), 7.14 (t, 1H), 7.03-6.92 (m, 5H), 5.91 (dd, 1H), 4.96 (s, 1H), 3.84 (s, 3H), 3.66 (dd, 1H), 3.23 (dd, 1H)

Example 364

1-(2-chloro-phenyl)-5-(2-fluoro-4'-methylsulfanyl-biphenyl-4-yl)-3-[di-(trifluoromethyl)-hydroxy-methyl]-4,5-dihydro-1H-pyrazole $^1$H NMR (400 MHz, CDCl$_3$) 7.31 (d, 2H), 7.29-7.26 (m, 4H), 7.20 (d, 1H), 7.14 (t, 1H), 7.03-6.94 (m, 3H), 5.89 (dd, 1H), 4.90 (s, 1H), 3.66 (dd, 1H), 3.22 (dd, 1H), 2.50 (s, 3H)

Example 365

1-(2-chloro-phenyl)-5-(2-fluoro-4'-methylsulfonyl-biphenyl-4-yl)-3-[di-(trifluoromethyl)-hydroxy-methyl]-4,5-dihydro-1H-pyrazole $^1$H NMR (400 MHz, CDCl$_3$) 7.98 (d, 2H), 7.65 (d, 2H), 7.34-7.22 (m, 3H), 7.15 (t, 1H), 7.07-7.00 (m, 3H), 5.93 (dd, 1H), 4.90 (s, 1H), 3.69 (dd, 1H), 3.22 (dd, 1H), 3.08 (s, 3H)

Example 366

1-(2-chloro-phenyl)-5-(2,4'-difluoro-biphenyl-4-yl)-3-[di-(trifluoromethyl)-hydroxy-methyl]-4,5-dihydro-1H-pyrazole $^1$H NMR (400 MHz, CDCl$_3$) 7.42 (m, 2H), 0.7.30-7.21 (m, 3H), 7.16-7.10 (m, 3H), 7.07-6.95 (m, 3H), 5.92 (dd, 1H), 4.95 (s, 1H), 3.68 (dd, 1H), 3.23 (dd, 1H)

Example 367

1-(2-chloro-phenyl)-5-(2-fluoro-2'-isopropoxy-biphenyl-4-yl)-3-[di-(trifluoromethyl)-hydroxy-methyl]-4,5-dihydro-1H-pyrazole $^1$H NMR (400 MHz, CDCl$_3$) 7.31 (d, 2H), 7.27-7.10 (m, 4H), 7.01-6.88 (m, 5H), 5.90 (dd, 1H), 4.98 (s, 1H), 4.35 (m, 1H), 3.68 (dd, 1H), 3.29 (dd, 1H), 1.12 (d, 6H)

Example 368

1-(2-chloro-phenyl)-5-[3-fluoro-4-(6-methoxy-pyridin-3-yl)-phenyl]-3-[di-(trifluoromethyl)-hydroxy-methyl]-4,5-dihydro-1H-pyrazole $^1$H NMR (400 MHz, CDCl$_3$) 8.25 (s, 1H), 7.68 (d, 1H), 7.31-7.25 (m, 3H), 7.21 (d, 1H), 7.14 (t, 1H), 7.02-6.99 (m, 3H), 6.78 (d, 1H), 5.89 (dd, 1H), 4.90 (s, 1H), 3.96 (s, 3H), 3.67 (dd, 1H), 3.22 (dd, 1H)

Example 369

1-(2,4-difluoro-phenyl)-5-(3'-methylsulfanyl-biphenyl-4-yl)-3-[di-(trifluoromethyl)-hydroxy-methyl]-4,5-dihydro-1H-pyrazole 5-(4-Bromo-phenyl)-1-(2,4-difluoro-phenyl)-3-[di-(trifluoromethyl)-hydroxy-methyl]-4,5-dihydro-1H-pyrazole (50.0 mg, 0.10 mmol) prepared in Step 2 of Preparation 22, 3-(methylthio)-phenylboronic acid (25.0 mg, 0.15 mmol), Pd(PPh$_3$)$_4$ (11.5 mg, cat.), ethanol 0.5 mL and a 2N sodium carbonate solution (0.5 mL) were added to 1,2-dimethoxyethane (2.0 mL). The reaction mixture was stirred at 88° C. for 2 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/10) to give 6.1 mg of the titled compound as a yellow liquid.

$^1$H NMR (400 MHz, CDCl$_3$) 7.46 (d, 2H), 7.40 (s, 1H), 7.34-7.20 (m, 6H), 6.76-6.69 (m, 2H), 5.62 (dd, 1H), 4.87 (s, 1H), 3.63 (dd, 1H), 3.17 (dd, 1H), 2.51 (s, 3H)

Examples 370 to 375

The compounds of Examples 370 to 375 were prepared in accordance with the same procedures as in Example 369, except for using 5-(4-bromo-phenyl)-1-(2,4-difluoro-phenyl)-3-[di-(trifluoromethyl)-hydroxy-methyl]-4,5-dihydro-1H-pyrazole prepared in Step 2 of Preparation 22; and using each boronic acid corresponding to the compounds of Examples 370 to 375 instead of 3-(methylthio)-phenylboronic acid.

Example 370

1-(2,4-difluoro-phenyl)-5-(4-(6-methoxy-pyridin-3-yl)-phenyl)-3-[di-(trifluoromethyl)-hydroxy-methyl]-4,5-dihydro-1H-pyrazole $^1$H NMR (400 MHz, CDCl$_3$) 8.32 (s, 1H), 7.72 (d, 1H), 7.41 (d, 2H), 7.24-7.20 (m, 4H), 6.80-6.69 (m, 3H), 5.60 (dd, 1H), 4.88 (s, 1H), 3.97 (s, 3H), 3.64 (dd, 1H), 3.16 (dd, 1H)

Example 371

1-(2,4-difluoro-phenyl)-5-(2'-methyl-biphenyl-4-yl)-3-[di-(trifluoromethyl)-hydroxy-methyl]-4,5-dihydro-1H-pyrazole $^1$H NMR (400 MHz, CDCl$_3$) 7.27-7.12 (m, 9H), 6.75-6.70 (m, 2H), 5.60 (dd, 1H), 4.89 (s, 1H), 3.63 (dd, 1H), 3.21 (dd, 1H), 2.17 (s, 3H)

Example 372

1-(2,4-difluoro-phenyl)-5-(4-pyrimidin-5-yl-phenyl)-3-[di-(trifluoromethyl)-hydroxy-methyl]-4,5-dihydro-1H-pyrazole $^1$H NMR (400 MHz, CDCl$_3$) 9.19 (s, 1H), 8.89 (s, 2H), 7.49 (d, 2H), 7.31-7.24 (m, 4H), 6.78-6.69 (m, 2H), 5.66 (dd, 1H), 5.02 (s, 1H), 3.67 (dd, 1H), 3.16 (dd, 1H)

Example 373

1-(2,4-difluoro-phenyl)-5-(4'-tetrazol-1-yl-biphenyl-4-yl)-3-[di-(trifluoromethyl)-hydroxy-methyl]-4,5-dihydro-1H-pyrazole $^1$H NMR (400 MHz, CDCl$_3$) 9.01 (s, 1H), 7.79-7.72 (m, 4H), 7.52 (d, 2H), 7.29-7.20 (m, 3H), 6.78-6.70 (m, 2H), 5.65 (dd, 1H), 4.89 (s, 1H), 3.66 (dd, 1H), 3.17 (dd, 1H)

Example 374

1-(2,4-difluoro-phenyl)-5-[4-(1-methyl-1H-indol-2-yl)-phenyl]-3-[di-(trifluoromethyl)-hydroxy-methyl]-4,5-dihydro-1H-pyrazole $^1$H NMR (400 MHz, CDCl$_3$) 7.60 (d, 1H), 7.41 (d, 2H), 7.34 (d, 1H), 7.26-7.23 (m, 4H), 7.13 (dd, 1H), 6.79-6.71 (m, 2H), 6.52 (s, 1H), 5.63 (dd, 1H), 4.85 (s, 1H), 3.69 (s, 3H), 3.65 (dd, 1H), 3.19 (dd, 1H)

Example 375

5-[4-(1-benzenesulfonyl-1H-indol-2-yl)-phenyl]-1-(2,4-difluoro-phenyl)-3-[di-(trifluoromethyl)-hydroxy-methyl]-4,5-dihydro-1H-pyrazole $^1$H NMR (400 MHz, CDCl$_3$) 8.29 (d, 1H), 7.43-7.33 (m, 4H), 7.28-7.16 (m, 9H), 6.80-6.76 (m, 2H), 6.49 (s, 1H), 5.64 (dd, 1H), 4.85 (s, 1H), 3.67 (dd, 1H), 3.25 (dd, 1H)

Example 376

1-(2,4-difluoro-phenyl)-5-(4-(2-methyl-pyridin-3-yl)-phenyl)-3-[di-(trifluoromethyl)-hydroxy-methyl]-4,5-dihydro-1H-pyrazole Step 1: 1-(2,4-difluoro-phenyl)-5-[4-(4,4,5,5-tetramethyl-1,3,2-dioxaborolan-2-yl)-phenyl]-3-[di-(trifluoromethyl)-hydroxy-methyl]-4,5-dihydro-1H-pyrazole 5-(4-Bromo-phenyl)-1-(2,4-difluoro-phenyl)-3-[di-(trifluoromethyl)-hydroxy-methyl]-4,5-dihydro-1H-pyrazole (2.9 g, 5.66 mmol) prepared in Step 2 of Preparation 22, bis(pinacolato)diboron (3.45 g, 13.59 mmol), Pd(dppf)Cl$_2$ (0.28 g, 0.34 mmol), dppf (0.19 g, 0.34 mmol) and potassium acetate (3.34 g, 33.98 mmol) were added to 1,4-dioxane (30 mL). The reaction mixture was stirred at 80° C. for 2 hours and then filtered through celite pad. Distilled water was added to the filtrate, which was then extracted with diethyl ether three times. The combined extract was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/100) to give 2.5 g of the titled compound as a white liquid.

$^1$H NMR (400 MHz, CDCl$_3$) 7.42 (d, 2H), 7.22 (q, 1H), 7.01 (d, 2H), 6.77-6.68 (m, 2H), 5.52 (dd, 1H), 4.81 (s, 1H), 3.61 (dd, 1H), 3.10 (dd, 1H), 1.33 (s, 12H)

Step 2: 1-(2,4-difluoro-phenyl)-5-(4-(2-methyl-pyridin-3-yl)-phenyl)-3-[di-(trifluoromethyl)-hydroxy-methyl]-4,5-dihydro-1H-pyrazole To 3-bromo-2-methylpyridine (25.0 mg, 0.14 mmol), were added 1,2-dimethoxyethane (1.5 mL) and Pd(PPh$_3$)$_4$ (8.5 mg, cat.). To the reaction mixture, were added 1-(2,4-difluoro-phenyl)-5-[4-(4,4,5,5-tetramethyl-1,3,2-dioxaborolan-2-yl)-phenyl]-3-[di-(trifluoromethyl)-hydroxy-methyl]-4,5-dihydro-1H-pyrazole (40.0 mg, 0.07 mmol) prepared in Step 1, ethanol 364.0 uL, and a 2N sodium carbonate solution (364.0 uL). The reaction mixture was stirred at 88° C. for 2 hours. Distilled water was added to the reaction mixture, which was then extracted with diethyl ether two times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/5) to give 3.3 mg of the titled compound as a yellow liquid.

$^1$H NMR (400 MHz, CDCl$_3$) 8.48 (d, 1H), 7.44 (d, 1H), 7.24-7.14 (m, 6H), 6.77-6.70 (m, 2H), 5.61 (t, 1H), 5.08 (br, 1H), 3.65 (dd, 1H), 3.20 (dd, 1H), 2.41 (s, 3H)

Examples 377 to 397

The compounds of Examples 377 to 397 were prepared in accordance with the same procedures as in Step 2 of Example 376, except for using 1-(2,4-difluoro-phenyl)-5-[4-(4,4,5,5-tetramethyl-1,3,2-dioxaborolan-2-yl)-phenyl]-3-[di-(trifluoromethyl)-hydroxy-methyl]-4,5-dihydro-1H-pyrazole prepared in Step 1 of Example 376; and using each substituted aryl bromide corresponding to the compounds of Examples 377 to 397 instead of 3-bromo-2-methylpyridine.

Example 377

1-(2,4-difluoro-phenyl)-5-[4-(6-trifluoromethyl-pyridin-3-yl)-phenyl]-3-[di-(trifluoromethyl)-hydroxy-methyl]-4,5-dihydro-1H-pyrazole $^1$H NMR (400 MHz, CDCl$_3$) 8.88 (s, 1H), 7.97 (d, 1H), 7.73 (d, 1H), 7.51 (d, 2H), 7.29 (d, 2H), 7.25 (m, 1H), 6.78-6.70 (m, 2H), 5.65 (dd, 1H), 4.84 (s, 1H), 3.66 (dd, 1H), 3.16 (dd, 1H)

Example 378

1-(2,4-difluoro-phenyl)-5-[4-(5-methoxycarbonyl-pyridin-3-yl)-phenyl]-3-[di-(trifluoromethyl)-hydroxy-methyl]-4,5-dihydro-1H-pyrazole $^1$H NMR (400 MHz, CDCl$_3$) 9.17 (s, 1H), 8.92 (s, 1H), 8.41 (s, 1H), 7.53 (d, 2H), 7.29-7.26 (m, 6.75-6.70 (m, 2H), 5.64 (dd, 1H), 4.89 (s, 1H), 3.66 (dd, 1H), 3.17 (dd, 1H), 1.42 (t, 3H)

Example 379

1-(2,4-difluoro-phenyl)-5-[4-(5-formyl-6-methoxy-pyridin-3-yl)-phenyl)-3-[di-(trifluoromethyl)-hydroxy-methyl]-4,5-dihydro-1H-pyrazole $^1$H NMR (400 MHz, CDCl$_3$) 8.54 (s, 1H), 8.24 (s, 1H), 7.45 (d, 2H), 7.26-7.23 (m, 3H), 6.77-6.69 (m, 2H), 5.62 (dd, 1H), 4.87 (s, 1H), 4.13 (s, 3H), 3.64 (dd, 1H), 3.16 (dd, 1H)

Example 380

5-[4-(2-cyano-pyridin-3-yl)-phenyl]-1-(2,4-difluoro-phenyl)-3-[di-(trifluoromethyl)-hydroxy-methyl]-4,5-dihydro-1H-pyrazole $^1$H NMR (400 MHz, CDCl$_3$) 8.69 (d, 1H), 7.80 (d, 1H), 7.56 (t, 1H), 7.49 (d, 2H), 7.32 (d, 2H), 7.23 (m, 1H), 6.78-6.72 (m, 2H), 5.63 (dd, 1H), 4.86 (s, 1H), 3.65 (dd, 1H), 3.18 (dd, 1H)

Example 381

1-(2,4-difluoro-phenyl)-5-[4-(5-fluoro-pyridin-3-yl)-phenyl)-3-[di-(trifluoromethyl)-hydroxy-methyl]-4,5-dihydro-1H-pyrazole $^1$H NMR (400 MHz, CDCl$_3$) 8.60 (s, 1H), 8.44 (s, 1H), 7.52 (d, 1H), 7.47 (d, 2H), 7.27-7.23 (m, 3H), 6.77-6.69 (m, 2H), 5.64 (dd, 1H), 4.98 (s, 1H), 3.66 (dd, 1H), 3.16 (dd, 1H)

Example 382

1-(2,4-difluoro-phenyl)-5-[4-(6-methanesulfanyl-pyridin-3-yl)-phenyl]-3-[di-(trifluoromethyl)-hydroxy-methyl]-4,5-dihydro-1H-pyrazole $^1$H NMR (400 MHz, CDCl$_3$) 8.60 (s, 1H), 7.63 (d, 1H), 7.44 (d, 2H), 7.28-7.22 (m, 4H), 6.77-6.70 (m, 2H), 5.61 (dd, 1H), 4.86 (s, 1H), 3.64 (dd, 1H), 3.16 (dd, 1H), 2.59 (s, 3H)

Example 383

1-(2,4-difluoro-phenyl)-5-[4-(6-methoxy-4-methyl-pyridin-3-yl)-phenyl]-3-[di-(trifluoromethyl)-hydroxy-methyl]-4,5-dihydro-1H-pyrazole $^1$H NMR (400 MHz, CDCl$_3$) 7.91 (s, 1H), 7.22-7.17 (m, 5H), 6.75-6.71 (m, 2H), 6.62 (s, 1H), 5.61 (dd, 1H), 4.87 (s, 1H), 3.94 (s, 3H), 3.65 (dd, 1H), 3.20 (dd, 1H), 2.14 (s, 3H)

Example 384

1-(2,4-difluoro-phenyl)-5-[4-(6-fluoro-4-methyl-pyridin-3-yl)-phenyl]-3-[di-(trifluoromethyl)-hydroxy-methyl]-4,5-dihydro-1H-pyrazole $^1$H NMR (400 MHz, CDCl$_3$) 7.96 (s, 1H), 7.26-7.16 (m, 5H), 6.81 (s, 1H), 6.77-6.69 (m, 2H), 5.63 (dd, 1H), 4.88 (s, 1H), 3.65 (dd, 1H), 3.19 (dd, 1H), 2.22 (s, 3H)

Example 385

1-(2,4-difluoro-phenyl)-5-[4-pyridin-2-yl-phenyl]-3-[di-(trifluoromethyl)-hydroxy-methyl]-4,5-dihydro-1H-pyrazole $^1$H NMR (400 MHz, CDCl$_3$) 8.66 (s, 1H), 7.88 (d, 2H), 7.73 (t, 1H), 7.65 (d, 1H), 7.26-7.23 (m, 4H), 6.76-6.67 (m, 2H), 5.63 (dd, 1H), 4.93 (s, 1H), 3.64 (dd, 1H), 3.17 (dd, 1H)

Example 386

1-(2,4-difluoro-phenyl)-5-{4'-[(2-hydroxy-ethyl)-methyl-sulfamoyl]-biphenyl-4-yl}-3-[di-(trifluoromethyl)-hydroxy-methyl]-4,5-dihydro-1H-pyrazole $^1$H NMR (400 MHz, CDCl$_3$) 7.84 (d, 2H), 7.67 (d, 2H), 7.50 (d, 2H), 7.29-7.25 (m, 3H), 6.77-6.69 (m, 2H), 5.65 (dd, 1H), 4.89 (s, 1H), 3.78 (d, 2H), 3.66 (dd, 1H), 3.20 (d, 2H), 3.17 (dd, 1H), 2.86 (s, 3H)

Example 387

1-(2,4-difluoro-phenyl)-5-(3'-fluoro-4'-methanesulfonyl-biphenyl-4-yl)-3-[di-(trifluoromethyl)-hydroxy-methyl]-4,5-dihydro-1H-pyrazole $^1$H NMR (400 MHz, CDCl$_3$) 7.98 (t, 1H), 7.50-7.47 (m, 3H), 7.39 (d, 1H), 7.29-7.26 (m, 3H), 6.77-6.69 (m, 2H), 5.64 (dd, 1H), 4.83 (s, 1H), 3.66 (dd, 1H), 3.24 (s, 3H), 3.17 (dd, 1H)

Example 388

1-(2,4-difluoro-phenyl)-5-(3',5'-difluoro-4'-methanesulfonyl-biphenyl-4-yl)-3-[di-(trifluoromethyl)-hydroxy-methyl]-4,5-dihydro-1H-pyrazole $^1$H NMR (400 MHz, CDCl$_3$) 7.47 (d, 2H), 7.29-7.26 (m, 3H), 7.21 (d, 2H), 6.78-6.69 (m, 2H), 5.65 (dd, 1H), 4.82 (s, 1H), 3.66 (dd, 1H), 3.31 (s, 3H), 3.13 (dd, 1H)

Example 389

1-(2,4-difluoro-phenyl)-5-(2',6'-difluoro-4'-methanesulfonyl-biphenyl-4-yl)-3-[di-(trifluoromethyl)-hydroxy-methyl]-4,5-dihydro-1H-pyrazole $^1$H NMR (400 MHz, CDCl$_3$) 7.57 (d, 2H), 7.39 (d, 2H), 7.30-7.23 (m, 3H), 6.79-6.72 (m, 2H), 5.62 (dd, 1H), 3.65 (dd, 1H), 3.17 (dd, 1H), 3.11 (s, 3H)

Example 390

1-(2,4-difluoro-phenyl)-5-(3'-cyano-4'-methanesulfonyl-biphenyl-4-yl)-3-[di-(trifluoromethyl)-hydroxy-methyl]-4,5-dihydro-1H-pyrazole $^1$H NMR (400 MHz, CDCl$_3$) 8.22 (d, 1H), 8.03 (s, 1H), 7.92 (d, 1H), 7.51 (d, 2H), 7.31-7.26 (m, 3H), 6.79-6.69 (m, 2H), 5.67 (dd, 1H), 4.85 (s, 1H), 3.66 (dd, 1H), 3.31 (s, 3H), 3.15 (dd, 1H)

Example 391

1-(2,4-difluoro-phenyl)-5-[4-(5-methanesulfonyl-pyridin-2-yl)-phenyl]-3-[di-(trifluoromethyl)-hydroxy-methyl]-4,5-dihydro-1H-pyrazole $^1$H NMR (400 MHz, CDCl$_3$) 9.16 (s, 1H), 8.24 (d, 1H), 7.97 (d, 2H), 7.85 (d, 1H), 7.31-7.23 (m, 3H), 6.76-6.67 (m, 2H), 5.66 (dd, 1H), 4.87 (s, 1H), 3.66 (dd, 1H), 3.16 (dd, 1H), 3.12 (s, 3H)

Example 392

1-(2,4-difluoro-phenyl)-5-(4'-methanesulfonyl-3'-trifluoromethyl-biphenyl-4-yl)-3-[di-(trifluoromethyl)-hydroxy-methyl]-4,5-dihydro-1H-pyrazole $^1$H NMR (400 MHz, CDCl$_3$) 8.34 (d, 1H), 8.02 (s, 1H), 7.88 (d, 1H), 7.53 (d, 2H), 7.31-7.26 (m, 3H), 6.79-6.69 (m, 2H), 5.66 (dd, 1H), 4.84 (s, 1H), 3.67 (dd, 1H), 3.20 (s, 3H), 3.15 (dd, 1H)

Example 393

1-(2,4-difluoro-phenyl)-5-{[2',6'-difluoro-4'-(tetrazol-1-yl)-biphenyl]-4-yl}-3-[di-(trifluoromethyl)-hydroxy-methyl]-4,5-dihydro-1H-pyrazole $^1$H NMR (400 MHz, CDCl$_3$) 7.34 (d, 2H), 7.26-7.22 (m, 6H), 6.76-6.66 (m, 4H), 5.60 (dd, 1H), 4.83 (s, 1H), 3.63 (dd, 1H), 3.16 (dd, 1H)

Example 394

1-(2,4-difluoro-phenyl)-5-{4-[4-methyl-6-(tetrazol-1-yl)-pyridin-3-yl]-phenyl}-3-[di-(trifluoromethyl)-hydroxy-methyl]-4,5-dihydro-1H-pyrazole $^1$H NMR (400 MHz, CDCl$_3$) 9.53 (s, 1H), 8.28 (s, 1H), 7.99 (s, 1H), 7.30-7.26 (m, 5H), 6.80-6.72 (m, 2H), 5.65 (dd, 1H), 4.86 (s, 1H), 3.67 (dd, 1H), 3.20 (dd, 1H), 2.36 (s, 3H)

Example 395

5-{3'-[3-(N-BOC-N-methyl-amino)-propane-1-sulfonyl]-biphenyl-4-yl}-1-(2,4-difluoro-phenyl)-3-(di-(trifluoromethyl)-hydroxy-methyl)-4,5-dihydro-1H-pyrazole $^1$H NMR (400 MHz, CDCl$_3$) 8.04 (s, 1H), 7.86 (d, 1H), 7.80 (d, 1H), 7.67-7.57 (m, 1H), 7.51 (d, 2H), 7.26-7.24 (m, 3H), 6.77-6.68 (m, 2H), 5.64 (dd, 1H), 4.97 (brs, 1H), 3.66 (dd, 1H), 3.32-3.27 (m, 2H), 3.19-3.10 (m, 3H), 2.80 (s, 3H), 2.01-1.93 (m, 2H), 1.39 (s, 9H)

Example 396

1-(2,4-difluoro-phenyl)-5-(4'-dimethylsulfamoyl-biphenyl-4-yl)-3-(di-(trifluoromethyl)-hydroxy-methyl)-4,5-dihydro-1H-pyrazole $^1$H NMR (400 MHz, CDCl$_3$) 7.81 (d, 2H), 7.67 (d, 2H), 7.51 (d, 2H), 7.30-7.24 (m, 3H), 6.77-6.68 (m, 2H), 5.65 (dd, 1H), 4.90 (brs, 1H), 3.66 (dd, 1H), 3.16 (dd, 1H), 2.73 (s, 6H)

Example 397

1-(2,4-difluoro-phenyl)-5-{4'-[(2-hydroxy-ethyl)-methanesulfonyl-amino]biphenyl-4-yl}-3-(di-(trifluoromethyl)-hydroxy-methyl)-4,5-dihydro-1H-pyrazole $^1$H NMR (400 MHz, CDCl$_3$) 7.56 (d, 2H), 7.48-7.41 (m, 5H), 7.22 (d, 2H), 6.77-6.69 (m, 2H), 5.63 (dd, 1H), 4.88 (brs, 1H), 3.87 (t, 2H), 3.74-3.60 (m, 3H), 3.17 (dd, 1H), 2.99 (s, 3H), 1.93 (brs, 1H)

Example 398

1-(2,4-difluoro-phenyl)-5-[4-(1-BOC-1,2,3,6-tetrahydropyridin-4-yl)-phenyl]-3-[di-(trifluoromethyl)-hydroxy-methyl]-4,5-dihydro-1H-pyrazole 5-(4-Bromo-phenyl)-1-(2,4-difluoro-phenyl)-3-[di-(trifluoromethyl)-hydroxy-methyl]-4,5-dihydro-1H-pyrazole (2000.0 mg, 3.98 mmol) prepared in Step 2 of Preparation 22, tert-butyl 4-(4,4,5,5-tetramethyl-1,3,2-dioxaborolan-2-yl)-5,6-dihydropyridin-1(2H)-carboxylic acid (1475.0 mg, 4.77 mmol), Pd(dppf)Cl$_2$ (291.3 mg, cat.) and potassium carbonate (2746.0 mg, 19.88 mmol) were added to a mixed solvent of 1,4-dioxane (57.6 mL) and water (14.4 mL). The reaction mixture was stirred at 90° C. for 12 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/8) to give 1.6 g of the titled compound as a white solid.

$^1$H NMR (400 MHz, CDCl$_3$) 7.26-7.23 (m, 2H), 7.19 (q, 1H), 7.09 (d, 2H), 6.74-6.66 (m, 2H), 6.01 (br, 1H), 5.56 (dd, 1H), 4.88 (s, 1H), 4.04 (s, 2H), 3.59 (t, 2H), 3.55 (dd, 1H), 3.13 (dd, 1H), 2.45 (s, 2H), 1.47 (s, 9H)

Example 399

1-(2,4-difluoro-phenyl)-5-[4-(1,2,3,6-tetrahydropyridin-4-yl)-phenyl]-3-[di-(trifluoromethyl)-hydroxy-methyl]-4,5-dihydro-1H-pyrazole trifluoroacetate 1-(2,4-Difluoro-phenyl)-5-[4-(1-BOC-1,2,3,6-tetrahydropyridin-4-yl)-phenyl]-3-[di-(trifluoromethyl)-hydroxy-methyl]-4,5-dihydro-1H-pyrazole (800.0 mg, 1.32 mmol) prepared in Example 398 and trifluoroacetate (1.0 mL, 13.05 mmol) were added at 0° C. to dichloromethane (6.0 mL). The reaction mixture was stirred at room temperature for 3 hours and then concentrated under reduced pressure to give 800.0 mg of the titled compound as a yellow liquid.

$^1$H NMR (400 MHz, CD$_3$OD) 7.44 (q, 1H), 7.37 (d, 2H), 7.18 (d, 2H), 6.83-6.76 (m, 2H), 6.13 (s, 1H), 5.60 (d, 1H), 3.83 (s, 2H), 3.67 (dd, 1H), 3.44 (t, 2H), 3.09 (dd, 1H), 2.75 (s, 2H)

Example 400

1-(2,4-difluoro-phenyl)-5-[4-(1-methanesulfonyl-1,2,3,6-tetrahydropyridin-4-yl)-phenyl]-3-[di-(trifluoromethyl)-hydroxy-methyl]-4,5-dihydro-1H-pyrazole 1-(2,4-Difluoro-phenyl)-5-[4-(1,2,3,6-tetrahydropyridin-4-yl)-phenyl]-3-[di-(trifluoromethyl)-hydroxy-methyl]-4,5-dihydro-1H-pyrazole trifluoroacetate (30.0 mg, 0.05 mmol) prepared in Example 399, triethylamine (20.3 uL, 0.15 mmol) and methanesulfonyl chloride (4.6 uL, 0.06 mmol) were added at 0° C. to dichloromethane (1.0 mL). The reaction mixture was stirred at room temperature for 12 hours and then distilled water was added thereto. The reaction mixture was extracted with dichloromethane two times. The combined extract was washed with a 1N hydrochloric acid solution, a saturated solution of sodium carbonate, and brine, dried on anhydrous magnesium sulfate, and then concentrated under reduced pressure to give a yellow liquid residue. The resulting residue was purified by silica gel column chromatography (eluent: ethyl acetate/n-hexane=1/3) to give 2.1 mg of the titled compound as a yellow liquid.

$^1$H NMR (400 MHz, CDCl$_3$) 7.26-7.23 (m, 2H), 7.19 (q, 1H), 7.11 (d, 2H), 6.75-6.67 (m, 2H), 6.04 (s, 1H), 5.57 (dd, 1H), 4.83 (s, 1H), 3.94 (s, 2H), 3.55 (dd, 1H), 3.48 (t, 2H), 3.12 (dd, 1H), 2.84 (s, 3H), 2.60 (s, 2H)

Examples 401 to 403

The compounds of Examples 401 to 403 were prepared in accordance with the same procedures as in Example 400, except for using 1-(2,4-difluoro-phenyl)-5-[4-(1,2,3,6-tetrahydropyridin-4-yl)-phenyl]-3-[di-(trifluoromethyl)-hydroxy-methyl]-4,5-dihydro-1H-pyrazole trifluoroacetate prepared in Example 399; and using each sulfonyl chloride or acyl chloride corresponding to the compounds of Examples 401 to 403 instead of methanesulfonyl chloride.

Example 401

1-(2,4-difluoro-phenyl)-5-[4-(1-dimethylsulfamoyl-1,2,3,6-tetrahydropyridin-4-yl)-phenyl]-3-[di-(trifluoromethyl)-hydroxy-methyl]-4,5-dihydro-1H-pyrazole $^1$H NMR (400 MHz, CDCl$_3$) 7.26-7.23 (m, 2H), 7.19 (q, 1H), 7.10 (d, 2H), 6.75-6.67 (m, 2H), 6.03 (s, 1H), 5.57 (dd, 1H), 4.83 (s, 1H), 3.90 (s, 2H), 3.60 (dd, 1H), 3.47 (t, 2H), 3.12 (dd, 1H), 2.82 (s, 6H), 2.55 (s, 2H)

Example 402

1-(2,4-difluoro-phenyl)-5-[4-(1-isobutyryl-1,2,3,6-tetrahydropyridin-4-yl)-phenyl]-3-[di-(trifluoromethyl)-hydroxy-methyl]-4,5-dihydro-1H-pyrazole $^1$H NMR (400 MHz, CDCl$_3$) 7.26-7.23 (m, 2H), 7.19 (q, 1H), 7.10 (d, 2H), 6.75-6.67 (m, 2H), 6.07-6.01 (d, 1H), 5.57 (dd, 1H), 4.85 (s, 1H), 4.21-4.16 (d, 2H), 3.79-3.68 (d, 2H), 3.57 (dd, 1H), 3.12 (dd, 1H), 2.85-2.79 (m, 1H), 2.52-2.47 (d, 2H), 1.12 (d, 6H)

Example 403

1-(2,4-difluoro-phenyl)-5-[4-(1-dimethylcarbamoyl-1,2,3,6-tetrahydropyridin-4-yl)-phenyl]-3-[di-(trifluoromethyl)-hydroxy-methyl]-4,5-dihydro-1H-pyrazole $^1$H NMR (400 MHz, CDCl$_3$) 7.26-7.23 (m, 2H), 7.19 (q, 1H), 7.10 (d, 2H), 6.74-6.66 (m, 2H), 6.04 (s, 1H), 5.56 (dd, 1H), 4.87 (s, 1H), 3.89 (s, 2H), 3.59 (dd, 1H), 3.41 (t, 2H), 3.12 (dd, 1H), 2.84 (s, 6H), 2.51 (s, 2H)

Example 404

1-(2,4-difluoro-phenyl)-5-[4-(4-BOC-piperazin-1-yl)-phenyl]-3-[di-(trifluoromethyl)-hydroxy-methyl]-4,5-dihydro-1H-pyrazole 5-(4-Bromo-phenyl)-1-(2,4-difluoro-phenyl)-3-[di-(trifluoromethyl)-hydroxy-methyl]-4,5-dihydro-1H-pyrazole (500.0 mg, 0.99 mmol) prepared in Step 2 of Preparation 22, 1-BOC-piperazine (222.0 mg, 1.19 mmol), Pd$_2$(dba)$_3$ (45.0 mg, cat.), BINAP (62.0 mg, cat.) and sodium t-butoxide (143.0 mg, 1.49 mmol) were added to toluene (10.0 mL). The reaction mixture was stirred at 100° C. for 12 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/5) to give 340.0 mg of the titled compound as a yellow liquid.

$^1$H NMR (400 MHz, CDCl$_3$) 7.17 (dd, 1H), 7.01 (d, 2H), 6.77-6.65 (m, 4H), 5.49 (dd, 1H), 4.94 (s, 1H), 3.59-3.51 (m, 5H), 3.15-3.08 (m, 5H), 1.47 (s, 9H)

Example 405

1-(2,4-difluoro-phenyl)-5-[4-(piperazin-1-yl)-phenyl]-3-[di-(trifluoromethyl)-hydroxy-methyl]-4,5-dihydro-1H-pyrazole hydrochloride 1-(2,4-Difluoro-phenyl)-5-[4-(4-BOC-piperazin-1-yl)-phenyl]-3-[di-(trifluoromethyl)-hydroxy-methyl]-4,5-dihydro-1H-pyrazole (340.0 mg, 0.6 mmol) prepared in Example 404 was added to a saturated solution of hydrochloric acid in ethyl acetate (5.0 mL). The reaction mixture was stirred at room temperature for 2 hours and then concentrated under reduced pressure to give 300.0 mg of the titled compound as a pale yellow solid.

$^1$H NMR (400 MHz, CD$_3$OD) 7.31 (d, 1H), 7.21 (d, 1H), 7.11-7.09 (m, 3H), 6.94 (t, 1H), 6.84 (d, 2H), 5.83 (dd, 1H), 3.62 (dd, 1H), 3.30 (m, 8H), 3.14 (dd, 1H)

Example 406

1-(2,4-difluoro-phenyl)-5-[4-(4-methanesulfonyl-piperazin-1-yl)-phenyl]-3-[di-(trifluoromethyl)-hydroxy-methyl]-4,5-dihydro-1H-pyrazole 1-(2,4-Difluoro-phenyl)-5-[4-(piperazin-1-yl)-phenyl]-3-[di-(trifluoromethyl)-hydroxy-methyl]-4,5-dihydro-1H-pyrazole hydrochloride (30.0 mg, 0.06 mmol) prepared in Example 405, triethylamine (23.0 uL, 0.17 mmol) and methanesulfonyl chloride (5.0 uL, 0.07 mmol) were added to dichloromethane (1.0 mL). The reaction mixture was stirred at room temperature for 1 hour, washed with distilled water, 1N hydrochloride, a saturated solution of sodium hydrogen carbonate, and brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 10.0 mg of the titled compound as a yellow liquid.

$^1$H NMR (400 MHz, CDCl$_3$) 7.16 (dd, 1H), 7.03 (d, 2H), 6.77 (d, 2H), 6.74-6.66 (m, 2H), 5.51 (dd, 1H), 4.84 (s, 1H), 3.56 (dd, 1H), 3.35-3.31 (m, 4H), 3.25-3.22 (m, 4H), 3.10 (dd, 1H), 2.81 (s, 3H)

Example 407

1-(2,4-difluoro-phenyl)-5-[4-(4-dimethylsulfamoyl-piperazin-1-yl)-phenyl]-3-[di-(trifluoromethyl)-hydroxy-methyl]-4,5-dihydro-1H-pyrazole The titled compound was prepared in accordance with the same procedures as in Example 406, except for using 1-(2,4-difluoro-phenyl)-5-[4-(piperazin-1-yl)-phenyl]-3-[di-(trifluoromethyl)-hydroxy-methyl]-4,5-dihydro-1H-pyrazole hydrochloride prepared in Example 405; and using dimethylsulfamoyl chloride instead of methanesulfonyl chloride.

$^1$H NMR (400 MHz, CDCl$_3$) 7.18 (dd, 1H), 7.02 (d, 2H), 6.77-6.66 (m, 4H), 5.51 (dd, 1H), 4.87 (s, 1H), 3.56 (dd, 1H), 3.36-3.32 (m, 4H), 3.20-3.16 (m, 4H), 3.11 (dd, 1H), 2.85 (s, 6H)

Example 408

1-(2,4-difluoro-phenyl)-5-[4-(4-BOC-homopiperazin-1-yl)-phenyl]-3-[di-(trifluoromethyl)-hydroxy-methyl]-4,5-dihydro-1H-pyrazole 5-(4-Bromo-phenyl)-1-(2,4-difluoro-phenyl)-3-[di-(trifluoromethyl)-hydroxy-methyl]-4,5-dihydro-1H-pyrazole (500.0 mg, 0.99 mmol) prepared in Step 2 of Preparation 22, 1-BOC-homopiperazine (235.0 uL, 1.19 mmol), Pd$_2$(dba)$_3$ (45.0 mg, cat.), BINAP (62.0 mg, cat.) and sodium t-butoxide (143.0 mg, 1.49 mmol) were added to toluene (10.0 mL). The reaction mixture was stirred at 100° C. for 12 hours and filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/5) to give 250.0 mg of the titled compound as a yellow liquid.

$^1$H NMR (400 MHz, CDCl$_3$) 6.95 (d, 2H), 6.72-6.66 (m, 2H), 6.52 (d, 2H), 5.46 (dd, 1H), 4.93 (s, 1H), 3.56-3.47 (m, 7H), 3.29-3.08 (m, 3H), 1.91-1.87 (m, 2H), 1.35 (d, 9H)

Example 409

1-(2,4-difluoro-phenyl)-5-[4-(homopiperazin-1-yl)-phenyl]-3-[di-(trifluoromethyl)-hydroxy-methyl]-4,5-dihydro-1H-pyrazole hydrochloride 1-(2,4-Difluoro-phenyl)-5-[4-(4-BOC-homopiperazin-1-yl)-phenyl]-3-[di-(trifluoromethyl)-hydroxy-methyl]-4,5-dihydro-1H-pyrazole (340.0 mg, 0.6 mmol) prepared in Example 408 was added to a saturated solution of hydrochloric acid in ethyl acetate (5.0 mL). The reaction was stirred at room temperature for 2 hours and then concentrated under reduced pressure to give 250.0 mg of the titled compound as a pale yellow solid.

$^1$H NMR (400 MHz, CDCl$_3$) 7.40 (dd, 1H), 7.15 (d, 2H), 7.08 (d, 2H), 6.79-6.70 (m, 2H), 5.52 (dd, 1H), 3.90-3.87 (m, 2H), 3.66-3.54 (m, 5H), 3.37-3.35 (m, 2H), 3.04 (dd, 1H), 2.30-2.27 (m, 2H)

Example 410

1-(2,4-difluoro-phenyl)-5-[4-(4-methanesulfonyl-homopiperazin-1-yl)-phenyl]-3-[di-(trifluoromethyl)-hydroxy-methyl]-4,5-dihydro-1H-pyrazole 1-(2,4-Difluoro-phenyl)-5-[4-(homopiperazin-1-yl)-phenyl]-3-[di-(trifluoromethyl)-hydroxy-methyl]-4,5-dihydro-1H-pyrazole hydrochloride (30.0 mg, 0.06 mmol) prepared in Example 409, triethylamine (22.0 uL, 0.16 mmol) and methanesulfonyl chloride (5.0 uL, 0.07 mmol) were added to dichloromethane (1.0 mL). The reaction mixture was stirred at room temperature for 1 hour, washed with distilled water, 1N hydrochloride, a saturated solution of sodium hydrogen carbonate, and brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 10.0 mg of the titled compound as a yellow liquid.

$^1$H NMR (400 MHz, CDCl$_3$) 7.16 (dd, 1H), 6.96 (d, 2H), 6.73-6.66 (m, 2H), 6.52 (d, 2H), 5.47 (dd, 1H), 4.87 (s, 1H), 3.62-3.45 (m, 7H), 3.24-3.20 (m, 2H), 3.12 (dd, 1H), 2.66 (s, 3H), 2.05-1.97 (m, 2H)

Example 411

1-(2,4-difluoro-phenyl)-5-[4-(4-dimethylsulfamoyl-homopiperazin-1-yl)-phenyl]-3-[di-(trifluoromethyl)-hydroxy-methyl]-4,5-dihydro-1H-pyrazole The titled compound was prepared in accordance with the same procedures as in Example 410, except for using 1-(2,4-difluoro-phenyl)-5-[4-(homopiperazin-1-yl)-phenyl]-3-[di-(trifluoromethyl)-hydroxy-methyl]-4,5-dihydro-1H-pyrazole hydrochloride prepared in Example 409; and using dimethylsulfamoyl chloride instead of methanesulfonyl chloride.

$^1$H NMR (400 MHz, CDCl$_3$) 7.16 (dd, 1H), 6.96 (d, 2H), 6.73-6.66 (m, 2H), 6.51 (d, 2H), 5.47 (dd, 1H), 4.89 (s, 1H), 3.61-3.43 (m, 7H), 3.23 (t, 2H), 3.12 (dd, 1H), 2.64 (s, 6H), 2.00-1.96 (m, 2H)

Example 412

1-(2,4-difluoro-phenyl)-5-{3'-[3-(methyl-amino)-propane-1-sulfonyl]-biphenyl-4-yl}-3-[di-(trifluoromethyl)-hydroxy-methyl]-4,5-dihydro-1H-pyrazole To 5-{3'-[3-(N-BOC-N-methyl-amino)-propane-1-sulfonyl]-biphenyl-4-yl}-1-(2,4-difluoro-phenyl)-3-(di-(trifluoromethyl)-hydroxy-methyl)-4,5-dihydro-1H-pyrazole (23.0 mg, 0.03 mmol) prepared in Example 395, were added dichloromethane (0.5 mL) and trifluoroacetic acid (24.0 uL, 0.31 mmol). The reaction mixture was stirred at room temperature for 72 hours, washed with distilled water, 1N hydrochloride, a saturated solution of sodium hydrogen carbonate, and brine, dried on anhydrous magnesium sulfate, and then concentrated under reduced pressure to give 15.0 mg of the titled compound as a pale yellow liquid.

$^1$H NMR (400 MHz, CDCl$_3$) 8.04 (s, 1H), 7.90-7.77 (m, 2H), 7.66-7.48 (m, 3H), 7.28-7.23 (m, 3H), 6.75-6.68 (m, 2H), 5.60 (dd, 1H), 3.63 (dd, 1H), 3.24-3.11 (m, 3H), 3.01 (brs, 1H), 2.69-2.66 (m, 2H), 2.36 (s, 3H), 1.97-1.91 (m, 2H)

Example 413

1-(2,4-difluoro-phenyl)-5-[3'-methanesulfonyl-biphenyl-4-yl]-3-[di-(trifluoromethyl)-hydroxy-methyl]-4,5-dihydro-1H-pyrazole To a mixture of 1-(2,4-difluoro-phenyl)-5-(3'-methylsulfanyl-biphenyl-4-yl)-3-[di-(trifluoromethyl)-hydroxy-methyl]-4,5-dihydro-1H-pyrazole (43.0 mg, 0.08 mmol) prepared in Example 369 in dichloromethane (1.0 mL), was slowly added meta-chloroperbenzoic acid (77%, 45.0 mg, 0.18 mmol) at 0° C. The reaction mixture was stirred at room temperature for 30 minutes, quenched with a saturated solution of sodium hydrogen carbonate, and then extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/2) to give 7.5 mg of the titled compound as a pale yellow liquid.

$^1$H NMR (400 MHz, CDCl$_3$) 8.08 (s, 1H), 7.90 (d, 1H), 7.80 (d, 1H), 7.64 (t, 2H), 7.51 (d, 2H), 7.30-7.26 (m, 2H), 6.75-6.69 (m, 2H), 5.65 (dd, 1H), 3.66 (dd, 1H), 3.16 (dd, 1H), 3.07 (s, 3H)

Example 414

1-(2-chloro-phenyl)-5-{5-[3-(methylsulfanyl)-phenyl]-thiophen-2-yl}-3-[di-(trifluoromethyl)-hydroxy-methyl]-4,5-dihydro-1H-pyrazole 5-(5-Bromo-thiophen-2-yl)-1-(2-chloro-phenyl)-3-[di-(trifluoromethyl)-hydroxy-methyl]-4,5-dihydro-1H-pyrazole (100.0 mg, 0.20 mmol) prepared in Step 5 of Preparation 23, 3-methylthiophenylboronic acid (50.4 mg, 0.30 mmol), Pd(PPh$_3$)$_4$ (23.0 mg, 0.02 mmol), and a 2N sodium carbonate solution (1.0 mL) were added to a mixed solvent of 1,2-dimethoxyethane (2.0 mL) and ethanol (1.0 mL). The reaction mixture was stirred at 88° C. for 4 hours and then ethyl acetate was added thereto. The reaction mixture was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/5) to give 9.2 mg of the titled compound as a yellow liquid.

$^1$H NMR (400 MHz, CDCl$_3$) 7.30 (d, 2H), 7.25-7.11 (m, 5H), 7.08 (t, 1H), 6.98 (s, 1H), 6.76 (s, 1H), 6.19 (dd, 1H), 4.90 (s, 1H), 3.62 (dd, 1H), 3.37 (dd, 1H), 2.48 (s, 3H)

Examples 415 and 416

The compounds of Examples 415 and 416 were prepared in accordance with the same procedures as in Example 414, except for using 5-(5-bromo-thiophen-2-yl)-1-(2-chloro-phenyl)-3-[di-(trifluoromethyl)-hydroxy-methyl]-4,5-dihydro-1H-pyrazole prepared in Step 5 of Preparation 23; and using each boronic acid corresponding to the compounds of Examples 415 and 416 instead of 3-methylthiophenylboronic acid.

Example 415

1-(2-chloro-phenyl)-5-{5-[6-(methylsulfanyl)-pyridin-3-yl]-thiophen-2-yl}-3-[di-(trifluoromethyl)-hydroxy-methyl]-4,5-dihydro-1H-pyrazole $^1$H NMR (400 MHz, CDCl$_3$) 8.54 (s, 1H), 7.51 (d, 1H), 7.31 (d, 1H), 7.18 (d, 1H), 7.13-7.07 (m, 2H), 7.01 (t, 1H), 6.92 (s, 1H), 6.78 (s, 1H), 6.22 (dd, 1H), 4.96 (s, 1H), 3.63 (dd, 1H), 3.37 (dd, 1H), 2.55 (s, 3H)

Example 416

1-(2-chloro-phenyl)-5-[5-(1-BOC-1,2,3,6-tetrahydropyridin-4-yl)-thiophen-2-yl]-3-[di-(trifluoromethyl)-hydroxy-methyl]-4,5-dihydro-1H-pyrazole $^1$H NMR (400 MHz, CDCl$_3$) 7.29 (d, 1H), 7.18 (d, 1H), 7.11 (t, 1H), 7.03 (t, 1H), 6.66 (d, 1H), 6.59 (d, 1H), 6.15 (dd, 1H), 5.92 (br, 1H), 4.88 (s, 1H) 4.01 (s, 2H), 3.62 (dd, 1H), 3.55 (t, 2H), 3.33 (dd, 1H), 2.37 (m, 2H), 1.49 (s, 9H)

Example 417

1-(2-chloro-phenyl)-5-[5-(1,2,3,6-tetrahydropyridin-4-yl)-thiophen-2-yl]-3-[di-(trifluoromethyl)-hydroxy-methyl]-4,5-dihydro-1H-pyrazole hydrochloride 1-(2-Chloro-phenyl)-5-[5-(1-BOC-1,2,3,6-tetrahydropyridin-4-yl)-thiophen-2-yl]-3-[di-(trifluoromethyl)-hydroxy-methyl]-4,5-dihydro-1H-pyrazole (590.0 mg, 0.97 mmol) prepared in Example 416 was added to a saturated solution of hydrochloric acid in ethyl acetate (2.0 mL). The reaction mixture was stirred at room temperature for 2 hours and then concentrated under reduced pressure to give 590.0 mg of the titled compound as a yellow liquid.

$^1$H NMR (400 MHz, CD$_3$OD) 7.28 (d, 2H), 7.06 (t, 1H), 6.97 (t, 1H), 6.79-6.74 (m, 2H), 5.16 (dd, 1H), 5.97 (s, 1H), 3.75 (s, 2H), 3.63 (dd, 1H), 3.37 (t, 2H), 3.21 (dd, 1H), 2.66 (m, 2H)

Example 418

1-(2-chloro-phenyl)-5-[5-(1-methanesulfonyl-1,2,3, 6-tetra hydropyridin-4-yl)-thiophen-2-yl]-3-[di-(trifluoromethyl)-hydroxy-methyl]-4,5-dihydro-1H-pyrazole 1-(2-Chloro-phenyl)-5-[5-(1,2,3,6-tetrahydropyridin-4-yl)-thiophen-2-yl]-3-[di-(trifluoromethyl)-hydroxy-methyl]-4,5-dihydro-1H-pyrazole hydrochloride (30.0 mg, 0.06 mmol) prepared in Example 417, methanesulfonyl chloride (6.0 uL, 0.08 mmol), and triethylamine (38.0 uL, 0.28 mmol) were added to dichloromethane (1.0 mL). The reaction mixture was stirred at room temperature for 16 hours, washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/1) to give 5.0 mg of the titled compound as a yellow liquid.

$^1$H NMR (400 MHz, CDCl$_3$) 7.50 (d, 1H), 7.25 (d, 1H), 7.10 (t, 1H), 7.00 (d, 1H), 6.68 (s, 1H), 6.60 (s, 1H), 6.13 (d, 1H), 5.95 (s, 1H), 3.90 (brs, 2H), 3.63 (dd, 1H), 3.45-3.35 (m, 3H), 2.82 (s, 3H), 2.51 (brs, 2H)

Example 419

1-(2-chloro-phenyl)-5-{5-[3-(methylsulfonyl)-phenyl]-thiophen-2-yl}-3-[di-(trifluoromethyl)-hydroxy-methyl]-4,5-dihydro-1H-pyrazole To a mixture of 1-(2-chloro-phenyl)-5-{5-[3-(methylsulfanyl)-phenyl]-thiophen-2-yl}-3-[di-(trifluoromethyl)-hydroxy-methyl]-4,5-dihydro-1H-pyrazole (20.0 mg, 0.01 mmol) prepared in Example 414 in dichloromethane (1.0 mL), was slowly added meta-chloroperbenzoic acid (77%, 6.0 mg, 0.02 mmol) at 0° C. The reaction mixture was stirred at room temperature for 1 hour, quenched with a saturated solution of sodium hydrogen carbonate, and then extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/2) to give 10.0 mg of the titled compound as a yellow liquid.

$^1$H NMR (400 MHz, CDCl$_3$) 8.05 (s, 1H), 7.78 (d, 1H), 7.70 (d, 1H), 7.54 (t, 1H), 7.32 (d, 1H), 7.20 (d, 1H), 7.13-7.00 (m, 3H), 6.82 (d, 1H), 6.21 (dd, 1H), 4.89 (s, 1H), 3.62 (dd, 1H), 3.39 (dd, 1H), 3.06 (s, 3H)

Example 420

1-(2-chloro-phenyl)-5-{5-[6-(methylsulfonyl)-pyridin-3-yl]-thiophen-2-yl}-3-[di-(trifluoromethyl)-hydroxy-methyl]-4,5-dihydro-1H-pyrazole To a mixture of 1-(2-chloro-phenyl)-5-{5-[6-(methylsulfanyl)-pyridin-3-yl]-thiophen-2-yl}-3-[di-(trifluoromethyl)-hydroxy-methyl]-4,5-dihydro-1H-pyrazole (49.0 mg, 0.03 mmol) prepared in Example 415 in dichloromethane (1.0 mL), was slowly added meta-chloroperbenzoic acid (77%, 15.0 mg, 0.05 mmol) at 0° C. The reaction mixture was stirred at room temperature for 1 hour, quenched with a saturated solution of sodium hydrogen carbonate, and then extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/1) to give 17.0 mg of the titled compound as a yellow liquid.

$^1$H NMR (400 MHz, CDCl$_3$) 8.76 (s, 1H), 8.02 (d, 1H), 7.93 (d, 1H), 7.32 (d, 1H), 7.21-7.09 (m, 3H), 7.03 (t, 1H), 6.87 (s, 1H), 6.34 (dd, 1H), 4.89 (br, 1H), 3.68 (dd, 1H), 3.36 (dd, 1H), 3.21 (s, 3H)

Example 421

5-(2-chloro-phenyl)-1-[3'-(methylsulfanyl)-biphenyl-4-yl]-3-[di-(trifluoromethyl)-hydroxy-methyl]-4,5-dihydro-1H-pyrazole 1-(4-Bromo-phenyl)-5-(2-chloro-phenyl)-3-[di-(trifluoromethyl)-hydroxy-methyl]-4,5-dihydro-1H-pyrazole (50.0 mg, 0.10 mmol) prepared in Step 5 of Preparation 24, 3-methylthiophenylboronic acid (25.1 mg, 0.15 mmol), Pd(PPh$_3$)$_4$ (11.5 mg, 0.01 mmol), and a 2N sodium carbonate solution (0.5 mL) were added to a mixed solvent of 1,2-dimethoxyethane (2.0 mL) and ethanol (0.5 mL). The reaction mixture was stirred at 90° C. for 2 hours and then ethyl acetate was added thereto. The reaction mixture was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/10) to give 3.7 mg of the titled compound as a yellow liquid.

$^1$H NMR (400 MHz, CDCl$_3$) 7.44-7.38 (m, 3H), 7.32 (s, 1H), 7.27-7.22 (m, 4H), 7.16 (t, 2H), 6.96 (d, 2H), 5.89 (dd, 1H), 4.86 (s, 1H), 3.80 (dd, 1H), 2.93 (dd, 1H), 2.50 (s, 3H)

Example 422

5-(2-chloro-phenyl)-1-{4-[6-(methylsulfanyl)-pyridin-3-yl]-phenyl}-3-[di-(trifluoromethyl)-hydroxy-methyl]-4,5-dihydro-1H-pyrazole The titled compound was prepared in accordance with the same procedures as in Example 421, except for using 1-(4-bromo-phenyl)-5-(2-chloro-phenyl)-3-[di-(trifluoromethyl)-hydroxy-methyl]-4,5-dihydro-1H-pyrazole prepared in Step 5 of Preparation 24; and using 6-methylthiopyridin-3-ylboronic acid instead of 3-methylthiophenylboronic acid.

$^1$H NMR (400 MHz, CDCl$_3$) 8.60 (s, 1H), 7.71 (d, 1H), 7.46 (d, 1H), 7.41 (d, 2H), 7.30-7.20 (m, 3H), 7.14 (d, 1H), 6.99 (d, 2H), 5.88 (dd, 1H), 4.86 (s, 1H), 3.80 (dd, 1H), 2.93 (dd, 1H), 2.59 (s, 3H)

Example 423

5-(2-chloro-phenyl)-1-[4-(1-BOC-1,2,3,6-tetrahydro-pyridin-4-yl)-phenyl]-3-[di-(trifluoromethyl)-hydroxy-methyl]-4,5-dihydro-1H-pyrazole 1-(4-Bromo-phenyl)-5-(2-chloro-phenyl)-3-[di-(trifluoromethyl)-hydroxy-methyl]-4,5-dihydro-1H-pyrazole (500.0 mg, 1.00 mmol) prepared in Step 5 of Preparation 24, tert-butyl 4-(4,4,5,5-tetramethyl-1,3,2-dioxaborolan-2-yl)-5,6-dihydropyridin-1(2H)-carboxylic acid (370.0 mg, 1.20 mmol), potassium carbonate (690.0 mg, 4.98 mmol), and Pd(dppf)Cl$_2$ (73.0 mg, 0.10 mmol) were added to a mixed solvent of 1,4-dioxane (15.0 mL) and distilled water (4.0 mL). The reaction mixture was stirred at 85° C. for 16 hours. Distilled water was added to the reaction mixture, which was then extracted with ethyl acetate. The extract was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/5) to give 435.0 mg of the titled compound as a yellow liquid.

$^1$H NMR (400 MHz, CDCl$_3$) 7.45 (d, 1H), 7.29-7.17 (m, 4H), 7.12 (d, 1H), 6.86 (d, 2H), 5.92 (brs, 1H), 5.84 (dd, 1H), 4.86 (s, 1H), 4.04 (brs, 2H), 3.75 (dd, 1H), 3.60 (t, 2H), 2.90 (dd, 1H), 2.44 (brs, 2H), 1.48 (s, 9H)

Example 424

5-(2-chloro-phenyl)-1-[3'-(methylsulfonyl)-biphenyl-4-yl]-3-[di-(trifluoromethyl)-hydroxy-methyl]-4,5-dihydro-1H-pyrazole To a mixture of 5-(2-chloro-phenyl)-1-[3'-(methylsulfanyl)-biphenyl-4-yl]-3-[di-(trifluoromethyl)-hydroxy-methyl]-4,5-dihydro-1H-pyrazole (10.0 mg, 0.005 mmol) prepared in Example 421 in dichloromethane (1.0 mL), was slowly added meta-chloroperbenzoic acid (77%, 10.0 mg, 0.01 mmol) at 0° C. The reaction mixture was stirred at room temperature for 2 hours, quenched with a saturated solution of sodium hydrogen carbonate, and then extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/2) to give 8.0 mg of the titled compound as a yellow liquid.

$^1$H NMR (400 MHz, CDCl$_3$) 8.09 (s, 1H), 7.82 (d, 1H), 7.73 (d, 1H), 7.58 (t, 1H), 7.50-7.46 (m, 3H), 7.30-7.20 (m, 2H), 7.12 (d, 1H), 7.00 (d, 2H), 5.91 (dd, 1H), 4.90 (br, 1H), 3.82 (dd, 1H), 3.07 (s, 3H), 2.95 (dd, 1H)

Example 425

5-(2-chloro-phenyl)-1-{4-[6-(methylsulfonyl)-pyridin-3-yl]-phenyl}-3-[di-(trifluoromethyl)-hydroxy-methyl]-4,5-dihydro-1H-pyrazole To a mixture of 5-(2-chloro-phenyl)-1-{4-[6-(methylsulfanyl)-pyridin-3-yl]-phenyl}-3-[di-(trifluoromethyl)-hydroxy-methyl]-4,5-dihydro-1H-pyrazole (10.0 mg, 0.005 mmol) prepared in Example 422 in dichloromethane (1.0 mL), was slowly added meta-chloroperbenzoic acid (77%, 10.0 mg, 0.01 mmol) at 0° C. The reaction mixture was stirred at room temperature for 2 hours, quenched with a saturated solution of sodium hydrogen carbonate, and then extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 2.0 mg of the titled compound as a yellow liquid.

$^1$H NMR (400 MHz, CDCl$_3$) 8.86 (s, 1H), 8.09 (d, 1H), 8.02 (d, 1H), 7.50-7.47 (m, 3H), 7.30-7.20 (m, 3H), 7.11 (d, 1H), 7.04 (d, 2H), 5.91 (dd, 1H), 4.86 (br, 1H), 3.83 (dd, 1H), 3.24 (s, 3H), 2.97 (dd, 1H)

Example 426

5-(2-chloro-phenyl)-1-[4-(4-BOC-piperazin-1-yl)-phenyl]-3-[di-(trifluoromethyl)-hydroxy-methyl]-4,5-dihydro-1H-pyrazole 1-(4-Bromo-phenyl)-5-(2-chloro-phenyl)-3-[di-(trifluoromethyl)-hydroxy-methyl]-4,5-dihydro-1H-pyrazole (500.0 mg, 1.00 mmol) prepared in Step 5 of Preparation 24, 1-BOC-piperazine (241.0 mg, 1.30 mmol), Pd$_2$(dba)$_3$ (45.0 mg, 0.05 mmol), BINAP (62.0 mg, 0.10 mmol) and sodium t-butoxide (144.0 mg, 1.50 mmol) were added to toluene (10.0 mL). The reaction mixture was stirred at 100° C. for 12 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/2) to give 280.0 mg of the titled compound as a yellow liquid.

$^1$H NMR (400 MHz, CDCl$_3$) 7.44 (d, 1H), 7.28-7.19 (m, 3H), 6.87-6.80 (m, 4H), 5.75 (dd, 1H), 4.88 (s, 1H), 3.74 (dd, 1H), 3.54 (t, 4H), 2.99 (t, 4H), 2.86 (dd, 1H), 1.47 (s, 9H)

Example 427

5-(2-chloro-phenyl)-1-[4-(1,2,3,6-tetrahydropyridin-4-yl)-phenyl]-3-[di-(trifluoromethyl)-hydroxy-methyl]-4,5-dihydro-1H-pyrazole hydrochloride 5-(2-Chloro-phenyl)-1-[4-(1-BOC-1,2,3,6-tetrahydropyridin-4-yl)-phenyl]-3-[di-(trifluoromethyl)-hydroxy-methyl]-4,5-dihydro-1H-pyrazole (435.0 mg, 0.72 mmol) prepared in Example 423 was added to a saturated solution of hydrochloric acid in ethyl acetate (2.0 mL). The reaction mixture was stirred at room temperature for 2 hours and then concentrated under reduced pressure to give 400.0 mg of the titled compound as a yellow liquid.
$^1$H NMR (400 MHz, CD$_3$OD) 7.49 (d, 1H), 7.38-7.27 (m, 3H), 7.19 (t, 1H), 7.05 (d, 1H), 6.93 (d, 2H), 6.01 (s, 1H), 5.79 (dd, 1H), 3.84-3.76 (m, 3H), 3.42 (t, 2H), 2.86 (dd, 1H), 2.73 (brs, 2H)

Example 428

5-(2-chloro-phenyl)-1-[4-(piperazin-1-yl)-phenyl]-3-[di-(trifluoromethyl)-hydroxy-methyl]-4,5-dihydro-1H-pyrazole hydrochloride 5-(2-Chloro-phenyl)-1-[4-(4-BOC-piperazin-1-yl)-phenyl]-3-[di-(trifluoromethyl)-hydroxy-methyl]-4,5-dihydro-1H-pyrazole (280.0 mg, 0.46 mmol) prepared in Example 426 was added to a saturated solution of hydrochloric acid in ethyl acetate (2.0 mL). The reaction mixture was stirred at room temperature for 1 hour and then concentrated under reduced pressure to give 270.0 mg of the titled compound as a yellow liquid.
$^1$H NMR (400 MHz, CD$_3$OD) 7.49 (d, 1H), 7.29 (t, 1H), 7.24-7.18 (m, 3H), 7.07 (d, 1H), 6.98 (d, 2H), 5.76 (dd, 1H), 3.80 (dd, 1H), 3.58-3.48 (m, 8H), 2.86 (dd, 1H)

Example 429

5-(2-chloro-phenyl)-1-[4-(1-cyclopropanesulfonyl-1,2,3,6-tetrahydropyridin-4-yl)-phenyl]-3-[di-(trifluoromethyl)-hydroxy-methyl]-4,5-dihydro-1H-pyrazole 5-(2-Chloro-phenyl)-1-[4-(1,2,3,6-tetrahydropyridin-4-yl)-phenyl]-3-[di-(trifluoromethyl)-hydroxy-methyl]-4,5-dihydro-1H-pyrazole hydrochloride (20.0 mg, 0.04 mmol) prepared in Example 427, cyclopropanesulfonyl chloride (6.0 uL, 0.06 mmol), and triethylamine (26.0 uL, 0.19 mmol) were added to dichloromethane (1.0 mL). The reaction mixture was stirred at room temperature for 16 hours, washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/1) to give 15.0 mg of the titled compound as a yellow liquid.
$^1$H NMR (400 MHz, CDCl$_3$) 7.45 (d, 1H), 7.28-7.18 (m, 4H), 7.12 (d, 1H), 6.87 (d, 2H), 5.95 (s, 1H), 5.84 (dd, 1H), 4.85 (s, 1H), 4.00 (brs, 2H), 3.77 (dd, 1H), 3.54 (t, 2H), 2.93 (dd, 1H), 2.58 (brs, 2H), 2.33-2.26 (m, 1H), 1.22-1.17 (m, 2H), 1.01-0.95 (m, 2H)

Example 430

5-(2-chloro-phenyl)-1-[4-(4-cyclopropanesulfonyl-piperazin-1-yl)-phenyl]-3-[di-(trifluoromethyl)-hydroxy-methyl]-4,5-dihydro-1H-pyrazole 5-(2-Chloro-phenyl)-1-[4-(piperazin-1-yl)-phenyl]-3-[di-(trifluoromethyl)-hydroxy-methyl]-4,5-dihydro-1H-pyrazole hydrochloride (20.0 mg, 0.04 mmol) prepared in Example 428, cyclopropanesulfonyl chloride (6.0 uL, 0.06 mmol), and triethylamine (25.0 uL, 0.18 mmol) were added to dichloromethane (1.0 mL). The reaction mixture was stirred at room temperature for 16 hours, washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/1) to give 15.0 mg of the titled compound as a yellow liquid.
$^1$H NMR (400 MHz, CDCl$_3$) 7.44 (d, 1H), 7.28-7.17 (m, 3H), 6.88-6.81 (m, 4H), 5.75 (dd, 1H), 4.88 (s, 1H), 3.75 (dd, 1H), 3.44 (t, 4H), 3.13 (t, 4H), 2.87 (dd, 1H), 2.32-2.25 (m, 1H), 1.22-1.17 (m, 2H), 1.03-0.97 (m, 2H)

Example 431

5-(2-chloro-phenyl)-1-[3'-(methylsulfanyl)-biphenyl-3-yl]-3-[di-(trifluoromethyl)-hydroxy-methyl]-4,5-dihydro-1H-pyrazole 1-(3-Bromo-phenyl)-5-(2-chloro-phenyl)-3-[di-(trifluoromethyl)-hydroxy-methyl]-4,5-dihydro-1H-pyrazole (50.0 mg, 0.10 mmol) prepared in Step 2 of Preparation 25, 3-methylthiophenylboronic acid (20.0 mg, 0.15 mmol), Pd(PPh$_3$)$_4$ (11.5 mg, 0.01 mmol), and a 2N sodium carbonate solution (0.5 mL) were added to a mixed solvent of 1,2-dimethoxyethane (2.0 mL) and ethanol (0.5 mL). The reaction mixture was stirred at 90° C. for 2 hours and then ethyl acetate was added thereto. The reaction mixture was washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/10) to give 5.3 mg of the titled compound as a yellow liquid.
$^1$H NMR (400 MHz, CDCl$_3$) 7.46 (d, 1H), 7.34-7.17 (m, 8H), 7.09 (d, 2H), 6.87 (d, 1H), 5.90 (dd, 1H), 4.87 (s, 1H), 3.78 (dd, 1H), 2.94 (dd, 1H), 2.49 (s, 3H)

Examples 432 and 433

The compounds of Examples 432 and 433 were prepared in accordance with the same procedures as in Example 431, except for using 1-(3-bromo-phenyl)-5-(2-chloro-phenyl)-3-[di-(trifluoromethyl)-hydroxy-methyl]-4,5-dihydro-1H-pyrazole prepared in Step 2 of Preparation 25; and using each boronic acid corresponding to the compounds of Examples 432 and 433 instead of 3-methylthiophenylboronic acid.

Example 432

5-(2-chloro-phenyl)-1-{3-[6-(methylsulfanyl)-pyridin-3-yl]-phenyl}-3-[di-(trifluoromethyl)-hydroxy-methyl]-4,5-dihydro-1H-pyrazole $^1$H NMR (400 MHz, CDCl$_3$) 8.55 (s, 1H), 7.60 (d, 1H), 7.47 (d, 1H), 7.31-7.21 (m, 4H), 7.17 (d, 1H), 7.11 (s, 1H), 7.08 (d, 1H), 6.88 (d, 1H), 5.90 (dd, 1H), 4.84 (s, 1H), 3.80 (dd, 1H), 2.97 (dd, 1H), 2.59 (s, 3H)

Example 433

5-(2-chloro-phenyl)-1-[3-(1-BOC-1,2,3,6-tetrahydropyridin-4-yl)-phenyl]-3-[di-(trifluoromethyl)-hydroxy-methyl]-4,5-dihydro-1H-pyrazole $^1$H NMR (400 MHz, CDCl$_3$) 7.45 (d, 1H), 7.26-7.13 (m, 4H), 6.95 (s, 1H), 6.91 (d, 1H), 6.74 (d, 1H), 5.93 (br, 1H), 5.84 (dd, 1H), 4.88 (s, 1H), 4.04 (s, 2H), 3.77 (dd, 1H), 3.58 (t, 2H), 2.92 (dd, 1H), 2.40 (m, 2H), 1.47 (s, 9H)

Example 434

5-(2-chloro-phenyl)-1-[3'-(methylsulfonyl)-biphenyl-3-yl]-3-[di-(trifluoromethyl)-hydroxy-methyl]-4,5-dihydro-1H-pyrazole To a mixture of 5-(2-chloro-phenyl)-1-[3'-(methylsulfanyl)-biphenyl-3-yl]-3-[di-(trifluoromethyl)-hydroxy-methyl]-4,5-dihydro-1H-pyrazole (30.0 mg, 0.055 mmol) prepared in Example 431 in dichloromethane (1.0 mL), was slowly added meta-chloroperbenzoic acid (77%, 27.0 mg, 0.110 mmol) at 0° C. The reaction mixture was stirred at room temperature for 2 hours, quenched with a saturated solution of sodium hydrogen carbonate, and then extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/2) to give 15.0 mg of the titled compound as a yellow liquid.
$^1$H NMR (400 MHz, CDCl$_3$) 8.06 (s, 1H), 7.89 (d, 1H), 7.75 (d, 1H), 6.73 (t, 1H), 7.48 (d, 1H), 7.32-7.23 (m, 5H), 7.17 (d, 1H), 6.88 (d, 1H), 5.93 (dd, 1H), 4.88 (s, 1H), 3.80 (dd, 1H), 3.08 (s, 3H), 2.98 (dd, 1H)

Example 435

5-(2-chloro-phenyl)-1-{3-[6-(methylsulfonyl)-pyridin-3-yl]-phenyl}-3-[di-(trifluoromethyl)-hydroxy-methyl]-4,5-dihydro-1H-pyrazole To a mixture of 5-(2-chloro-phenyl)-1-{3-[6-(methylsulfanyl)-pyridin-3-yl]-phenyl}-3-[di-(trifluoromethyl)-hydroxy-methyl]-4,5-dihydro-1H-pyrazole (10.0 mg, 0.02 mmol) prepared in Example 432 in dichloromethane (1.0 mL), was slowly added meta-chloroperbenzoic acid (77%, 9.0 mg, 0.04 mmol) at 0° C. The reaction mixture was stirred at room temperature for 2 hours, quenched with a saturated solution of sodium hydrogen carbonate, and then extracted with dichloromethane three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 4.0 mg of the titled compound as a yellow liquid.
$^1$H NMR (400 MHz, CDCl$_3$) 8.80 (s, 1H), 8.12 (d, 1H), 7.99 (d, 1H), 7.48 (D, 1H), 7.31 (t, 1H), 7.27-7.23 (m, 2H), 7.16 (d, 1H), 7.12 (d, 2H), 6.99 (d, 1H), 5.92 (dd, 1H), 4.80 (s, 1H), 3.82 (dd, 1H), 3.26 (s, 3H), 2.97 (dd, 1H)

Example 436

5-(2-chloro-phenyl)-1-[3-(4-BOC-piperazin-1-yl)-phenyl]-3-[di-(trifluoromethyl)-hydroxy-methyl]-4,5-dihydro-1H-pyrazole 1-(3-Bromo-phenyl)-5-(2-chloro-phenyl)-3-[di-(trifluoromethyl)-hydroxy-methyl]-4,5-dihydro-1H-pyrazole (500.0 mg, 1.00 mmol) prepared in Step 2 of Preparation 25, 1-BOC-piperazine (275.0 mg, 1.49 mmol), Pd$_2$(dba)$_3$ (47.0 mg, 0.05 mmol), BINAP (63.0 mg, 0.10 mmol) and sodium t-butoxide (143.0 mg, 1.79 mmol) were added to toluene (12.0 mL). The reaction mixture was stirred at 100° C. for 12 hours and then filtered through celite pad. A saturated solution of ammonium chloride was added to the filtrate, which was then extracted with ethyl acetate three times. The combined extract was washed with brine, dried on anhydrous magnesium sulfate, and then concentrated under reduced pressure to give a yellow liquid residue. The resulting residue was purified by silica gel column chromatography (eluent: ethyl acetate/n-hexane=1/5) to give 95.0 mg the titled compound as a yellow liquid.
$^1$H NMR (400 MHz, CDCl$_3$) 7.44 (d, 1H), 7.25-7.19 (m, 2H), 7.14 (d, 1H), 7.07 (t, 1H), 6.54 (s, 1H), 6.47 (d, 1H), 6.33 (d, 1H), 5.84 (dd, 1H), 3.73 (dd, 1H), 3.53 (t, 4H), 3.06 (t, 4H), 2.90 (dd, 1H), 1.45 (s, 9H)

Example 437

5-(2-chloro-phenyl)-1-[3-(1-methylsulfonyl-1,2,3,6-tetrahydropyridin-4-yl)-phenyl]-3-[di-(trifluoromethyl)-hydroxy-methyl]-4,5-dihydro-1H-pyrazole 5-(2-Chloro-phenyl)-1-[3-(1-BOC-1,2,3,6-tetrahydropyridin-4-yl)-phenyl]-3-[di-(trifluoromethyl)-hydroxy-methyl]-4,5-dihydro-1H-pyrazole (350.0 mg, 0.71 mmol) prepared in Example 433 was added to a saturated solution of hydrochloric acid in ethyl acetate (3.0 mL). The reaction mixture was stirred at room temperature for 1 hour and then concentrated under reduced pressure to give 400.0 mg of 5-(2-chloro-phenyl)-1-[3-(1,2,3,6-tetrahydropyridin-4-yl)-phenyl]-3-[di-(trifluoromethyl)-hydroxy-methyl]-4,5-dihydro-1H-pyrazole hydrochloride as a yellow liquid.
The 5-(2-chloro-phenyl)-1-[3-(1,2,3,6-tetrahydropyridin-4-yl)-phenyl]-3-[di-(trifluoromethyl)-hydroxy-methyl]-4,5-dihydro-1H-pyrazole hydrochloride (30.0 mg, 0.055 mmol) in the form of a yellow liquid, methanesulfonyl chloride (7.6 mg, 0.066 mmol), and triethylamine (31.0 uL, 0.221 mmol) were added to dichloromethane (1.0 mL). The reaction mixture was stirred at room temperature for 16 hours, washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=2/1) to give 14.0 mg of the titled compound as a yellow liquid.
$^1$H NMR (400 MHz, CDCl$_3$) 7.47 (d, 1H), 7.28-7.13 (m, 4H), 6.91-6.89 (m, 2H), 6.78 (d, 1H), 5.97 (s, 1H), 5.96 (dd, 1H), 4.85 (s, 1H), 3.93 (t, 2H), 3.76 (dd, 1H), 3.49 (t, 2H), 2.96 (dd, 1H), 2.86 (s, 3H), 2.55 (m, 2H)

Example 438

5-(2-chloro-phenyl)-1-[3-(1-cyclopropanesulfonyl-1,2,3,6-tetrahydropyridin-4-yl)-phenyl]-3-[di-(trifluoromethyl)-hydroxy-methyl]-4,5-dihydro-1H-pyrazole 5-(2-Chloro-phenyl)-1-[3-(1-BOC-1,2,3,6-tetrahydropyridin-4-yl)-phenyl]-3-[di-(trifluoromethyl)-hydroxy-methyl]-4,5-dihydro-1H-pyrazole (350.0 mg, 0.71 mmol) prepared in Example 433 was added to a saturated solution of hydrochloric acid in ethyl acetate (3.0 mL). The reaction mixture was stirred at room temperature for 1 hour and then concentrated under reduced pressure to give 400.0 mg of 5-(2-chloro-phenyl)-1-[3-(1,2,3,6-tetrahydropyridin-4-yl)-phenyl]-3-[di-(trifluoromethyl)-hydroxy-methyl]-4,5-dihydro-1H-pyrazole hydrochloride as a yellow liquid.
The 5-(2-chloro-phenyl)-1-[3-(1,2,3,6-tetrahydropyridin-4-yl)-phenyl]-3-[di-(trifluoromethyl)-hydroxy-methyl]-4,5-dihydro-1H-pyrazole hydrochloride (30.0 mg, 0.055 mmol)

in the form of a yellow liquid, cyclopropanesulfonyl chloride (9.3 mg, 0.066 mmol), and triethylamine (31.0 uL, 0.221 mmol) were added to dichloromethane (1.0 mL). The reaction mixture was stirred at room temperature for 16 hours, washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/2) to give 14.0 mg of the titled compound as a yellow liquid.

$^1$H NMR (400 MHz, CDCl$_3$) 7.47 (d, 1H), 7.28-7.13 (m, 4H), 6.91-6.89 (m, 2H), 6.80 (d, 1H), 5.96 (s, 1H), 5.88 (dd, 1H), 4.85 (s, 1H), 3.98 (t, 2H), 3.76 (dd, 1H), 3.53 (t, 2H), 2.96 (dd, 1H), 2.53 (m, 2H), 2.30 (m, 1H), 1.24 (m, 2H), 1.02 (m, 2H)

Example 439

5-(2-chloro-phenyl)-1-[3-(4-methylsulfonyl-piperazin-1-yl)-phenyl]-3-[di-(trifluoromethyl)-hydroxymethyl]-4,5-dihydro-1H-pyrazole 5-(2-Chloro-phenyl)-1-[3-(4-BOC-piperazin-1-yl)-phenyl]-3-[di-(trifluoromethyl)-hydroxy-methyl]-4,5-dihydro-1H-pyrazole (100.0 mg, 0.20 mmol) prepared in Example 436 was added to a saturated solution of hydrochloric acid in ethyl acetate (3.0 mL). The reaction mixture was stirred at room temperature for 1 hour and then concentrated under reduced pressure to give 400.0 mg of 5-(2-chloro-phenyl)-1-[3-(piperazin-1-yl)-phenyl]-3-[di-(trifluoromethyl)-hydroxy-methyl]-4,5-dihydro-1H-pyrazole hydrochloride as a yellow liquid.

The 5-(2-chloro-phenyl)-1-[3-(piperazin-1-yl)-phenyl]-3-[di-(trifluoromethyl)-hydroxy-methyl]-4,5-dihydro-1H-pyrazole hydrochloride (30.0 mg, 0.055 mmol) in the form of a yellow liquid, methanesulfonyl chloride (7.6 mg, 0.066 mmol), and triethylamine (31.0 uL, 0.221 mmol) were added to dichloromethane (1.0 mL). The reaction mixture was stirred at room temperature for 16 hours, washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/2) to give 15.0 mg of the titled compound as a yellow liquid.

$^1$H NMR (400 MHz, CDCl$_3$) 7.44 (d, 1H), 7.28-7.08 (m, 5H), 6.52 (s, 1H), 6.47 (d, 1H), 6.40 (d, 1H), 5.83 (dd, 1H), 4.85 (s, 1H), 3.75 (dd, 1H), 3.34 (d, 4H), 3.21 (d, 4H), 2.89 (dd, 1H), 2.80 (s, 3H)

Example 440

5-(2-chloro-phenyl)-1-[3-(4-cyclopropanesulfonyl-piperazin-1-yl)-phenyl]-3-[di-(trifluoromethyl)-hydroxy-methyl]-4,5-dihydro-1H-pyrazole 5-(2-Chloro-phenyl)-1-[3-(4-BOC-piperazin-1-yl)-phenyl]-3-[di-(trifluoromethyl)-hydroxy-methyl]-4,5-dihydro-1H-pyrazole (100.0 mg, 0.20 mmol) prepared in Example 436 was added to a saturated solution of hydrochloric acid in ethyl acetate (3.0 mL). The reaction mixture was stirred at room temperature for 1 hour and then concentrated under reduced pressure to give 400.0 mg of 5-(2-chloro-phenyl)-1-[3-(piperazin-1-yl)-phenyl]-3-[di-(trifluoromethyl)-hydroxy-methyl]-4,5-dihydro-1H-pyrazole hydrochloride as a yellow liquid.

The 5-(2-chloro-phenyl)-1-[3-(piperazin-1-yl)-phenyl]-3-[di-(trifluoromethyl)-hydroxy-methyl]-4,5-dihydro-1H-pyrazole hydrochloride (30.0 mg, 0.055 mmol) in the form of a yellow liquid, cyclopropanesulfonyl chloride (9.3 mg, 0.066 mmol), and triethylamine (31.0 uL, 0.221 mmol) were added to dichloromethane (1.0 mL). The reaction mixture was stirred at room temperature for 16 hours, washed with distilled water and brine, dried on anhydrous magnesium sulfate, and then concentrated under reduced pressure to give a yellow liquid residue. The resulting residue was purified by silica gel column chromatography (eluent: ethyl acetate/n-hexane=1/2) to give 15.0 mg of the titled compound as a yellow liquid.

$^1$H NMR (400 MHz, CDCl$_3$) 7.44 (d, 1H), 7.28-7.08 (m, 5H), 6.52 (s, 1H), 6.47 (d, 1H), 6.40 (d, 1H), 5.83 (dd, 1H), 4.85 (s, 1H), 3.75 (dd, 1H), 3.34 (d, 4H), 3.21 (d, 4H), 2.89 (dd, 1H), 2.26 (m, 1H), 1.24 (m, 2H), 1.01 (m, 2H)

Test Example

Assay for Transcriptional Activity of LXRβ

The ligand-binding domain (LBD) cDNA of human LXRβ was inserted into an expression vector (pFA, Stratagene, USA) site adjacent to the yeast GAL4 transcription factor DNA binding domain to prepare an expression construct (pFA-hLXRβ/GAL4) (Willey et al., Genes & Development 9 1033-1045 (1995). The GAL4-responsive luciferase reporter plasmid, i.e., pUAS (Stratagene, USA), contained five copies of the GAL4 response element placed adjacent to the promoter and the luciferase reporter gene. The pFA-hLXRβ/GAL4 and pUAS were introduced into mammalian cells through transient transfection, followed by measuring the transcriptional activity of LXRβ.

HEK293 cells (human kidney cells, sATCC, CRL-1573) were incubated at a T-75 flask containing a DMEM supplemented with 10% fetal bovine serum (FBS) in a 37° C., until they reach about 70~80% confluency. The culture media containing the cells was added to each well of a 96-well plate in a density of 5×10$^4$ cells per well. The pFA-hLXRβ/GAL4 and pUAS was transfected to the cells using a cationic-lipid transfection reagent (Lipofectamine™, Invitrogen), through culturing at 37° C. for 3 hours for transient transfection according to the manufacturer's instruction. The test compounds were dissolved in dimethyl sulfoxide (DMSO) in the concentrations of 50, 30, 10, 3, 1, 0.3, 0.1, 0.03, and 0.01 μM and then cells were treated with the prepared compound-containing solution (100 μl). The cells were incubated at 37° C. for 24 hours. After removal of the medium from each well, the lysis buffer (25 mM Tricine pH7.8, 2 mM DTT, 2 mM EGTA, 10% glycerol, 1% Triton X-100) was added with the amount of 20 μl per each well, and the plate was stirred at room temperature for 15 minutes. The luciferase reagent (prepared by adding 10 ml of the luciferase buffer (Promega) to 1 vial of the luciferase substrate (Promega)) was added to each well with the amount of 100 μl per well, followed by assaying with a luminometer according to the manufacturer's instruction.

The dose-response curve for calculating the EC$_{50}$ values of the test compounds on the increase of transcriptional activity of LXRβ was prepared using the known LXR agonist (i.e., N-(2,2,2-trifluoro-ethyl)-N-[4-(2,2,2-trifluoro-1-hydroxy-1-trifluoromethyl-ethyl)-phenyl]-benzenesulfonamide) as a positive control and the vehicle (DMSO) as a negative control. The dose-response curve was produced from the 9-point curve having different concentrations at a 1/2 log unit. The EC$_{50}$ value of a test compound, which is defined as a concentration for initiating the reaction corresponding to the half value between the Top value (i.e., the maximum value) and the Bottom value (baseline), was calculated according to the following equation.

$$Y = \text{Bottom} + (\text{Top} - \text{Bottom})/(1 + 10^{((\log EC50 - X)*\text{Hill Slope})}).$$

In the above equation, Y is the observed value; X is the log concentration; Hill Slope is the slope of the curve; and Top and Bottom are the maximum value of test compound and the baseline value, respectively.

The following tables 1 and 2 show the $EC_{50}$ values of the test compounds measured as in the above. In the tables 1 and 2, each $EC_{50}$ value represents an average value obtained from three independent tests.

TABLE 1

| No. | EC50 (nM) | Emax (fold) |
|---|---|---|
| 5 | 330 | 48 |
| 15 | 14850 | 23 |
| 18 | 692 | 103 |
| 30 | 8572 | 66 |
| 31 | 5664 | 28 |
| 41 | 1655 | 89 |
| 42 | 593 | 103 |
| 51 | 2480 | 61 |
| 52 | 546 | 56 |
| 53 | 746 | 61 |
| 54 | 6434 | 17 |
| 55 | 4904 | 73 |
| 56 | 2219 | 78 |
| 57 | 4771 | 39 |
| 60 | 20070 | 11 |
| 62 | 1160 | 59 |
| 64 | 1297 | 48 |
| 68 | 192 | 75 |
| 69 | 1096 | 83 |
| 70 | 466 | 62 |
| 71 | 1232 | 20 |
| 72 | 15199 | 9 |
| 73 | 1069 | 13 |
| 74 | 2960 | 29 |
| 75 | 1122 | 63 |
| 76 | 189 | 84 |
| 77 | 7180 | 57 |
| 78 | 2498 | 25 |
| 79 | 747 | 46 |
| 81 | 1400 | 78 |
| 86 | 958 | 45 |
| 87 | 91 | 46 |
| 88 | 819 | 72 |
| 89 | 382 | 106 |
| 90 | 2647 | 33 |
| 91 | 1460 | 44 |
| 92 | 344 | 81 |
| 94 | 19000 | 27 |
| 96 | 3360 | 67 |
| 97 | 3092 | 69 |
| 105 | 6311 | 55 |
| 106 | 1157 | 85 |
| 108 | 993 | 44 |
| 111 | 4154 | 41 |
| 112 | 8524 | 57 |
| 129 | 7992 | 44 |
| 130 | 10300 | 34 |
| 131 | 12800 | 45 |
| 138 | 501 | 153 |
| 139 | 368 | 110 |
| 140 | 1770 | 143 |
| 141 | 18 | 127 |
| 142 | 181 | 73 |
| 145 | 885 | 107 |
| 146 | 842 | 105 |
| 149 | 303 | 124 |
| 157 | 397 | 96 |
| 162 | 2930 | 59 |
| 165 | 225 | 157 |
| 166 | 7054 | 56 |

TABLE 1-continued

| No. | EC50 (nM) | Emax (fold) |
|---|---|---|
| 168 | 6118 | 30 |
| 172 | 1024 | 73 |
| 173 | 2488 | 102 |
| 174 | 543 | 119 |
| 177 | 26 | 57 |
| 178 | 543 | 82 |
| 180 | 513 | 118 |
| 183 | 3280 | 79 |
| 184 | 2837 | 81 |
| 188 | 304 | 107 |
| 189 | 2717 | 56 |
| 191 | 6698 | 50 |
| 194 | 3626 | 95 |
| 206 | 1400 | 87 |
| 207 | 6144 | 16 |
| 208 | 6068 | 22 |
| 209 | 5107 | 20 |
| 210 | 4470 | 25 |
| 211 | 509 | 29 |
| 212 | 1619 | 9 |
| 229 | 76 | 126 |
| 230 | 36 | 137 |
| 231 | 8 | 107 |
| 232 | 70 | 77 |
| 233 | 21 | 72 |
| 234 | 13 | 49 |
| 235 | 31 | 63 |
| 236 | 49 | 71 |
| 237 | 119 | 81 |
| 240 | 157 | 44 |
| 241 | 3348 | 47 |
| 242 | 14120 | 89 |
| 243 | 617 | 112 |
| 244 | 298 | 100 |
| 245 | 2427 | 57 |
| 246 | 1415 | 47 |
| 247 | 2035 | 33 |
| 248 | 2476 | 43 |
| 249 | 784 | 115 |
| 250 | 625 | 107 |
| 251 | 1952 | 96 |
| 252 | 2353 | 62 |
| 253 | 1069 | 55 |
| 254 | 7062 | 50 |
| 255 | 1080 | 58 |
| 256 | 729 | 51 |
| 257 | 1845 | 57 |
| 258 | 302 | 62 |
| 259 | 519 | 57 |
| 260 | 1871 | 47 |
| 261 | 699 | 54 |
| 262 | 6865 | 92 |
| 263 | 1271 | 72 |
| 265 | 239 | 97 |
| 266 | 1393 | 80 |
| 267 | 442 | 59 |
| 268 | 452 | 88 |
| 269 | 7930 | 44 |
| 270 | 437 | 48 |
| 271 | 547 | 45 |
| 272 | 2250 | 24 |
| 273 | 1152 | 45 |
| 274 | 1012 | 55 |
| 276 | 1238 | 87 |
| 277 | 364 | 65 |
| 278 | 731 | 68 |
| 279 | 931 | 67 |
| 280 | 556 | 81 |
| 281 | 1790 | 66 |
| 283 | 270 | 51 |
| 284 | 635 | 56 |
| 285 | 62 | 73 |
| 286 | 632 | 36 |
| 287 | 519 | 47 |
| 288 | 727 | 40 |
| 289 | 320 | 32 |
| 290 | 161 | 29 |

TABLE 1-continued

| No. | EC50 (nM) | Emax (fold) |
|---|---|---|
| 298 | 304 | 88 |
| 299 | 316 | 83 |
| 300 | 635 | 53 |

TABLE 2

| No. | EC50 (nM) | Emax (fold) |
|---|---|---|
| 301 | 479 | 73 |
| 302 | 849 | 45 |
| 304 | 521 | 104 |
| 305 | 304 | 66 |
| 306 | 1253 | 59 |
| 307 | 5466 | 52 |
| 308 | 495 | 36 |
| 309 | 1938 | 84 |
| 310 | 1147 | 78 |
| 312 | 2540 | 46 |
| 313 | 1121 | 56 |
| 314 | 883 | 59 |
| 315 | 1490 | 59 |
| 316 | 706 | 43 |
| 319 | 1829 | 39 |
| 320 | 1656 | 17 |
| 322 | 778 | 64 |
| 323 | 344 | 54 |
| 324 | 3745 | 37 |
| 325 | 800 | 53 |
| 326 | 550 | 51 |
| 329 | 2027 | 39 |
| 334 | 295 | 102 |
| 335 | 136 | 94 |
| 336 | 1471 | 72 |
| 337 | 1070 | 80 |
| 338 | 850 | 87 |
| 339 | 1110 | 71 |
| 340 | 780 | 101 |
| 341 | 353 | 112 |
| 342 | 4069 | 21 |
| 343 | 617 | 81 |
| 344 | 989 | 53 |
| 345 | 71 | 42 |
| 347 | 42 | 62 |
| 348 | 991 | 45 |
| 349 | 772 | 60 |
| 353 | 473 | 94 |
| 355 | 4133 | 43 |
| 358 | 719 | 90 |
| 359 | 630 | 92 |
| 360 | 10190 | 45 |
| 361 | 632 | 39 |
| 362 | 580 | 72 |
| 363 | 1215 | 50 |
| 365 | 283 | 68 |
| 367 | 312 | 59 |
| 368 | 1916 | 57 |
| 369 | 666 | 28 |
| 370 | 821 | 36 |
| 371 | 636 | 34 |
| 372 | 412 | 42 |
| 373 | 551 | 39 |
| 374 | 678 | 60 |
| 376 | 325 | 39 |
| 377 | 890 | 15 |
| 378 | 744 | 30 |
| 379 | 745 | 35 |
| 380 | 450 | 38 |
| 381 | 448 | 50 |
| 382 | 772 | 44 |
| 383 | 368 | 49 |
| 384 | 94 | 46 |
| 385 | 771 | 60 |
| 386 | 170 | 35 |

TABLE 2-continued

| No. | EC50 (nM) | Emax (fold) |
|---|---|---|
| 387 | 47 | 27 |
| 388 | 60 | 25 |
| 389 | 503 | 29 |
| 390 | 318 | 55 |
| 391 | 173 | 26 |
| 392 | 147 | 26 |
| 393 | 790 | 8 |
| 394 | 83 | 50 |
| 395 | 0.4 | 83 |
| 396 | 145 | 83 |
| 398 | 1811 | 12 |
| 400 | 379 | 38 |
| 401 | 785 | 45 |
| 402 | 1022 | 23 |
| 403 | 1170 | 22 |
| 404 | 5274 | 15 |
| 406 | 966 | 53 |
| 407 | 731 | 58 |
| 410 | 154 | 74 |
| 411 | 461 | 62 |
| 412 | 727 | 53 |
| 413 | 156 | 49 |
| 414 | 193 | 125 |
| 415 | 346 | 100 |
| 416 | 1115 | 90 |
| 417 | 1031 | 58 |
| 418 | 373 | 106 |
| 419 | ND | 82 |
| 420 | ND | 80 |
| 431 | 2237 | 17 |
| 433 | 6599 | 13 |
| 434 | 354 | 30 |
| 435 | 965 | 25 |
| 437 | 932 | 13 |
| 438 | 1933 | 6 |

\* In the tables 1 and 2, the Emax represents the fold value in comparison with the control (i.e., the DMSO-treated group).

As shown in Tables 1 and 2, the compounds of the present invention effectively increase the LXR transcriptional activity, and therefore they can be usefully applied for preventing or treating a dysfunction in cholesterol metabolism, including cholesterol gallstone, hyperlipidemia, and coronary atherosclerosis.

The invention claimed is:

1. A compound of Formula 1 or its pharmaceutically acceptable salt:

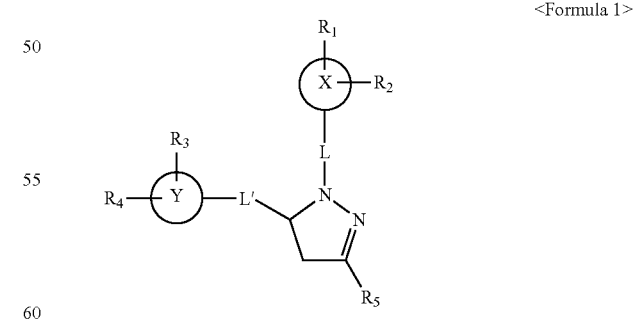

<Formula 1> wherein,
L is $-(CH_2)_n-$, n is 0 or 1,
L' is $-(CH_2)_n-$, n is 0,
Ring X is a $C_3 \sim C_6$ cycloalkyl ring; benzene; pyridine; or pyridazine,
Ring Y is benzene; pyridine; or thiophene, $R_1$ and $R_3$ are, independently each other, hydrogen or halogen, $R_2$ and $R_4$ are, independently each other, hydrogen; halogen; a $C_1\sim C_5$ alkyl group optionally substituted with one or more halogens; a $C_1\sim C_5$ alkoxy group; an aryl group; a heteroaryl group; or a heterocyclic group, when $R_2$ and $R_4$ are, independently each other, an aryl group, a heteroaryl group or a heterocyclic group, the aryl group, the heteroaryl group or the heterocyclic group is optionally substituted with one or more substituents selected from the group consisting of halogen; hydroxyl; cyano; azido; $C_1\sim C_5$ alkyl optionally substituted with one or more substituents selected from the group consisting of halogen, hydroxy, and hydroxyimino; $C_2\sim C_6$ alkenyl; $C_2\sim C_6$ alkynyl; $C_3\sim C_6$ cycloalkyl; aryl; heteroaryl; heterocyclic; —$SO_3H$; —$SO_2R$; —SOR; —SR;

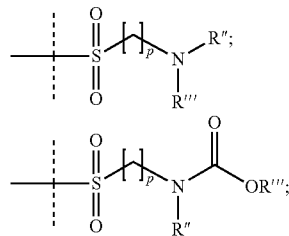

—OR; —COR; —$CO_2R$; —OC(=O)R; —$OCO_2R$; —OC(=O)NRR'; —NR"C(=O)R'''; —NR"C(=O)OR'''; —NR"$SO_2$R'''; —CONR"R'''; and —NR"R''', R and R' are, independently each other, hydrogen; a $C_1\sim C_5$ alkyl group optionally substituted with one or more substituents selected from the group consisting of halogen, hydroxy and $C_3\sim C_6$ cycloalkyl; a $C_3\sim C_6$ cycloalkyl group; an aryl group optionally substituted with one or more halogens; an aralkyl group; a heteroaryl group; or a heterocyclic group, R" and R''' are, independently each other, hydrogen; a $C_1\sim C_5$ alkyl group optionally substituted with one or more substituents selected from the group consisting of halogen and hydroxy; a $C_3\sim C_6$ cycloalkyl group; or an aryl group, p is 0, 1, 2, 3, 4, or 5, and $R_5$ is $CF_2CF_3$ or $C(CF_3)_2OH$.

2. The compound or its pharmaceutically acceptable salt of claim 1, wherein Ring Y is benzene.

3. The compound or its pharmaceutically acceptable salt of claim 1, wherein Ring Y is pyridine.

4. The compound or its pharmaceutically acceptable salt of claim 1, wherein Ring Y is thiophene.

5. The compound or its pharmaceutically acceptable salt of claim 1, wherein $R_5$ is $CF_2CF_3$.

6. The compound or its pharmaceutically acceptable salt of claim 5, wherein

L is —$(CH_2)_n$—, n is 0 or 1,

L' is —$(CH_2)_n$—, n is 0,

Ring X is a $C_3\sim C_6$ cycloalkyl ring; benzene; pyridine; or pyridazine,

Ring Y is benzene; pyridine; or thiophene, $R_1$ and $R_3$ are, independently each other, hydrogen or halogen, $R_2$ is hydrogen; halogen; a $C_1\sim C_5$ alkyl group optionally substituted with one or more halogens; a $C_1\sim C_5$ alkoxy group; a phenyl group; a pyridinyl group; a 1,2,3,6-tetrahydropyridinyl group; or a piperazinyl group, when $R_2$ is a phenyl group, a pyridinyl group, a 1,2,3,6-tetrahydropyridinyl group, or a piperazinyl group, the phenyl group, the pyridinyl group, the 1,2,3,6-tetrahydropyridinyl group, or the piperazinyl group is optionally substituted with one or more substituents selected from the group consisting of $C_1\sim C_5$ alkylthio; $C_1\sim C_5$ alkylsulfonyl; $C_3\sim C_6$ cycloalkylsulfonyl; $C_1\sim C_5$ alkoxycarbonyl;

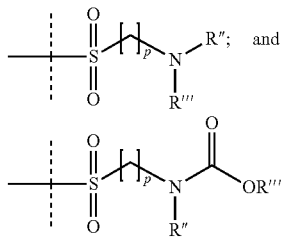

(wherein, R" and R''' are, independently each other, hydrogen; or a $C_1\sim C_5$ alkyl group optionally substituted with hydroxy, and p is 0, 1, 2, or 3), $R_4$ is halogen; a phenyl group; a heteroaryl group selected from the group consisting of pyrazolyl, pyridinyl, pyrimidinyl, and quinolinyl; or a heterocyclic group selected from the group consisting of pyrrolidinyl, 2-oxo-pyrrolidinyl, 1,2,3,6-tetrahydropyridinyl, piperidinyl, piperazinyl, morpholinyl, and homopiperazinyl, when $R_4$ is a phenyl group, the phenyl group is optionally substituted with one or more substituents selected from the group consisting of halogen; hydroxy; cyano; $C_1\sim C_5$ alkyl optionally substituted with one or more substituents selected from the group consisting of halogen, hydroxy, and hydroxyimino; $C_1\sim C_5$ alkoxy; $C_1\sim C_5$ alkylthio; $C_1\sim C_5$ alkylsulfonyl; $C_1\sim C_5$ alkylsulfinyl; $C_1\sim C_5$ alkylcarbonyl; triazolyl; tetrazolyl; —NR"R'''; —NR"$SO_2$R''';

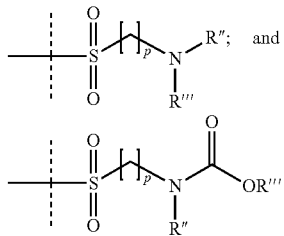

(wherein, p, R" and R''' are the same as defined in the above), when $R_4$ is a heteroaryl group or a heterocyclic group, the heteroaryl group or the heterocyclic group is optionally substituted with one or more substituents selected from the group consisting of halogen; cyano; hydroxy; $C_1\sim C_5$ alkyl optionally substituted with one or more substituents selected from the group consisting of halogen and hydroxy; $C_1\sim C_5$ alkoxy; formyl; $C_1\sim C_5$ alkylthio; $C_1\sim C_5$ alkylsulfonyl optionally substituted with trifluoromethyl; $C_3\sim C_6$ cycloalkylsulfonyl; mono or di-$C_1\sim C_5$ alkylaminosulfonyl; $C_1\sim C_5$ alkylcarbonyl; $C_1\sim C_5$ alkoxycarbonyl; mono or di-$C_1\sim C_5$ alkylaminocarbonyl; amino; $C_1\sim C_5$ alkylsulfonylamino; $C_3\sim C_6$ cycloalkylsulfonylamino; and $C_1\sim C_5$ alkoxycarbonylamino.

7. The compound or its pharmaceutically acceptable salt of claim 5, wherein $R_3$ is hydrogen.

8. The compound or its pharmaceutically acceptable salt of claim 5, wherein $R_3$ is halogen; and Ring X and Ring Y are benzene.

9. The compound or its pharmaceutically acceptable salt of claim 5, wherein $R_3$ and $R_4$ are halogen; Ring X and Ring Y are benzene; $R_2$ is a phenyl group, a pyridinyl group, a 1,2,3,6-tetrahydropyridinyl group, or a piperazinyl group [where the phenyl group, the pyridinyl group, the 1,2,3,6-tetrahydropyridinyl group, or the piperazinyl group is optionally substituted with one or more substituents selected from the group consisting of $C_1$~$C_5$ alkylthio; $C_1$~$C_5$ alkylsulfonyl; $C_3$~$C_6$ cycloalkylsulfonyl; $C_1$~$C_5$ alkoxycarbonyl;

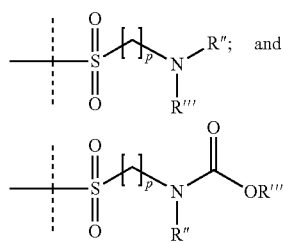

(wherein, R" and R'" are, independently each other, hydrogen; or $C_1$~$C_5$ alkyl optionally substituted with hydroxy, and p is 0, 1, 2, or 3)].

10. The compound or its pharmaceutically acceptable salt of claim 1, wherein $R_5$ is $C(CF_3)_2OH$.

11. The compound or its pharmaceutically acceptable salt of claim 10, wherein
n is 0,
Ring X is benzene,
Ring Y is benzene; pyridine; or thiophene,
$R_1$ and $R_3$ are, independently each other, hydrogen or halogen,
$R_2$ is halogen; a phenyl group; a pyridinyl group; a 1,2,3,6-tetrahydropyridinyl group; or a piperazinyl group,
when $R_2$ is a phenyl group, a pyridinyl group, a 1,2,3,6-tetrahydropyridinyl group, or a piperazinyl group, the phenyl group, the pyridinyl group, the 1,2,3,6-tetrahydropyridinyl group, or the piperazinyl group is optionally substituted with one or more substituents selected from the group consisting of $C_1$~$C_5$ alkylthio; $C_1$~$C_5$ alkylsulfonyl; $C_3$~$C_6$ cycloalkylsulfonyl; and $C_1$~$C_5$ alkoxycarbonyl,
$R_4$ is halogen; a phenyl group; a heteroaryl group selected from the group consisting of furanyl, pyridinyl, pyrimidinyl, indolyl, benzofuranyl, benzothienyl, and quinolinyl; or a heterocyclic group selected from the group consisting of 1,2,3,6-tetrahydropyridinyl, piperidinyl, piperazinyl, 1,1-dioxo-thiomorpholinyl, and homopiperazinyl,
when $R_4$ is a phenyl group, the phenyl group is optionally substituted with one or more substituents selected from the group consisting of halogen; hydroxy; cyano; $C_1$~$C_5$ alkyl optionally substituted with one or more substituents selected from the group consisting of halogen and hydroxy; $C_1$~$C_5$ alkoxy optionally substituted with one or more halogens; $C_1$~$C_5$ alkylthio; $C_1$~$C_5$ alkylsulfonyl; $C_1$~$C_5$ alkylsulfinyl; $C_1$~$C_5$ alkylcarbonyl; hydroxycarbonyl; triazolyl; tetrazolyl; —NR"R'"; —NR"SO$_2$R'"; —NR"C(=O)R'";

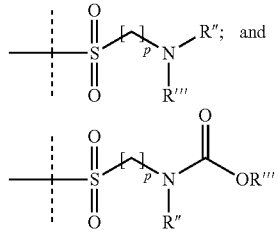

(wherein, R" and R'" are, independently each other, hydrogen, $C_1$~$C_5$ alkyl optionally substituted with hydroxy, or $C_3$~$C_6$ cycloalkyl, and p is 0, 1, 2, or 3),
when $R_4$ is a heteroaryl group or a heterocyclic group, the heteroaryl group or the heterocyclic group is optionally substituted with one or more substituents selected from the group consisting of halogen; cyano; $C_1$~$C_5$ alkyl optionally substituted with one or more halogens; $C_1$~$C_5$ alkoxy; formyl; $C_1$~$C_5$ alkylthio; $C_1$~$C_5$ alkylsulfonyl alkyl optionally substituted with one or more halogens; $C_3$~$C_6$ cycloalkylsulfonyl; benzenesulfonyl; pyrrolidin-1-yl-sulfonyl; mono or di-$C_1$~$C_5$ alkylaminosulfonyl; $C_1$~$C_5$ alkylcarbonyl optionally substituted with hydroxy; $C_3$~$C_6$ cycloalkylcarbonyl; $C_3$~$C_6$ cycloalkyl-$C_1$~$C_5$ alkylcarbonyl; benzoyl optionally substituted with halogen; benzylcarbonyl; thiophenecarbonyl; $C_1$~$C_5$ alkoxycarbonyl; hydroxycarbonyl; mono or di-$C_1$~$C_5$ alkylaminocarbonyl; amino; $C_3$~$C_6$ cycloalkylsulfonylamino; $C_1$~$C_5$ alkoxycarbonylamino; and tetrazolyl.

12. The compound or its pharmaceutically acceptable salt of claim 10, wherein $R_3$ is hydrogen.

13. The compound or its pharmaceutically acceptable salt of claim 10, wherein $R_3$ is halogen; and Ring X and Ring Y are benzene.

14. The compound or its pharmaceutically acceptable salt of claim 10, wherein $R_3$ is hydrogen; $R_4$ is halogen; Ring X and Ring Y are benzene; $R_2$ is a phenyl group, a pyridinyl group, a 1,2,3,6-tetrahydropyridinyl group, or a piperazinyl group (where the phenyl group, the pyridinyl group, the 1,2,3,6-tetrahydropyridinyl, or the piperazinyl group is optionally substituted with one or more substituents selected from the group consisting of $C_1$~$C_5$ alkylthio; $C_1$~$C_5$ alkylsulfonyl; $C_3$~$C_6$ cycloalkylsulfonyl; and $C_1$~$C_5$ alkoxycarbonyl).

15. The compound or its pharmaceutically acceptable salt of claim 1, which is selected from the group consisting of:
1-(2-chloro-phenyl)-5-(4'-(methylsulfanyl)-biphenyl-4-yl)-3-pentafluoroethyl-4,5-dihydro-1H-pyrazole;
1-(2-chloro-phenyl)-3-pentafluoroethyl-5-[4'-(trifluoromethyl)-biphenyl-4-yl]-4,5-dihydro-1H-pyrazole;
1-(2-chloro-phenyl)-5-[4'-(N,N-dimethylamino)-biphenyl-4-yl]-3-pentafluoroethyl-4,5-dihydro-1H-pyrazole;
1-(2-chloro-phenyl)-5-[2'-(methylsulfonyl)-biphenyl-4-yl]-3-pentafluoroethyl-4,5-dihydro-1H-pyrazole;
1-(2-chloro-phenyl)-5-[3'-(methylsulfonyl)-biphenyl-4-yl]-3-pentafluoroethyl-4,5-dihydro-1H-pyrazole;
1-(2-chloro-phenyl)-5-[4'-(methylsulfonyl)-biphenyl-4-yl]-3-pentafluoroethyl-4,5-dihydro-1H-pyrazole;
1-(2-chloro-phenyl)-5-[3'-(methylsulfinyl)-biphenyl-4-yl]-3-pentafluoroethyl-4,5-dihydro-1H-pyrazole;
1-(2-chloro-phenyl)-5-[4'-(methylsulfinyl)-biphenyl-4-yl]-3-pentafluoroethyl-4,5-dihydro-1H-pyrazole;
1-(2-chloro-phenyl)-5-[4-(1-BOC-1,2,3,6-tetrahydropyridin-4-yl)-phenyl]-3-pentafluoroethyl-4,5-dihydro-1H-pyrazole;

1-(2-chloro-phenyl)-5-[4-(1,2,3,6-tetrahydropyridin-4-yl)-phenyl]-3-pentafluoroethyl-4,5-dihydro-1H-pyrazole trifluoroacetate;
1-(2-chloro-phenyl)-5-[4-(1-methanesulfonyl-1,2,3,6-tetrahydropyridin-4-yl)-phenyl]-3-pentafluoroethyl-4,5-dihydro-1H-pyrazole;
1-(2-chloro-phenyl)-5-(3'-methylsulfanyl-biphenyl-4-yl)-3-pentafluoroethyl-4,5-dihydro-1H-pyrazole;
1-(2,4-dichloro-phenyl)-5-(3'-methylsulfanyl-biphenyl-4-yl)-3-pentafluoroethyl-4,5-dihydro-1H-pyrazole;
1-(2,4-difluoro-phenyl)-5-(3'-methylsulfanyl-biphenyl-4-yl)-3-pentafluoroethyl-4,5-dihydro-1H-pyrazole;
1-(2-chloro-benzyl)-5-(3'-methylsulfanyl-biphenyl-4-yl)-3-pentafluoroethyl-4,5-dihydro-1H-pyrazole;
1-(2,4-dichloro-phenyl)-5-(3'-methanesulfonyl-biphenyl-4-yl)-3-pentafluoroethyl-4,5-dihydro-1H-pyrazole;
1-(2,4-dichloro-phenyl)-5-(3'-methanesulfinyl-biphenyl-4-yl)-3-pentafluoroethyl-4,5-dihydro-1H-pyrazole;
1-(2,4-difluoro-phenyl)-5-(3'-methanesulfonyl-biphenyl-4-yl)-3-pentafluoroethyl-4,5-dihydro-1H-pyrazole;
1-(2-chloro-phenyl)-5-[5-(3-acetyl-phenyl)-pyridin-2-yl]-3-pentafluoroethyl-4,5-dihydro-1H-pyrazole;
1-(2-chloro-phenyl)-5-[5-(4-methoxy-phenyl)-pyridin-2-yl]-3-pentafluoroethyl-4,5-dihydro-1H-pyrazole;
1-(2-chloro-phenyl)-5-[5-(3-methylsulfanyl-phenyl)-pyridin-2-yl]-3-pentafluoroethyl-4,5-dihydro-1H-pyrazole;
1-(2-chloro-phenyl)-5-[5-(4-methanesulfonyl-phenyl)-pyridin-2-yl]-3-pentafluoroethyl-4,5-dihydro-1H-pyrazole;
1-(4-chloro-phenyl)-5-(4'-methylsulfanyl-biphenyl-3-yl)-3-pentafluoroethyl-4,5-dihydro-1H-pyrazole;
1-(3-chloro-phenyl)-5-(4'-methylsulfanyl-biphenyl-3-yl)-3-pentafluoroethyl-4,5-dihydro-1H-pyrazole;
1-(2,4-dichloro-phenyl)-5-(4'-methylsulfanyl-biphenyl-3-yl)-3-pentafluoroethyl-4,5-dihydro-1H-pyrazole;
5-(4'-methylsulfanyl-biphenyl-3-yl)-3-pentafluoroethyl-1-(2-trifluoromethyl-phenyl)-4,5-dihydro-1H-pyrazole;
5-(4'-methylsulfanyl-biphenyl-3-yl)-3-pentafluoroethyl-1-ortho-tolyl-4,5-dihydro-1H-pyrazole;
1-(2-methoxy-phenyl)-5-(4'-methylsulfanyl-biphenyl-3-yl)-3-pentafluoroethyl-4,5-dihydro-1H-pyrazole;
5-(4'-methylsulfanyl-biphenyl-3-yl)-3-pentafluoroethyl-1-phenyl-4,5-dihydro-1H-pyrazole;
1-(2,4-difluoro-phenyl)-5-(4'-methylsulfanyl-biphenyl-3-yl)-3-pentafluoroethyl-4,5-dihydro-1H-pyrazole;
1-(4-chloro-2-fluoro-phenyl)-5-(4'-methylsulfanyl-biphenyl-3-yl)-3-pentafluoroethyl-4,5-dihydro-1H-pyrazole;
1-(2-chloro-benzyl)-5-(4'-methylsulfanyl-biphenyl-3-yl)-3-pentafluoroethyl-4,5-dihydro-1H-pyrazole;
1-cyclohexyl-5-(4'-methylsulfanyl-biphenyl-3-yl)-3-pentafluoroethyl-4,5-dihydro-1H-pyrazole;
1-(pyridin-2-yl)-5-(4'-methylsulfanyl-biphenyl-3-yl)-3-pentafluoroethyl-4,5-dihydro-1H-pyrazole;
1-(6-chloro-pyridazin-3-yl)-5-(4'-methylsulfanyl-biphenyl-3-yl)-3-pentafluoroethyl-4,5-dihydro-1H-pyrazole;
1-benzyl-5-(4'-methylsulfanyl-biphenyl-3-yl)-3-pentafluoroethyl-4,5-dihydro-1H-pyrazole;
1-(3-chloro-phenyl)-5-(4'-methanesulfinyl-biphenyl-3-yl)-3-pentafluoroethyl-4,5-dihydro-1H-pyrazole;
1-(3-chloro-phenyl)-5-(4'-methanesulfonyl-biphenyl-3-yl)-3-pentafluoroethyl-4,5-dihydro-1H-pyrazole;
1-(4-chloro-phenyl)-5-(4'-methanesulfonyl-biphenyl-3-yl)-3-pentafluoroethyl-4,5-dihydro-1H-pyrazole;
1-(4-chloro-phenyl)-5-(4'-methanesulfinyl-biphenyl-3-yl)-3-pentafluoroethyl-4,5-dihydro-1H-pyrazole;
1-(2,4-dichloro-phenyl)-5-(4'-methanesulfonyl-biphenyl-3-yl)-3-pentafluoroethyl-4,5-dihydro-1H-pyrazole;
1-(2,4-dichloro-phenyl)-5-(4'-methanesulfinyl-biphenyl-3-yl)-3-pentafluoroethyl-4,5-dihydro-1H-pyrazole;
5-(4'-methanesulfonyl-biphenyl-3-yl)-3-pentafluoroethyl-1-(2-trifluoromethyl-phenyl)-4,5-dihydro-1H-pyrazole;
5-(4'-methanesulfinyl-biphenyl-3-yl)-3-pentafluoroethyl-1-(2-trifluoromethyl-phenyl)-4,5-dihydro-1H-pyrazole;
5-(4'-methanesulfonyl-biphenyl-3-yl)-3-pentafluoroethyl-1-ortho-tolyl-4,5-dihydro-1H-pyrazole;
5-(4'-methanesulfonyl-biphenyl-3-yl)-3-pentafluoroethyl-1-(2-methoxy-phenyl)-4,5-dihydro-1H-pyrazole;
1-(pyridin-2-yl)-5-(4'-methanesulfonyl-biphenyl-3-yl)-3-pentafluoroethyl-4,5-dihydro-1H-pyrazole;
1-(6-chloro-pyridazin-3-yl)-5-(4'-methanesulfonyl-biphenyl-3-yl)-3-pentafluoroethyl-4,5-dihydro-1H-pyrazole;
1-benzyl-5-(4'-methanesulfonyl-biphenyl-3-yl)-3-pentafluoroethyl-4,5-dihydro-1H-pyrazole;
5-(4'-methanesulfonyl-biphenyl-3-yl)-3-pentafluoroethyl-1-phenyl-4,5-dihydro-1H-pyrazole;
1-(2,4-difluoro-phenyl)-5-(4'-methanesulfonyl-biphenyl-3-yl)-3-pentafluoroethyl-4,5-dihydro-1H-pyrazole;
1-(2,4-difluoro-phenyl)-5-(4'-methanesulfinyl-biphenyl-3-yl)-3-pentafluoroethyl-4,5-dihydro-1H-pyrazole;
1-(4-chloro-2-fluoro-phenyl)-5-(4'-methanesulfonyl-biphenyl-3-yl)-3-pentafluoroethyl-4,5-dihydro-1H-pyrazole;
1-(2-chloro-benzyl)-5-(4'-methanesulfonyl-biphenyl-3-yl)-3-pentafluoroethyl-4,5-dihydro-1H-pyrazole;
1-(2,4-difluoro-phenyl)-5-[3-(6-fluoro-pyridin-3-yl)-phenyl]-3-pentafluoroethyl-4,5-dihydro-1H-pyrazole;
1-(2,4-difluoro-phenyl)-5-[3-(6-methoxy-pyridin-3-yl)-phenyl]-3-pentafluoroethyl-4,5-dihydro-1H-pyrazole;
1-(2,4-difluoro-phenyl)-3-pentafluoroethyl-5-[3-(5-pyrimidyl)-phenyl]-4,5-dihydro-1H-pyrazole;
1-(2,4-difluoro-phenyl)-3-pentafluoroethyl-5-[4'-(1-tetrazolyl)-biphenyl-3-yl]-4,5-dihydro-1H-pyrazole;
1-(2,4-difluoro-phenyl)-3-pentafluoroethyl-5-[3-(1H-pyrazol-4-yl)-phenyl]-4,5-dihydro-1H-pyrazole;
5-[3-(1-BOC-1,2,3,6-tetrahydropyridin-4-yl)-phenyl]-1-(2,4-difluoro-phenyl)-3-pentafluoroethyl-4,5-dihydro-1H-pyrazole;
1-(2,4-difluoro-phenyl)-5-[3-(1,2,3,6-tetrahydropyridin-4-yl)-phenyl]-3-pentafluoroethyl-4,5-dihydro-1H-pyrazole trifluoroacetate;
1-(2,4-difluoro-phenyl)-5-[3-(1-methanesulfonyl-1,2,3,6-tetrahydropyridin-4-yl)-phenyl]-3-pentafluoroethyl-4,5-dihydro-1H-pyrazole;
1-(2,4-difluoro-phenyl)-5-[3-(1-isobutyryl-1,2,3,6-tetrahydropyridin-4-yl)-phenyl]-3-pentafluoroethyl-4,5-dihydro-1H-pyrazole;
1-(2,4-difluoro-phenyl)-5-[3-(1-dimethylcarbamoyl-1,2,3,6-tetrahydropyridin-4-yl)-phenyl]-3-pentafluoroethyl-4,5-dihydro-1H-pyrazole;
1-(2,4-difluoro-phenyl)-5-[3-(morpholin-4-yl)-phenyl]-3-pentafluoroethyl-4,5-dihydro-1H-pyrazole;
1-(2,4-difluoro-phenyl)-3-pentafluoroethyl-5-(3-pyrrolidin-1-yl-phenyl)-4,5-dihydro-1H-pyrazole;
1-(2,4-difluoro-phenyl)-3-pentafluoroethyl-5-[3-(piperidin-1-yl)-phenyl]-4,5-dihydro-1H-pyrazole;
5-(2',5'-difluoro-4'-methanesulfonyl-biphenyl-3-yl)-1-(2,4-difluoro-phenyl)-3-pentafluoroethyl-4,5-dihydro-1H-pyrazole;

1-(2,4-difluoro-phenyl)-5-(4'-methanesulfonyl-3'-trifluoromethyl-biphenyl-3-yl)-3-pentafluoroethyl-4,5-dihydro-1H-pyrazole;
5-[3'-cyano-4'-(methanesulfonyl)-biphenyl-3-yl]-1-(2,4-difluoro-phenyl)-3-pentafluoroethyl-4,5-dihydro-1H-pyrazole;
1-(2,4-difluoro-phenyl)-5-(3-(2-methyl-pyridin-3-yl)-phenyl)-3-pentafluoroethyl-4,5-dihydro-1H-pyrazole;
1-(2,4-difluoro-phenyl)-3-pentafluoroethyl-5-(3-(2-trifluoromethyl-pyridin-5-yl)-phenyl)-4,5-dihydro-1H-pyrazole;
1-(2,4-difluoro-phenyl)-5-(3-(3-formyl-2-methoxy-pyridin-5-yl)-phenyl)-3-pentafluoroethyl-4,5-dihydro-1H-pyrazole;
1-(2,4-difluoro-phenyl)-5-(3-(5-fluoro-pyridin-3-yl)-phenyl)-3-pentafluoroethyl-4,5-dihydro-1H-pyrazole;
1-(2,4-difluoro-phenyl)-5-(3-(2-methoxy-pyridin-3-yl)-phenyl)-3-pentafluoroethyl-4,5-dihydro-1H-pyrazole;
1-(2,4-difluoro-phenyl)-5-[3'-fluoro-4'-(hydroxymethyl)-5'-(methylsulfonyl)-biphenyl-3-yl]-3-pentafluoroethyl-4,5-dihydro-1H-pyrazole;
1-(2,4-difluoro-phenyl)-5-[3-(2-methylsulfanyl-pyridin-5-yl)-phenyl]-3-pentafluoroethyl-4,5-dihydro-1H-pyrazole;
5-[3-(2-cyano-pyridin-5-yl)-phenyl]-1-(2,4-difluoro-phenyl)-3-pentafluoroethyl-4,5-dihydro-1H-pyrazole;
1-(2,4-difluoro-phenyl)-5-[3-(5-formyl-pyridin-2-yl)-phenyl]-3-pentafluoroethyl-4,5-dihydro-1H-pyrazole;
1-(2,4-difluoro-phenyl)-5-[3-(6-hydroxy-pyridin-3-yl)-phenyl]-3-pentafluoroethyl-4,5-dihydro-1H-pyrazole;
1-(2,4-difluoro-phenyl)-5-[3-(5-methanesulfonyl-pyridin-2-yl)-phenyl]-3-pentafluoroethyl-4,5-dihydro-1H-pyrazole;
1-(2,4-difluoro-phenyl)-5-[3-(2,5-difluoro-4-[1,2,4]triazol-1-yl-phenyl)-phenyl]-3-pentafluoroethyl-4,5-dihydro-1H-pyrazole;
1-(2,4-difluoro-phenyl)-5-{3-[(2-hydroxy-ethyl)-methyl-sulfamoyl]-biphenyl-3-yl}-3-pentafluoroethyl-4,5-dihydro-1H-pyrazole;
1-(2,4-difluoro-phenyl)-5-{4'-[(2-hydroxy-ethyl)-(methanesulfonyl)-amino]-biphenyl-3-yl}-3-pentafluoroethyl-4,5-dihydroxy-1H-pyrazole;
5-{3'-[3-(N-BOC-N-methyl-amino)-propane-1-sulfonyl]-biphenyl-3-yl}-1-(2,4-difluoro-phenyl)-3-pentafluoroethyl-4,5-dihydro-1H-pyrazole;
5-{4'-[3-(N-BOC-N-methyl-amino)-propane-1-sulfonyl]-biphenyl-3-yl}-1-(2,4-difluoro-phenyl)-3-pentafluoroethyl-4,5-dihydro-1H-pyrazole;
1-(2,4-difluoro-phenyl)-5-(3'-dimethylsulfamoyl-biphenyl-3-yl)-3-pentafluoroethyl-4,5-dihydro-1H-pyrazole;
1-(2,4-difluoro-phenyl)-5-{4'-[(2-hydroxy-ethyl)-methyl-sulfamoyl]-biphenyl-3-yl}-3-pentafluoroethyl-4,5-dihydro-1H-pyrazole;
1-(2,4-difluoro-phenyl)-5-{3'-[3-(N-methyl-amino)-propane-1-sulfonyl]-biphenyl-3-yl}-3-pentafluoroethyl-4,5-dihydro-1H-pyrazole;
1-(2,4-difluoro-phenyl)-5-[3-(5-hydroxymethyl-6-methoxy-pyridin-3-yl)-phenyl]-3-pentafluoroethyl-4,5-dihydro-1H-pyrazole;
1-(2,4-difluoro-phenyl)-5-[3-(5-hydroxymethyl-pyridin-2-yl)-phenyl]-3-pentafluoroethyl-4,5-dihydro-1H-pyrazole;
1-(2,4-difluoro-phenyl)-5-[3-(6-methanesulfonyl-pyridin-3-yl)-phenyl]-3-pentafluoroethyl-4,5-dihydro-1H-pyrazole;
1-(2,4-difluoro-phenyl)-5-[3-(2-methanesulfonyl-pyrimidin-5-yl)-phenyl]-3-pentafluoroethyl-4,5-dihydro-1H-pyrazole;
5-biphenyl-3-yl-1-(2,4-difluoro-phenyl)-3-pentafluoroethyl-4,5-dihydro-1H-pyrazole;
5-[3-(4-BOC-piperazin-1-yl)-phenyl]-1-(2,4-difluoro-phenyl)-3-pentafluoroethyl-4,5-dihydro-1H-pyrazole;
1-(2,4-difluoro-phenyl)-5-[3-(4-methanesulfonyl-piperazin-1-yl)-phenyl]-3-pentafluoroethyl-4,5-dihydro-1H-pyrazole;
5-[3-(4-cyclopropanesulfonyl-piperazin-1-yl)-phenyl]-1-(2,4-difluoro-phenyl)-3-pentafluoroethyl-4,5-dihydro-1H-pyrazole;
5-{3-[4-(N-BOC-amino)-piperidin-1-yl]-phenyl}-1-(2,4-difluoro-phenyl)-3-pentafluoroethyl-4,5-dihydro-1H-pyrazole;
5-[3-(4-amino-piperidin-1-yl)-phenyl]-1-(2,4-difluoro-phenyl)-3-pentafluoroethyl-4,5-dihydro-1H-pyrazole hydrochloride;
1-(2,4-difluoro-phenyl)-5-[3-(4-methanesulfonylamino-piperidin-1-yl)-phenyl]-3-pentafluoroethyl-4,5-dihydro-1H-pyrazole;
1-(2-chloro-phenyl)-3-pentafluoroethyl-5-(3'-trifluoromethyl-biphenyl-3-yl)-4,5-dihydro-1H-pyrazole;
1-(2-chloro-phenyl)-5-(4'-methoxy-biphenyl-3-yl)-3-pentafluoroethyl-4,5-dihydro-1H-pyrazole;
1-(2-chloro-phenyl)-5-(4'-fluoro-biphenyl-3-yl)-3-pentafluoroethyl-4,5-dihydro-1H-pyrazole;
1-(2-chloro-phenyl)-5-(4'-dimethylamino-biphenyl-3-yl)-3-pentafluoroethyl-4,5-dihydro-1H-pyrazole;
1-(2-chloro-phenyl)-5-(4'-methylsulfanyl-biphenyl-3-yl)-3-pentafluoroethyl-4,5-dihydro-1H-pyrazole;
1-(2-chloro-phenyl)-5-(4'-methylsulfonyl-biphenyl-3-yl)-3-pentafluoroethyl-4,5-dihydro-1H-pyrazole;
5-(4'-acetyl-biphenyl-3-yl)-1-(2-chloro-phenyl)-3-pentafluoroethyl-4,5-dihydro-1H-pyrazole;
1-(2-chloro-phenyl)-5-[4'-(1-hydroxy-ethyl)-biphenyl-3-yl]-3-pentafluoroethyl-4,5-dihydro-1H-pyrazole;
1-(2-chloro-phenyl)-5-[4'-(1-hydroxyimino-ethyl)-biphenyl-3-yl]-3-pentafluoroethyl-4,5-dihydro-1H-pyrazole;
5-(2'-acetyl-biphenyl-3-yl)-1-(2-chloro-phenyl)-3-pentafluoroethyl-4.5-dihydro-1H-pyrazole;
1-(2-chloro-phenyl)-5-(3'-hydroxy-biphenyl-3-yl)-3-pentafluoroethyl-4.5-dihydro-1H-pyrazole;
1-(2-chloro-phenyl)-5-(3',4'-dimethoxy-biphenyl-3-yl)-3-pentafluoroethyl-4.5-dihydro-1H-pyrazole;
1-(2-chloro-phenyl)-5-(3-pyrimidin-5-yl-phenyl)-3-pentafluoroethyl-4.5-dihydro-1H-pyrazole;
1-(2-chloro-phenyl)-3-pentafluoroethyl-5-(3-quinolin-3-yl-phenyl)-4.5-dihydro-1H-pyrazole;
1-(2-chloro-phenyl)-5-[3-(6-methoxy-pyridin-3-yl)-phenyl]-3-pentafluoroethyl-4.5-dihydro-1H-pyrazole;
5-[3-(1-BOC-1,2,3,6-tetrahydropyridin-4-yl)-phenyl]-1-(2-chloro-phenyl)-3-pentafluoroethyl-4,5-dihydro-1H-pyrazole;
1-(2-chloro-phenyl)-5-[3-(1,2,3,6-tetrahydropyridin-4-yl)-phenyl]-3-pentafluoroethyl-4,5-dihydro-1H-pyrazole trifluoroacetate;
1-(2-chloro-phenyl)-5-[3-(1-methanesulfonyl-1,2,3,6-tetrahydropyridin-4-yl)-phenyl]-3-pentafluoroethyl-4,5-dihydro-1H-pyrazole;
5-[3-(4-BOC-piperazin-1-yl)-phenyl]-1-(2-chloro-phenyl)-3-pentafluoroethyl-4,5-dihydro-1H-pyrazole;
1-(2-chloro-phenyl)-5-[3-(4-methanesulfonyl-piperazin-1-yl)-phenyl]-3-pentafluoroethyl-4,5-dihydro-1H-pyrazole;

1-(2-chloro-phenyl)-5-[3-(4-dimethylsulfamoyl-piperazin-1-yl)-phenyl]-3-pentafluoroethyl-4,5-dihydro-1H-pyrazole;

1-(2-chloro-phenyl)-5-[3-(4-isobutyryl-piperazin-1-yl)-phenyl]-3-pentafluoroethyl-4,5-dihydro-1H-pyrazole;

1-(2-chloro-phenyl)-5-[3-(4-dimethylcarbamoyl-piperazin-1-yl)-phenyl]-3-pentafluoroethyl-4,5-dihydro-1H-pyrazole;

5-[3-(4-BOC-homopiperazin-1-yl)-phenyl]-1-(2-chloro-phenyl)-3-pentafluoroethyl-4,5-dihydro-1H-pyrazole;

1-(2-chloro-phenyl)-5-[3-(4-methanesulfonyl-homopiperazin-1-yl)-phenyl]-3-pentafluoroethyl-4,5-dihydro-1H-pyrazole;

1-(2-chloro-phenyl)-5-[3-(4-dimethylsulfamoyl-homopiperazin-1-yl)-phenyl]-3-pentafluoroethyl-4,5-dihydro-1H-pyrazole;

1-(2-chloro-phenyl)-5-[3-(4-isobutyryl-homopiperazin-1-yl)-phenyl]-3-pentafluoroethyl-4,5-dihydro-1H-pyrazole;

1-(2-chloro-phenyl)-5-[3-(4-dimethylcarbamoyl-homopiperazin-1-yl)-phenyl]-3-pentafluoroethyl-4,5-dihydro-1H-pyrazole;

1-(2,4-difluoro-phenyl)-5-(6-fluoro-4'-methanesulfonyl-biphenyl-3-yl)-3-pentafluoroethyl-4,5-dihydro-1H-pyrazole;

1-(2,4-difluoro-phenyl)-5-[4-fluoro-3-(6-chloro-pyridin-3-yl)-phenyl]-3-pentafluoroethyl-4,5-dihydro-1H-pyrazole;

1-(2,4-difluoro-phenyl)-5-[4-fluoro-3-(6-methoxy-pyridin-3-yl)-phenyl]-3-pentafluoroethyl-4,5-dihydro-1H-pyrazole;

1-(2,4-difluoro-phenyl)-5-[4-fluoro-3-(pyrimidin-5-yl)-phenyl]-3-pentafluoroethyl-4,5-dihydro-1H-pyrazole;

1-(2,4-difluoro-phenyl)-5-(4-fluoro-3-pyrrolidin-1-yl-phenyl)-3-pentafluoroethyl-4,5-dihydro-1H-pyrazole;

1-(2,4-difluoro-phenyl)-5-[6-fluoro-(4'-tetrazol-1-yl)-biphenyl-3-yl]-3-pentafluoroethyl-4,5-dihydro-1H-pyrazole;

1-(2,4-difluoro-phenyl)-5-(4-fluoro-3-morpholin-4-yl-phenyl)-3-pentafluoroethyl-4,5-dihydro-1H-pyrazole;

1-(2,4-difluoro-phenyl)-5-(4-fluoro-3-piperidin-1-yl-phenyl)-3-pentafluoroethyl-4,5-dihydro-1H-pyrazole;

1-(2,4-difluoro-phenyl)-5-[4-fluoro-3-(2-oxo-pyrrolidin-1-yl)-phenyl]-3-pentafluoroethyl-4,5-dihydro-1H-pyrazole;

1-(2,4-difluoro-phenyl)-5-(4-fluoro-3'-(methylsulfanyl)biphenyl-3-yl)-3-pentafluoroethyl-4,5-dihydro-1H-pyrazole;

1-(2,4-difluoro-phenyl)-5-(4-fluoro-4'-methylsulfonyl-biphenyl-3-yl)-3-pentafluoroethyl-4,5-dihydro-1H-pyrazole;

1-(2,4-difluoro-phenyl)-5-[6-fluoro-3-(6-methylsulfanyl-pyridin-3-yl)-phenyl]-3-pentafluoroethyl-4,5-dihydro-1H-pyrazole;

1-(2,4-difluoro-phenyl)-5-(4-fluoro-3'-methanesulfonyl-biphenyl-3-yl)-3-pentafluoroethyl-4,5-dihydroxy-1H-pyrazole;

1-(2,4-difluoro-phenyl)-5-[6-fluoro-3-(6-methanesulfonyl-pyridin-3-yl)-phenyl]-3-pentafluoroethyl-4,5-dihydro-1H-pyrazole;

1-(2,4-difluoro)-5-[2-fluoro-5-(4-BOC-piperazin-1-yl)-phenyl]-3-pentafluoroethyl-4,5-dihydro-1H-pyrazole;

1-(2,4-difluoro)-5-[2-fluoro-5-(piperazin-1-yl)-phenyl]-3-pentafluoroethyl-4,5-dihydro-1H-pyrazole hydrochloride;

1-(2,4-difluoro)-5-[2-fluoro-5-(4-methanesulfonyl-piperazin-1-yl)-phenyl]-3-pentafluoroethyl-4,5-dihydro-1H-pyrazole;

1-(2,4-difluoro)-5-[2-fluoro-5-(4-cyclopropanesulfonyl-piperazin-1-yl)-phenyl]-3-pentafluoroethyl-4,5-dihydro-1H-pyrazole;

1-(2,4-difluoro-phenyl)-5-[2-fluoro-5-(1-BOC-1,2,3,6-tetrahydropyridin-4-yl)-phenyl]-3-pentafluoroethyl-4,5-dihydro-1H-pyrazole;

1-(2,4-difluoro-phenyl)-5-[2-fluoro-5-(1,2,3,6-tetrahydropyridin-4-yl)-phenyl]-3-pentafluoroethyl-4,5-dihydro-1H-pyrazole hydrochloride;

1-(2,4-difluoro-phenyl)-5-[2-fluoro-5-(1-methanesulfonyl-1,2,3,6-tetrahydropyridin-4-yl)-phenyl]-3-pentafluoroethyl-4,5-dihydro-1H-pyrazole;

5-[2-(2-acetyl-phenyl)-pyridin-6-yl]-1-(2-chloro-phenyl)-3-pentafluoroethyl-4,5-dihydro-1H-pyrazole;

1-(2-chloro-phenyl)-5-[2-(4-methoxy-phenyl)-pyridin-6-yl]-3-pentafluoroethyl-4,5-dihydro-1H-pyrazole;

1-(2-chloro-phenyl)-5-[2-(3-methylsulfanyl-phenyl)-pyridin-6-yl]-3-pentafluoroethyl-4,5-dihydro-1H-pyrazole;

1-(2-chloro-phenyl)-5-[2-(4-methylsulfanyl-phenyl)-pyridin-6-yl]-3-pentafluoroethyl-4,5-dihydro-1H-pyrazole;

1-(2-chloro-phenyl)-5-[2-(4-methanesulfonyl-phenyl)-pyridin-6-yl]-3-pentafluoroethyl-4,5-dihydro-1H-pyrazole;

5-[2-(1-BOC-1,2,3,6-tetrahydropyridin-4-yl)-pyridin-6-yl]-1-(2-chloro-phenyl)-3-pentafluoroethyl-4,5-dihydro-1H-pyrazole;

1-(2-chloro-phenyl)-5-[2-(4-methanesulfinyl-phenyl)-pyridin-6-yl]-3-pentafluoroethyl-4,5-dihydro-1H-pyrazole;

1-(2-chloro-phenyl)-5-[2-(3-methanesulfonyl-phenyl)-pyridin-6-yl]-3-pentafluoroethyl-4,5-dihydro-1H-pyrazole;

1-(2-chloro-phenyl)-5-[2-(1-methanesulfonyl-1,2,3,6-tetrahydropyridin-4-yl)-pyridin-6-yl]-3-pentafluoroethyl-4,5-dihydro-1H-pyrazole;

1-(2-chloro-phenyl)-5-[2-(1-dimethylsulfamoyl-1,2,3,6-tetrahydropyridin-4-yl)-pyridin-6-yl]-3-pentafluoroethyl-4,5-dihydro-1H-pyrazole;

1-(2,4-difluoro-phenyl)-5-[3-(3-methylsulfanyl-phenyl)-pyridin-5-yl]-3-pentafluoroethyl-4,5-dihydro-1H-pyrazole;

1-(2,4-difluoro-phenyl)-5-[3-(4-methylsulfanyl-phenyl)-pyridin-5-yl]-3-pentafluoroethyl-4,5-dihydro-1H-pyrazole;

1-(2,4-difluoro-phenyl)-5-[3-(4-methanesulfonyl-phenyl)-pyridin-5-yl]-3-pentafluoroethyl-4,5-dihydro-1H-pyrazole;

1-(2,4-difluoro-phenyl)-5-[3-(6-methylsulfanyl-pyridin-3-yl)-pyridin-5-yl]-3-pentafluoroethyl-4,5-dihydro-1H-pyrazole;

5-[3-(1-BOC-1,2,3,6-tetrahydropyridin-4-yl)-pyridin-5-yl]-1-(2,4-difluoro-phenyl)-3-pentafluoroethyl-4,5-dihydro-1H-pyrazole;

1-(2,4-difluoro-phenyl)-5-[3-(3-methanesulfonyl-phenyl)-pyridin-5-yl]-3-pentafluoroethyl-4,5-dihydro-1H-pyrazole;

1-(2,4-difluoro-phenyl)-5-[3-(6-methanesulfonyl-pyridin-3-yl)-pyridin-5-yl]-3-pentafluoroethyl-4,5-dihydro-1H-pyrazole;

1-(2,4-difluoro-phenyl)-5-[3-(1,2,3,6-tetrahydropyridin-4-yl)-pyridin-5-yl]-3-pentafluoroethyl-4,5-dihydro-1H-pyrazole hydrochloride;

1-(2,4-difluoro-phenyl)-5-[3-(1-cyclopropanesulfonyl-1,2,3,6-tetrahydropyridin-4-yl)-pyridin-5-yl]-3-pentafluoroethyl-4,5-dihydro-1H-pyrazole;

5-[3-(4-BOC-piperazin-1-yl)-pyridin-5-yl]-1-(2,4-difluoro-phenyl)-3-pentafluoroethyl-4,5-dihydro-1H-pyrazole;

1-(2,4-difluoro-phenyl)-5-[3-(piperazin-1-yl)-pyridin-5-yl]-3-pentafluoroethyl-4,5-dihydro-1H-pyrazole hydrochloride;

1-(2,4-difluoro-phenyl)-5-[3-(4-methanesulfonyl-piperazin-1-yl)-pyridin-5-yl]-3-pentafluoroethyl-4,5-dihydro-1H-pyrazole;

1-(2,4-difluoro-phenyl)-5-[4-(3-methylsulfanyl-phenyl)-pyridin-2-yl]-3-pentafluoroethyl-4,5-dihydro-1H-pyrazole;

1-(2,4-difluoro-phenyl)-5-[4-(4-methylsulfanyl-phenyl)-pyridin-2-yl]-3-pentafluoroethyl-4,5-dihydro-1H-pyrazole;

1-(2,4-difluoro-phenyl)-5-[4-(4-methanesulfonyl-phenyl)-pyridin-2-yl]-3-pentafluoroethyl-4,5-dihydro-1H-pyrazole;

1-(2,4-difluoro-phenyl)-5-[4-(6-methylsulfanyl-pyridin-3-yl)-pyridin-2-yl]-3-pentafluoroethyl-4,5-dihydro-1H-pyrazole;

5-[4-(1-BOC-1,2,3,6-tetrahydropyridin-4-yl)-pyridin-2-yl]-1-(2,4-difluoro-phenyl)-3-pentafluoroethyl-4,5-dihydro-1H-pyrazole;

1-(2,4-difluoro-phenyl)-5-[4-(3-methanesulfonyl-phenyl)-pyridin-2-yl]-3-pentafluoroethyl-4,5-dihydro-1H-pyrazole;

1-(2,4-difluoro-phenyl)-5-[4-(6-methanesulfonyl-pyridin-3-yl)-pyridin-2-yl]-3-pentafluoroethyl-4,5-dihydro-1H-pyrazole;

1-(2,4-difluoro-phenyl)-5-[4-(1,2,3,6-tetrahydropyridin-4-yl)-pyridin-2-yl]-3-pentafluoroethyl-4,5-dihydro-1H-pyrazole hydrochloride;

1-(2,4-difluoro-phenyl)-5-[4-(1-methanesulfonyl-1,2,3,6-tetrahydropyridin-4-yl)-pyridin-2-yl]-3-pentafluoroethyl-4,5-dihydro-1H-pyrazole;

5-[4-(4-BOC-piperazin-1-yl)-pyridin-2-yl]-1-(2,4-difluoro-phenyl)-3-pentafluoroethyl-4,5-dihydro-1H-pyrazole;

1-(2,4-difluoro-phenyl)-5-[4-(piperazin-1-yl)-pyridin-2-yl]-3-pentafluoroethyl-4,5-dihydro-1H-pyrazole hydrochloride;

1-(2,4-difluoro-phenyl)-5-[4-(4-methanesulfonyl-piperazin-1-yl)-pyridin-2-yl]-3-pentafluoroethyl-4,5-dihydro-1H-pyrazole;

1-(2,4-difluoro-phenyl)-5-[4-(4-cyclopropanesulfonyl-piperazin-1-yl)-pyridin-2-yl]-3-pentafluoroethyl-4,5-dihydro-1H-pyrazole;

1-(2,4-difluoro-phenyl)-5-[2-(3-methylsulfanyl-phenyl)-pyridin-4-yl]-3-pentafluoroethyl-4,5-dihydro-1H-pyrazole;

-(2,4-difluoro-phenyl)-5-[2-(6-methylsulfanyl-pyridin-3-yl)-pyridin-4-yl]-3-pentafluoroethyl-4,5-dihydro-1H-pyrazole;

5-[2-(1-BOC-1,2,3,6-tetrahydropyridin-4-yl)-pyridin-4-yl]-1-(2,4-difluoro-phenyl)-3-pentafluoroethyl-4,5-dihydro-1H-pyrazole;

1-(2,4-difluoro-phenyl)-5-[2-(3-methanesulfonyl-phenyl)-pyridin-4-yl]-3-pentafluoroethyl-4,5-dihydro-1H-pyrazole;

1-(2,4-difluoro-phenyl)-5-[2-(6-methanesulfonyl-pyridin-3-yl)-pyridin-4-yl]-3-pentafluoroethyl-4,5-dihydro-1H-pyrazole;

1-(2,4-difluoro-phenyl)-5-[2-(1,2,3,6-tetrahydropyridin-4-yl)-pyridin-4-yl]-3-pentafluoroethyl-4,5-dihydro-1H-pyrazole hydrochloride;

1-(2,4-difluoro-phenyl)-5-[2-(1-methanesulfonyl-1,2,3,6-tetrahydropyridin-4-yl)-pyridin-4-yl]-3-pentafluoroethyl-4,5-dihydro-1H-pyrazole;

5-[2-(4-BOC-piperazin-1-yl)-pyridin-4-yl]-1-(2,4-difluoro-phenyl)-3-pentafluoroethyl-4,5-dihydro-1H-pyrazole;

1-(2,4-difluoro-phenyl)-5-[2-(piperazin-1-yl)-pyridin-4-yl]-3-pentafluoroethyl-4,5-dihydro-1H-pyrazole hydrochloride;

1-(2,4-difluoro-phenyl)-5-[2-(4-methanesulfonyl-piperazin-1-yl)-pyridin-4-yl]-3-pentafluoroethyl-4,5-dihydro-1H-pyrazole;

1-(2,4-difluoro-phenyl)-5-{5-[3-(rnethylsulfanyl)-phenyl]-thiophen-2-yl}-3-pentafluoroethyl-4,5-dihydro-1H-pyrazole;

1-(2,4-difluoro-phenyl)-5-[5-(6-methylsulfanyl-pyridin-3-yl)-thiophen-2-yl]-3-pentafluoroethyl-4,5-dihydro-1H-pyrazole;

5-[5-(1-BOC-1,2,3,6-tetrahydropyridin-4-yl)-thiophen-2-yl]-1-(2,4-difluoro-phenyl)-3-pentafluoroethyl-4,5-dihydro-1H-pyrazole;

1-(2,4-difluoro-phenyl)-5-{5-[3-(methylsulfonyl)-phenyl]-thiophen-2-yl}-3-pentafluoroethyl-4,5-dihydro-1H-pyrazole;

1-(2,4-difluoro-phenyl)-5-[5-(6-methanesulfonyl-pyridin-3-yl)-thiophen-2-yl]-3-pentafluoroethyl-4,5-dihydro-1H-pyrazole;

1-(2,4-difluoro-phenyl)-5-[5-(1-methanesulfonyl-1,2,3,6-tetrahydropyridin-4-yl)-thiophen-2-yl]-3-pentafluoroethyl-4,5-dihydro-1H-pyrazole;

1-(2,4-difluoro-phenyl)-5-[5-(1-dimethylsulfamoyl-1,2,3,6-tetrahydropyridin-4-yl)-thiophen-2-yl]-3-pentafluoroethyl-4,5-dihydro-1H-pyrazole;

5-[5-(4-BOC-piperazin-1-yl)-thiophen-2-yl]-1-(2,4-difluoro-phenyl)-3-pentafluoroethyl-4,5-dihydro-1H-pyrazole;

1-(2,4-difluoro-phenyl)-5-[5-(4-methanesulfonyl-piperazin-1-yl)-thiophen-2-yl]-3-pentafluoroethyl-4,5-dihydro-1H-pyrazole;

5-(2,4-difluoro-phenyl)-1-[3'-(methylsulfanyl)-biphenyl-3-yl]-3-pentafluoroethyl-4,5-dihydro-1H-pyrazole;

1-[3-(1-BOC-1,2,3,6-tetrahydropyridin-4-yl)-phenyl]-5-(2,4-difluoro-phenyl)-3-pentafluoroethyl-4,5-dihydro-1H-pyrazole;

5-(2,4-difluoro-phenyl)-1-[3'-(methylsulfonyl)-biphenyl-3-yl]-3-pentafluoroethyl-4,5-dihydro-1H-pyrazole;

5-(2,4-difluoro-phenyl)-1-[3-(5-methanesulfonyl-pyridin-3-yl)-phenyl]-3-pentafluoroethyl-4,5-dihydro-1H-pyrazole;

5-(2,4-difluoro-phenyl)-1-[3-(6-methanesulfonyl-pyridin-2-yl)-phenyl]-3-pentafluoroethyl-4,5-dihydro-1H-pyrazole;

5-(2,4-difluoro-phenyl)-1-[3-(6-dimethylsulfamoyl-pyridin-2-yl)-phenyl]-3-pentafluoroethyl-4,5-dihydro-1H-pyrazole;

5-(2,4-difluoro-phenyl)-1-{3'-[(2-hydroxy-ethyl)-methylsulfamoyl]-biphenyl-3-yl}-3-pentafluoroethyl-4,5-dihydro-1H-pyrazole;

5-(2,4-difluoro-phenyl)-1-{3'-[3-(N-BOC-N-methylamino)-propane-1-sulfonyl]-biphenyl-3-yl}-3-pentafluoroethyl-4,5-dihydro-1H-pyrazole;

5-(2,4-difluoro-phenyl)-1-[3'-(3-methylamino-propane-1-sulfonyl)-biphenyl-3-yl]-3-pentafluoroethyl-4,5-dihydro-1H-pyrazole hydrochloride;

5-(2,4-difluoro-phenyl)-1-[3-(1,2,3,6-tetrahydropyridin-4-yl)-phenyl]-3-pentafluoroethyl-4,5-dihydro-1H-pyrazole hydrochloride;

5-(2,4-difluoro-phenyl)-1-[3-(1-methanesulfonyl-1,2,3,6-tetrahydropyridin-4-yl)-phenyl]-3-pentafluoroethyl-4,5-dihydro-1H-pyrazole;

1-[3-(4-BOC-piperazin-1-yl)-phenyl]-5-(2,4-difluoro-phenyl)-3-pentafluoroethyl-4,5-dihydro-1H-pyrazole;

5-(2,4-difluoro-phenyl)-1-[3-(piperazin-1-yl)-phenyl]-3-pentafluoroethyl-4,5-dihydro-1H-pyrazole hydrochloride;

5-(2,4-difluoro-phenyl)-1-[3-(4-methanesulfonyl-piperazin-1-yl)-phenyl]-3-pentafluoroethyl-4,5-dihydro-1H-pyrazole;

5-(2,4-difluoro-phenyl)-1-[3'-(methylsulfanyl)-biphenyl-4-yl]-3-pentafluoroethyl-4,5-dihydro-1H-pyrazole;

5-(2,4-difluoro-phenyl)-1-[4-(6-methylsulfanyl-pyridin-3-yl)-phenyl]-3-pentafluoroethyl-4,5-dihydro-1H-pyrazole;

1-[4-(1-BOC-1,2,3,6-tetrahydropyridin-4-yl)-phenyl]-5-(2,4-difluoro-phenyl)-3-pentafluoroethyl-4,5-dihydro-1H-pyrazole;

5-(2,4-difluoro-phenyl)-1-[3'-(methylsulfonyl)-biphenyl-4-yl]-3-pentafluoroethyl-4,5-dihydro-1H-pyrazole;

5-(2,4-difluoro-phenyl)-1-[4-(6-methanesulfonyl-pyridin-3-yl)-phenyl]-3-pentafluoroethyl-4,5-dihydro-1H-pyrazole;

5-(2'-acetyl-biphenyl-3-yl)-1-(2-chloro-phenyl)-3-[di-(trifluoromethyl)-hydroxy-methyl]-4,5-dihydro-1H-pyrazole;

5-(3'-acetyl-biphenyl-3-yl)-1-(2-chloro-phenyl)-3-[di-(trifluoromethyl)-hydroxy-methyl]-4,5-dihydro-1H-pyrazole;

5-(4'-acetyl-biphenyl-3-yl)-1-(2-chloro-phenyl)-3-[di-(trifluoromethyl)-hydroxy-methyl]-4,5-dihydro-1H-pyrazole;

1-(2-chloro-phenyl)-5-[4'-(methylsulfonyl)-biphenyl-3-yl]-3-[di-(trifluoromethyl)-hydroxy-methyl]-4,5-dihydro-1H-pyrazole;

1-(2-chloro-phenyl)-5-[3-'-(1-hydroxy-1-methyl-ethyl)-biphenyl-3-yl]-3-[di-(trifluoromethyl)-hydroxy-methyl]-4,5-dihydro-1H-pyrazole;

1-(2-chloro-phenyl)-5-[4'-(1-hydroxy-1-methyl-ethyl)-biphenyl-3-yl]-3-[di-(trifluoromethyl)-hydroxy-methyl]-4,5-dihydro-1H-pyrazole;

1-(2-chloro-phenyl)-5-[3-(1-BOC-1,2,3,6-tetrahydropyridin-4-yl)-phenyl]-3-[di-(trifluoromethyl)-hydroxy-methyl]-4,5-dihydro-1H-pyrazole;

1-(2-chloro-phenyl)-5-[3-(1,2,3,6-tetrahydropyridin-4-yl)-phenyl]-3-[di-(trifluoromethyl)-hydroxy-methyl]-4,5-dihydro-1H-pyrazole trifluoroacetate;

5-[3-(1-acetyl-1,2,3,6-tetrahydropyridin-4-yl)-phenyl]-1-(2-chloro-phenyl)-3-[di-(trifluoromethyl)-hydroxy-methyl]-4,5-dihydro-1H-pyrazole;

1-(2-chloro-phenyl)-5-{3-[1-(2-cyclopentyl-acetyl)-1,2,3,6-tetrahydropyridin-4-yl]-phenyl}-3-[di-(trifluoromethyl)-hydroxy-methyl]-4,5-dihydro-1H-pyrazole;

1-(2-chloro-phenyl)-5-{3-[1-(3-cyclopentyl-propionyl)-1,2,3,6-tetrahydropyridin-4-yl]-phenyl}-3-[di-(trifluoromethyl)-hydroxy-methyl]-4,5-dihydro-1H-pyrazole;

1-(2-chloro-phenyl)-5-{3-[1-(thiophene-2-carbonyl)-1,2,3,6-tetrahydropyridin-4-yl]-phenyl}-3-[di-(trifluoromethyl)-hydroxy-methyl]-4,5-dihydro-1H-pyrazole;

5-[3-(1-benzoyl-1,2,3,6-tetrahydropyridin-4-yl)-phenyl]-1-(2-chloro-phenyl)-3-[di-(trifluoromethyl)-hydroxy-methyl]-4,5-dihydro-1H-pyrazole;

1-(2-chloro-phenyl)-5-[3-(1-phenylacetyl-1,2,3,6-tetrahydropyridin-4-yl)-phenyl]-3-[di-(trifluoromethyl)-hydroxy-methyl]-4,5-dihydro-1H-pyrazole;

5-{3-[1-(4-chloro-benzoyl)-1,2,3,6-tetrahydropyridin-4-yl]-phenyl}-1-(2-chloro-phenyl)-3-[di-(trifluoromethyl)-hydroxy-methyl]-4,5-dihydro-1H-pyrazole;

1-(2-chloro-phenyl)-5-[3-(1-methanesulfonyl-1,2,3,6-tetrahydropyridin-4-yl)-phenyl]-3-[di-(trifluoromethyl)-hydroxy-methyl]-4,5-dihydro-1H-pyrazole;

1-(2-chloro-phenyl)-5-[3-(1-trifluoromethanesulfonyl-1,2,3,6-tetrahydropyridin-4-yl)-phenyl]-3-[di-(trifluoromethyl)-hydroxy-methyl]-4,5-dihydro-1H-pyrazole;

1-(2-chloro-phenyl)-5-[3-(1-dimethylsulfamoyl-1,2,3,6-tetrahydropyridin-4-yl)-phenyl]-3-[di-(trifluoromethyl)-hydroxy-methyl]-4,5-dihydro-1H-pyrazole;

5-(2'-acetyl-biphenyl-4-yl)-1-(2-chloro-phenyl)-3-[di-(trifluoromethyl)-hydroxy-methyl]-4,5-dihydro-1H-pyrazole;

1-(2-chloro-phenyl)-5-(4'-methoxy-biphenyl-4-yl)-3-[di-(trifluoromethyl)-hydroxy-methyl]-4,5-dihydro-1H-pyrazole;

1-(2-chloro-phenyl)-5-[4'-(methylsulfanyl)-biphenyl-4-yl]-3-[di-(trifluoromethyl)-hydroxy-methyl]-4,5-dihydro-1H-pyrazole;

1-(2-chloro-phenyl)-5-[4'-(methanesulfonyl)-biphenyl-4-yl]-3-[di-(trifluoromethyl)-hydroxy-methyl]-4,5-dihydro-1H-pyrazole;

1-(2-chloro-phenyl)-5-(2',6'-dimethoxy-biphenyl-4-yl)-3-[di-(trifluoromethyl)-hydroxy-methyl]-4,5-dihydro-1H-pyrazole;

1-(2-chloro-phenyl)-5-(4'-fluoro-biphenyl-4-yl)-3-[di-(trifluoromethyl)-hydroxy-methyl]-4,5-dihydro-1H-pyrazole;

1-(2-chloro-phenyl)-5-[4'-(trifluoromethyl)-biphenyl-4-yl]-3-[di-(trifluoromethyl)-hydroxy-methyl]-4,5-dihydro-1H-pyrazole;

1-(2-chloro-phenyl)-5-[3'-(trifluoromethoxy)-biphenyl-4-yl]-3-[di-(trifluoromethyl)-hydroxy-methyl]-4,5-dihydro-1H-pyrazole;

1-(2-chloro-phenyl)-5-(2'-methyl-biphenyl-4-yl)-3-[di-(trifluoromethyl)-hydroxy-methyl]-4,5-dihydro-1H-pyrazole;

1-(2-chloro-phenyl)-5-(4'-methyl-biphenyl-4-yl)-3-[di-(trifluoromethyl)-hydroxy-methyl]-4,5-dihydro-1H-pyrazole;

1-(2-chloro-phenyl)-5-(3'-ethoxy-biphenyl-4-yl)-3-[di-(trifluoromethyl)-hydroxy-methyl]-4,5-dihydro-1H-pyrazole;

1-(2-chloro-phenyl)-5-(3'-hydroxy-biphenyl-4-yl)-3-[di-(trifluoromethyl)-hydroxy-methyl]-4,5-dihydro-1H-pyrazole;

5-(3'-amino-biphenyl-4-yl)-1-(2-chloro-phenyl)-3-[di-(trifluoromethyl)-hydroxy-methyl]-4,5-dihydro-1H-pyrazole;

1-(2-chloro-phenyl)-5-(4'-dimethylamino-biphenyl-4-yl)-3-[di-(trifluoromethyl)-hydroxy-methyl]-4,5-dihydro-1H-pyrazole;

5-(2'-chloro-4'-methoxy-biphenyl-4-yl)-1-(2-chloro-phenyl)-3-[di-(trifluoromethyl)-hydroxy-methyl]-4,5-dihydro-1H-pyrazole;

5-(3'-chloro-4'-fluoro-biphenyl-4-yl)-1-(2-chloro-phenyl)-3-[di-(trifluoromethyl)-hydroxy-methyl]-4,5-dihydro-1H-pyrazole;

1-(2-chloro-phenyl)-5-(4-furan-3-yl-phenyl)-3-[di-(trifluoromethyl)-hydroxy-methyl]-4,5-dihydro-1H-pyrazole;

1-(2-chloro-phenyl)-5-(4-pyrimidin-5-yl-phenyl)-3-[di-(trifluoromethyl)-hydroxy-methyl]-4,5-dihydro-1H-pyrazole;

1-(2-chloro-phenyl)-5-(4-quinolin-3-yl-phenyl)-3-[di-(trifluoromethyl)-hydroxy-methyl]-4,5-dihydro-1H-pyrazole;

1-(2-chloro-phenyl)-5-[4-(6-methoxy-pyridin-3-yl)-phenyl]-3-[di-(trifluoromethyl)-hydroxy-methyl]-4,5-dihydro-1H-pyrazole;

1-(2-chloro-phenyl)-5-[4-(2-fluoro-pyridin-3-yl)-phenyl]-3-[di-(trifluoromethyl)-hydroxy-methyl]-4,5-dihydro-1H-pyrazole;

5-(4-benzofuran-2-yl-phenyl)-1-(2-chloro-phenyl)-3-[di-(trifluoromethyl)-hydroxy-methyl]-4,5-dihydro-1H-pyrazole;

5-(4-benzo[b]thiophen-2-yl-phenyl)-1-(2-chloro-phenyl)-3-[di-(trifluoromethyl)-hydroxy-methyl]-4,5-dihydro-1H-pyrazole;

5-(4'-carboxy-biphenyl-4-yl)-1-(2-chloro-phenyl)-3-[di-(trifluoromethyl)-hydroxy-methyl]-4,5-dihydro-1H-pyrazole;

1-(2-chloro-phenyl)-5-(2'-fluoro-4'-methyl-biphenyl-4-yl)-3-[di-(trifluoromethyl)-hydroxy-methyl]-4,5-dihydro-1H-pyrazole;

1-(2-chloro-phenyl)-5-[4-(6-methylsulfanyl-pyridin-3-yl)-phenyl]-3-[di-(trifluoromethyl)-hydroxy-methyl]-4,5-dihydro-1H-pyrazole;

1-(2-chloro-phenyl)-5-[4-(6-cyano-pyridin-3-yl)-phenyl]-3-[di-(trifluoromethyl)-hydroxy-methyl]-4,5-dihydro-1H-pyrazole;

1-(2-chloro-phenyl)-5-[4-(6-fluoro-pyridin-3-yl)-phenyl]-3-[di-(trifluoromethyl)-hydroxy-methyl]-4,5-dihydro-1H-pyrazole;

1-(2-chloro-phenyl)-5-[4-(6-ethoxy-pyridin-3-yl)-phenyl]-3-[di-(trifluoromethyl)-hydroxy-methyl]-4,5-dihydro-1H-pyrazole;

1-(2-chloro-phenyl)-5-[4-(6-methoxy-4-methyl-pyridin-3-yl)-phenyl]-3-[di-(trifluoromethyl)-hydroxy-methyl]-4,5-dihydro-1H-pyrazole;

1-(2-chloro-phenyl)-5-[4-(4-methyl-pyridin-3-yl)-phenyl]-3-[di-(trifluoromethyl)-hydroxy-methyl]-4,5-dihydro-1H-pyrazole;

1-(2-chloro-phenyl)-5-[4-(6-trifluoromethyl-pyridin-3-yl)-phenyl]-3-[di-(trifluoromethyl)-hydroxy-methyl]-4,5-dihydro-1H-pyrazole;

1-(2-chloro-phenyl)-5-[4-(5-methoxycarbonyl-pyridin-3-yl)-phenyl]-3-[di-(trifluoromethyl)-hydroxy-methyl]-4,5-dihydro-1H-pyrazole;

1-(2-chloro-phenyl)-5-[4-(5-formyl-6-methoxy-pyridin-3-yl)-phenyl]-3-[di-(trifluoromethyl)-hydroxy-methyl]-4,5-dihydro-1H-pyrazole;

1-(2-chloro-phenyl)-5-[4-(5-methyl-pyridin-3-yl)-phenyl]-3-[di-(trifluoromethyl)-hydroxy-methyl]-4,5-dihydro-1H-pyrazole;

1-(2-chloro-phenyl)-5-[4-(6-methyl-pyridin-2-yl)-phenyl]-3-[di-(trifluoromethyl)-hydroxy-methyl]-4,5-dihydro-1H-pyrazole;

1-(2-chloro-phenyl)-5-[4-(pyridin-3-yl)-phenyl]-3-[di-(trifluoromethyl)-hydroxy-methyl]-4,5-dihydro-1H-pyrazole;

1-(2-chloro-phenyl)-5-[4-(5-cyano-pyridin-3-yl)-phenyl]-3-[di-(trifluoromethyl)-hydroxy-methyl]-4,5-dihydro-1H-pyrazole;

1-(2-chloro-phenyl)-5-[4-(2-methoxy-pyrimidin-5-yl)-phenyl]-3-[di-(trifluoromethyl) hydroxy-methyl]-4,5-dihydro-1H-pyrazole;

1-(2-chloro-phenyl)-5-[4-(2,4-dimethoxy-pyrimidin-5-yl)-phenyl]-3-[di-(trifluoromethyl)-hydroxy-methyl]-4,5-dihydro-1H-pyrazole;

1-(2-chloro-phenyl)-5-[4-(2-chloro-pyrimidin-5-yl)-phenyl]-3-[di-(trifluoromethyl)-hydroxy-methyl]-4,5-dihydro-1H-pyrazole;

1-(2-chloro-phenyl)-5-{4'-[(2-hydroxy-ethyl)-methanesulfonyl-amino]-biphenyl-4-yl}-3-[di-(trifluoromethyl)-hydroxy-methyl]-4,5-dihydro-1H-pyrazole;

1-(2-chloro-phenyl)-5-{3'-[(2-hydroxy-ethyl)-methylsulfamoyl]-biphenyl-4-yl}-3-[di-(trifluoromethyl)-hydroxy-methyl]-4,5-dihydro-1H-pyrazole;

1-(2-chloro-phenyl)-5-(3'-dimethylsulfamoyl-biphenyl-4-yl)-3-[di-(trifluoromethyl)-hydroxy-methyl]-4,5-dihydro-1H-pyrazole;

5-{3'-[3-(N-BOC-N-methyl-amino)-propane-1-sulfonyl]-biphenyl-4-yl}-1-(2-chloro-phenyl)-3-[di-(trifluoromethyl)-hydroxy-methyl]-4,5-dihydro-1H-pyrazole;

1-(2-chloro-phenyl)-5-{4-[6-(methylsulfonyl)-pyridin-2-yl]-phenyl}-3-[di-(trifluoromethyl)-hydroxy-methyl]-4,5-dihydro-1H-pyrazole;

1-(2-chloro-phenyl)-5-[2',5'-difluoro-4'-(1H-1,2,4-triazol-1-yl)-biphenyl-4-yl]-3-[di-(trifluoromethyl)-hydroxy-methyl]-4,5-dihydro-1H-pyrazole;

1-(2-chloro-phenyl)-5-[2',6'-difluoro-4'-(methylsulfonyl)-biphenyl-4-yl]-3-[di-(trifluoromethyl)-hydroxy-methyl]-4,5-dihydro-1H-pyrazole;

1-(2-chloro-phenyl)-5-[4'-(methylsulfonyl)-2'-(trifluoromethyl)-biphenyl-4-yl]-3-[di-(trifluoromethyl)-hydroxy-methyl]-4,5-dihydro-1H-pyrazole;

1-(2-chloro-phenyl)-5-[3'-cyano-4'-(methylsulfonyl)-biphenyl-4-yl]-3-[di-(trifluoromethyl)-hydroxy-methyl]-4,5-dihydro-1H-pyrazole;

1-(2-chloro-phenyl)-5-[4-(1-BOC-1,2,3,6-tetrahydropyridin-4-yl)-phenyl]-3-[di-(trifluoromethyl)-hydroxy-methyl]-4,5-dihydro-1H-pyrazole;

1-(2-chloro-phenyl)-5-[4-(1,2,3,6-tetrahydropyridin-4-yl)-phenyl]-3-[di-(trifluoromethyl)-hydroxy-methyl]-4,5-dihydro-1H-pyrazole trifluoroacetate;

1-(2-chloro-phenyl)-5-[4-(1-acetyl-1,2,3,6-tetrahydropyridin-4-yl)-phenyl]-3-[di-(trifluoromethyl)-hydroxy-methyl]-4,5-dihydro-1H-pyrazole;

1-(2-chloro-phenyl)-5-{4-[1-(2-thiophenecarbonyl)-1,2,3,6-tetrahydropyridin-4-yl]-phenyl}-3-[di-(trifluoromethyl)-hydroxy-methyl]-4,5-dihydro-1H-pyrazole;

1-(2-chloro-phenyl)-5-[4-(1-benzoyl-1,2,3,6-tetrahydropyridin-4-yl)-phenyl]-3-[di-(trifluoromethyl)-hydroxy-methyl]-4,5-dihydro-1H-pyrazole;

1-(2-chloro-phenyl)-5-[4-(1-phenylacetyl-1,2,3,6-tetrahydropyridin-4-yl)-phenyl]-3-[di-(trifluoromethyl)-hydroxy-methyl]-4,5-dihydro-1H-pyrazole;

1-(2-chloro-phenyl)-5-{4-[1-(4-chlorobenzoyl)-1,2,3,6-tetrahydropyridin-4-yl]-phenyl}-3-[di-(trifluoromethyl)-hydroxy-methyl]-4,5-dihydro-1H-pyrazole;

1-(2-chloro-phenyl)-5-[4-(1-methanesulfonyl-1,2,3,6-tetrahydropyridin-4-yl)-phenyl]-3-[di-(trifluoromethyl)-hydroxy-methyl]-4,5-dihydro-1H-pyrazole;

1-(2-chloro-phenyl)-5-[4-(1-ethanesulfonyl-1,2,3,6-tetrahydropyridin-4-yl)-phenyl]-3-[di-(trifluoromethyl)-hydroxy-methyl]-4,5-dihydro-1H-pyrazole;

1-(2-chloro-phenyl)-5-{4-[1-(propane-1-sulfonyl)-1,2,3,6-tetrahydropyridin-4-yl]-phenyl}-3-[di-(trifluoromethyl)-hydroxy-methyl]-4,5-dihydro-1H-pyrazole;

1-(2-chloro-phenyl)-5-{4-[1-(propane-2-sulfonyl)-1,2,3,6-tetrahydropyridin-4-yl]-phenyl}-3-[di-(trifluoromethyl)-hydroxy-methyl]-4,5-dihydro-1H-pyrazole;

1-(2-chloro-phenyl)-5-{4-[1-(2-methyl-propane-1-sulfonyl)-1,2,3,6-tetrahydropyridin-4-yl]-phenyl}-3-[di-(trifluoromethyl)-hydroxy-methyl]-4,5-dihydro-1H-pyrazole;

1-(2-chloro-phenyl)-5-[4-(1-trifluoromethanesulfonyl-1,2,3,6-tetrahydropyridin-4-yl)-phenyl]-3-[di-(trifluoromethyl)-hydroxy-methyl]-4,5-dihydro-1H-pyrazole;

1-(2-chloro-phenyl)-5-[4-(1-cyclopropanesulfonyl-1,2,3,6-tetrahydropyridin-4-yl)-phenyl]-3-[di-(trifluoromethyl)-hydroxy-methyl]-4,5-dihydro-1H-pyrazole;

1-(2-chloro-phenyl)-5-{4-[1-dimethylsulfamoyl-1,2,3,6-tetrahydropyridin-4-yl]-phenyl}-3-[di-(trifluoromethyl)-hydroxy-methyl]-4,5-dihydro-1H-pyrazole;

1-(2-chloro-phenyl)-5-[4-(1-cyclopentanesulfonyl-1,2,3,6-tetrahydropyridin-4-yl)-phenyl]-3-[di-(trifluoromethyl)-hydroxy-methyl]-4,5-dihydro-1H-pyrazole;

1-(2-chloro-phenyl)-5-[4-(1-cyclohexanesulfonyl-1,2,3,6-tetrahydropyridin-4-yl)-phenyl]-3-[di-(trifluoromethyl)-hydroxy-methyl]-4,5-dihydro-1H-pyrazole;

1-(2-chloro-phenyl)-5-{4-[1-(pyrrolidine-1-sulfonyl)-1,2,3,6-tetrahydropyridin-4-yl]-phenyl}-3-[di-(trifluoromethyl)-hydroxy-methyl]-4,5-dihydro-1H-pyrazole;

5-(3'-acetaminobiphenyl-4-yl)-1-(2-chloro-phenyl)-3-[di-(trifluoromethyl)-hydroxy-methyl]-4,5-dihydro-1H-pyrazole;

5-(3'-methanesulfonyl-aminobiphenyl-4-yl)-1-(2-chloro-phenyl)-3-[di-(trifluoromethyl)-hydroxy-methyl]-4,5-dihydro-1H-pyrazole;

1-(2-chloro-phenyl)-5-[4-(4-BOC-piperazin-1-yl)-phenyl]-3-[di-(trifluoromethyl)-hydroxy-methyl]-4,5-dihydro-1H-pyrazole;

1-(2-chloro-phenyl)-5-[4-(4-methanesulfonyl-piperazin-1-yl)-phenyl]-3-[di-(trifluoromethyl)-hydroxy-methyl]-4,5-dihydro-1H-pyrazole;

1-(2-chloro-phenyl)-5-[4-(4-ethanesulfonyl-piperazin-1-yl)-phenyl]-3-[di-(trifluoromethyl)-hydroxy-methyl]-4,5-dihydro-1H-pyrazole;

1-(2-chloro-phenyl)-5-[4-(4-isopropylsulfonyl-piperazin-1-yl)-phenyl]-3-[di-(trifluoromethyl)-hydroxy-methyl]-4,5-dihydro-1H-pyrazole;

1-(2-chloro-phenyl)-5-[4-(4-cyclopropanesulfonyl-piperazin-1-yl)-phenyl]-3-[di-(trifluoromethyl)-hydroxy-methyl]-4,5-dihydro-1H-pyrazole;

1-(2-chloro-phenyl)-5-[4-(4-dimethylsulfamoyl-piperazin-1-yl)-phenyl]-3-[di-(trifluoromethyl)-hydroxy-methyl]-4,5-dihydro-1H-pyrazole;

1-(2-chloro-phenyl)-5-[4-(4-isobutyryl-piperazin-1-yl)-phenyl]-3-[di-(trifluoromethyl)-hydroxy-methyl]-4,5-dihydro-1H-pyrazole;

1-(2-chloro-phenyl)-5-[4-(4-dimethylcarbamoyl-piperazin-1-yl)-phenyl]-3-[di-(trifluoromethyl)-hydroxy-methyl]-4,5-dihydro-1H-pyrazole;

1-(2-chloro-phenyl)-5-{4-[4-(pyrrolidine-1-sulfonyl)-piperazin-1-yl]-phenyl}-3-[di-(trifluoromethyl)-hydroxy-methyl]-4,5-dihydro-1H-pyrazole;

1-(2-chloro-phenyl)-5-{4-[4-(2-hydroxy-2-methyl-propionyl)-piperazin-1-yl]-phenyl}-3-(di-(trifluoromethyl)-hydroxy-methyl]-4,5-dihydro-1H-pyrazole;

1-(2-chloro-phenyl)-5-[4-(4-BOC-homopiperazin-1-yl)-phenyl]-3-[di-(trifluoromethyl)-hydroxy-methyl]-4,5-dihydro-1H-pyrazole;

1-(2-chloro-phenyl)-5-[4-(4-methanesulfonyl-homopiperazin-1-yl)-phenyl]-3-[di-(trifluoromethyl)-hydroxy-methyl]-4,5-dihydro-1H-pyrazole;

1-(2-chloro-phenyl)-5-[4-(4-ethanesulfonyl-homopiperazin-1-yl)-phenyl]-3-[di-(trifluoromethyl)-hydroxy-methyl]-4,5-dihydro-1H-pyrazole;

1-(2-chloro-phenyl)-5-[4-(4-isopropylsulfonyl-homopiperazin-1-yl)-phenyl]-3-[di-(trifluoromethyl)-hydroxy-methyl]-4,5-dihydro-1H-pyrazole;

1-(2-chloro-phenyl)-5-[4-(4-cyclopropanesulfonyl-homopiperazin-1-yl)-phenyl]-3-[di-(trifluoromethyl)-hydroxy-methyl]-4,5-dihydro-1H-pyrazole;

1-(2-chloro-phenyl)-5-[4-(4-dimethylsulfamoyl-homopiperazin-1-yl)-phenyl]-3-[di-(trifluoromethyl)-hydroxy-methyl]-4,5-dihydro-1H-pyrazole;

1-(2-chloro-phenyl)-5-[4-(4-isobutyryl-homopiperazin-1-yl)-phenyl]-3-[di-(trifluoromethyl)-hydroxy-methyl]-4,5-dihydro-1H-pyrazole;

1-(2-chloro-phenyl)-5-[4-(4-dimethylcarbamoyl-homopiperazin-1-yl)-phenyl]-3-[di-(trifluoromethyl)-hydroxy-methyl]-4,5-dihydro-1H-pyrazole;

1-(2-chloro-phenyl)-5-[4-(1,1-dioxo-thiomorpholin-4-yl)-phenyl]-3-[di-(trifluoromethyl)-hydroxy-methyl]-4,5-dihydro-1H-pyrazole;

1-(2-chloro-phenyl)-5-{4-[4-(N-BOC-amino)-piperidin-1-yl]-phenyl}-3-[di-(trifluoromethyl)-hydroxy-methyl]-4,5-dihydro-1H-pyrazole;

1-(2-chloro-phenyl)-5-{4-[4-amino-piperidin-1-yl]-phenyl}-3-[di-(trifluoromethyl)-hydroxy-methyl]-4,5-dihydro-1H-pyrazole hydrochloride;

1-(2-chloro-phenyl)-5-[4-(4-cyclopropanesulfonylamino-piperidin-1-yl)-phenyl]-3-[di-(trifluoromethyl)-hydroxy-methyl]-4,5-dihydro-1H-pyrazole;

1-(2-chloro-phenyl)-5-[4-(5-carboxypyridin-3-yl)-phenyl]-3-[di-(trifluoromethyl)-hydroxy-methyl]-4,5-dihydro-1H-pyrazole;

1-(2-chloro-phenyl)-5-{3-[3-(methyl-amino)-propane-1-sulfonyl]-biphenyl-4-yl}-3-[di-(trifluoromethyl)-hydroxy-methyl]-4,5-dihydro-1H-pyrazole;

1-(2-chloro-phenyl)-5-[4-(6-methanesulfonyl-pyridin-3-yl)-phenyl]-3-[di-(trifluoromethyl)-hydroxy-methyl]-4,5-dihydro-1H-pyrazole;

5-(3'-ethoxy-biphenyl-4-yl)-1-(2-fluoro-phenyl)-3-[di-(trifluoromethyl)-hydroxy-methyl]-4,5-dihydro-1H-pyrazole;

5-(3'-ethoxy-biphenyl-4-yl)-1-(2,4-difluoro-phenyl)-3-[di-(trifluoromethyl)-hydroxy-methyl]-4,5-dihydro-1H-pyrazole;

1-(2-chloro-phenyl)-5-(3-fluoro-3'-methylsulfanyl-biphenyl-4-yl)-3-[di-(trifluoromethyl)-hydroxy-methyl]-4,5-dihydro-1H-pyrazole;

1-(2-chloro-phenyl)-5-(3'-ethoxy-3-fluoro-biphenyl-4-yl)-3-[di-(trifluoromethyl)-hydroxy-methyl]-4,5-dihydro-1H-pyrazole;

1-(2-chloro-phenyl)-5-(3-fluoro-2'-methyl-biphenyl-4-yl)-3-[di-(trifluoromethyl)-hydroxy-methyl]-4,5-dihydro-1H-pyrazole;

1-(2-chloro-phenyl)-5-(4'-acetyl-3-fluoro-biphenyl-4-yl)-3-[di-(trifluoromethyl)-hydroxy-methyl]-4,5-dihydro-1H-pyrazole;

1-(2-chloro-phenyl)-5-[2-fluoro-4-(1-BOC-1,2,3,6-tetrahydropyridin-4-yl)-phenyl]-3-[di-(trifluoromethyl)-hydroxy-methyl]-4,5-dihydro-1H-pyrazole;

1-(2-chloro-phenyl)-5-[2-fluoro-4-(6-methoxy-pyridin-3-yl)-phenyl]-3-[di-(trifluoromethyl)-hydroxy-methyl]-4,5-dihydro-1H-pyrazole;

1-(2-chloro-phenyl)-5-(3,4'-difluoro-biphenyl-4-yl)-3-[di-(trifluoromethyl)-hydroxy-methyl]-4,5-dihydro-1H-pyrazole;

1-(2-chloro-phenyl)-5-(3-fluoro-3'-methanesulfinyl-biphenyl-4-yl)-3-[di-(trifluoromethyl)-hydroxy-methyl]-4,5-dihydro-1H-pyrazole;

1-(2-chloro-phenyl)-5-[3-fluoro-4'-(1-hydroxy-1-methyl-ethyl)-biphenyl-4-yl]-3-[di-(trifluoromethyl)-hydroxy-methyl]-4,5-dihydro-1H-pyrazole;

1-(2-chloro-phenyl)-5-(3-fluoro-3'-methanesulfonyl-biphenyl-4-yl)-3-[di-(trifluoromethyl)-hydroxy-methyl]-4,5-dihydro-1H-pyrazole;

5-[6-(2-acetyl-phenyl)-pyridin-3-yl]-1-(2-chloro-phenyl)-3-[di-(trifluoromethyl)-hydroxy-methyl]-4,5-dihydro-1H-pyrazole;

1-(2-chloro-phenyl)-5-[6-(3-methoxy-phenyl)-pyridin-3-yl]-3-[di-(trifluoromethyl)-hydroxy-methyl]-4,5-dihydro-1H-pyrazole;

1-(2-chloro-phenyl)-5-[6-(4-methylsulfanyl-phenyl)-pyridin-3-yl]-3-[di-(trifluoromethyl)-hydroxy-methyl]-4,5-dihydro-1H-pyrazole;

1-(2-chloro-phenyl)-5-[6-(4-methanesulfonyl-phenyl)-pyridin-3-yl]-3-[di-(trifluoromethyl)-hydroxy-methyl]-4,5-dihydro-1H-pyrazole;

1-(2-chloro-phenyl)-5-[6-(6-methoxy-pyridin-3-yl)-pyridin-3-yl]-3-[di-(trifluoromethyl)-hydroxy-methyl]-4,5-dihydro-1H-pyrazole;

1-(2-chloro-phenyl)-5-[6-(4-fluoro-phenyl)-pyridin-3-yl]-3-[di-(trifluoromethyl)-hydroxy-methyl]-4,5-dihydro-1H-pyrazole;

1-(2-chloro-phenyl)-5-[6-(1-BOC-1,2,3,6-tetrahydropyridin-4-yl)-pyridin-3-yl]-3-[di-(trifluoromethyl)-hydroxy-methyl]-4,5-dihydro-1H-pyrazole;

1-(2-chloro-phenyl)-5-[6-(4-BOC-piperazin-1-yl)-pyridin-3-yl]-3-[di-(trifluoromethyl)-hydroxy-methyl]-4,5-dihydro-1H-pyrazole;

1-(2-chloro-phenyl)-5-[6-(1,2,3,6-tetrahydropyridin-4-yl)-pyridin-3-yl]-3-[di-(trifluoromethyl)-hydroxy-methyl]-4,5-dihydro-1H-pyrazole hydrochloride;

1-(2-chloro-phenyl)-5-[6-(piperazin-1-yl)-pyridin-3-yl]-3-[di-(trifluoromethyl)-hydroxy-methyl]-4,5-dihydro-1H-pyrazole hydrochloride;

1-(2-chloro-phenyl)-5-[6-(1-methanesulfonyl-1,2,3,6-tetrahydropyridin-4-yl)-pyridin-3-yl]-3-[di-(trifluoromethyl)-hydroxy-methyl]-4,5-dihydro-1H-pyrazole;

1-(2-chloro-phenyl)-5-[6-(1-cyclopropanesulfonyl-1,2,3,6-tetrahydropyridin-4-yl)-pyridin-3-yl]-3-[di-(trifluoromethyl)-hydroxy-methyl]-4,5-dihydro-1H-pyrazole;

1-(2-chloro-phenyl)-5-[6-(4-methanesulfonyl-piperazin-1-yl)-pyridin-3-yl]-3-[di-(trifluoromethyl)-hydroxy-methyl]-4,5-dihydro-1H-pyrazole;

5-(3'-acetyl-2-fluoro-biphenyl-4-yl)-1-(2-chloro-phenyl)-3-[di-(trifluoromethyl)-hydroxy-methyl]-4,5-dihydro-1H-pyrazole;

5-(4'-acetyl-2-fluoro-biphenyl-4-yl)-1-(2-chloro-phenyl)-3-[di-(trifluoromethyl)-hydroxy-methyl]-4,5-dihydro-1H-pyrazole;

1-(2-chloro-phenyl)-5-(2-fluoro-4'-methoxy-biphenyl-4-yl)-3-[di-(trifluoromethyl)-hydroxy-methyl]-4,5-dihydro-1H-pyrazole;

1-(2-chloro-phenyl)-5-(2-fluoro-4'-methylsulfanyl-biphenyl-4-yl)-3-[di-(trifluoromethyl)-hydroxy-methyl]-4,5-dihydro-1H-pyrazole;

1-(2-chloro-phenyl)-5-(2-fluoro-4'-methylsulfonyl-biphenyl-4-yl)-3-[di-(trifluoromethyl)-hydroxy-methyl]-4,5-dihydro-1H-pyrazole;

1-(2-chloro-phenyl)-5-(2,4'-difluoro-biphenyl-4-yl)-3-[di-(trifluoromethyl)-hydroxy-methyl]-4,5-dihydro-1H-pyrazole;

1-(2-chloro-phenyl)-5-(2-fluoro-2'-isopropoxy-biphenyl-4-yl)-3-[di-(trifluoromethyl)-hydroxy-methyl]-4,5-dihydro-1H-pyrazole;

1-(2-chloro-phenyl)-5-[3-fluoro-4-(6-methoxy-pyridin-3-yl)-phenyl]-3-[di-(trifluoromethyl)-hydroxy-methyl]-4,5-dihydro-1H-pyrazole;

1-(2,4-difluoro-phenyl)-5-(3'-methylsulfanyl-biphenyl-4-yl)-3-[di-(trifluoromethyl)-hydroxy-methyl]-4,5-dihydro-1H-pyrazole;

1-(2,4-difluoro-phenyl)-5-(4-(6-methoxy-pyridin-3-yl)-phenyl)-3-[di-(trifluoromethyl)-hydroxy-methyl]-4,5-dihydro-1H-pyrazole;

1-(2,4-difluoro-phenyl)-5-(2'-methyl-biphenyl-4-yl)-3-[di-(trifluoromethyl)-hydroxy-methyl]-4,5-dihydro-1H-pyrazole;

1-(2,4-difluoro-phenyl)-5-(4-pyrimidin-5-yl-phenyl)-3-[di-(trifluoromethyl)-hydroxy-methyl]-4,5-dihydro-1H-pyrazole;

1-(2,4-difluoro-phenyl)-5-(4'-tetrazol-1-yl-biphenyl-4-yl)-3-[di-(trifluoromethyl)-hydroxy-methyl]-4,5-dihydro-1H-pyrazole;

1-(2,4-difluoro-phenyl)-5-[4-(1-methyl-1H-indol-2-yl)-phenyl]-3-[di-(trifluoromethyl)-hydroxy-methyl]-4,5-dihydro-1H-pyrazole;

5-[4-(1-benzenesulfonyl-1H-indol-2-yl)-phenyl]-1-(2,4-difluoro-phenyl)-3-[di-(trifluoromethyl)-hydroxy-methyl]-4,5-dihydro-1H-pyrazole;

1-(2,4-difluoro-phenyl)-5-(4-(2-methyl-pyridin-3-yl)-phenyl)-3-[di-(trifluoromethyl)-hydroxy-methyl]-4,5-dihydro-1H-pyrazole;

1-(2,4-difluoro-phenyl)-5-[4-(6-trifluoromethyl-pyridin-3-yl)-phenyl]-3-[di-(trifluoromethyl)-hydroxy-methyl]-4,5-dihydro-1H-pyrazole;

1-(2,4-difluoro-phenyl)-5-[4-(5-methoxycarbonyl-pyridin-3-yl)-phenyl]-3-[di-(trifluoromethyl)-hydroxy-methyl]-4,5-dihydro-1H-pyrazole;

1-(2,4-difluoro-phenyl)-5-[4-(5-formyl-6-methoxy-pyridin-3-yl)-phenyl]-3-[di-(trifluoromethyl)-hydroxy-methyl]-4,5-dihydro-1H-pyrazole;

5-[4-(2-cyano-pyridin-3-yl)-phenyl]-1-(2,4-difluoro-phenyl)-3-[di-(trifluoromethyl)-hydroxy-methyl]-4,5-dihydro-1H-pyrazole;

1-(2,4-difluoro-phenyl)-5-[4-(5-fluoro-pyridin-3-yl)-phenyl]-3-[di-(trifluoromethyl)-hydroxy-methyl]-4,5-dihydro-1H-pyrazole;

1-(2,4-difluoro-phenyl)-5-[4-(6-methanesulfanyl-pyridin-3-yl)-phenyl]-3-[di-(trifluoromethyl)-hydroxy-methyl]-4,5-dihydro-1H-pyrazole;

1-(2,4-difluoro-phenyl)-5-[4-(6-methoxy-4-methyl-pyridin-3-yl)-phenyl]-3-[di-(trifluoromethyl)-hydroxy-methyl]-4,5-dihydro-1H-pyrazole;

1-(2,4-difluoro-phenyl)-5-[4-(6-fluoro-4-methyl-pyridin-3-yl)-phenyl]-3-[di-(trifluoromethyl)-hydroxy-methyl]-4,5-dihydro-1H-pyrazole;

1-(2,4-difluoro-phenyl)-5-[4-pyridin-2-yl-phenyl]-3-[di-(trifluoromethyl)-hydroxy-methyl]-4,5-dihydro-1H-pyrazole;

1-(2,4-difluoro-phenyl)-5-{4'-[(2-hydroxy-ethyl)-methyl-sulfamoyl]-biphenyl-4-yl}-3-[di-(trifluoromethyl)-hydroxy-methyl]-4,5-dihydro-1H-pyrazole;

1-(2,4-difluoro-phenyl)-5-(3'-fluoro-4'-methanesulfonyl-biphenyl-4-yl)-3-[di-(trifluoromethyl)-hydroxy-methyl]-4,5-dihydro-1H-pyrazole;

1-(2,4-difluoro-phenyl)-5-(3',5'-difluoro-4'-methanesulfonyl-biphenyl-4-yl)-3-[di-(trifluoromethyl)-hydroxy-methyl]-4,5-dihydro-1H-pyrazole;

1-(2,4-difluoro-phenyl)-5-(2',6'-difluoro-4'-methanesulfonyl-biphenyl-4-yl)-3-[di-(trifluoromethyl)-hydroxy-methyl]-4,5-dihydro-1H-pyrazole;

1-(2,4-difluoro-phenyl)-5-(3'-cyano-4'-methanesulfonyl-biphenyl-4-yl)-3-[di-(trifluoromethyl)-hydroxy-methyl]-4,5-dihydro-1H-pyrazole;

1-(2,4-difluoro-phenyl)-5-[4-(5-methanesulfonyl-pyridin-2-yl)-phenyl]-3-[di-(trifluoromethyl)-hydroxy-methyl]-4,5-dihydro-1H-pyrazole;

1-(2,4-difluoro-phenyl)-5-(4'-methanesulfonyl-3'-trifluoromethyl-biphenyl-4-yl)-3-[di-(trifluoromethyl)-hydroxy-methyl]-4,5-dihydro-1H-pyrazole;

1-(2,4-difluoro-phenyl)-5-{[2',6'-difluoro-4'-(tetrazol-1-yl)-biphenyl]-4-yl}-3-[di-(trifluoromethyl)-hydroxy-methyl]-4,5-dihydro-1H-pyrazole;

1-(2,4-difluoro-phenyl)-5-{4-[4-methyl-6-(tetrazol-1-yl)-pyridin-3-yl]-phenyl}-3-[di-(trifluoromethyl)-hydroxy-methyl]-4,5-dihydro-1H-pyrazole;

5-{3'-[3-(N-BOC-N-methyl-amino)-propane-1-sulfonyl]-biphenyl-4-yl}-1-(2,4-difluoro-phenyl)-3-(di-(trifluoromethyl)-hydroxy-methyl)-4,5-dihydro-1H-pyrazole;

1-(2,4-difluoro-phenyl)-5-(4'-dimethylsulfamoyl-biphenyl-4-yl)-3-(di-(trifluoromethyl)-hydroxy-methyl)-4,5-dihydro-1H-pyrazole;

1-(2,4-difluoro-phenyl)-5-{4'-[(2-hydroxy-ethyl)-methanesulfonyl-amino]biphenyl-4-yl}-3-(di-(trifluoromethyl)-hydroxy-methyl)-4,5-dihydro-1H-pyrazole;

1-(2,4-difluoro-phenyl)-5-[4-(1-BOC-1,2,3,6-tetrahydropyridin-4-yl)-phenyl]-3-[di-(trifluoromethyl)-hydroxy-methyl]-4,5-dihydro-1H-pyrazole;

1-(2,4-difluoro-phenyl)-5-[4-(1,2,3,6-tetrahydropyridin-4-yl)-phenyl]-3-[di-(trifluoromethyl)-hydroxy-methyl]-4,5-dihydro-1H-pyrazole trifluoroacetate;

1-(2,4-difluoro-phenyl)-5-[4-(1-methanesulfonyl-1,2,3,6-tetrahydropyridin-4-yl)-phenyl]-3-[di-(trifluoromethyl)-hydroxy-methyl]-4,5-dihydro-1H-pyrazole;

1-(2,4-difluoro-phenyl)-5-[4-(1-dimethylsulfamoyl-1,2,3,6-tetrahydropyridin-4-yl)-phenyl]-3-[di-(trifluoromethyl)-hydroxy-methyl]-4,5-dihydro-1H-pyrazole;

1-(2,4-difluoro-phenyl)-5-[4-(1-isobutyryl-1,2,3,6-tetrahydropyridin-4-yl)-phenyl]-3-[di-(trifluoromethyl)-hydroxy-methyl]-4,5-dihydro-1H-pyrazole;

1-(2,4-difluoro-phenyl)-5-[4-(1-dimethylcarbamoyl-1,2,3,6-tetrahydropyridin-4-yl)-phenyl]-3-[di-(trifluoromethyl)-hydroxy-methyl]-4,5-dihydro-1H-pyrazole;

1-(2,4-difluoro-phenyl)-5-[4-(4-BOC-piperazin-1-yl)-phenyl]-3-[di-(trifluoromethyl)-hydroxy-methyl]-4,5-dihydro-1H-pyrazole;

1-(2,4-difluoro-phenyl)-5-[4-(piperazin-1-yl)-phenyl]-3-[di-(trifluoromethyl)-hydroxy-methyl]-4,5-dihydro-1H-pyrazole hydrochloride;

1-(2,4-difluoro-phenyl)-5-[4-(4-methanesulfonyl-piperazin-1-yl)-phenyl]-3-[di-(trifluoromethyl)-hydroxy-methyl]-4,5-dihydro-1H-pyrazole;

1-(2,4-difluoro-phenyl)-5-[4-(4-dimethylsulfamoyl-piperazin-1-yl)-phenyl]-3-[di-(trifluoromethyl)-hydroxy-methyl]-4,5-dihydro-1H-pyrazole;

1-(2,4-difluoro-phenyl)-5-[4-(4-BOC-homopiperazin-1-yl)-phenyl]-3-[di-(trifluoromethyl)-hydroxy-methyl]-4,5-dihydro-1H-pyrazole;

1-(2,4-difluoro-phenyl)-5-[4-(homopiperazin-1-yl)-phenyl]-3-[di-(trifluoromethyl)-hydroxy-methyl]-4,5-dihydro-1H-pyrazole hydrochloride;

1-(2,4-difluoro-phenyl)-5-[4-(4-methanesulfonyl-homopiperazin-1-yl)-phenyl]-3-[di-(trifluoromethyl)-hydroxy-methyl]-4,5-dihydro-1H-pyrazole;

1-(2,4-difluoro-phenyl)-5-[4-(4-dimethylsulfamoyl-homopiperazin-1-yl)-phenyl]-3-[di-(trifluoromethyl)-hydroxy-methyl]-4,5-dihydro-1H-pyrazole;

1-(2,4-difluoro-phenyl)-5-{3'-[3-(methyl-amino)-propane-1-sulfonyl]-biphenyl-4-yl}-3-[di-(trifluoromethyl)-hydroxy-methyl]-4,5-dihydro-1H-pyrazole;

1-(2,4-difluoro-phenyl)-5-[3'-methanesulfonyl-biphenyl-4-yl]-3-[di-(trifluoromethyl)-hydroxy-methyl]-4,5-dihydro-1H-pyrazole;

1-(2-chloro-phenyl)-5-{5-[3-(methylsulfanyl)-phenyl]-thiophen-2-yl}-3-[di-(trifluoromethyl)-hydroxy-methyl]-4,5-dihydro-1H-pyrazole;

1-(2-chloro-phenyl)-5-{5-[6-(methylsulfanyl)-pyridin-3-yl]-thiophen-2-yl}-3-[di-(trifluoromethyl)-hydroxy-methyl]-4,5-dihydro-1H-pyrazole;

1-(2-chloro-phenyl)-5-[5-(1-BOC-1,2,3,6-tetrahydropyridin-4-yl)-thiophen-2-yl]-3-[di-(trifluoromethyl)-hydroxy-methyl]-4,5-dihydro-1H-pyrazole;

1-(2-chloro-phenyl)-5-[5-(1,2,3,6-tetrahydropyridin-4-yl)-thiophen-2-yl]-3-[di-(trifluoromethyl)-hydroxy-methyl]-4,5-dihydro-1H-pyrazole hydrochloride;

1-(2-chloro-phenyl)-5-[5-(1-methanesulfonyl-1,2,3,6-tetrahydropyridin-4-yl)-thiophen-2-yl]-3-[di-(trifluoromethyl)-hydroxy-methyl]-4,5-dihydro-1H-pyrazole;

1-(2-chloro-phenyl)-5-{5-[3-(methylsulfonyl)-phenyl]-thiophen-2-yl}-3-[di-(trifluoromethyl)-hydroxy-methyl]-4,5-dihydro-1H-pyrazole;

1-(2-chloro-phenyl)-5-{5-[6-(methylsulfonyl)-pyridin-3-yl]-thiophen-2-yl}-3-[di-(trifluoromethyl)-hydroxy-methyl]-4,5-dihydro-1H-pyrazole;

5-(2-chloro-phenyl)-1-[3'-(methylsulfanyl)-biphenyl-4-yl]-3-[di-(trifluoromethyl)-hydroxy-methyl]-4,5-dihydro-1H-pyrazole;

5-(2-chloro-phenyl)-1-{4-[6-(methylsulfanyl)-pyridin-3-yl]-phenyl}-3-[di-(trifluoromethyl)-hydroxy-methyl]-4,5-dihydro-1H-pyrazole;

5-(2-chloro-phenyl)-1-[4-(1-BOC-1,2,3,6-tetrahydropyridin-4-yl)-phenyl]-3-[di-(trifluoromethyl)-hydroxy-methyl]-4,5-dihydro-1H-pyrazole;

5-(2-chloro-phenyl)-1-[3'-(methylsulfonyl)-biphenyl-4-yl]-3-[di-(trifluoromethyl)-hydroxy-methyl]-4,5-dihydro-1H-pyrazole;

5-(2-chloro-phenyl)-1-{4-[6-(methylsulfonyl)-pyridin-3-yl]-phenyl}-3-[di-(trifluoromethyl)-hydroxy-methyl]-4,5-dihydro-1H-pyrazole;

5-(2-chloro-phenyl)-1-[4-(4-BOC-piperazin-1-yl)-phenyl]-3-[di-(trifluoromethyl)-hydroxy-methyl]-4,5-dihydro-1H-pyrazole;

5-(2-chloro-phenyl)-1-[4-(1,2,3,6-tetrahydropyridin-4-yl)-phenyl]-3-[di-(trifluoromethyl)-hydroxy-methyl]-4,5-dihydro-1H-pyrazole hydrochloride;

5-(2-chloro-phenyl)-1-[4-(piperazin-1-yl)-phenyl]-3-[di-(trifluoromethyl)-hydroxy-methyl]-4,5-dihydro-1H-pyrazole hydrochloride;

5-(2-chloro-phenyl)-1-[4-(1-cyclopropanesulfonyl-1,2,3,6-tetrahydropyridin-4-yl)-phenyl]-3-[di-(trifluoromethyl)-hydroxy-methyl]-4,5-dihydro-1H-pyrazole;

5-(2-chloro-phenyl)-1-[4-(4-cyclopropanesulfonyl-piperazin-1-yl)-phenyl]-3-[di-(trifluoromethyl)-hydroxy-methyl]-4,5-dihydro-1H-pyrazole;

5-(2-chloro-phenyl)-1-[3'-(methylsulfanyl)-biphenyl-3-yl]-3-[di-(trifluoromethyl)-hydroxy-methyl]-4,5-dihydro-1H-pyrazole;

5-(2-chloro-phenyl)-1-{3-[6-(methylsulfanyl)-pyridin-3-yl]-phenyl}-3-[di-(trifluoromethyl)-hydroxy-methyl]-4,5-dihydro-1H-pyrazole;

5-(2-chloro-phenyl)-1-[3-(1-BOC-1,2,3,6-tetrahydropyridin-4-yl)-phenyl]-3-[di-(trifluoromethyl)-hydroxy-methyl]-4,5-dihydro-1H-pyrazole;

5-(2-chloro-phenyl)-1-[3'-(methylsulfonyl)-biphenyl-3-yl]-3-[di-(trifluoromethyl)-hydroxy-methyl]-4,5-dihydro-1H-pyrazole;

5-(2-chloro-phenyl)-1-{3-[6-(methylsulfonyl)-pyridin-3-yl]-phenyl}-3-[di-(trifluoromethyl)-hydroxy-methyl]-4,5-dihydro-1H-pyrazole;

5-(2-chloro-phenyl)-1-[3-(4-BOC-piperazin-1-yl)-phenyl]-3-[di-(trifluoromethyl)-hydroxy-methyl]-4,5-dihydro-1H-pyrazole;

5-(2-chloro-phenyl)-1-[3-(1-methylsulfonyl-1,2,3,6-tetrahydropyridin-4-yl)-phenyl]-3-[di-(trifluoromethyl)-hydroxy-methyl]-4, 5-dihydro-1H-pyrazole;

5-(2-chloro-phenyl)-1-[3-(1-cyclopropanesulfonyl-1,2,3,6-tetrahydropyridin-4-yl)-phenyl]-3-[di-(trifluoromethyl)-hydroxy-methyl]-4, 5-dihydro-1H-pyrazole;

5-(2-chloro-phenyl)-1-[3-(4-methylsulfonyl-piperazin-1-yl)-phenyl]-3-[di-(trifluoromethyl)-hydroxy-methyl]-4,5-dihydro-1H-pyrazole; and 5-(2-chloro-phenyl)-1-[3-(4-cyclopropanesulfonyl-piperazin-1-yl)-phenyl]-3-[di-(trifluoromethyl)-hydroxy-methyl]-4,5-dihydro-1H-pyrazole.

16. A pharmaceutical composition comprising a therapeutically effective amount of a compound of Formula 1 or its pharmaceutically acceptable salt according to claim 1; and a pharmaceutically acceptable carrier.

17. The pharmaceutical composition according to claim 16, wherein the composition is to treat dysfunction in cholesterol metabolism selected from the group consisting of cholesterol gallstone, hyperlipidemia, and coronary atherosclerosis.

\* \* \* \* \*